US006951872B2

(12) United States Patent
Jacobson et al.

(10) Patent No.: US 6,951,872 B2
(45) Date of Patent: Oct. 4, 2005

(54) MONOCYCLIC OR BICYCLIC CARBOCYCLES AND HETEROCYCLES AS FACTOR XA INHIBITORS

(75) Inventors: Irina C. Jacobson, Sammamish, WA (US); Ruth R. Wexler, Chadds Ford, PA (US); Suanne Nakajima, Cambridge, MA (US); Mimi L. Quan, Yardley, PA (US); Shuaige Wang, West Chester, PA (US); Joanne M. Smallheer, Yardley, PA (US); Jennifer Qiao, Princeton, NJ (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/730,170

(22) Filed: Dec. 8, 2003

(65) Prior Publication Data
US 2004/0132718 A1 Jul. 8, 2004

Related U.S. Application Data

(62) Division of application No. 10/003,125, filed on Oct. 29, 2001, now Pat. No. 6,710,058.
(60) Provisional application No. 60/246,107, filed on Nov. 6, 2000, and provisional application No. 60/313,552, filed on Aug. 20, 2001.

(51) Int. Cl.$^7$ .................... C07D 211/06; A61K 31/445; A61P 7/02
(52) U.S. Cl. ...................... 514/319; 546/205
(58) Field of Search ........................... 546/205; 514/319

(56) References Cited

U.S. PATENT DOCUMENTS

| 5,032,602 A | 7/1991 | Fey et al. |
| 5,252,584 A | 10/1993 | Carling et al. |
| 5,998,447 A | 12/1999 | Stilz et al. |
| 6,020,357 A | 2/2000 | Pinto et al. |

FOREIGN PATENT DOCUMENTS

| EP | 454444 A | 10/1991 |
| EP | 522606 A | 1/1993 |
| EP | 908764 A | 4/1999 |
| WO | WO 9514012 A | 5/1995 |
| WO | WO 9730708 A | 8/1997 |
| WO | WO 9736900 A | 10/1997 |
| WO | WO 9740024 A | 10/1997 |
| WO | WO 9809987 A | 3/1998 |
| WO | WO 9831670 A | 7/1998 |
| WO | WO 9857633 A | 12/1998 |
| WO | WO 9931506 A | 7/1999 |
| WO | WO 9931507 A | 7/1999 |
| WO | WO 9932477 A | 7/1999 |
| WO | WO 9942455 A | 8/1999 |
| WO | WO 0047207 | 8/2000 |
| WO | WO 0069826 A | 11/2000 |
| WO | WO 0069832 A | 11/2000 |
| WO | WO 0069833 A | 11/2000 |
| WO | WO 0069834 A | 11/2000 |
| WO | WO 0147919 A | 7/2001 |
| WO | WO 0200651 | 1/2002 |

Primary Examiner—Bruck Kifle
(74) Attorney, Agent, or Firm—Jing G. Sun; David H. Vance

(57) ABSTRACT

The present application describes monocyclic or bicyclic carbocycles and heterocycles and derivatives thereof of Formula I:

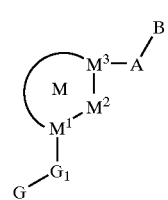

or pharmaceutically acceptable salt forms thereof, which are useful as inhibitors of factor Xa.

21 Claims, No Drawings

MONOCYCLIC OR BICYCLIC CARBOCYCLES AND HETEROCYCLES AS FACTOR XA INHIBITORS

CROSS-REFERENCE TO RELATED APPLICATIONS

This application is a Divisional of U.S. Ser. No. 10/003,125, filed Oct. 29, 2001 now U.S. Pat. No. 6,710,058, now allowed, which in turn claims the priority benefit of U.S. Provisional Application No. 60/246,107, filed Nov. 6, 2000, and Provisional Application No. 60/313,552, filed Aug. 20, 2001, all of which are expressly incorporated fully herein by reference.

FIELD OF THE INVENTION

This invention relates generally to monocyclic or bicyclic carbocycles and heterocycles, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

U.S. Pat. No. 5,032,602 shows 2-pyridones of the following formula.

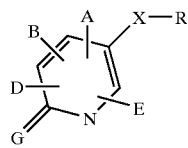

These compounds are inhibitors of HMG-COA reductase. These compounds are not described as being useful for inhibiting factor Xa and are not considered to be part of the present invention.

WO97/36900 describes inhibitors of farnesyl-protein transferase of the formula.

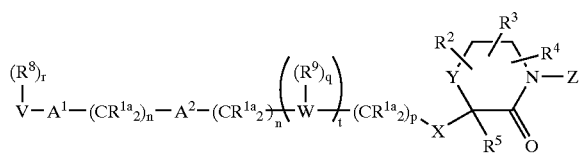

WO97/36900 does not consider inhibition of factor Xa however. The compounds of WO97/36900 are not considered to be part of the present invention.

WO99/31506 and WO99/31507 describe solution phase syntheses of lactams of the formula.

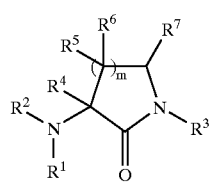

The lactams described in WO99/31506 and WO99/31507 are not considered to be part of the present invention.

WO95/14012 illustrates protease inhibitors of the formula.

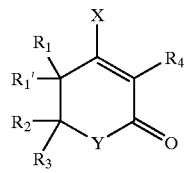

This formula represents pyrones when Y is unsubstituted or substituted nitrogen. However, the compounds of WO95/14012 are not considered to be part of the present invention.

EP 0,908,764 depicts photographic developers of the formula below.

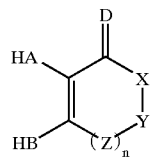

Careful selection of variables can lead one to pyrones. But, the compounds of EP 0,908,764 are not considered to be part of the present invention.

U.S. Pat. No. 5,252,584 shows hydroxyquinolones of the following formula.

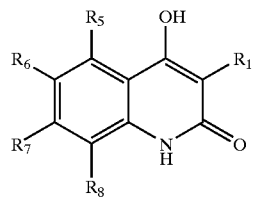

$R^1$ can be a substituted pyrone. These compounds are not described as being useful for inhibiting factor Xa and are not considered to be part of the present invention.

EP 0,454,444 describes glutarimide derivatives of the following formula.

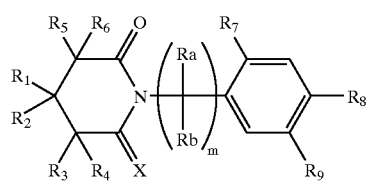

X can be O, $R_1$ can be an alkyl, alkoxy, or halo-substituted benzyl, and $R_9$ can be a cyclic moiety. These compounds are indicated to be herbicides. The compounds of EP 0,454,444 are not considered to be part of the present invention.

WO99/42455 illustrates antiviral agents of the formula.

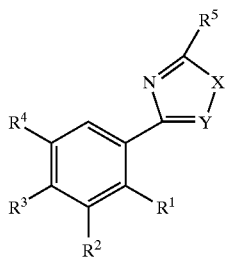

R¹ can potentially be a cyclic amide substituted by an aryl amine. The ring containing X and Y is a 5 or 6-membered heteroaromatic ring. The compounds shown in WO99/42455 are not considered to be part of the present invention.

U.S. Pat. No. 5,998,447 shows heterocycles of the following formula.

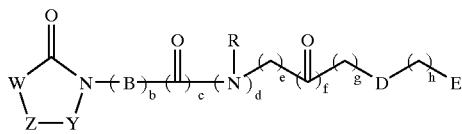

B can be phenylene; W can be substituted phenylalkylene; c, d, e, f, g, and h can all be 0; and, E can be tetrazole. These compounds are inhibitors of leucocyte adhesion and/or antagonists of VLA-4. Tetrazole substituted compounds of this sort are not considered to be part of the present invention.

EP 0,522,606 depicts pyridine derivatives of the following formula.

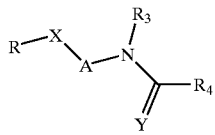

R can be substituted pyridine, X can be O, A is a carbon atom that can be part of a ring (i.e., a 1,1-substituted ring), Y can be O, and $R_3$ and $R_4$ can combine for form a cyclic lactam containing an optionally substituted aralkyl. Compounds of this sort are not considered to be part of the present invention.

WO99/32477 illustrates Factor Xa inhibitors containing at least three aryl or heterocyclic groups separated by two linking groups, an example of which is shown below.

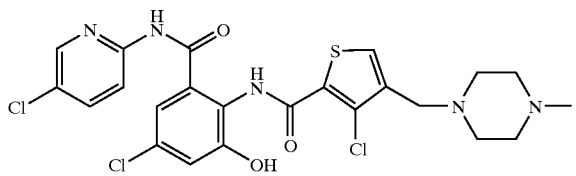

Dual linker compounds of this sort are not considered to be part of the present invention.

WO00/69826, WO00/69832, WO00/69833, and WO00/69834 relate to coagulation cascade inhibitors that are 1,3-disubsituted pyridones of the formula shown below, or aza-substituted derivatives.

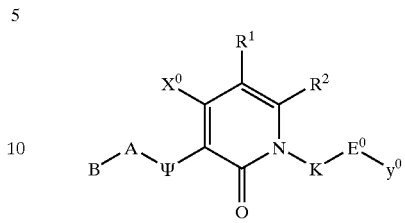

B and $Y^0$ are preferably cyclic moieties. A, Ψ, K, and $E^0$ are preferably linkers. Pyridones and aza-pyridones of this sort are not considered to be part of the present invention.

WO01/47919 discloses factor Xa inhibitors that are substituted oxazolidinones of the formula shown below:

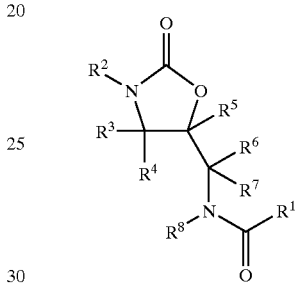

$R^1$ is thienyl or benzothienyl. Oxazolidinones of this sort are not considered to be part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel monocyclic or bicyclic carbocycles and heterocycles which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel compounds for use in therapy.

It is another object of the present invention to provide the use of novel compounds for the manufacture of a medicament for the treatment of a thromboembolic disorder.

These and other objects, which will become apparent during the following detailed description, have been achieved by the inventors' discovery that the presently claimed monocyclic or bicyclic carbocycles and heterocycles, or pharmaceutically acceptable salt or prodrug forms thereof, are effective factor Xa inhibitors.

DETAILED DESCRIPTION OF PREFERRED EMBODIMENTS

[1] Thus, in an embodiment, the present invention provides a novel compound of Formula I:

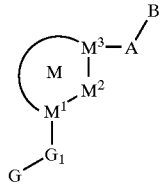

or a stereoisomer or pharmaceutically acceptable salt thereof, wherein;

ring M, including $M^1$, $M^2$, and $M^3$, is a 5, 6, or 7 membered non-aromatic carbocycle or 5, 6, or 7 membered non-aromatic heterocycle, consisting of: carbon atoms, 0–3 N, and 0–1 heteroatoms selected from O and $S(O)_p$, provided that ring M consists of a total of 0–3 O, $S(O)_p$ and N;

alternatively, ring M is an aromatic heterocycle selected from 2-pyridinone, 3-pyridazinone, 4-pyrimidinone, 2-pyrazinone, pyrimidine-2,4-dione, pyridazine-3,6-dione, 1H-quinolin-2-one, 1,4-dihydro-pyrrolo[3,2-b]pyridin-5-one and 1,4-dihydro-imidazo[4,5-b]pyridin-5-one;

ring M is substituted with 0–2 $R^{1a}$, 0–1 Z, and 0–2 carbonyl groups, and, comprises: 0–2 double bonds;

provided that ring M is other than an isoxazoline, isothiazoline, pyrazoline, triazoline, tetrazoline, 3-phenyl-substituted pyrrolidine, 3-phenyl-substituted pyrroline, 3-phenyl-substituted isoxazolidine, or 4-phenyl-substituted isoxazolidine;

G is a group of formula IIa or IIb:

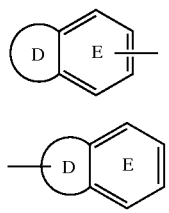

$G_1$ is selected from $(CR^{3a}R^{3b})_{1-5}$, $(CR^{3a}R^{3b})_{0-2}CR^{3a}=CR^{3a}$ $(CR^{3a}R^{3b})_{0-2}$, $(CR^{3a}R^{3b})_{0-2}C\equiv C(CR^{3a}R^{3b})_{0-2}$, $(CR^{3a}R^{3b})_u C(O)(CR^{3a}R^{3b})_w$, $(CR^{3a}R^{3b})_u C(O)O$ $(CR^{3a}R^{3b})_w$, $(CR^{3a}R^{3b})_u OC(O)(CR^{3a}R^{3b})_w$, $(CR^{3a}R^{3b})_u$ $(CR^{3a}R^{3b})_w$, $(CR^{3a}R^{3b})_u NR^{3e}(CR^{3a}R^{3b})_w$, $(CR^{3a}R^{3b})_u C(O)NR^3$ $(CR^{3a}R^{3b})_w$, $(CR^{3a}R^{3b})_u NR^3 C(O)$ $(CR^{3a}R^{3b})_w$, $(CR^{3a}R^{3b})_u C(O)NR^3$ $(CR^{3a}R^{3b})_w$, $(CR^{3a}R^{3b})_u NR^3 C(O)O$ $(CR^{3a}R^{3b})_w$, $(CR^{3a}R^{3b})_u NR^3 C(O)NR^3$ $(CR^{3a}R^{3b})_w$, $(CR^{3a}R^{3b})_u NR^3 C(S)NR^3 (CR^{3a}R^{3b})_w$, $(CR^{3a}R^{3b})_u S$ $(CR^{3a}R^{3b})_w$, $(CR^{3a}R^{3b})_u S(O)$ $(CR^{3a}R^{3b})_w$, $(CR^{3a}R^{3b})_u S$ $(O)_2(CR^{3a}R^{3b})_w$, $(CR^{3a}R^{3b})_u S(O)NR^3$ $(CR^{3a}R^{3b})_w$, $(CR^{3a}R^{3b})_u NR^3 S(O)_2$ $(CR^{3a}R^{3b})_w$, $(CR^{3a}R^{3b})_u S(O)_2$ $NR^3$ $(CR^{3a}R^{3b})_w$, $(CR^{3a}R^{3b})_u NR^3 S(O)_2 NR^3 (CR^{3a}R^{3b})_w$, and $(CR^{3a}R^{3b})_u S(O)_2 NR^3 C(O)NR^3 (CR^{3a}R^{3b})_w$, wherein u+W total 0, 1, 2, 3, or 4, provided that $G_1$ does not form a N—N or N—O bond with either group to which it is attached;

ring D, including the two atoms of Ring E to which it is attached, is a 5–6 membered non-aromatic ring consisting of carbon atoms, 0–1 double bonds, and 0–2 N, and D is substituted with 0–2 R;

alternatively, ring D, including the two atoms of Ring E to which it is attached, is a 5–6 membered aromatic system consisting of carbon atoms and 0–2 heteroatoms selected from the group consisting of N, O, and $S(O)_p$, and D is substituted with 0–2 R;

E is selected from phenyl, pyridyl, pyrimidyl, pyrazinyl, and pyridazinyl, and is substituted with 0–2 R;

R is selected from $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)$ $NR^7R^9$, $NHC(=NR^8)NR^7R^9$, $NR^8 CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_t C(O)H$, $(CR^8R^9)_t C(O)R^{2c}$, $(CR^8R^9)_t NR^7R^8$, $(CR^8R^9)_t C(O)NR^7R^8$, $(CR^8R^9)_t OR^{3a}$, $(CR^8R^9)_t NR^7 C(O)$ $R^7$, $(CR^8R^9)_t S(O)_p NR^7R^8$, $(CR^8R^9)_t NR^7 S(O)_p R^{3f}$, $(CR^8R^9)_t S(O)R^{3c}$, $(CR^8R^9)_t S(O)_2 R^{3c}$, and $OCF_3$;

alternatively, the bridging portion of ring D is absent, and ring E is selected from phenyl, thienyl, pyridyl, pyrimidyl, pyrazinyl, and pyridazinyl, and ring E is substituted with $R^a$ and $R^b$;

alternatively, ring E is substituted with a 5–6 membered aromatic heterocycle consisting of: carbon atoms and 1–4 heteroatoms selected from the group consisting of N, O, and $S(O)_p$, and said aromatic heterocycle is substituted with $R^a$ and $R^b$;

alternatively, ring E is substituted with a 5–6 membered non-aromatic hetercocyle consisting of: carbon atoms and 1–4 heteroatoms selected from the group consisting of N, O, and $S(O)_p$, and said non-aromatic hetercocyle is substituted with $R^a$ and $R^b$, 0–2 carbonyl groups and containing 0–2 double bonds;

$R^a$ and $R^b$, at each occurrence, are independently selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8 CH(=NR^7)$, $NH_2$, $NH(C_{1-3}$ alkyl), $N(C_{1-3}$ alkyl$)_2$, $C(=NH)NH_2$, $CH_2NH_2$, $CH_2NH$ $(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_t C(O)H$, $(CR^8R^9)_t C(O)R^{2c}$, $(CR^8R^9)_t NR^7R^8$, $(CR^8R^9)_t C(O)NR^7R^8$, $(CR^8R^9)_t OR^{3a}$, $(CR^8R^9)_t NR^7 C(O)$ $R^{3f}$, $(CR^8R^9)_t S(O)_p NR^7R^8$, $(CR^8R^9)_t NR^7 S(O)_p R^{3f}$, $(CR^8R^9)_t S(O)R^{3c}$, $(CR^8R^9)_t S(O)_2 R^{3C}$, and $OCF_3$;

alternatively, $R^a$ and $R^b$ combine to form methylenedioxy or ethylenedioxy;

alternatively, the bridging portion of ring D is absent, and ring E is selected from pyrrolyl, pyrazolyl, imidazolyl, isoxazolyl, oxazolyl, triazolyl, thienyl, and thiazolyl, and ring E is substituted with 0–2 $R^c$;

$R^c$ is selected from $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)$ $NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rNR^7R^8$, $(CR^8R^9)_rC(O)NR^7R^8$, $(CR^8R^9)_rC(O)H$, $(CR^8R^9)_rC(O)R^{2c}$, $(CR^8R^9)_rNR^7C(O)R^7$, $(CR^8R^9)_rS(O)_p$ $NR^7R^8$, $(CR^8R^9)_rNR^7S(O)_pR^{3f}$, $(CR^8R^9)_rS(O)R^{3f}$, $(CR^8R^9)_rS(O)_2R^{3f}$, and $OCF_3$;

A is selected from:

$C_{3-10}$ carbocyclic residue substituted with 0–2 $R^4$, and

5–12 membered heterocyclic system containing from 1–4 heteroatoms selected from the group consisting of N, O, and S substituted with 0–2 $R^4$;

provided that B and ring M are attached to different atoms on A;

B is selected from: Y and X—Y;

X is selected from $-(CR^2R^{2a})_{1-4}-$, $-CR^2(CR^2R^{2b})(CH_2)_t-$, $-C(°)-C(=NR^{1c})-$, $-CR^2(NR^{1c}R^2)-$, $-CR^2(OR^2)-$, $-CR^2(SR^2)-$, $-C(O)CR^2R^{2a}-$, $-CR^2R^{2a}C(O)$, $-S-$, $-S(O)-$, $-S(O)_2-$, $SCR^2R^{2a}$, $-S(O)CR^2R^{2a}-$, $-S(O)_2CR^2R^{2a}-$, $CR^2R^{2a}S-$, $-CR^2R^{2a}S(O)-$, $-CR^2R^{2a}S(O)_2-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}-$, $-CR^2R^{2a}NR^2-$, O, $-CR^2R^{2a}-$, and $-OCR^2R^{2a}-$;

Y is selected from:

$-(CH_2)_rNR^2R^{2a}$, provided that X—Y do not form a N—N, O—N, or S—N bond, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

provided that B and Y are other than tetrazolyl;

Z is selected from H, $S(O)_2NHR^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$; $C_{2-6}$ alkenyl substituted with 0–2 $R^{1a}$; $C_{2-6}$ alkynyl substituted with 0–2 $R^{1a}$; cycloalkyl($C_{0-4}$ alkyl)-substituted with 0–3 $R^{1a}$; heterocyclyl($C_{0-4}$ alkyl)-substituted with 0–3 $R^{1a}$; aryl($C_{0-4}$ alkyl)-substituted with 0–3 $R^{1a}$; heteroaryl($C_{0-4}$ alkyl)-substituted with 0–3 $R^{1a}$;

$R^{1a}$, is selected from H, $-(CH_2)_r-R^{1b}$, $-CH=CH-R^{1b}$, $NCH_2R^{1c}$, $OCH_2R^{1c}$, $S(O)_pCH_2R^{1c}$, $NH(CH_2)_2(CH_2)_t$ $R^{1b}$, $O(CH_2)_2(CH_2)_tR^{1b}$, and $S(CH_2)_2(CH_2)_tR^{1b}$, provided that $R^{1a}$ forms other than an N-halo, N—N, N—S, N—O, or N—CN bond with the group to which it is attached;

alternatively, when two $R^{1a}$s are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–1 Z, comprising: 0–3 double bonds;

$R^{1b}$ is selected from H, $C_{1-3}$ alkyl, F, Cl, Br, I, CN, CHO, $(CF_2)_rCF_3$, $(CH_2)_rOR^2$, $NR^2R^{2a}$, $C(O)R^{2c}$, $C(O)OR^2$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^{2c}(O)NHR^{2b}$, $NR^{2c}(O)_2R^{2a}$, $OC(O)NR^{2a}R^{2b}$, $C(O)NR^2R^{2a}$, $C(O)NR^2(CH_2)_r$ $OR^2$, $SO_2NR^2R^{2a}$, $NR^2SO_2R^{2b}$, $C_{3-10}$ carbocycle substituted with 0–2 $R^{4a}$, and 5–10 membered heterocycle consisting of carbon atoms and from 1–4 heteroatoms selected from the group consisting of N, O, and $S(O)_p$ substituted with 0–2 $R^{4a}$, provided that $R^{1b}$ forms other than an N-halo, N—N, N—S, N—O, or N—CN bond with the group to which it is attached;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl optionally substituted with 0–2 $R^{4b}$, benzyl, a $C_{3-10}$ carbocyclic-$(CH_2)_r$—residue substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl optionally substituted with 0–2 $R^{4b}$, benzyl, a $C_{3-10}$ carbocyclic-$(CH_2)_r$— residue substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{2b}$, at each occurrence, is selected from $CF_3$, $C_{1-4}$ alkoxy, $C_{1-6}$ alkyl, benzyl, $C_{3-10}$ carbocyclic-$(CH_2)_r$—residue substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-10}$ carbocyclic-$(CH_2)_r$— residue substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

$R^3$, at each occurrence, is selected from H, $C_{1-6}$ alkyl substituted with 0–2 $R^{1a}$; $C_{2-6}$ alkenyl substituted with 0–2 $R^{1a}$; $C_{2-6}$ alkynyl substituted with 0–2 $R^{1a}$; cycloalkyl($C_{0-4}$ alkyl)- substituted with 0–3 $R^{1a}$; heterocyclyl($C_{0-4}$ alkyl)- substituted with 0–3 $R^{1a}$; aryl ($C_{0-4}$ alkyl)- substituted with 0–3 $R^{1a}$; heteroaryl($C_{0-4}$ alkyl)- substituted with 0–3 $R^{1a}$;

$R^{3a}$ and $R^{3b}$, at each occurrence, are independently selected from H, $C_{1-4}$ alkyl, phenyl, and benzyl;

$R^{3c}$, at each occurrence, is selected from $C_{1-4}$ alkyl, phenyl, and benzyl;

$R^{3d}$, at each occurrence, is selected from H and $C_{1-4}$ alkyl;

$R^{3e}$, is selected from H, $S(O)_2NHR^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$; $C_{2-6}$ alkenyl substituted with 0–2 $R^{1a}$; $C_{2-6}$ alkynyl substituted with 0–2 $R^{1a}$; cycloalkyl($C_{0-4}$ alkyl)-substituted with 0–3 $R^{1a}$; heterocyclyl($C_{0-4}$ alkyl)-substituted with 0–3 $R^{1a}$; aryl($C_{0-4}$ alkyl)-substituted with 0–3 $R^{1a}$; heteroaryl($C_{0-4}$ alkyl)-substituted with 0–3 $R^{1a}$;

$R^{3f}$, at each occurrence, is selected from: $C_{1-6}$ alkyl substituted with 0–2 $R^{1a}$; $C_{2-6}$ alkenyl substituted with 0–2 $R^{1a}$; $C_{2-6}$ alkynyl substituted with 0–2 $R^{1a}$; cycloalkyl($C_{0-4}$ alkyl)-substituted with 0–3 $R^{1a}$; heterocyclyl($C_{0-4}$ alkyl)-substituted with 0–3 $R^{1a}$; aryl($C_{0-4}$ alkyl)-substituted with 0–3 $R^{1a}$; heteroaryl($C_{0-4}$ alkyl)-substituted with 0–3 $R^{1a}$;

$R^4$, at each occurrence, is selected from H, $=O$, $(CH_2)_rOR^2$, F, Cl, Br, I, $C_{1-4}$ alkyl, $-CN$, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^{3f})NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^{3f}$, $S(O)_pR^{3f}$, $(CF_2)_rCF_3$, $NCH_2R^{1c}$, $OCH_2R^{1c}$, $SCH_2R^{1c}$, $N(CH_2)_2(CH_2)_tR^{1b}$, $O(CH_2)_2(CH_2)_tR^{1b}$, $S(CH_2)_2(CH_2)_tR^{1b}$, and 5–6 membered carbocycle substituted with 0–1 $R^5$, and a 5–6 membered heterocycle consisting of: carbon atoms and 1–4 heteroatoms selected from the group consisting of N, O, and $S(O)_p$ substituted with 0–1 $R^5$;

$R^{4a}$, at each occurrence, is selected from H, =O, $(CH_2)_r$ $OR^2$, $(CH_2)_r$—F, $(CH_2)_r$—Br, $(CH_2)_r$—Cl, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $(CH_2)_rN=CHOR^3$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^{3f}$, $S(O)_pR^{3f}$, $(CF_2)_rCF_3$, and 5–6 membered carbocycle substituted with 0–1 $R^5$, and a 5–6 membered heterocycle consisting of: carbon atoms and 1–4 heteroatoms selected from the group consisting of N, O, and $S(O)_p$ substituted with 0–1 $R^5$;

$R^{4b}$, at each occurrence, is selected from H, =O, $(!CH_2)_r$ $OR^3$, $(CH_2)_r$—F, $(CH_2)_r$—Cl, $(CH_2)_r$—Br, $(CH_2)_r$—I, $C_{1-4}$ alkyl, $(CH_2)_r$—CN, $(CH_2)_r$—$NO_2$, $(CH_2)_rNR^3R^{3a}$, $(CH_2)_rC(O)R^3$, $(CH_2)_rC(O)OR^{3c}$, $(CH_2)_r$—$NR^3C(O)R^{3a}$, $(CH_2)_r$—$C(O)NR^3R^{3a}$, $(CH_2)_r$—$NR^3C(O)NR^3R^{3a}$, $(CH_2)_r$—$C(=NR^3)_rNR^3R^{3a}$, $(CH_2)_r$—$NR^3C(=NR^3)NR^3R^{3a}$, $(CH_2)_r$—$SO_2NR^3R^{3a}$, $(CH_2)_r$—$NR^3SO_2NR^3R^{3a}$, $(CH_2)_r$—$NR^3SO_2$—$C_{1-4}$ alkyl, $(CH_2)_r$—$NR^3SO_2CF_3$, $(CH_2)_r$—$NR^3SO_2$-phenyl, $(CH_2)_r$—$S(O)_pCF_3$, $(CH_2)_r$—$S(O)_p$—$C_{1-4}$ alkyl, $(CH_2)_r$—$S(O)_p$-phenyl, and $(CF_2)_rCF_3$;

$R^5$, at each occurrence, is selected from H, $C_{1-6}$ alkyl, =O, $(CH_2)_rOR^3$, F, Cl, Br, I, CN, $NO_2$, $(CH_2)_rNR^3R^{3a}$, $(CH_2)_rC(O)R^3$, $(CH_2)_rC(O)OR^{3a}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR_3SO_2$-$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5–10 membered saturated, partially saturated or unsaturated ring which contains 0–2 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
p, at each occurrence, is selected from 0, 1, and 2;
r, at each occurrence, is selected from 0, 1, 2, and 3; and
t, at each occurrence, is selected from 0, 1, 2, and 3;
provided that when ring M is piperidin-2,6-dione and A is phenyl, then:
  (i) one of $R^a$ and $R^b$ is other than halo, alkyl, alkoxy, and $CF_3$;
  (ii) B is phenyl and $R^{4a}$ is other than alkyl;
  (iii) B is pyridyl or imidazolyl; or
  (iv) X is present and is C(O);
provided that when ring M is oxazolidinone and $G_1$ is $CONHCH_2$, then G is other than thienyl or benzothienyl.

[2] In a preferred embodiment, the present invention provides a novel compound, wherein the compound is selected from the group:

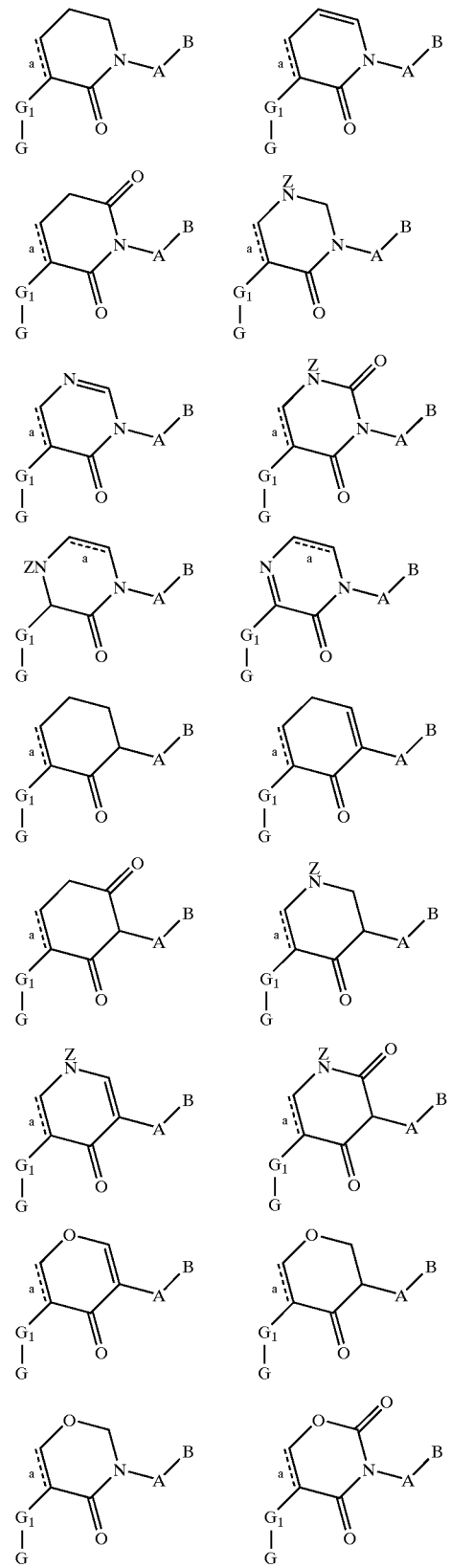

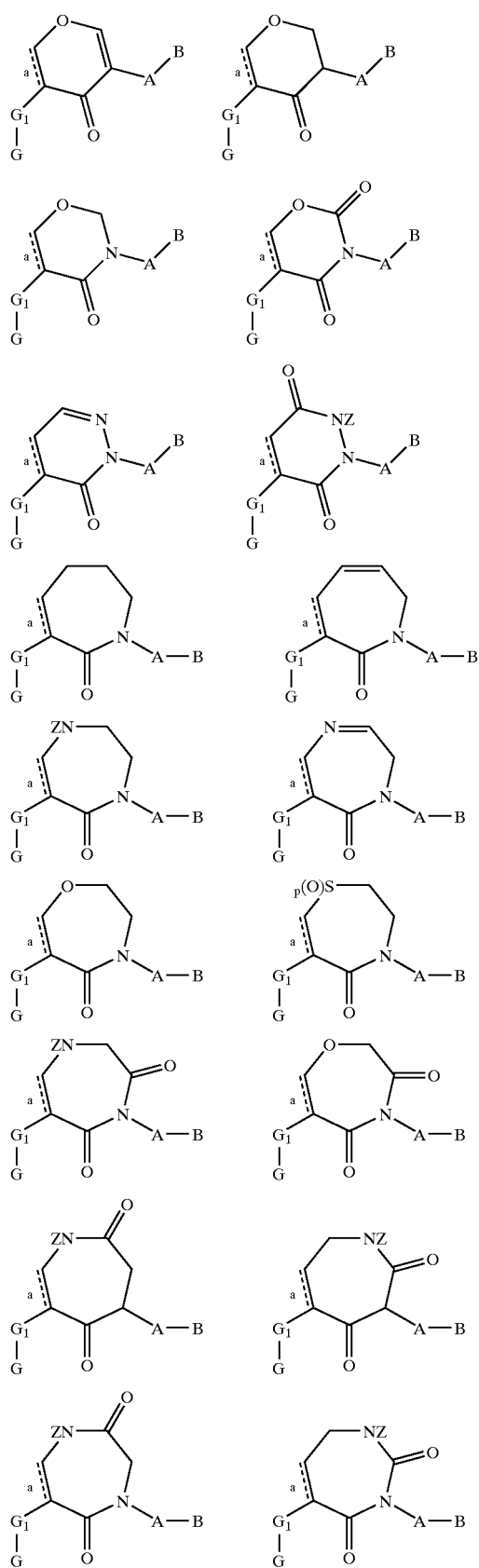
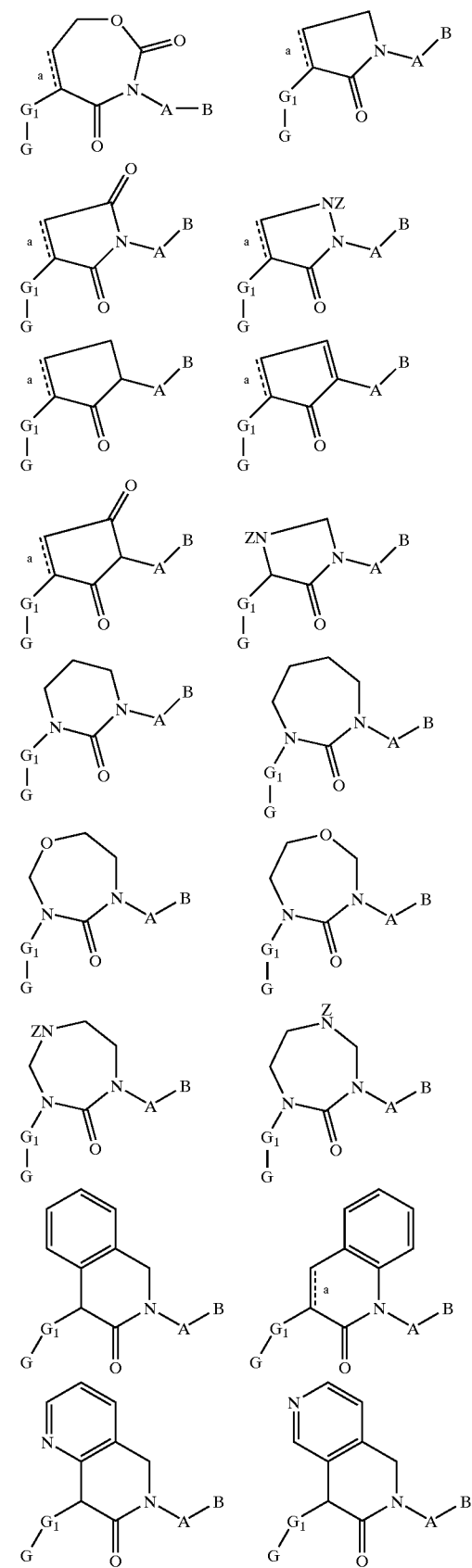

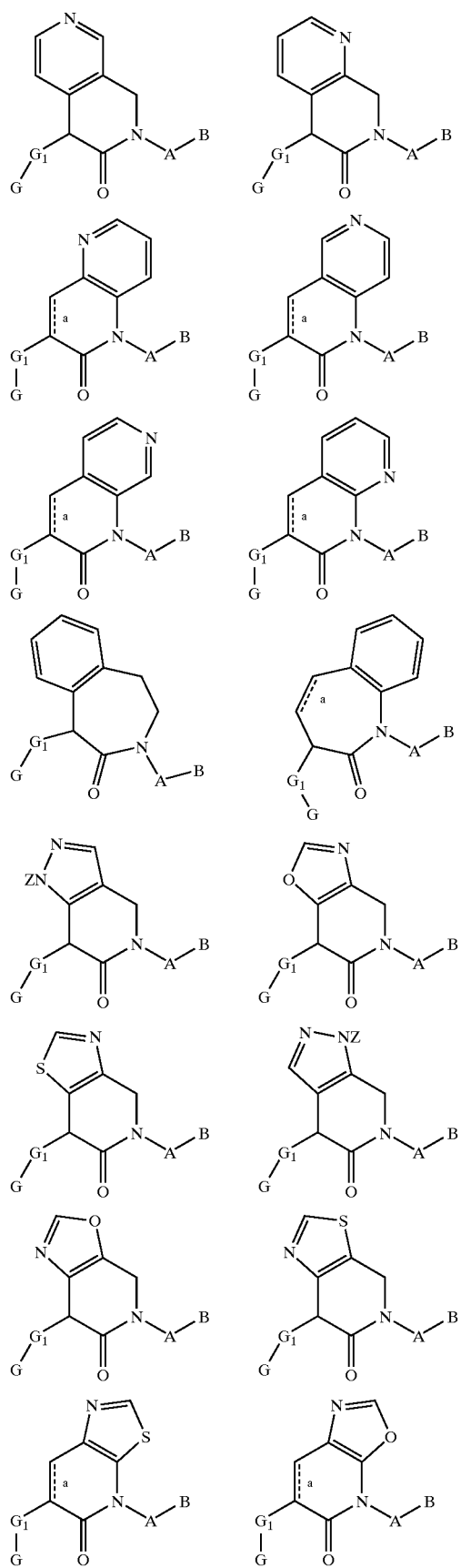
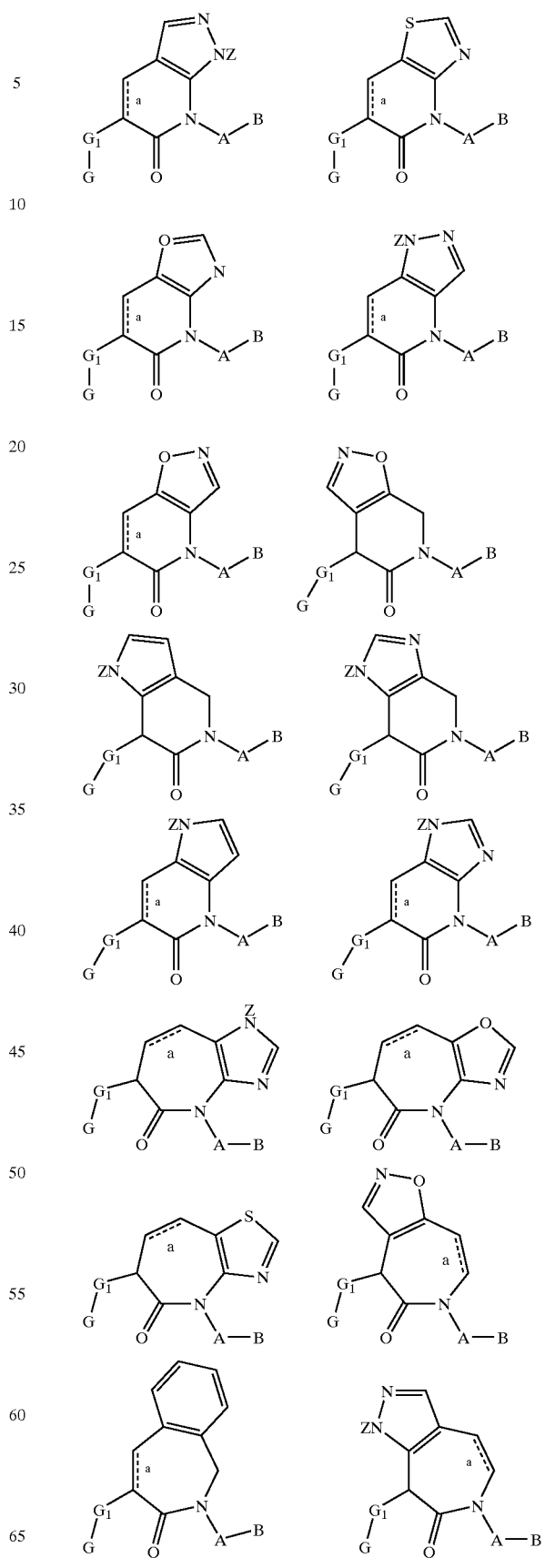

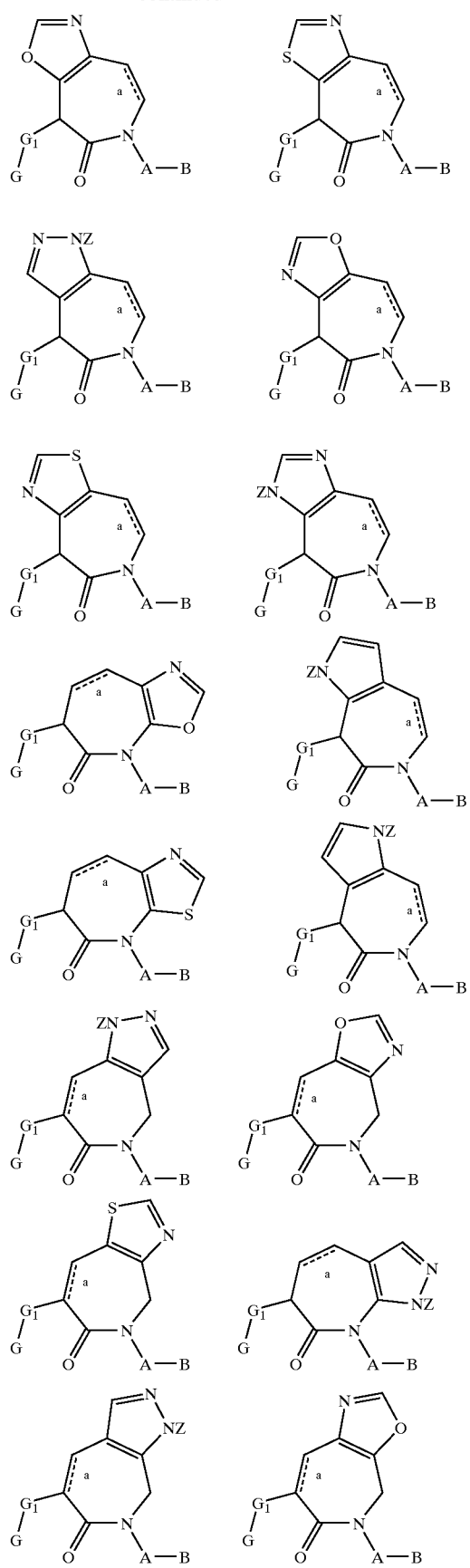
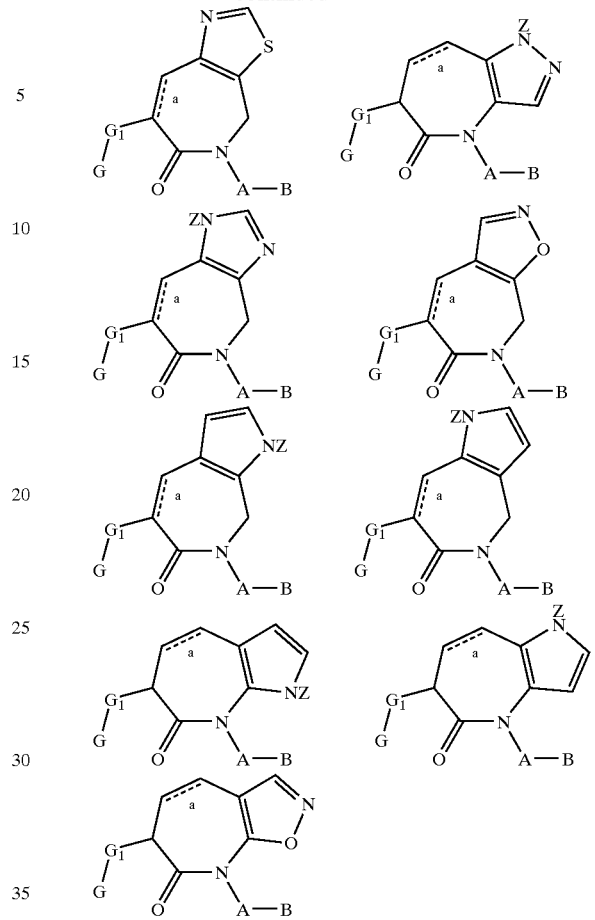

wherein the above formulas are substituted with 0–2 $R^{1a}$ and "a" is a single or double bond;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y and X—Y;

X is selected from —$(CR^2R^{2a})_{1-4}$—, —C(O)—, —C(=$NR^{1c}$), —$CR^2(NR^{1c}R^2)$—, —C(O)$CR^2R^{2a}$—, —$CR^2R^{2a}$C(O)—, —C(O)$NR^2$—, —$NR^2$C(O)—, —C(O)$NR^2CR^2R^{2a}$—, —$NR^2$C(O)$CR^2R^{2a}$—, —$CR^2R^{2a}$C(O)$NR^2$—, —$CR^2R^{2a}NR^2$C(O)—, —$NR^2$C(O)$NR^2$—, —$NR^2$—, —$NR^2CR^2R^{2a}$—, —$CR^2R^{2a}NR^2$—, O, —$CR^2R^{2a}$—, and —$OCR^2R^{2a}$—;

Y is —$(CH_2)_rNR^2R^{2a}$, provided that X—Y do not form a N—N or O—N bond;

alternatively, Y is selected from one of the following carbocyclic and heterocyclic systems which are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl; and alternatively, Y is selected from the following bicyclic heteroaryl ring systems:

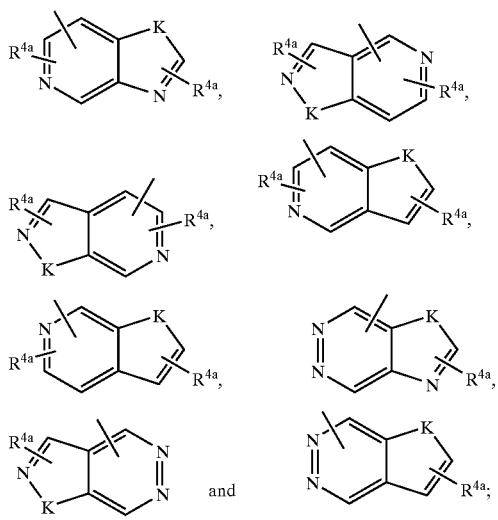

K is selected from O, S, NH, and N.

[3] In another preferred embodiment, the present invention provides a novel compound, wherein the compound is selected from the group:

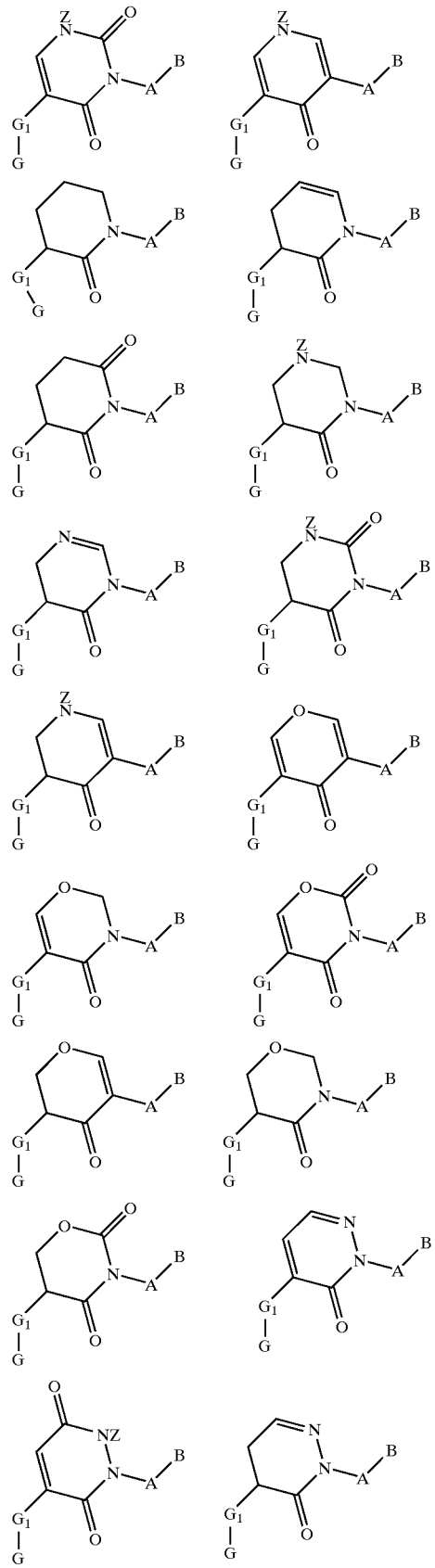

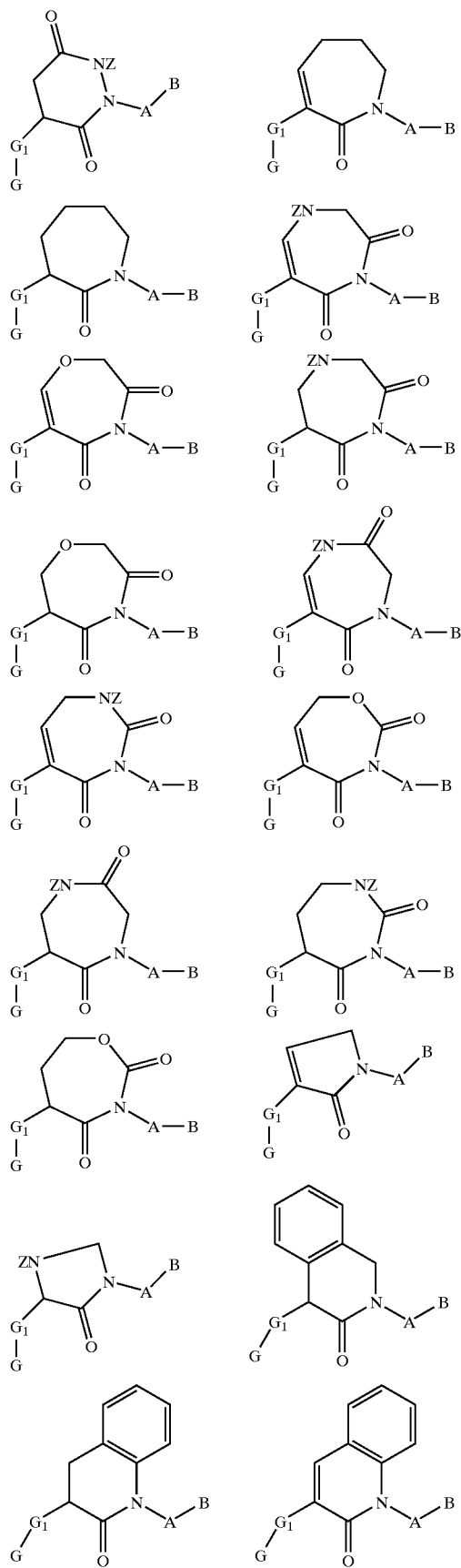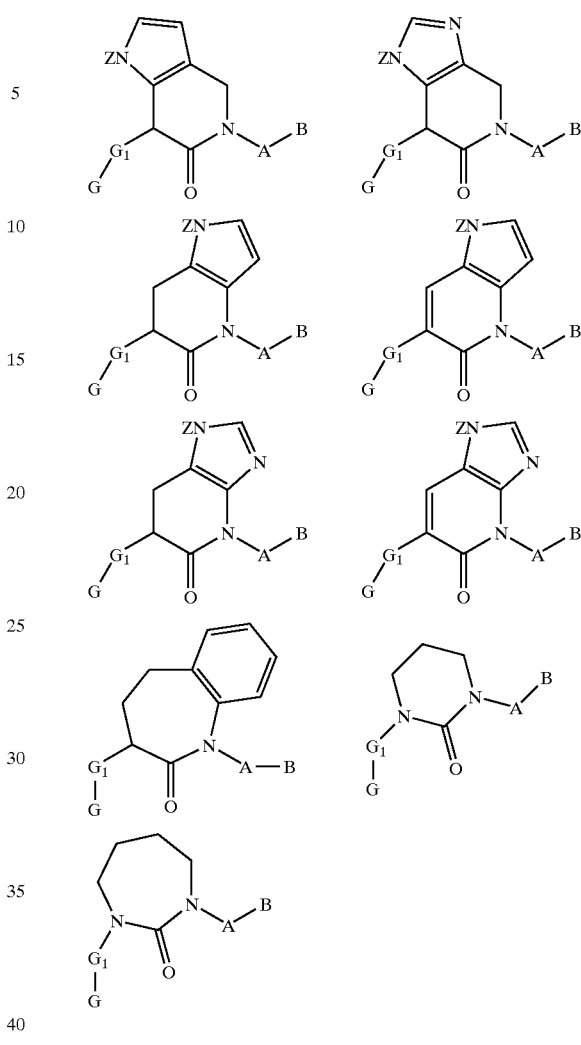
wherein compounds of the above formulas are substituted with 0–2 $R^{1a}$; and
G is selected from the group:
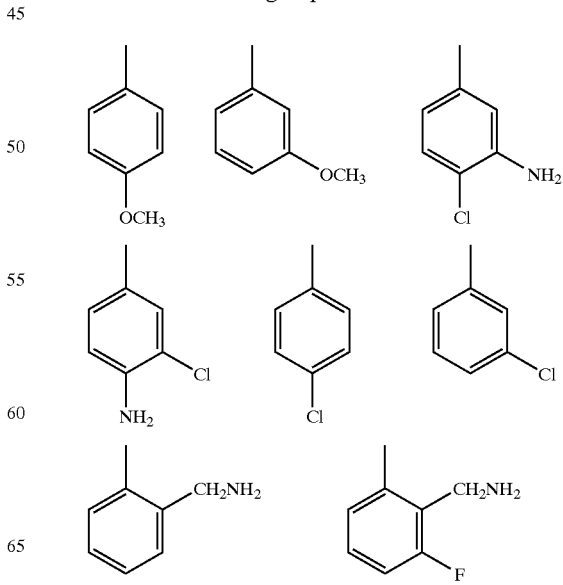

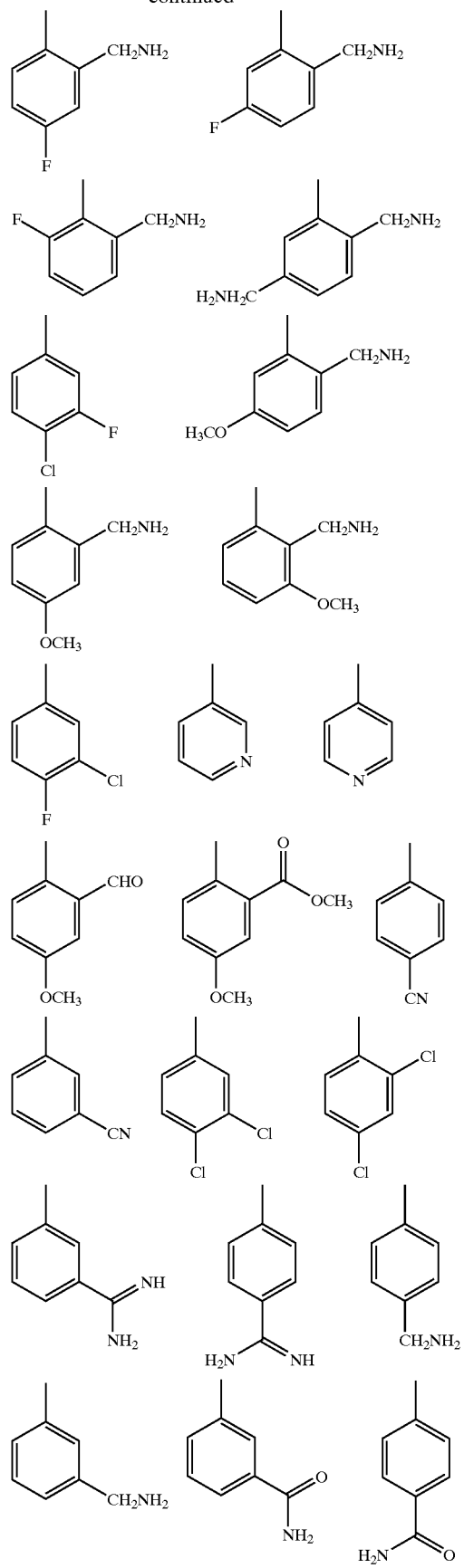
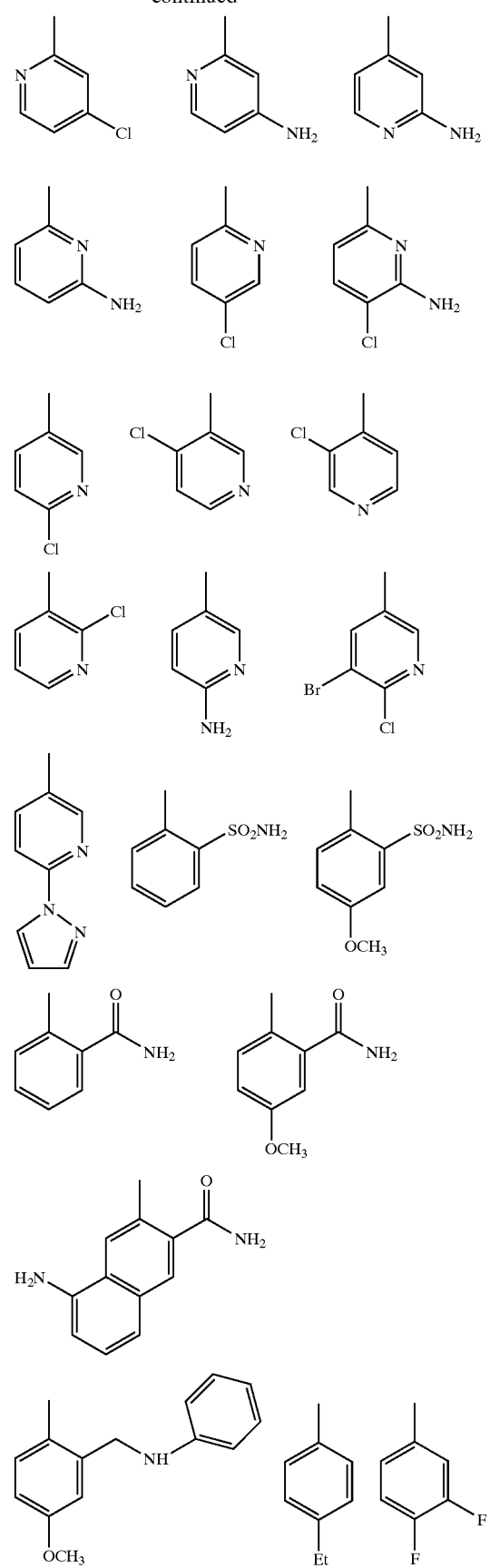

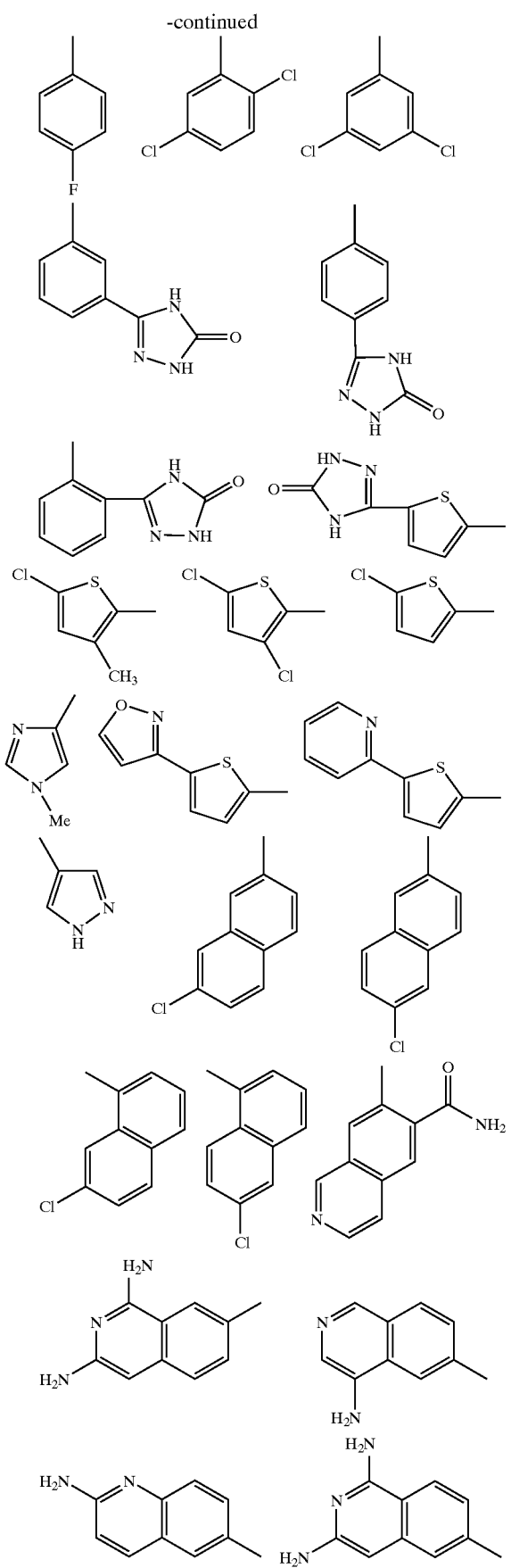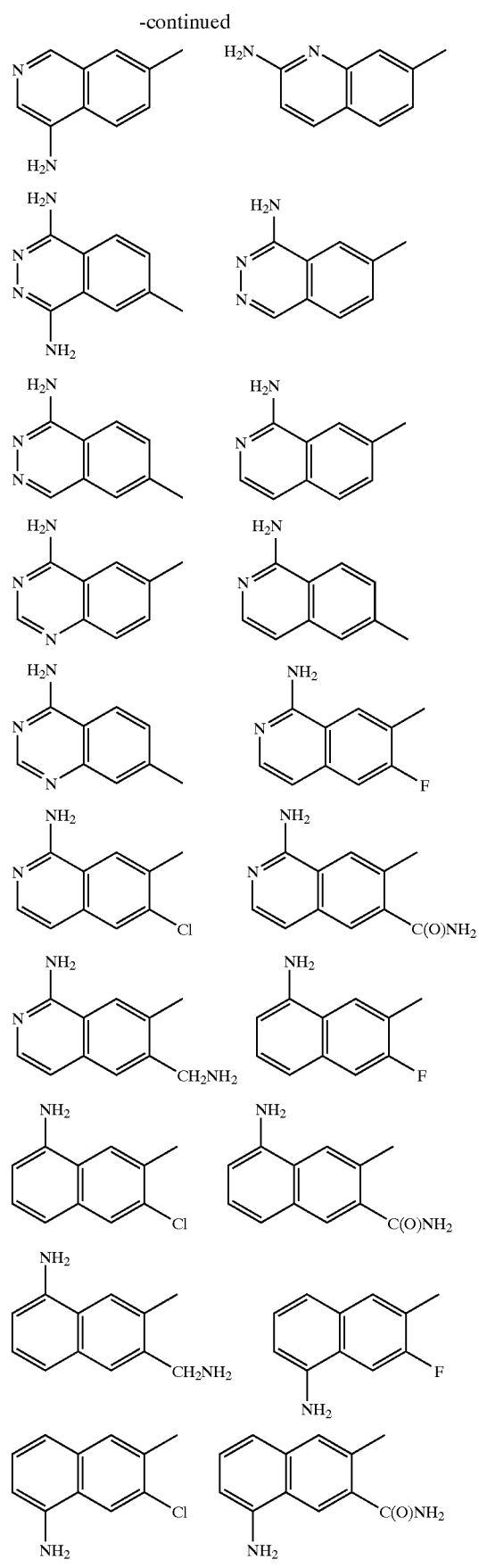

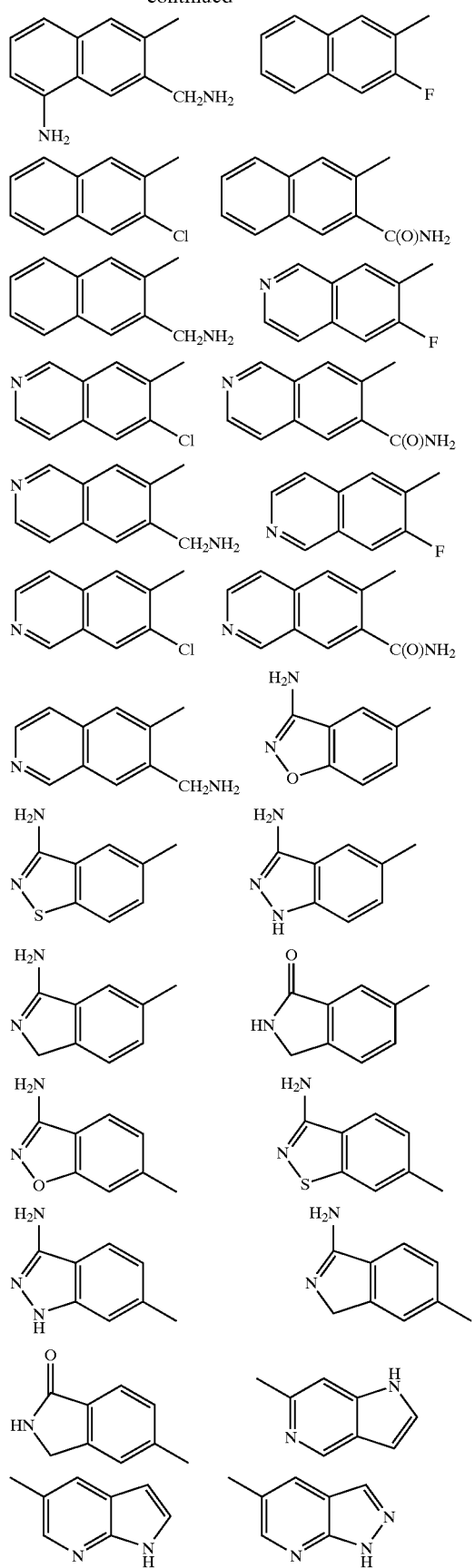
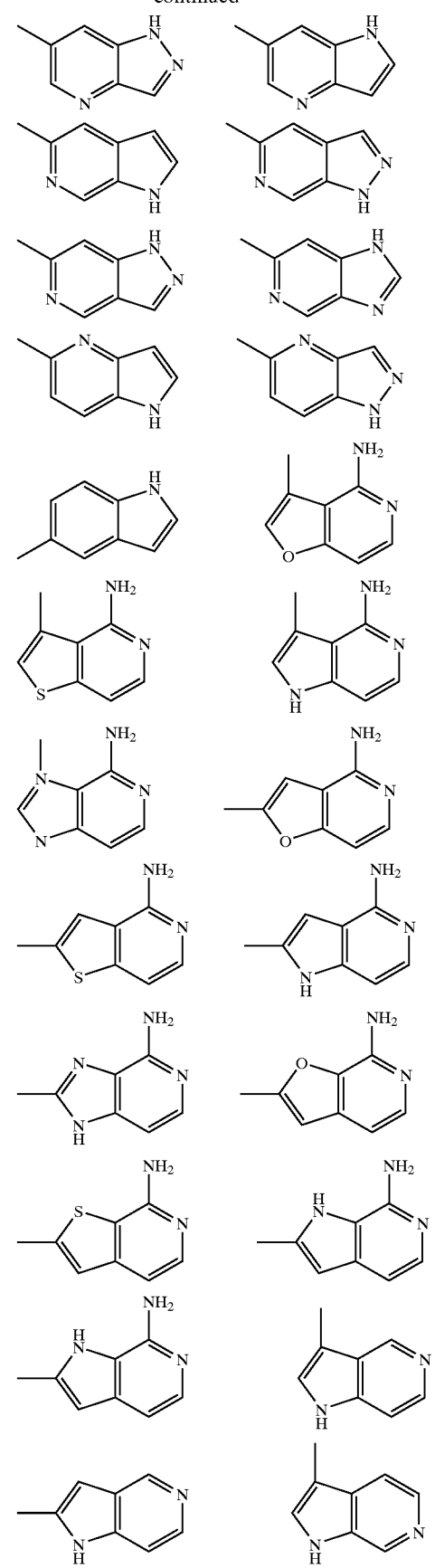

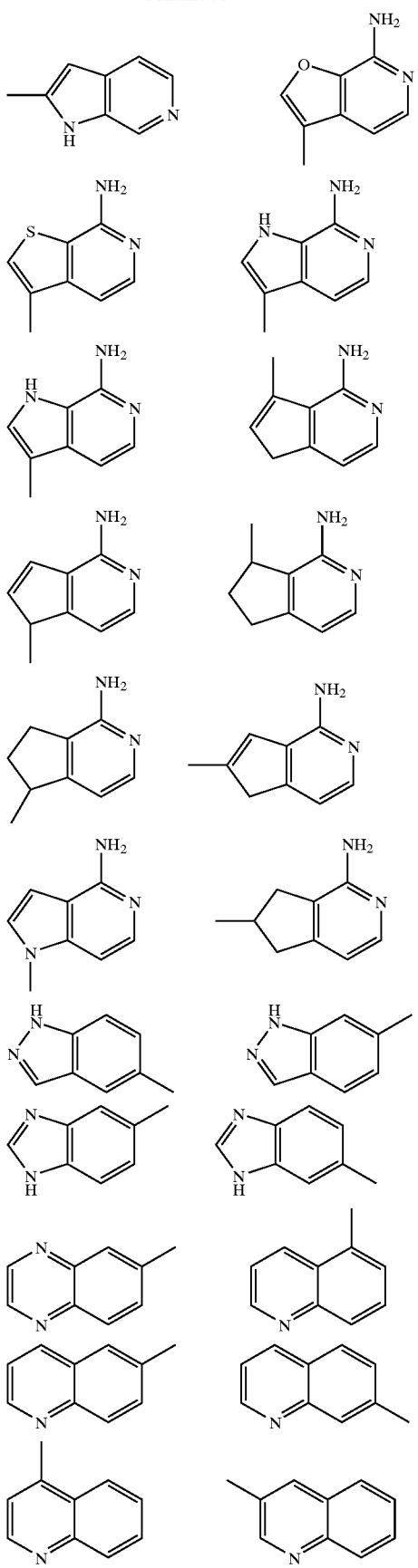
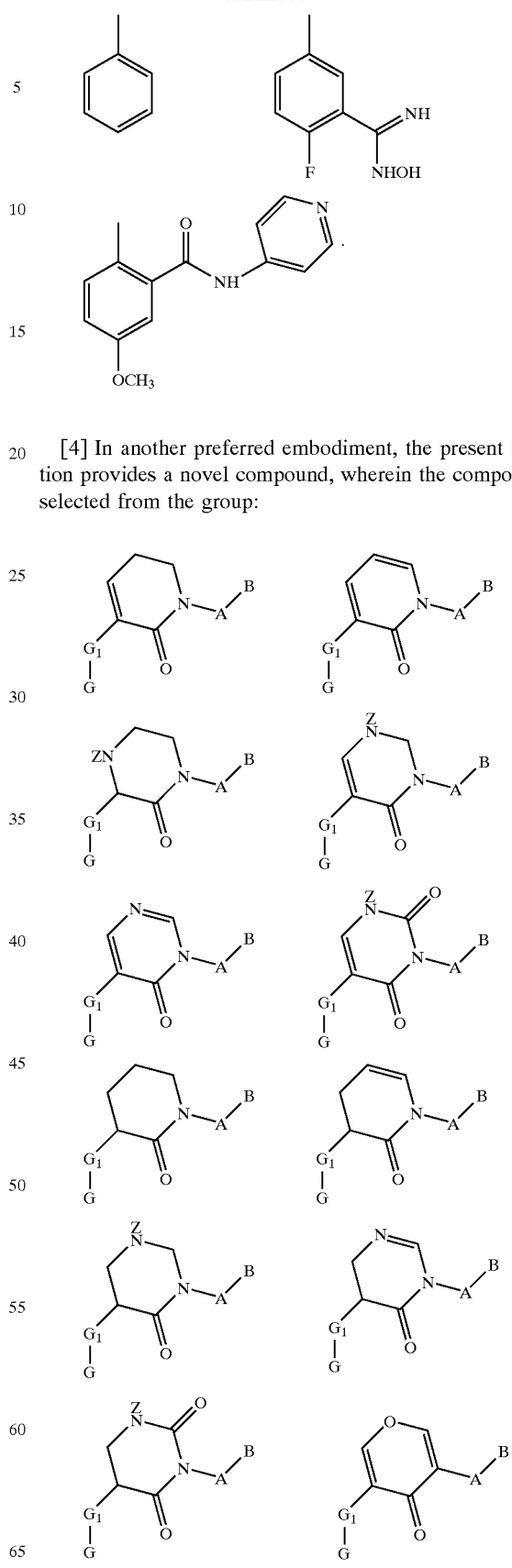
[4] In another preferred embodiment, the present invention provides a novel compound, wherein the compound is selected from the group:

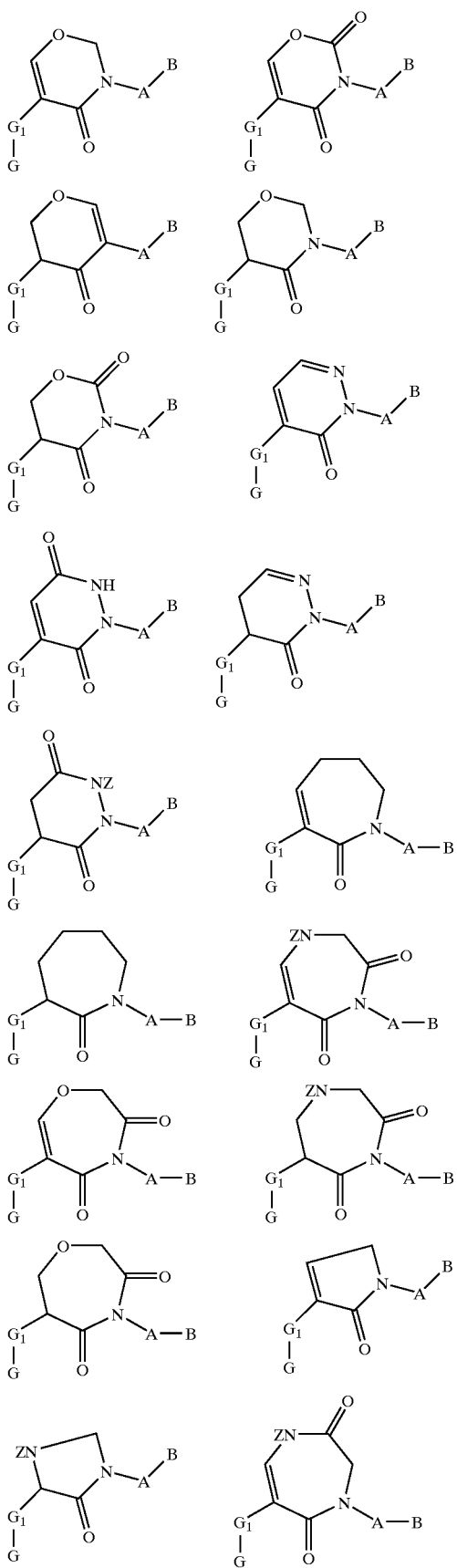
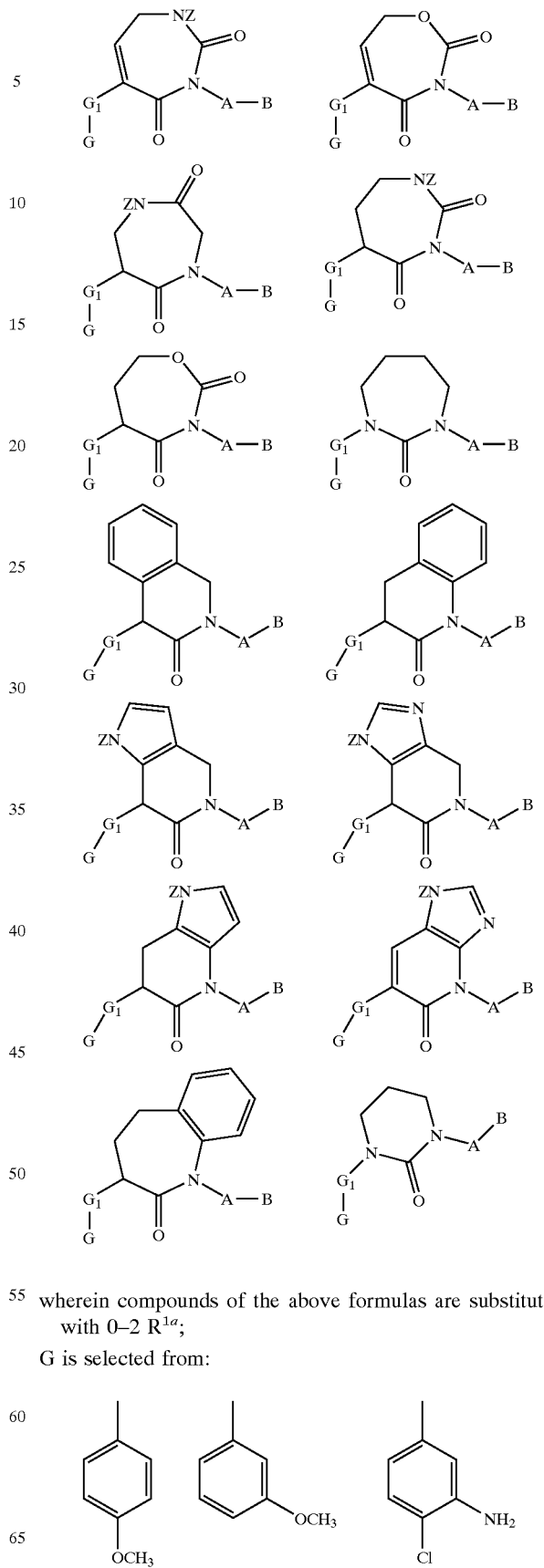
wherein compounds of the above formulas are substituted with 0–2 $R^{1a}$;
G is selected from:

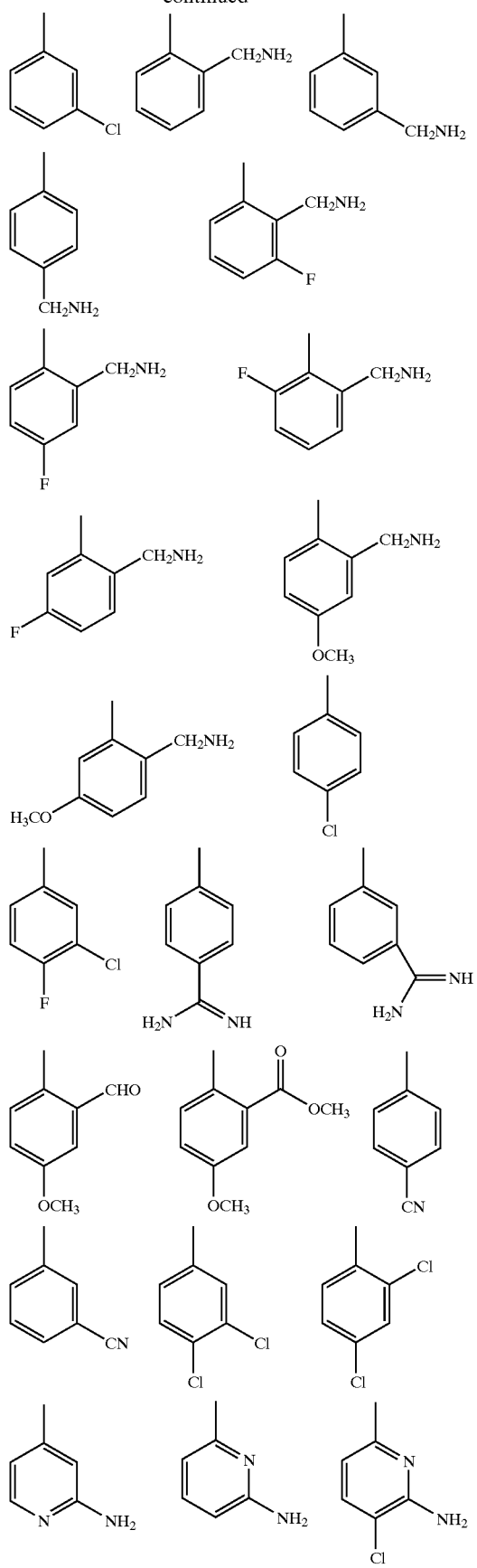
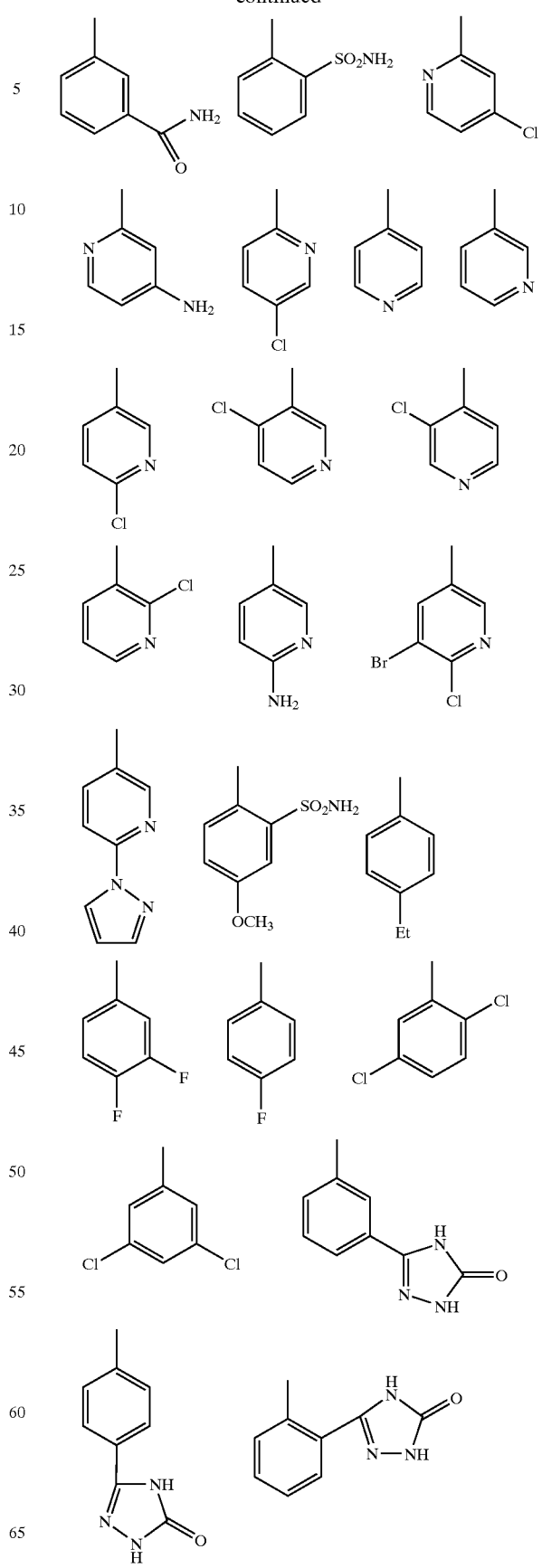

-continued
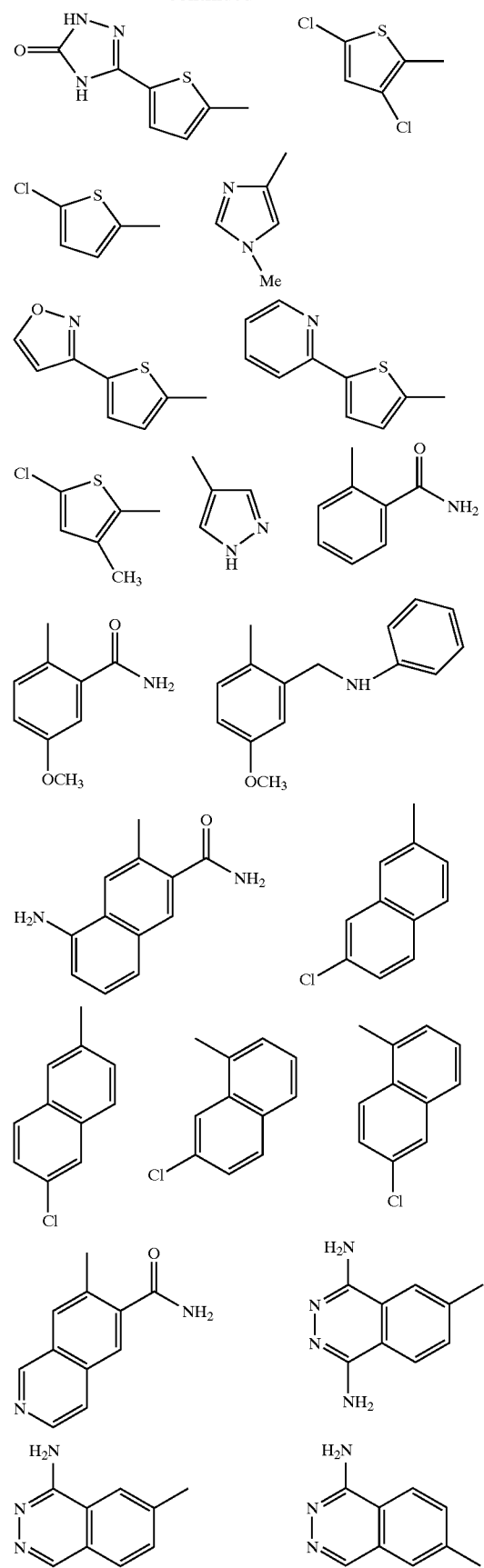
-continued
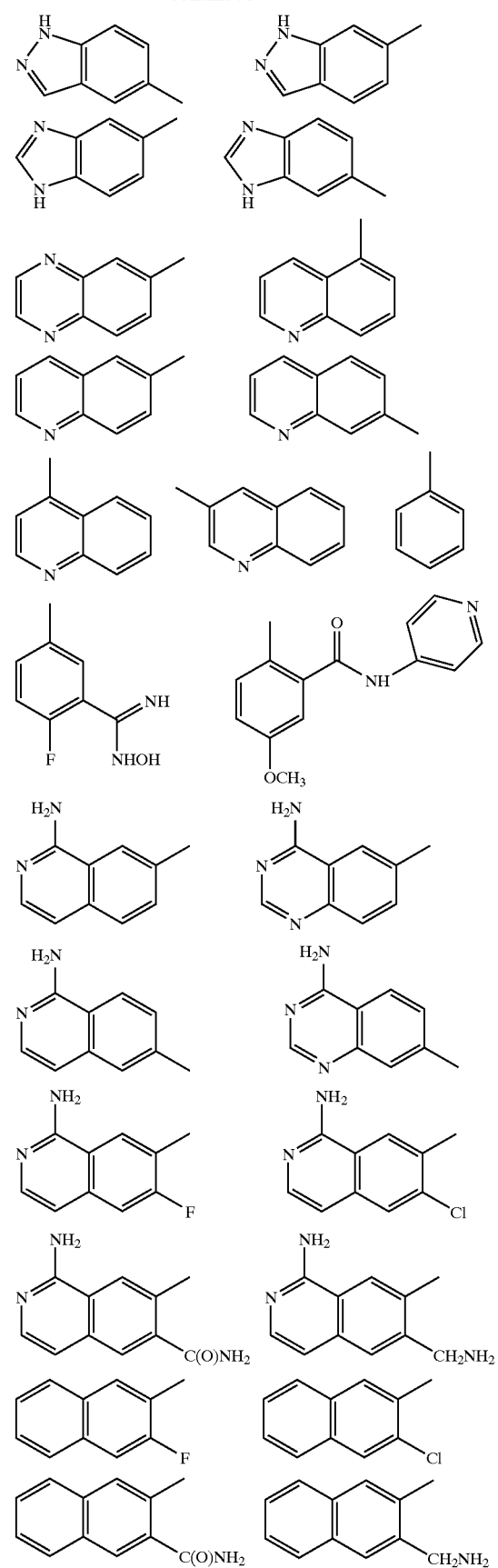

-continued

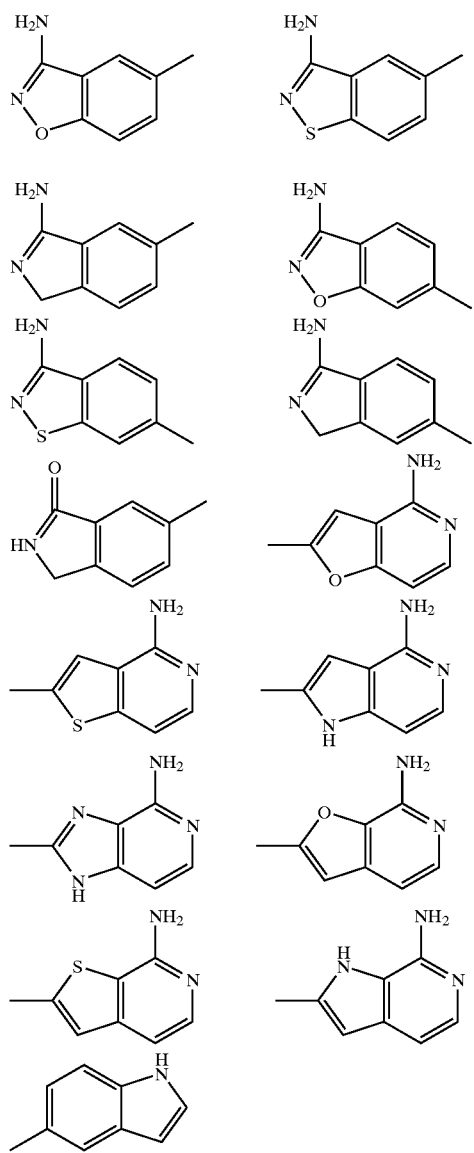

G₁ is selected from $(CR^{3a}R^{3b})_{1-2}$, $CR^3{=}CR^3$, $C{\equiv}C$, $(CHR^{3a})_uC(O)(CHR^{3a})_w$, $(CHR^{3a})_uC(O)O(CHR^{3a})_w$, $(CHR^{3a})_u(CHR^{3a})_w$, $(CHR^{3a})_uNR^{3e}(CHR^{3a})_w$, $(CHR^{3a})_uC(O)NR^3(CHR^{3a})_w$, $(CHR^{3a})_uNR^3C(O)(CHR^{3a})_w$, $(CHR^{3a})_uS(O)_2(CHR^{3a})_w$, $(CHR^{3a})_uNR^3S(O)_2(CHR^{3a})_w$, and $(CHR^{3a})_uS(O)_2NR^3(CHR^{3a})_w$, wherein u+w total 0, 1, or 2, provided that G₁ does not form a N—N or N—O bond with either group to which it is attached;

R³, at each occurrence, is selected from H,
- $C_{1-4}$ alkyl substituted with 0–2 $R^{1a}$;
- $C_{2-4}$ alkenyl substituted with 0–2 $R^{1a}$;
- $C_{2-4}$ alkynyl substituted with 0–2 $R^{1a}$;
- $C_{3-7}$ cycloalkyl($C_{0-2}$ alkyl)-substituted with 0–3 $R^{1a}$;
- heterocyclyl($C_{0-2}$ alkyl)-substituted with 0–3 $R^{1a}$;
- aryl($C_{0-2}$ alkyl)-substituted with 0–3 $R^{1a}$;
- heteroaryl($C_{0-2}$ alkyl)-substituted with 0–3 $R^{1a}$;

$R^{3a}$, at each occurrence, is selected from H, $C_{1-4}$ alkyl, and benzyl; and $R^{3b}$, at each occurrence, is selected from H, $C_{1-4}$ alkyl, and benzyl.

[5] In another preferred embodiment, the present invention provides a novel compound, wherein;

G is selected from:

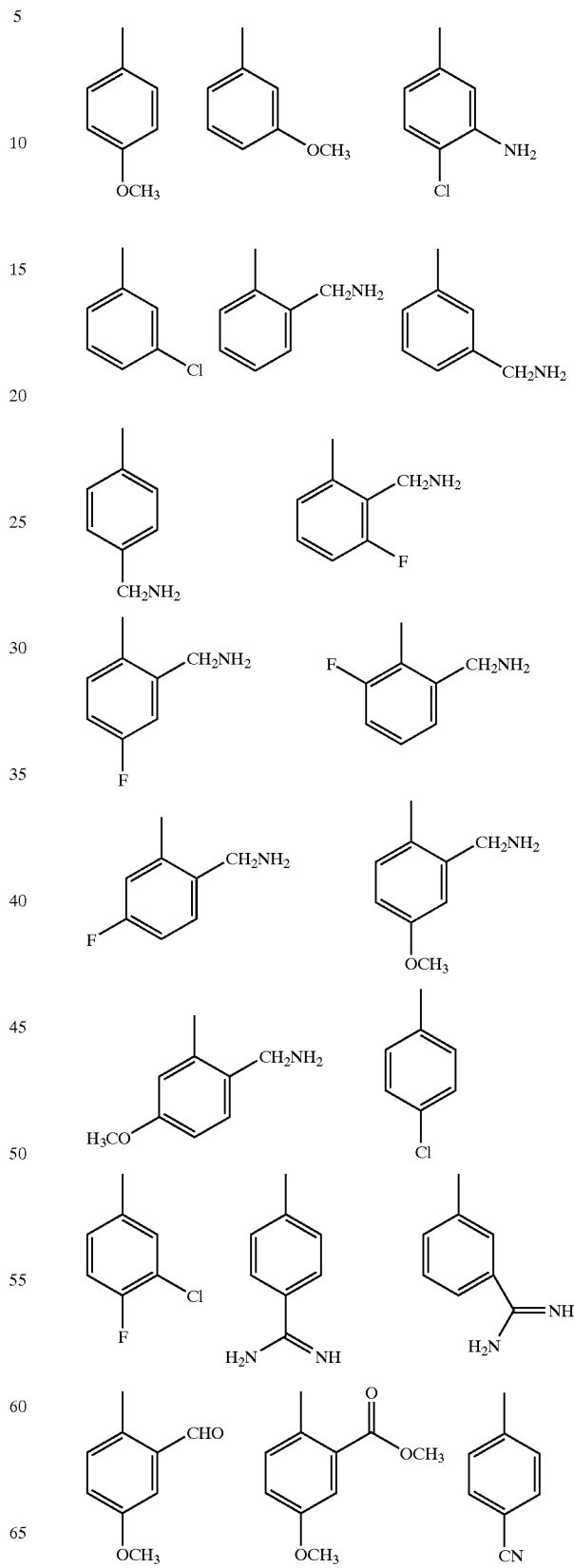

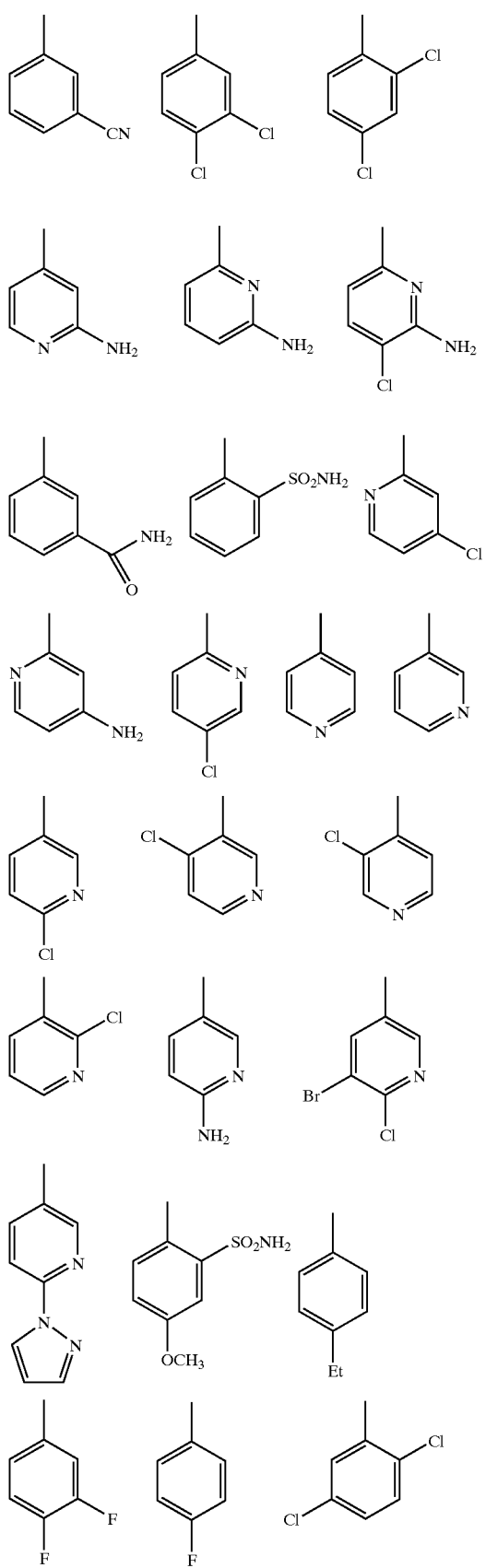
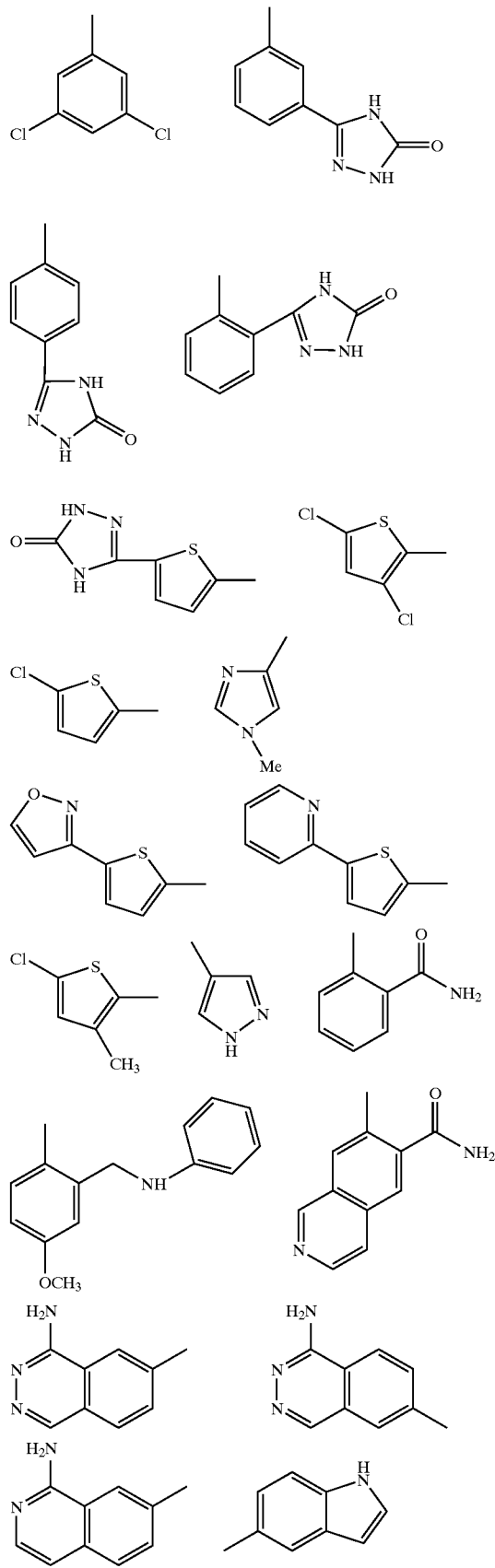

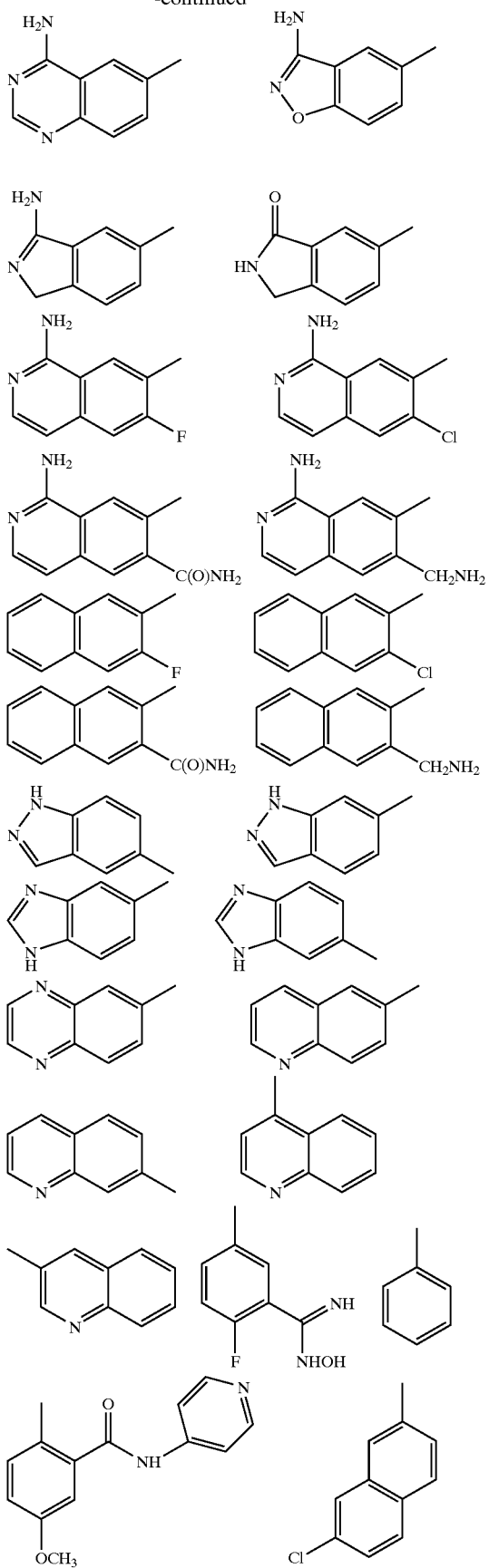

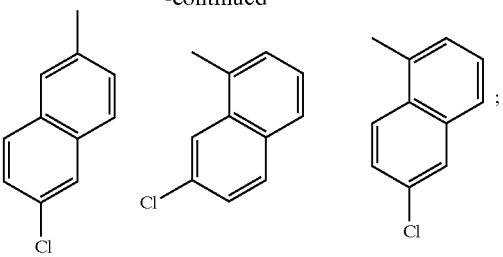

A is selected from phenyl, piperidinyl, pyridyl, and pyrimidyl, and is substituted with 0–2 $R^4$; and, B is selected from phenyl, pyrrolidino, N-pyrrolidinocarbonyl, morpholino, N-morpholino-carbonyl, 1,2,3-triazolyl, imidazolyl, and benzimidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$, and $CH_2CH_3$;

alternatively, $R^2$ and $R^{2a}$, together with the atom to which they are attached, combine to form pyrrolidine substituted with 0–2 $R^{4b}$ or piperidine substituted with 0–2 $R^{4b}$;

$R^4$, at each occurrence, is selected from H, OH, $OR^2$, $(CH_2)OR^2$, $(CH_2)_2OR^2$, F, Br, Cl, I, $C_{1-4}$ alkyl, $NR^2R^{2a}$, $(CH_2)NR^2R^{2a}$, $(CH_2)_2NR^2R^{2a}$, $CF_3$, and $(CF_2)CF_3$;

$R^{4a}$ is selected from H, $C_{1-4}$ alkyl, $CF_3$, $OR^2$, $(CH_2)OR^2$, $(CH_2)_2OR^2$, $NR^2R^{2a}$, $(CH_2)NR^2R^{2a}$, $(CH_2)_2NR^2R^{2a}$, $SR^5$, $S(O)R^5$, $S(O)_2R^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

[6] In a further preferred embodiment, the present invention provides a novel compound, wherein;

A is selected from the group: phenyl, piperidinyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N,N-diethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, 2-(N-(3-hydroxypyrrolidinyl)methyl)phenyl, and 2-(N-(2-hydroxyethyl)methylamino)-methyl)phenyl.

In another preferred embodiment, the present invention provides a novel compound, wherein the compound is selected from the group:

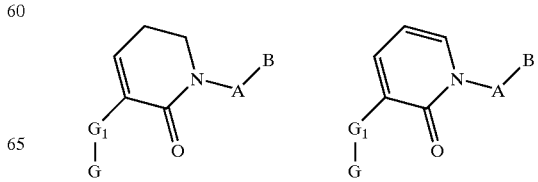

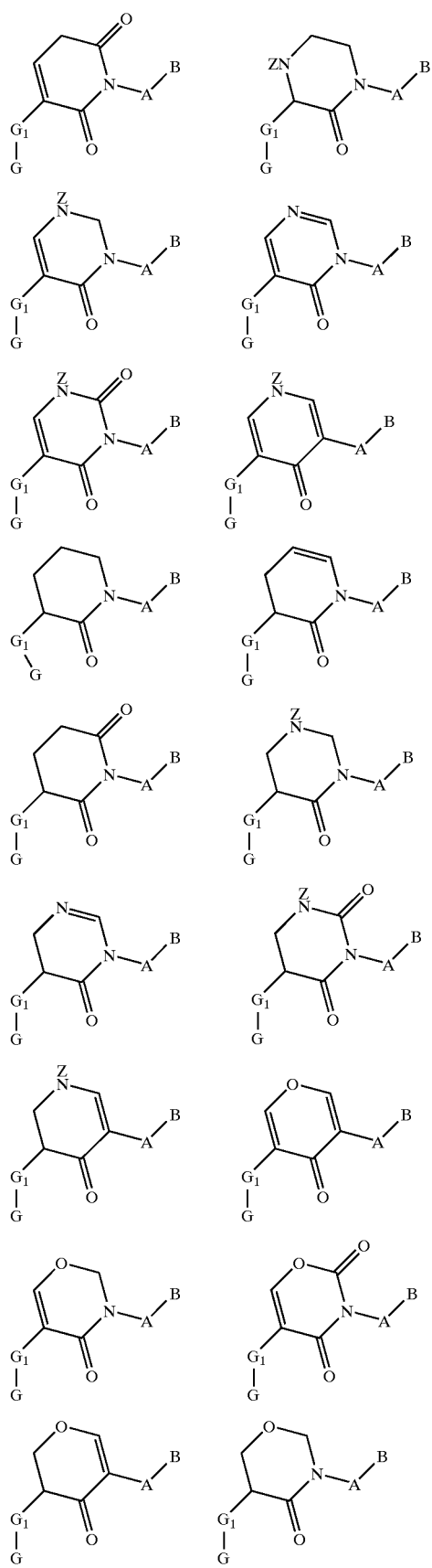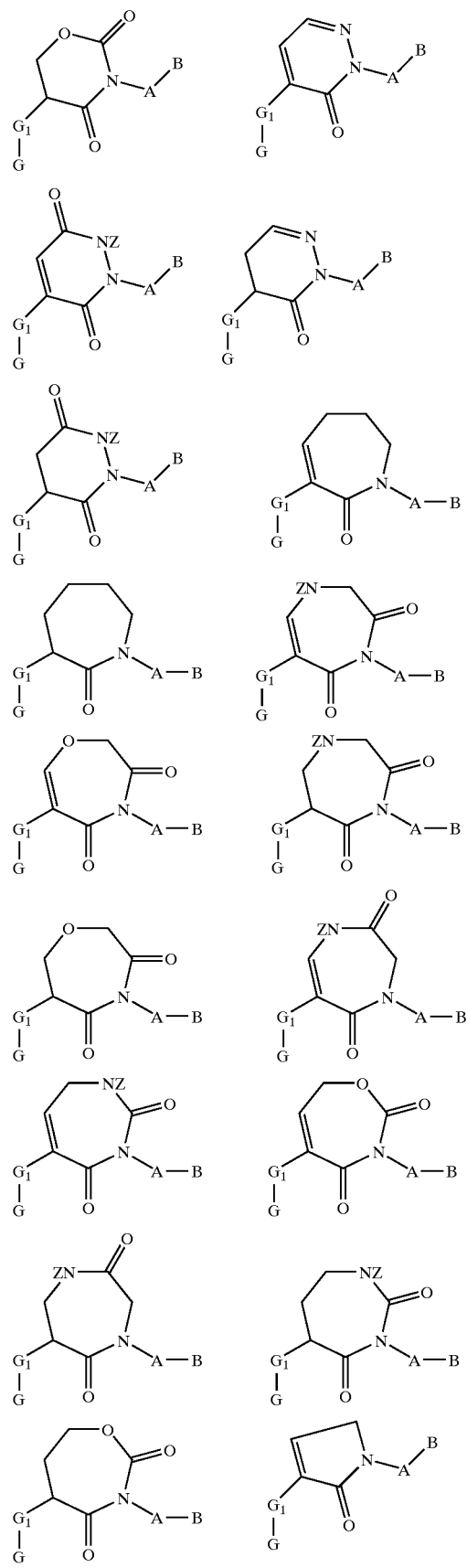

wherein compounds of the above formulas are substituted with 0–2 $R^{1a}$.

In another preferred embodiment, the present invention provides a novel compound, wherein the compound is selected from:

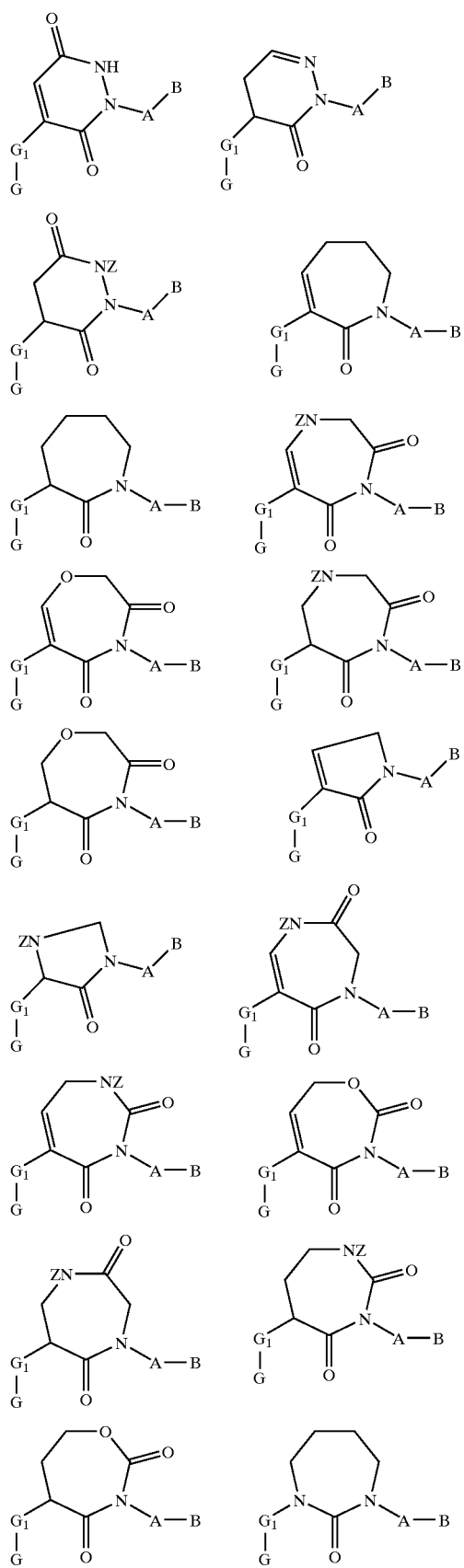
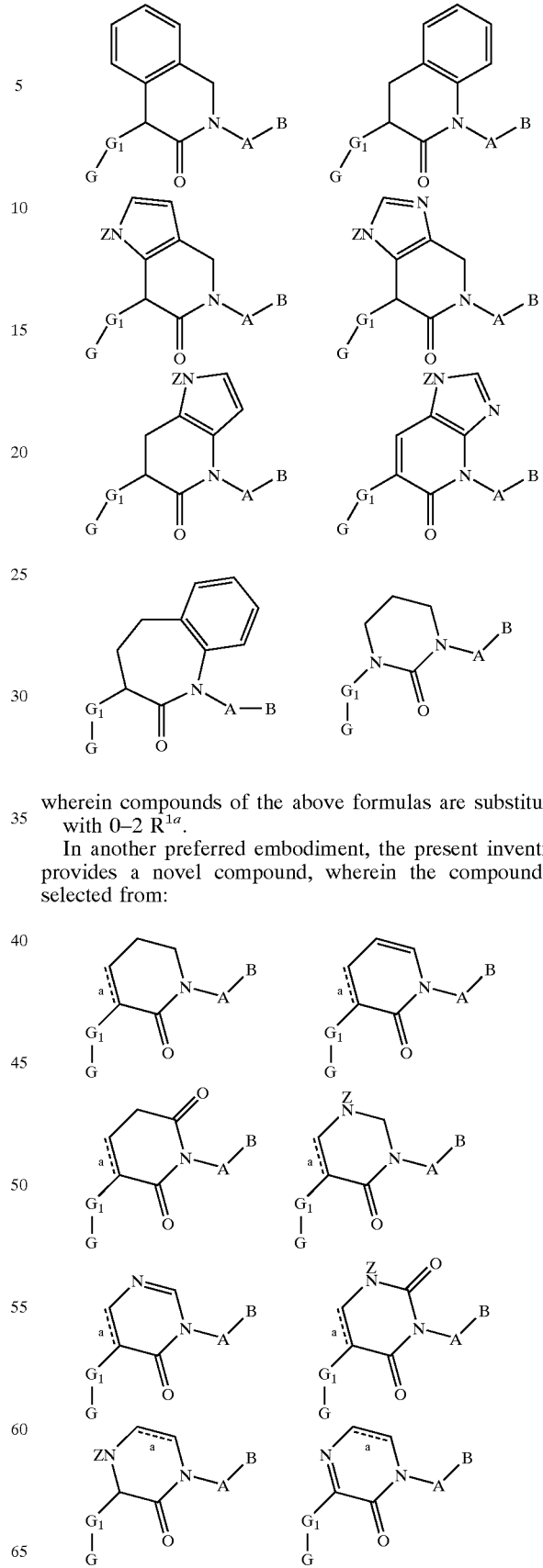
wherein compounds of the above formulas are substituted with 0–2 $R^{1a}$.
In another preferred embodiment, the present invention provides a novel compound, wherein the compound is selected from:
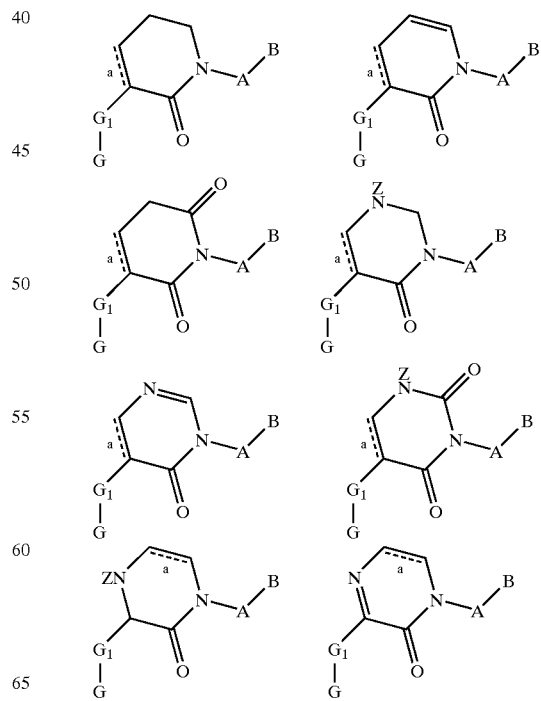

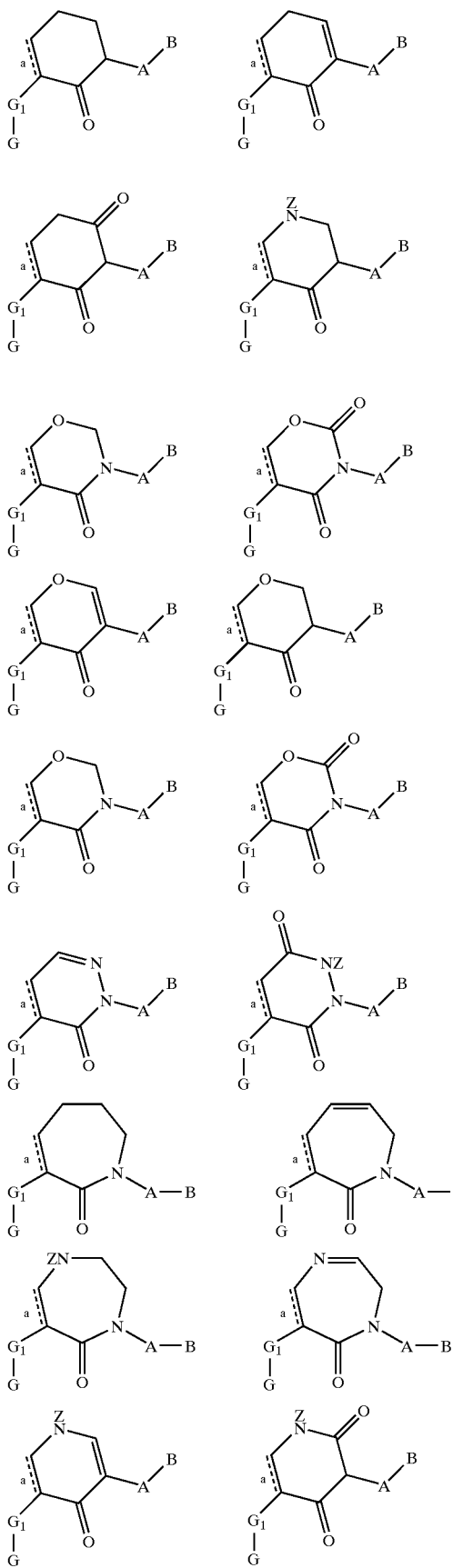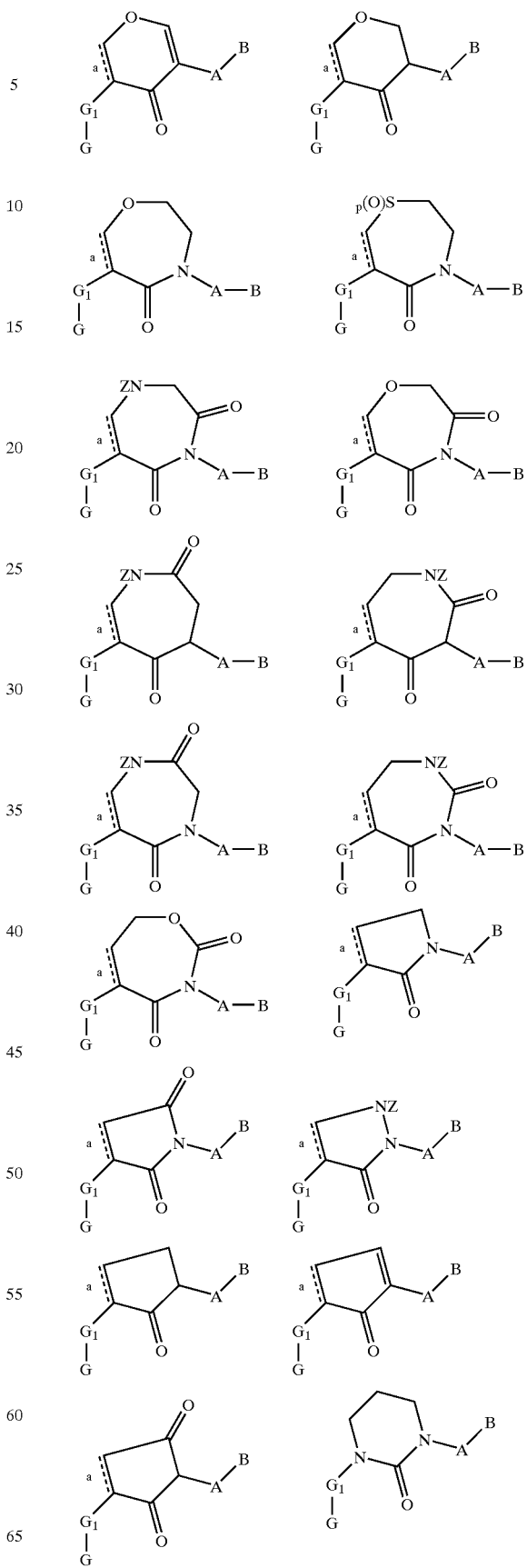

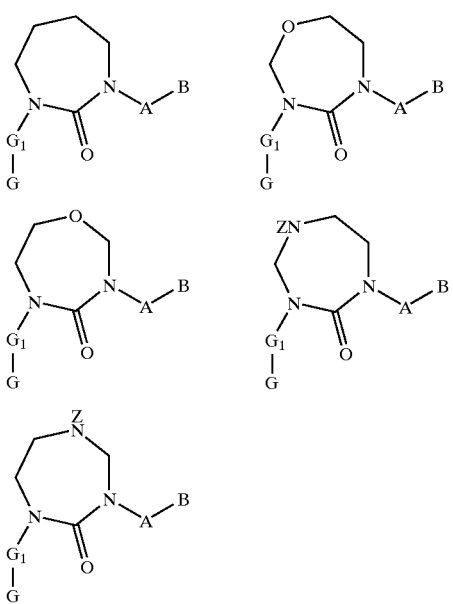
wherein the above formulas are substituted with 0–2 $R^{1a}$ and "a" is a single or double bond.
In another preferred embodiment, the present invention provides a novel compound, wherein the compound is selected from the group:
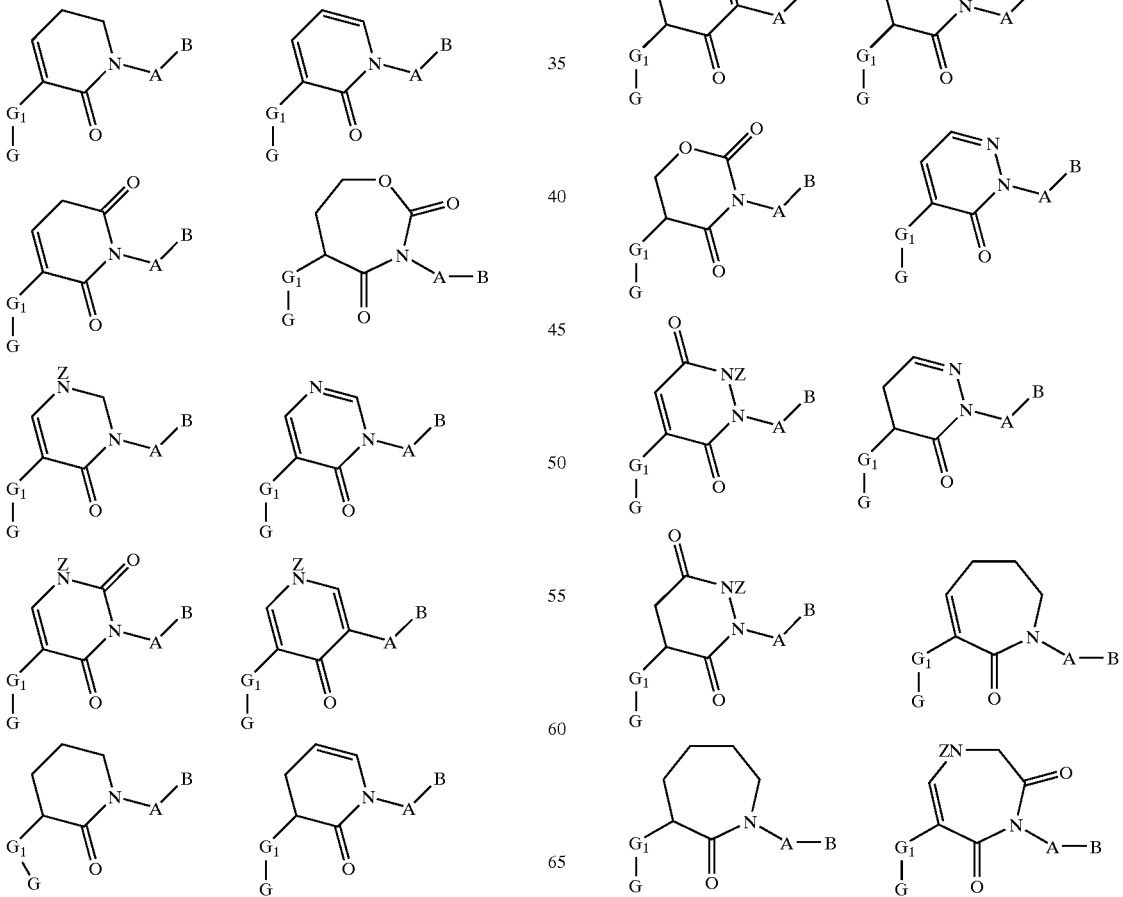
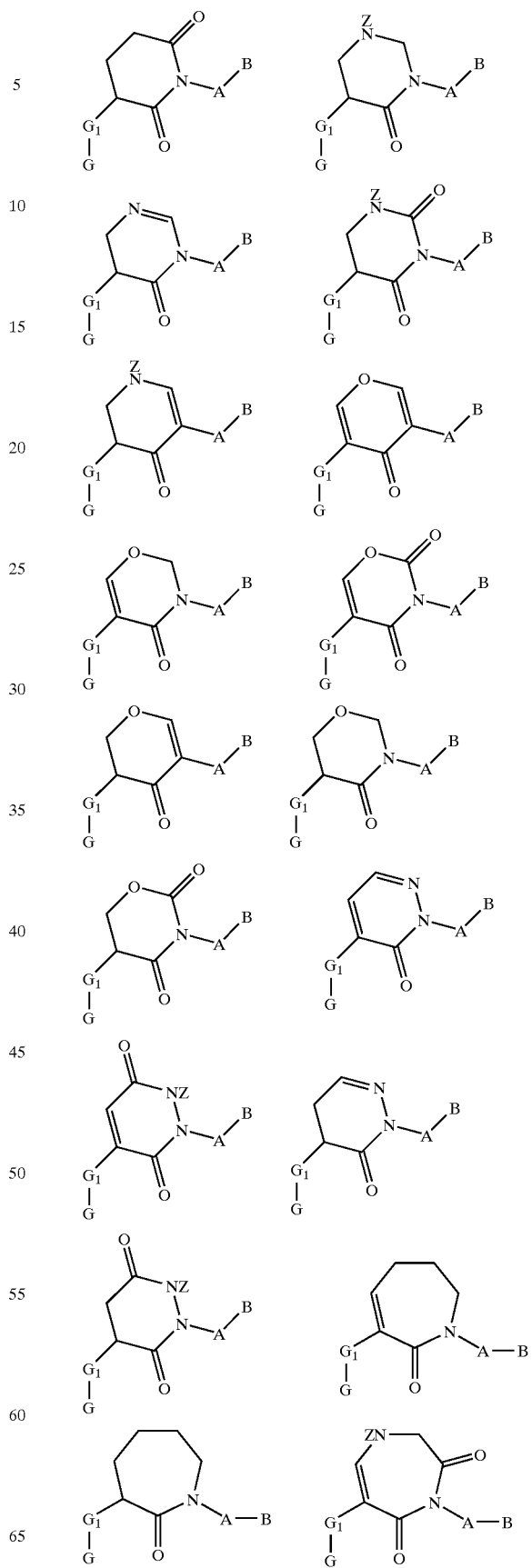

wherein compounds of the above formulas are substituted with 0–2 $R^{1a}$.

In another preferred embodiment, the present invention provides a novel compound, wherein the compound is selected from:

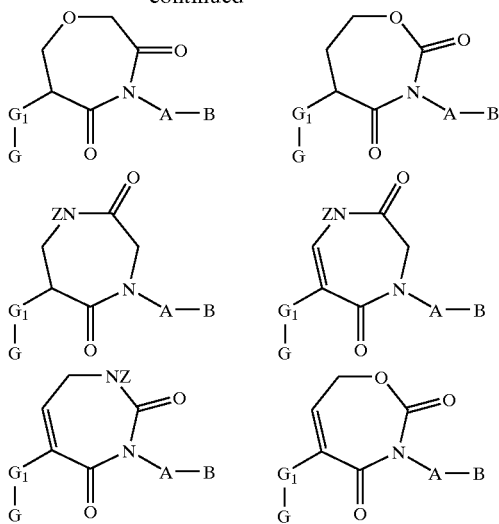

wherein compounds of the above formulas are substituted with 0–2 $R^{1a}$.

In another preferred embodiment, the present invention provides a novel compound, wherein the compound is selected from:

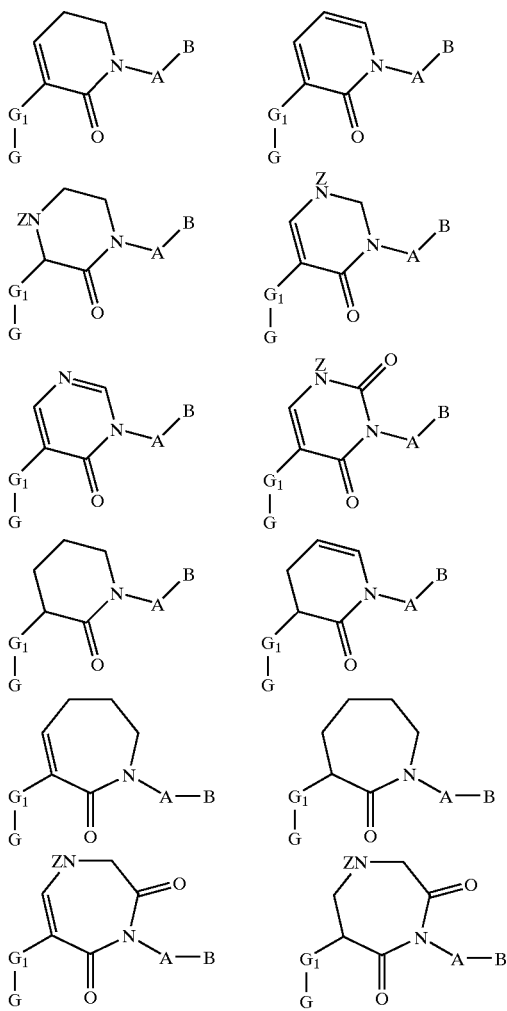

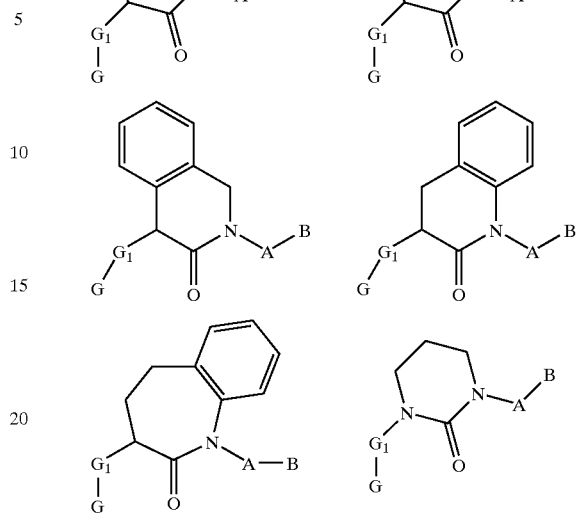

wherein compounds of the above formulas are substituted with 0–2 $R^{1a}$.

In another preferred embodiment, the present invention provides a novel compound, wherein the compound is selected from:

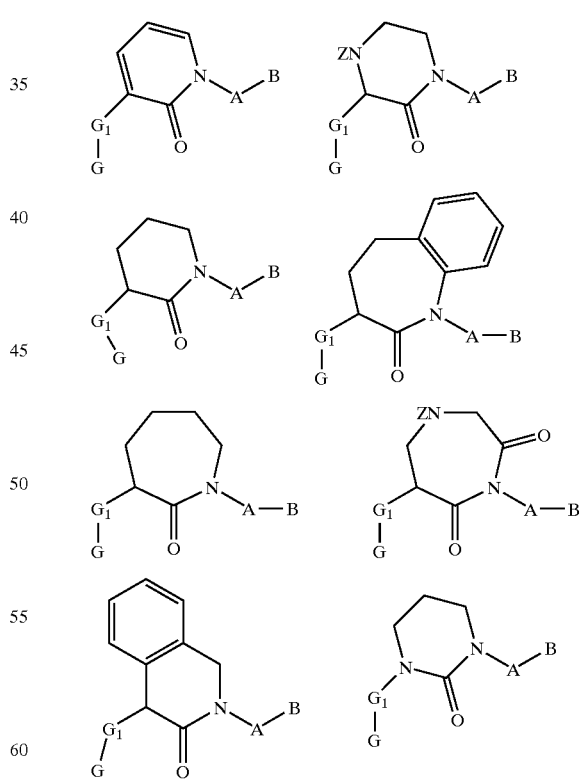

wherein compounds of the above formulas are substituted with 0–2 $R^{1a}$.

In another preferred embodiment, the present invention provides a novel compound, wherein;

G is selected from the group:
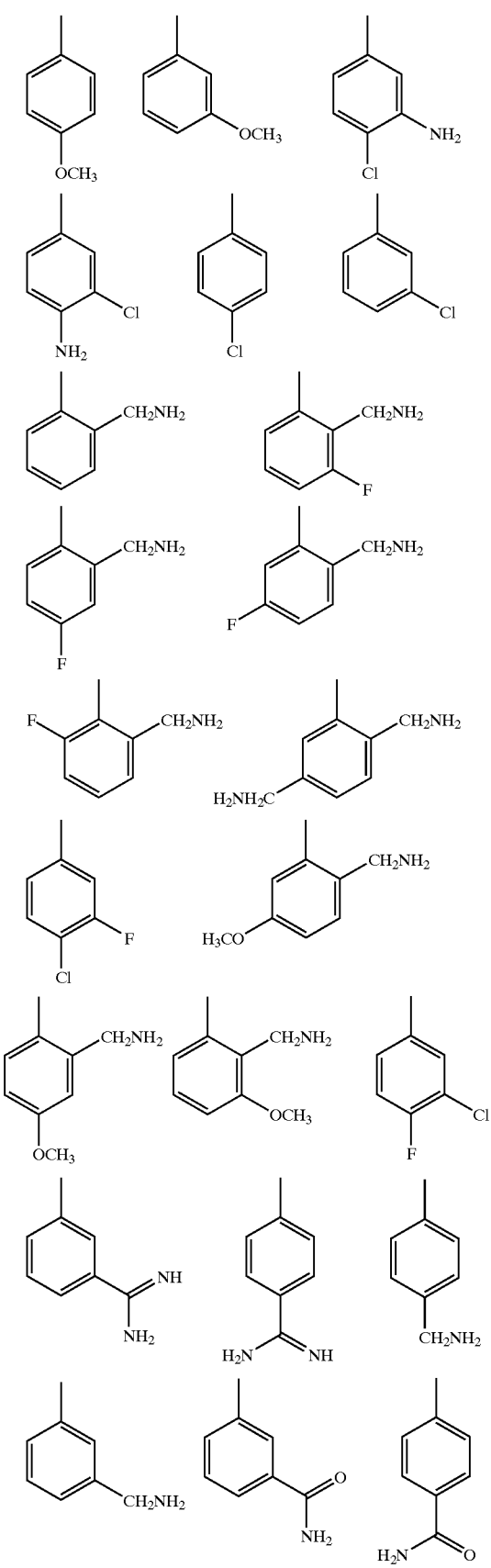
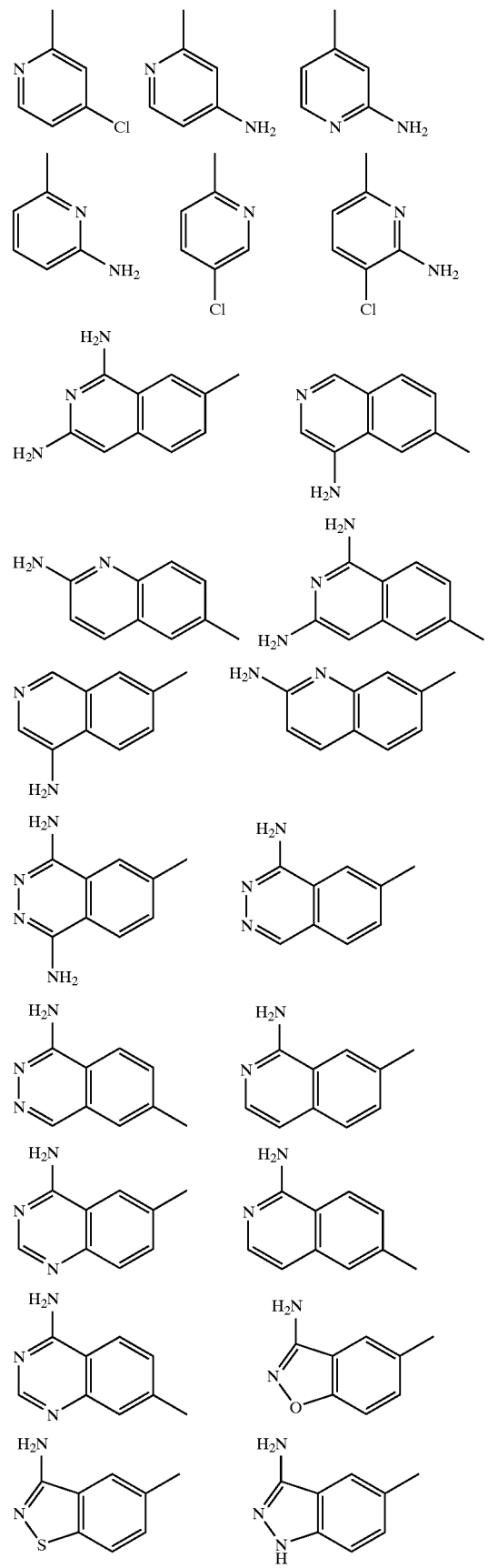

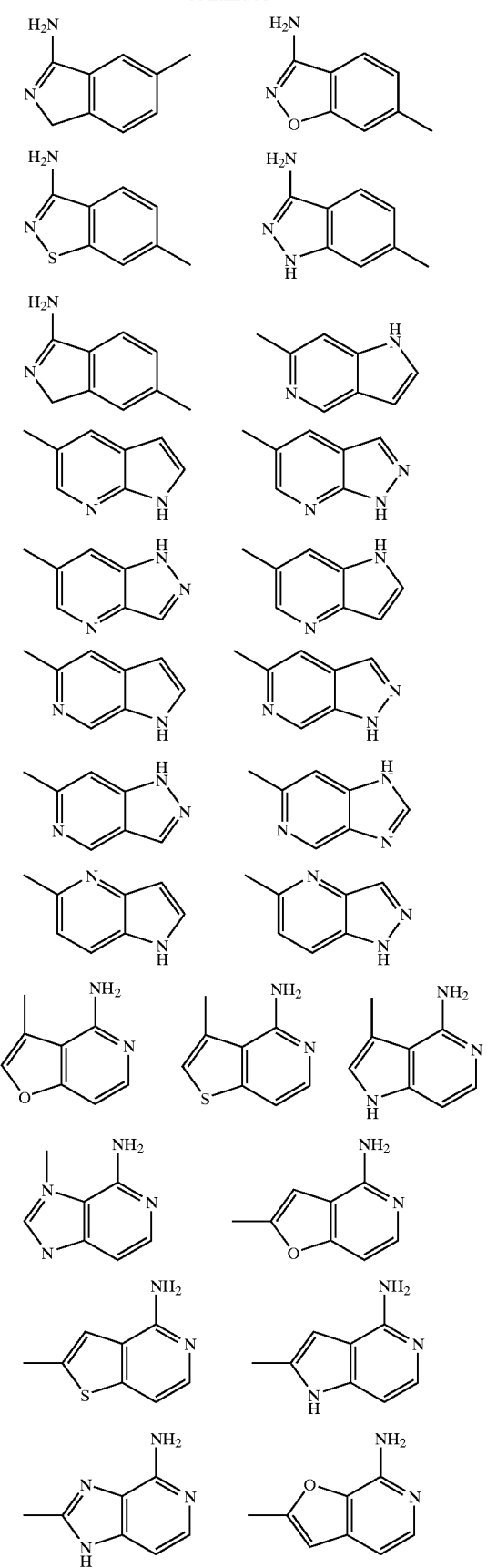
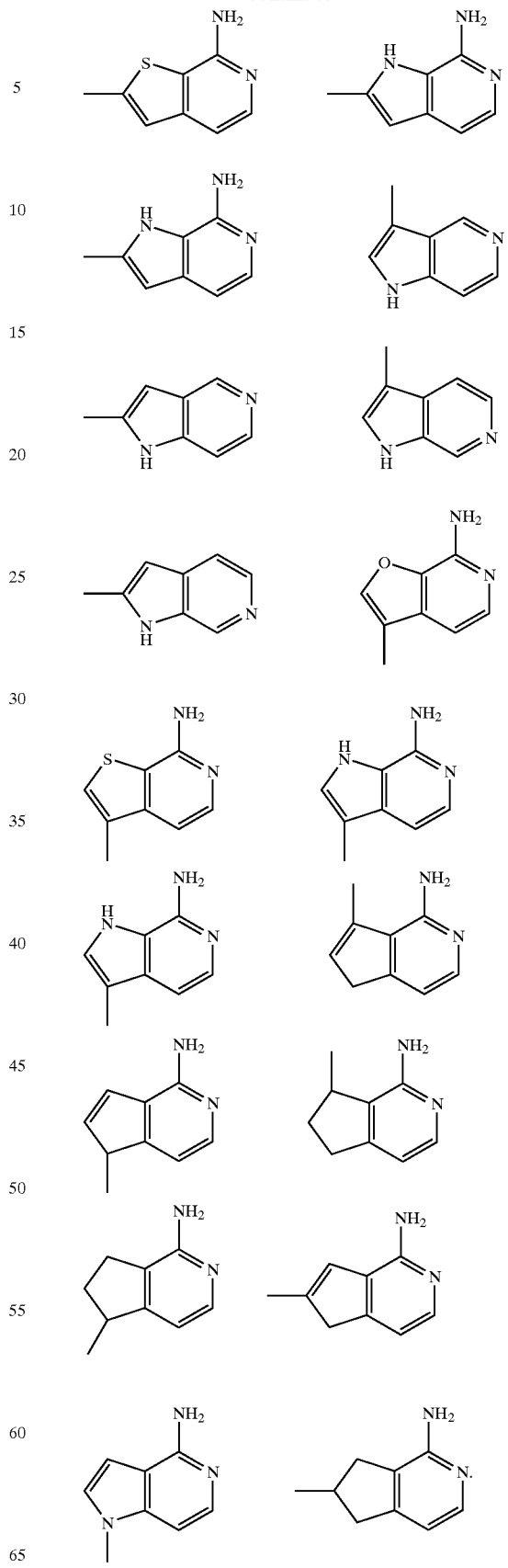

In another preferred embodiment, the present invention provides a novel compound, wherein;
G is selected from the group:
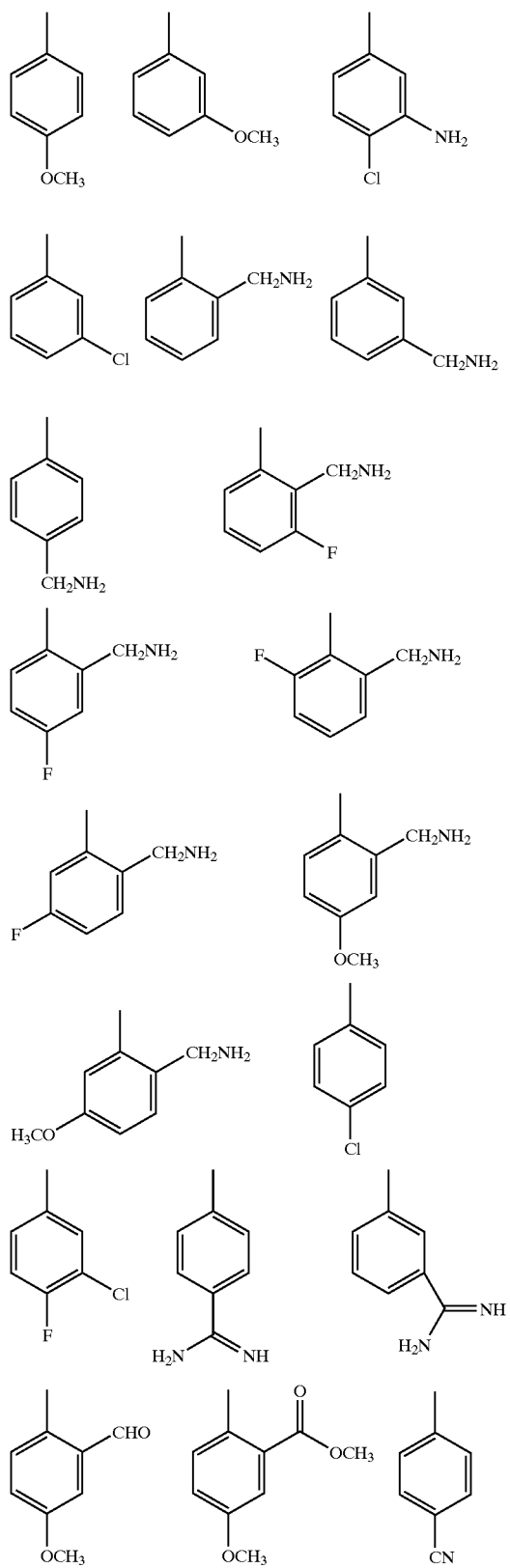
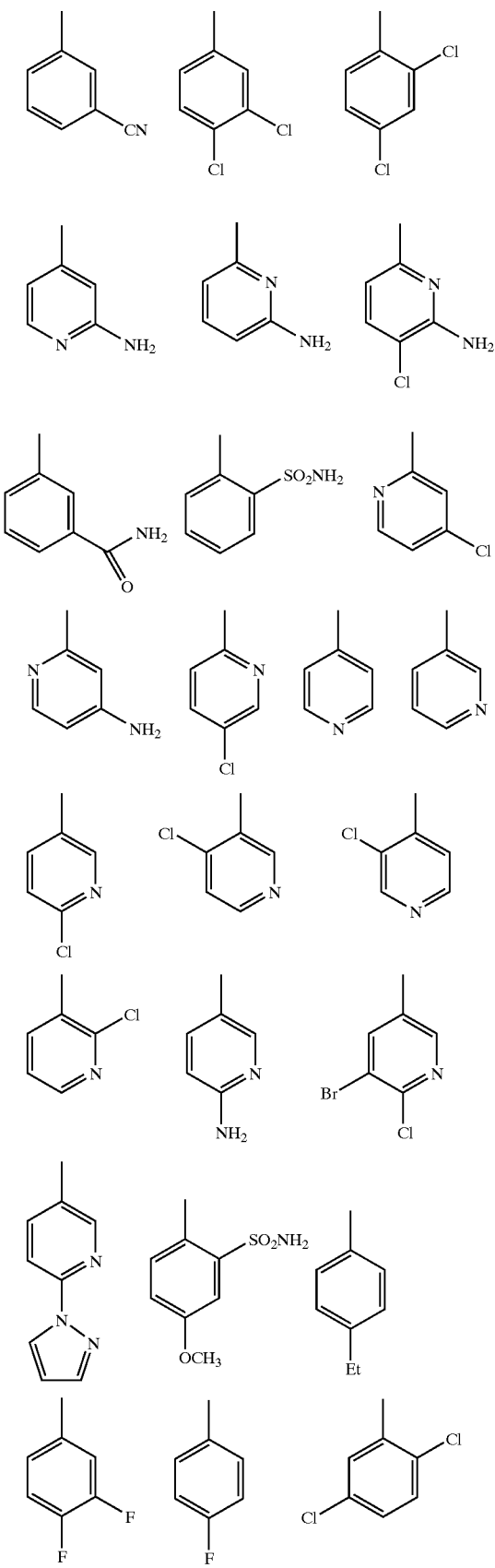

-continued
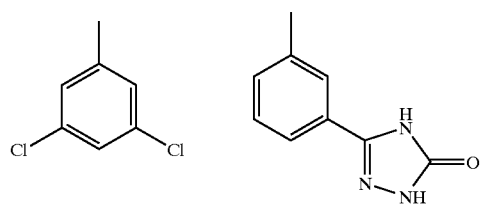
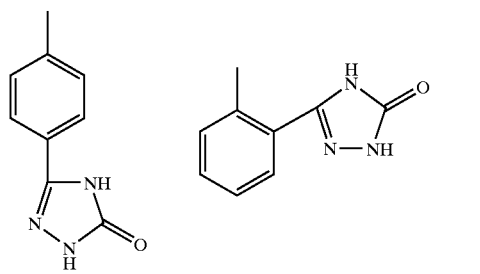
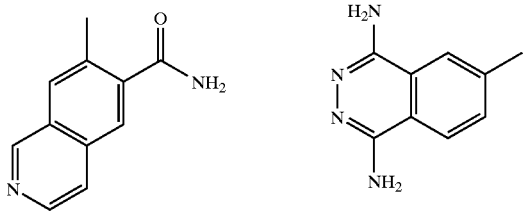
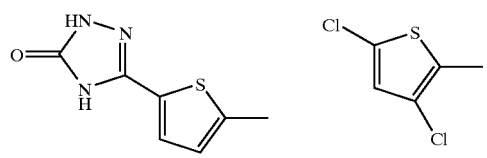
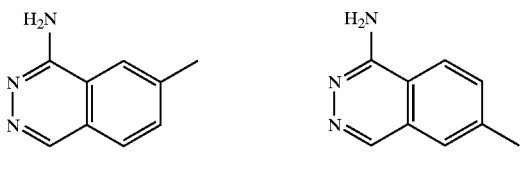
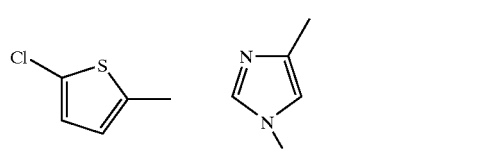
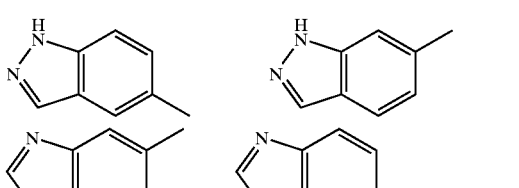
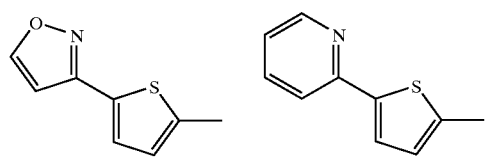
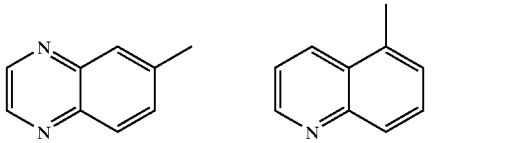
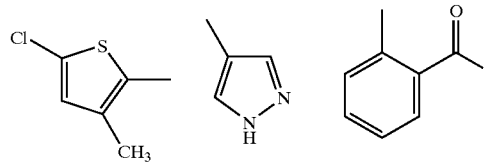
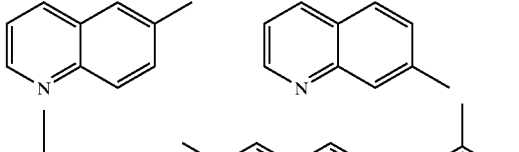
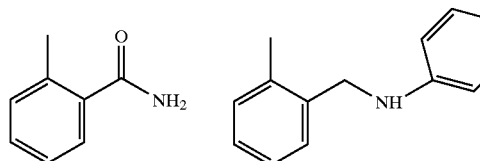
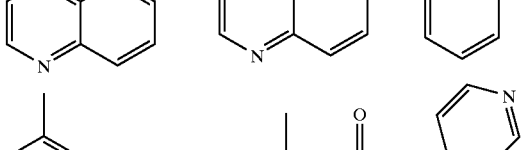
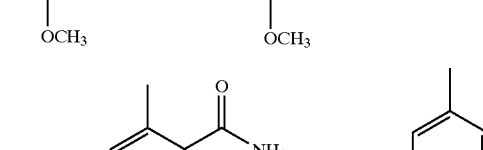
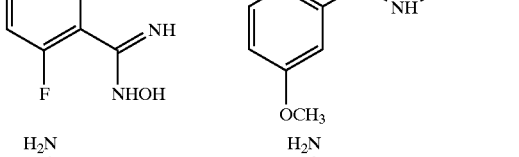
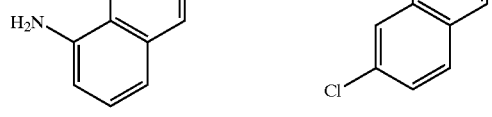
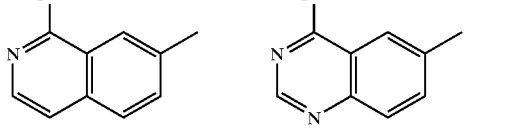

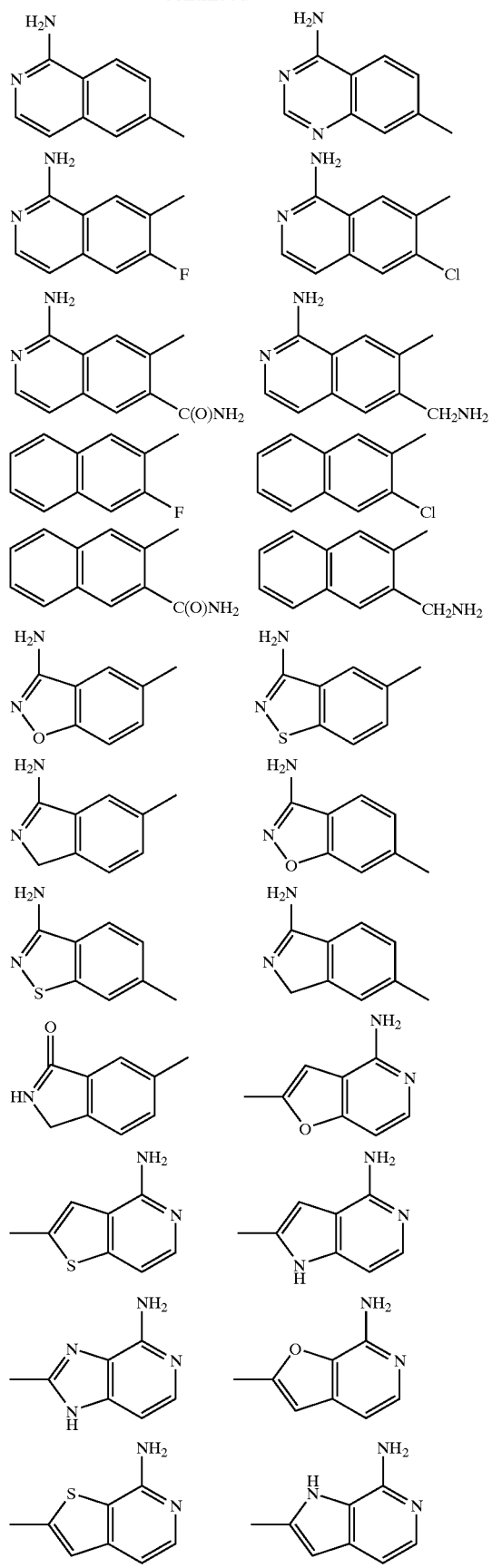
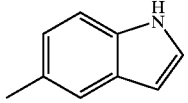
In another preferred embodiment, the present invention provides a novel compound, wherein;
G is selected from the group:
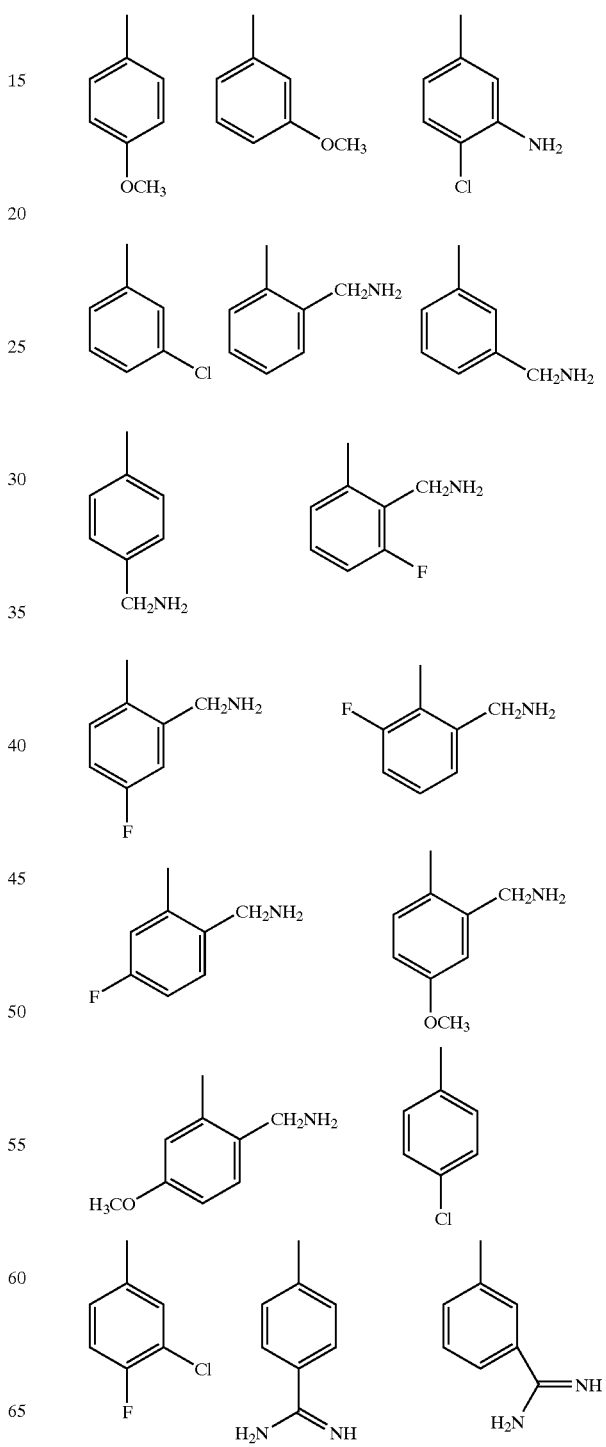

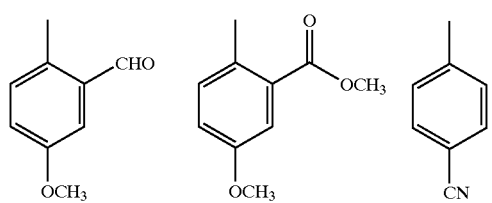
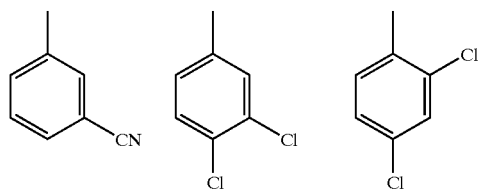
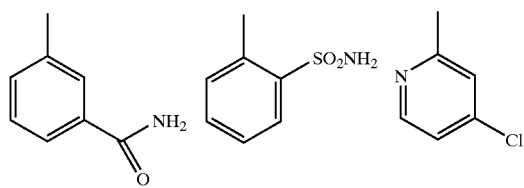
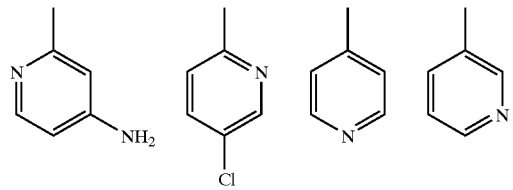
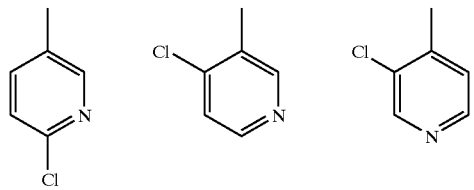
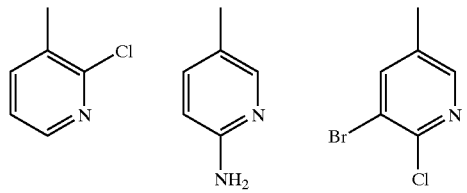
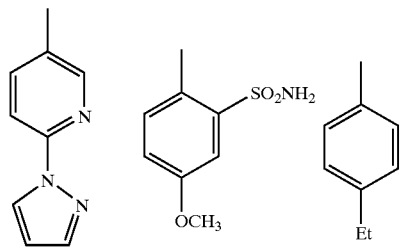
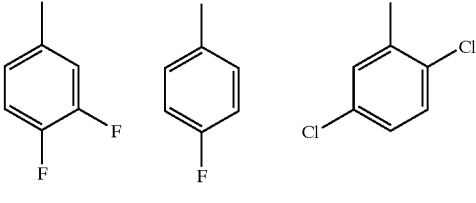
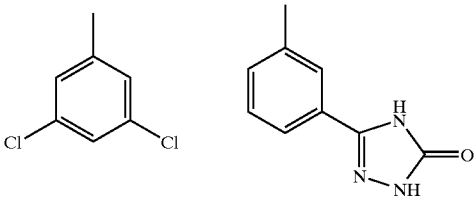
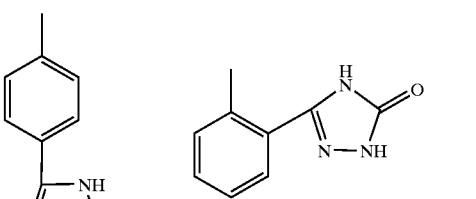
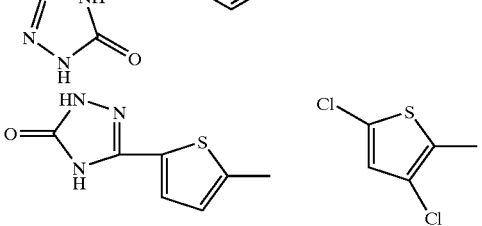
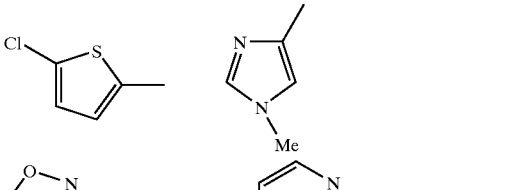
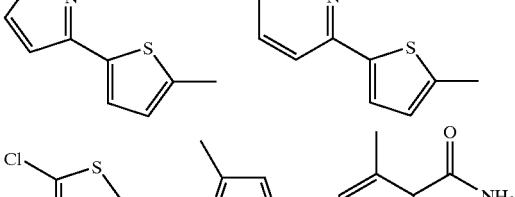
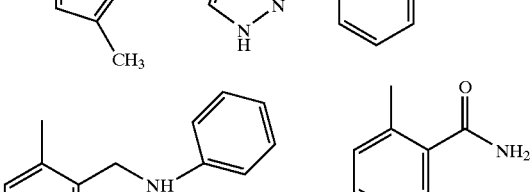
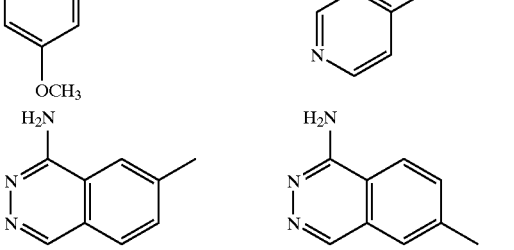

-continued
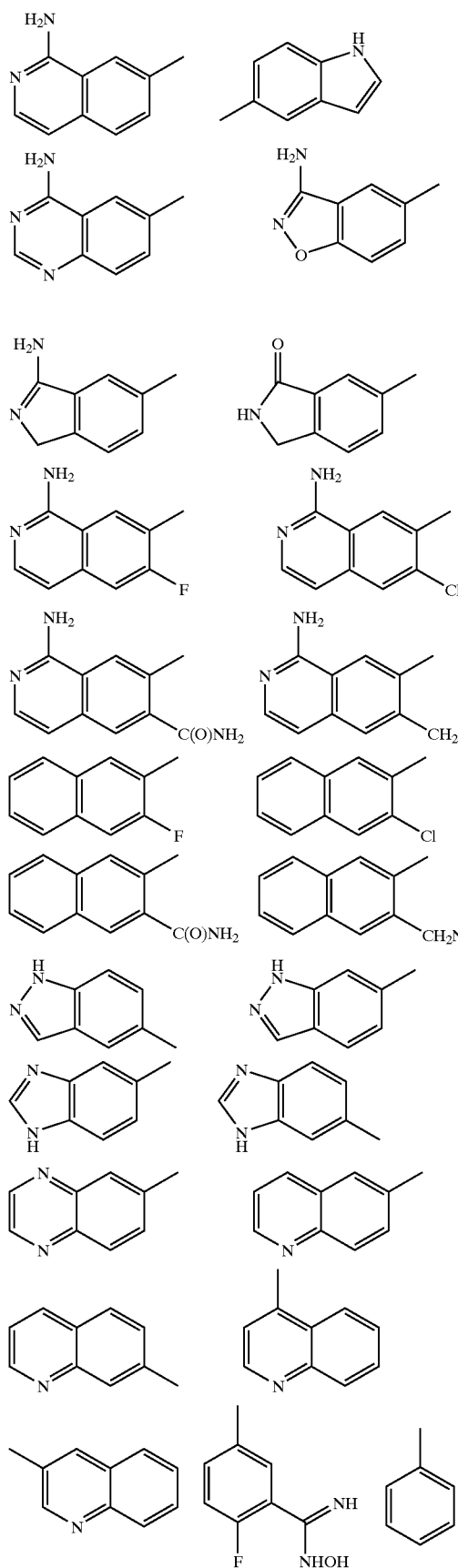
-continued
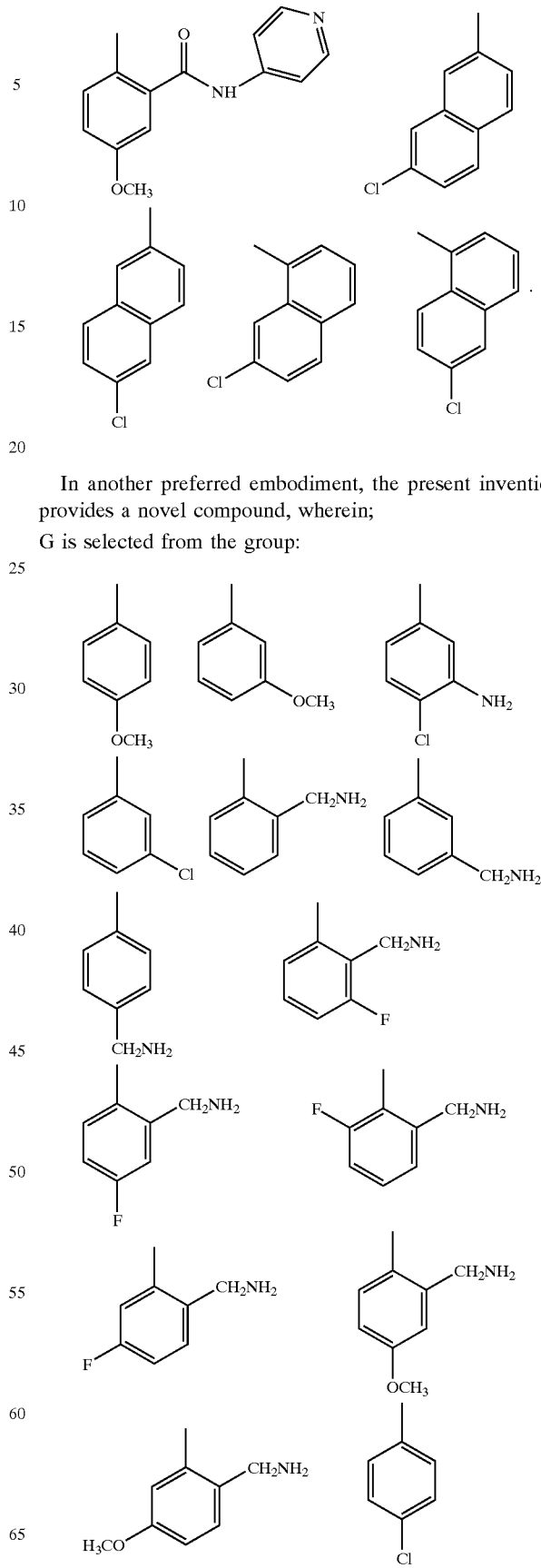
In another preferred embodiment, the present invention provides a novel compound, wherein;
G is selected from the group:

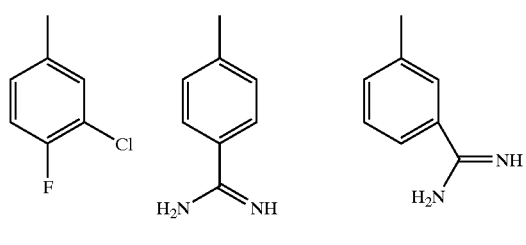
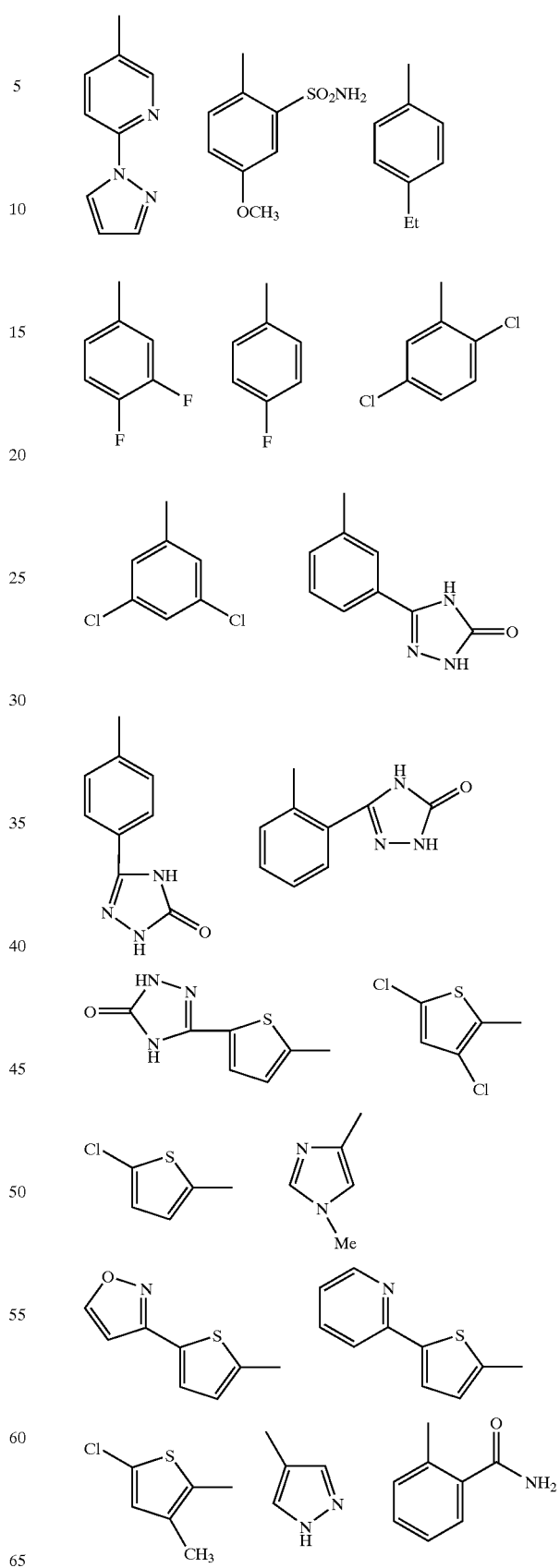

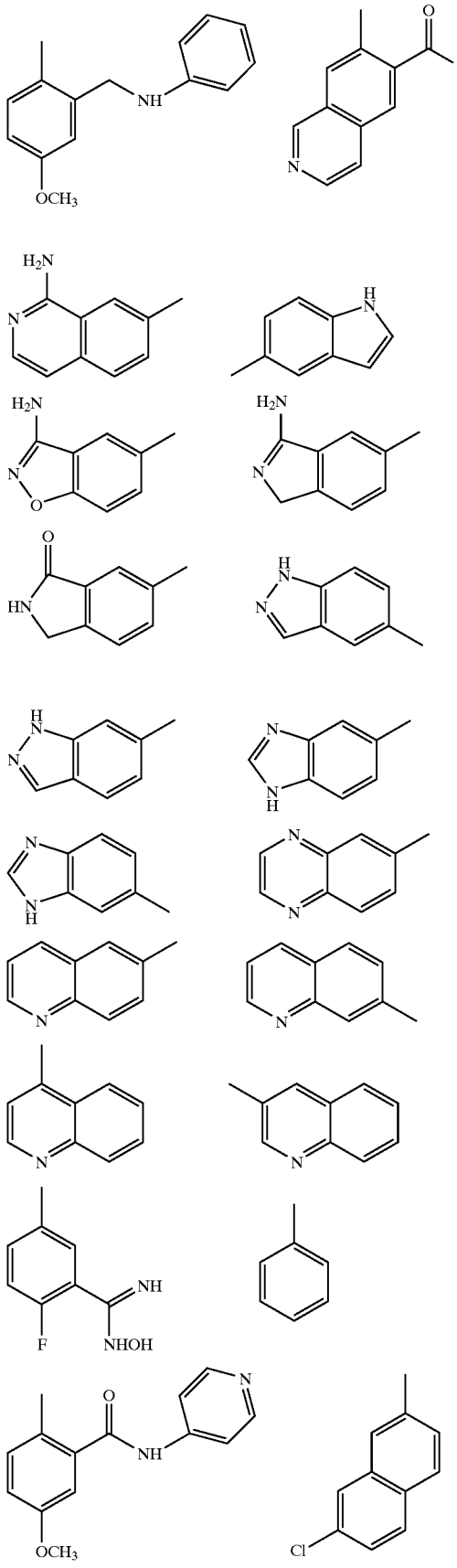

In another preferred embodiment, the present invention provides a novel compound, wherein;

$G_1$ is selected from $(CR^{3a}R^{3b})_{1-2}$, $CR^3\!=\!CR^3$, $C\!\equiv\!C$, $(CHR^{3a})_uC(O)(CHR^{3a})_w$, $(CHR^{3a})_uC(O)O(CHR^{3a})_w$, $(CHR^{3a})_uO(CHR^{3a})_w$, $(CHR^{3a})_uNR^{3e}(CHR^{3a})_w$, $(CHR^{3a})_uC(O)NR^3(CHR^{3a})_w$, $(CHR^{3a})_uNR^3C(O)(CHR^{3a})_w$, $(CHR^{3a})_uNR^3S(O)_2(CHR^{3a})_w$, $(CHR^{3a})_uNR^3S(O)_2(CHR^{3a})_w$, and $(CHR^{3a})_uS(O)_2NR^3(CHR^{3a})_w$, wherein u+w total 0, 1, or 2, provided that $G_1$ does not form a N—N or N—O bond with either group to which it is attached.

In another preferred embodiment, the present invention provides a novel compound, wherein;

A is selected from one of the following carbocyclic and heterocyclic systems which are substituted with 0–2 $R^4$;
phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl.

In another preferred embodiment, the present invention provides a novel compound, wherein;

A is selected from phenyl, piperidinyl, pyridyl, and pyrimidyl, and is substituted with 0–2 $R^4$.

In another preferred embodiment, the present invention provides a novel compound, wherein;

A is selected from the group: phenyl, piperidinyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl.

In another preferred embodiment, the present invention provides a novel compound, wherein;

B is selected from: Y and X—Y;
X is selected from —$(CR^2R^{2a})_{1-4}$—, —C(O)—, —C(=NR^{1c})—, —CR^2(NR^{1c}R^2)—, —C(O)CR^2R^{2a}—, —CR^2R^{2a}C(O)—, —C(O)NR^2—, —NR^2C(O)—, —C(O)NR^2CR^2R^{2a}—, —NR^2C(O)CR^2R^{2a}—, —CR^2R^{2a}C(O)NR^2—, —CR^2R^{2a}NR^2C(O)—, —NR^2C(O)NR^2—, —NR^2—, —NR^2CR^2R^{2a}—, —CR^2R^{2a}NR^2—, O, —CR^2R^{2a}O—, and —OCR^2R^{2a}—;
Y is —$(CH_2)_rNR^2R^{2a}$, provided that X—Y do not form a N—N or O—N bond;
alternatively, Y is selected from one of the following carbocyclic and heterocyclic systems which are substituted with 0–2 $R^{4a}$;
cyclopropyl, cyclopentyl, cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl; and alternatively, Y is selected from the following bicyclic heteroaryl ring systems:

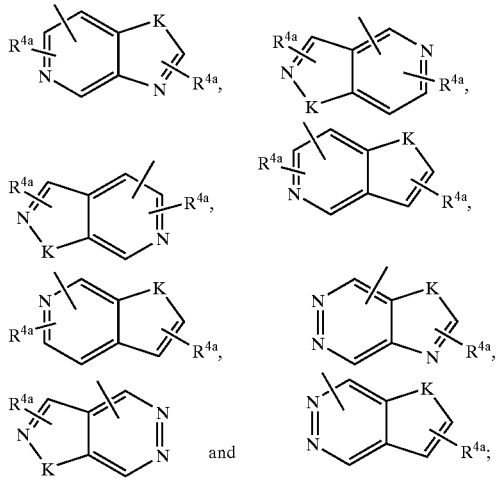

K is selected from O, S, NH, and N.

In another preferred embodiment, the present invention provides a novel compound, wherein;

B is selected from phenyl, pyrrolidino, N-pyrrolidino-carbonyl, morpholino, N-morpholino-carbonyl, 1,2,3-triazolyl, imidazolyl, and benzimidazolyl, and is substituted with 0–1 $R^{4a}$.

In another preferred embodiment, the present invention provides a novel compound, wherein;

B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N,N-diethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, 2-(N-(3-hydroxypyrrolidinyl)methyl)phenyl, and 2-(N-(2-hydroxyethyl)methylamino)-methyl)phenyl.

In another preferred embodiment, the present invention provides a novel compound, wherein;

R is selected from $C_{1-4}$ alkyl, F, Cl, Br, I, OH, $OCH_3$, $OCH_2CH_3$, $OCH(CH_3)_2$, $OCH_2CH_2CH_3$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), and $CH_2CH_2N(C_{1-3}$ alkyl)$_2$.

In another preferred embodiment, the present invention provides a novel compound, wherein;

$R^a$ and $R^b$, at each occurrence, are independently selected from H, $C_{1-4}$ alkyl, F, Cl, Br, I, OH, $OCH_3$, $OCH_2CH_3$, $OCH(CH_3)_2$, $OCH_2CH_2CH_3$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), and $CH_2CH_2N(C_{1-3}$ alkyl)$_2$; and alternatively, $R^a$ and $R^b$ combine to form methylenedioxy or ethylenedioxy.

In another preferred embodiment, the present invention provides a novel compound, wherein;

$R^c$ is selected from $C_{1-4}$ alkyl, F, Cl, Br, I, OH, $OCH_3$, $OCH_2CH_3$, $OCH(CH_3)2$, $OCH_2CH_2CH_3$, CN, $C(=NR^8)NR^7R^9$, $NHC(=NR^8)NR^7R^9$, $NR^8CH(=NR^7)$, $(CR^8R^9)_tNR^7R^8$, and $(CR^8R^9)_tC(O)NR^7R^8$.

In another preferred embodiment, the present invention provides a novel compound, wherein;

$R^3$, at each occurrence, is selected from H, $C_{1-4}$ alkyl substituted with 0–2 $R^{1a}$; $C_{2-4}$ alkenyl substituted with 0–2 $R^{1a}$; $C_{2-4}$ alkynyl substituted with 0–2 $R^{1a}$; $C_{3-7}$ cycloalkyl($C_{0-2}$ alkyl)-substituted with 0–3 $R^{1a}$; heterocyclyl($C_{0-2}$ alkyl)-substituted with 0–3 $R^{1a}$; aryl($C_{0-2}$ alkyl)-substituted with 0–3 $R^{1a}$; heteroaryl($C_{0-2}$ alkyl)-substituted with 0–3 $R^{1a}$.

In another preferred embodiment, the present invention provides a novel compound, wherein;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^{3f}$, $S(O)_pR^{3f}$, $(CF_2)_rCF_3$, $NCH_2R^{1c}$, $OCH_2R^{1c}$, $SCH_2R^{1b}$, $N(CH_2)_2(CH_2)_rR^{1b}$, $O(CH_2)_2(CH_2)_tR^{1b}$, and $S(CH_2)_2(CH_2)_rR^{1b}$.

In another preferred embodiment, the present invention provides a novel compound, wherein;

$R^4$, at each occurrence, is selected from H, OH, $OR^2$, $(CH_2)OR^2$, $(CH_2)_2OR^2$, F, Br, Cl, I, $C_{1-4}$ alkyl, $NR^2R^{2a}$, $(CH_2)NR^2R^{2a}$, $(CH_2)_2NR^2R^{2a}$, $CF_3$, and $(CF_2)CF_3$.

In another preferred embodiment, the present invention provides a novel compound, wherein;

$R^{4a}$, at each occurrence, is selected from H, =O, $(CH_2)_rOR^2$, $(CH_2)_r$—F, $(CH_2)_r$—Br, $(CH_2)_r$—Cl, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $(CH_2)_rN=CHOR^3$, $C(O)NH(CH_2)_2NR^2R^{2a}$, $NR^2C(O)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^{3f}$, $S(O)_nR^{3f}$, and $(CF_2)_rCF_3$.

In another preferred embodiment, the present invention provides a novel compound, wherein;

$R^{4a}$ is selected from H, $C_{1-4}$ alkyl, $CF_3$, $OR^2$, $(CH_2)OR^2$, $(CH_2)_2OR^2$, $NR^2R^{2a}$, $(CH_2)NR^2R^{2a}$, $(CH_2)_2NR^2R^{2a}$, $SR^5$, $S(O)R^5$, $S(O)_2R^5$, $SO_2NR^2R^{2a}$, and 1-$CF_3$-tetrazol-2-yl.

In another preferred embodiment, the present invention provides a novel compound, wherein;

$R^{4b}$, at each occurrence, is selected from H, =O, $(CH_2)_rOR^3$, F, Cl, Br, I, $C_{1-4}$ alkyl, CN, $NO_2$, $(CH_2)_rNR^3R^{3a}$, $(CH_2)_rC(O)R^3$, $(CH_2)_rC(O)OR^{3C}$, $NR^3C(O)R^{3a}$, $C(O)NR^3R^{3a}$, $NR^3C(O)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, —$S(O)_p$—$C_{1-4}$ alkyl, $S(O)_p$-phenyl, and $(CF_2)_rCF_3$.

In another preferred embodiment, the present invention provides a novel compound, wherein;

$R^{4b}$, at each occurrence, is selected from H. $CH_3$, and OH.

In another preferred embodiment, the present invention provides a novel compound, wherein;

$R^5$, at each occurrence, is selected from H, $C_{1-6}$ alkyl, =O, $CF_3$, phenyl substituted with 0–2 $R^6$, naphthyl substituted with 0–2 $R^6$, and benzyl substituted with 0–2 $R^6$.

In another-preferred embodiment, the present invention provides a novel compound, wherein;

$R^5$, at each occurrence, is selected from $CF_3$, $C_{1-6}$ alkyl, phenyl, and benzyl.

[7] In an even further preferred embodiment, the present invention provides a novel compound selected from:

3-({1-[3-fluoro-2'-(methylsulfonyl)-[1,1']-biphenyl-4-yl]-2-oxo-3-piperidinyl}oxy)benzonitrile;

3-({1-[3-fluoro-2'-(methylsulfonyl)-[1,1']-biphenyl-4-yl]-2-oxo-3-piperidinyl}oxy)benzene-carboximidamide;

4-({1-[3-fluoro-2'-(methylsulfonyl)-[1,1']-biphenyl-4-yl]-2-oxo-3-piperidinyl}oxy)benzene-carboximidamide;

3-({1-[2-[(dimethylamino)methyl]-3-fluoro-[1,1']-biphenyl-4-yl]-2-oxo-3-piperidinyl}oxy)benzonitrile;

3-({1-[2-[(dimethylamino)methyl]-3-fluoro-[1,1']-biphenyl-4-yl]-2-oxo-3-piperidinyl}oxy)benzene-carboximidamide;

3-({1-[2'-[(dimethylamino)methyl]-[1,1']-biphenyl-4-yl]-2-oxo-3-piperidinyl}oxy)benzene-carboximidamide;

3-({1-[2-[(dimethylamino)methyl]-3-fluoro-[1,1']-biphenyl-4-yl]-2-oxo-3-piperidinyl}amino)benzene-carboximidamide;

2,4-dichloro-N-{1-[3-fluoro-2'-(methylsulfonyl)-[1,1']-biphenyl-4-yl]-2-oxo-3-piperidinyl}benzamide;

3-chloro-N-{1-[3-fluoro-2'-(methylsulfonyl)-[1,1']-biphenyl-4-yl]-2-oxo-3-piperidinyl}-N-methyl-benzamide;

3,4-dichloro-N-{1-[3-fluoro-2'-(methylsulfonyl)-[1,1']-biphenyl-4-yl]-2-oxo-3-piperidinyl}-benzamide;

4-fluoro-N-{1-[3-fluoro-2'-(methylsulfonyl)-[1,1']-biphenyl-4-yl]-2-oxo-3-piperidinyl}-benzamide;

4-chloro-N-{1-[3-fluoro-2'-(methylsulfonyl)-[1,1']-biphenyl-4-yl]-2-oxo-3-piperidinyl}-benzamide;

2-chloro-N-{1-[3-fluoro-2'-(methylsulfonyl)-[1,1']-biphenyl-4-yl]-2-oxo-3-piperidinyl}-isonicotinamide;

6-chloro-N-{1-[3-fluoro-2'-(methylsulfonyl)-[1,1']-biphenyl-4-yl]-2-oxo-3-piperidinyl}-nicotinamide;

N-{1-[3-fluoro-2'-(methylsulfonyl)-[1,1']-biphenyl-4-yl]-2-oxo-3-piperidinyl}-6-(1H-pyrazol-1-yl)nicotinamide;

1-[3-fluoro-2'-(methylsulfonyl)-[1,1']-biphenyl-4-yl]-2-oxo-3-piperidinyl-2-chloronicotinate;

1-[3-fluoro-2'-(methylsulfonyl)-[1,1']-biphenyl-4-yl]-2-oxo-3-piperidinyl4-methoxybenzoate;

2-({1-[3-fluoro-2'-(methylsulfonyl)-[1,1']-biphenyl-4-yl]-2-oxo-3-piperidinyl}oxy)-5-methoxybenzaldehyde;

3-[{5-chloro-2-pyridynyl)amino]-1-[3-fluoro-2'-(methylsulfonyl)-[1,1']-biphenyl-4-yl]-2-piperidinone;

1-[3-fluoro-2'-(methylsulfonyl)-[1,1']-biphenyl-4-yl}-3(4-methoxyphenoxy)-2-piperidinone;

2-({1-[3-fluoro-2'-(methylsulfonyl)-[1,1']-biphenyl-4-yl]-2-oxo-3-piperidinyl}oxy)-5-methoxybenzoate;

3-[3-(aminomethyl)phenoxy]-1-[3-fluoro-2'-(methylsulfonyl)-[1,1 ]-biphenyl-4-yl]-2-piperidinone;

3-{[2-(anilinomethyl)-4-methoxyphenyl]oxo}-1-[3-fluoro-2'-(methylsulfonyl)-[1,1']-biphenyl-4-yl]-2-piperidinone;

3-chloro-N-{1-[3-fluoro-2'-(methylsulfonyl)-[1,1']-biphenyl-4-yl]-2-oxo-3-piperidinyl}-benzamide;

N-benzyl-4-chloro-N-{1-[3-fluoro-2'-(methylsulfonyl)-[1,1']-biphenyl-4-yl]-2-oxo-3-piperidinyl}-benzamide;

N-{1-[3-fluoro-2'-(methylthio)-[1,1']-biphenyl-4-yl]-2-oxo-3-piperidinyl}-1H-indole-5-carboxamide;

N-{1-[3-fluoro-2'-(methylthio)-[1,1']-biphenyl-4-yl]-2-oxo-3-piperidinyl}-1H-pyrazole-4-carboxamide;

N-{1-[3-fluoro-2'-(methylthio)-[1,1']-biphenyl-4-yl]-2-oxo-3-piperidinyl}-isonicotinamide;

N-{1-[3-fluoro-2'-(methylthio)-[1,1']-biphenyl-4-yl]-2-oxo-3-piperidinyl}-nicotinamide;

6-amino-N-{1-[3-fluoro-2'-(methylthio)-[1,1']-biphenyl-4-yl]-2-oxo-3-piperidinyl}-nicotinamide;

6-amino-N-{1-[3-fluoro-2'-(methylthio)-[1,1']-biphenyl-4-yl]-2-oxo-3-piperidinyl}-nicotinamide;

3-{[{1-[2'-aminosulfonyl-[1,1']-biphenyl-4-yl]-2-oxo-3-piperidinyl}(benzyl)amino]sulfonyl}benzenecarboximidamide;

3-{[{1-(3-fluoro-2'-aminosulfonyl)-[1,1']-biphenyl-4-yl]-2-oxo-3-piperidinyl}(benzyl)amino]sulfonyl}benzenecarboximidamide;

3-{N-benzyl-N-[2-oxo-1-(2'-sulfamoyl-biphenyl-4-yl)-piperidin-3-yl]-sulfamoyl}-benzamidine;

4-chloro-N-[1-3-fluoro-1-(2'-methylsulfonyl-biphenyl-4-yl)-2-oxo-piperidin-3-yl]-benzenesulfonamide;

6-chloro-N-[1-(3-fluoro-2'-methylsulfonyl-biphenyl-4-yl)-2-oxo-piperidin-3-yl]-naphthalene-2-sulfonamide;

7-chloro-N-[1-(3-fluoro-2'-methylsulfonyl-biphenyl-4-yl)-2-oxo-piperidin-3-yl]-naphthalene-2-sulfonamide;

5-chloro-N-[1-(3-fluoro-2'-methylsulfonyl-biphenyl-4-yl)-2-oxo-piperidin-3-yl]-thiophene-2-sulfonamide;

5-(3-isoxazolyl)-[1-3-fluoro-(2'-methylsulfonyl-biphenyl-4-yl)-2-oxo-piperidin-3-yl]-thiophene-2-sulfonamide;

4-fluoro-N-[1-(3-fluoro-1-2'-methylsulfonyl-biphenyl-4-yl)-2-oxo-piperidin-3-yl]-benzenesulfonamide;

N-[1-(3-fluoro-1-2'-methylsulfonyl-biphenyl-4-yl)-2-oxo-piperidin-3-yl]-4-methoxyl-benzenesulfonamide;

4-ethyl-N-[1-(3-fluoro-1-2'-methylsulfonyl-biphenyl-4-yl)-2-oxo-piperidin-3-yl]-benzenesulfonamide;

N-[3-fluoro-1-(2'-methylsulfonyl-biphenyl-4-yl)-2-oxo-piperidin-3-yl]-3-methoxyl-benzenesulfonamide;

5-bromo-6-chloro-[3-fluoro-1-(2'-methanesulfonyl-biphenyl-4-yl)-2-oxo-piperidin-3-yl]-pyridine-3-sulfonamide;

5-(2-pyridyl)-[3-fluoro-1-(2'-methanesulfonyl-biphenyl-4-yl)-2-oxo-piperidin-3-yl]-thiophene-2-sulfonamide;

3,4-difluoro-N-[3-fluoro-1-(2'-methanesulfonyl-biphenyl-4-yl)-2-oxo-piperidin-3-yl]-benzenesulfonamide;

3-chloro-N-[3-fluoro-1-(2'-methylsulfonyl-biphenyl-4-yl)-2-oxo-piperidin-3-yl]-benzenesulfonamide;

3,5-dichloro-[3-fluoro-1-(2'-methanesulfonyl-biphenyl-4-yl)-2-oxo-piperidin-3-yl]-thiophene-2-sulfonamide;

3-cyano-N-[3-fluoro-1-(2'-methanesulfonyl-biphenyl-4-yl)-2-oxo-piperidin-3-yl]-benzenesulfonamide;

3-chloro-4-fluoro-N-[3-fluoro-1-(2'-methanesulfonyl-biphenyl-4-yl)-2-oxo-piperidin-3-yl]-benzenesulfonamide 1-methyl-[3-fluoro-1-(2'-methanesulfonyl-biphenyl-4-yl)-2-oxo-piperidin-3-yl]-imidazole-4-sulfonamide;

2,5-dichloro-N-[3-fluoro-1-(2'-methylsulfonyl-biphenyl-4-yl)-2-oxo-piperidin-3-yl]-benzenesulfonamide;

3,5-dichloro-N-[3-fluoro-1-(2'-methylsulfonyl-biphenyl-4-yl)-2-oxo-piperidin-3-yl]-benzenesulfonamide;

5-chloro-N-[1-(2'-diethylaminomethyl-3-fluoro-biphenyl-4-yl)-2-oxo-piperidin-3-yl]-thiophene-2-sulfonamide;

5-chloro-N-[1-(3-fluoro-1-2'-pyrrolidin-1-ylmethyl-biphenyl-4-yl)-2-oxo-piperidin-3-yl]-thiophene-2-sulfonamide;

5-chloro-N-{1-[3-fluoro-1-2'-(3-hydroxypyrrolidin-1-ylmethyl)-biphenyl-4-yl]-2-oxo-piperidin-3-yl}-thiophene-2-sulfonamide;

5-chloro-N-{1-[3-fluoro-1-2'-(4-hydroxypiperidin-1-ylmethyl)-biphenyl-4-yl]-2-oxo-piperidin-3-yl}-thiophene-2-sulfonamide;

N-benzyl-5-chloro-N-[1-(2'-diethylaminomethyl-3-fluoro-biphenyl-4-yl)-2-oxo-piperidin-3-yl]-thiophene-2-sulfonamide;

N-benzyl-5-chloro-N-[1-(3-fluoro-1-2'-pyrrolidin-1-ylmethyl-biphenyl-4-yl)-2-oxo-piperidin-3-yl]-thiophene-2-sulfonamide;

N-benzyl-5-chloro-N-{1-[3-fluoro-1-2'-(3-hydroxypyrrolidin-1-ylmethyl)-biphenyl-4-yl]-2-oxo-piperidin-3-yl}-thiophene-2-sulfonamide;
N-benzyl-5-chloro-N-{1-[3-fluoro-1-2'-(4-hydroxypiperidin-1-ylmethyl)-biphenyl-4-yl]-2-oxo-piperidin-3-yl}-thiophene-2-sulfonamide;
5-chloro-[3-fluoro-1-(2'-{[(2-hydroxy-ethyl)-methyl-amino]-methyl}-biphenyl-4-yl)-2-oxo-piperidin-3-yl]-thiophene-2-sulfonamide;
3-amino-N-[1-(3-fluoro-2'-methanesulfonyl-biphenyl-4-yl)-2-oxo-piperidin-3-yl]-benzo[d]isoxazole-5-sulfonamide;
3-(3-amino-benzo[d]isoxazol-5-ylamino)-1-(3-fluoro-2'-methanesulfonyl-biphenyl-4-yl)-piperidin-2-one;
2-fluoro-5-[1-(3-fluoro-2'-methanesulfonyl-biphenyl-4-yl)-2-oxo-piperidin-3-ylamino]-N-hydroxy-benzamidine;
1-(3-fluoro-2'-methanesulfonyl-biphenyl-4-yl)-3-[3-(5-oxo-4,5-dihydro-1H-[1,2,4]triazol-3-yl)-phenylamino]-piperidin-2-one;
N-benzyl-4-chloro-N-[1-(2'-methanesulfonyl-biphenyl-4-yl)-2-oxo-piperidin-3-yl]-benzenesulfonamide;
4-chloro-N-methyl-N-[1-(2'-methanesulfonyl-biphenyl-4-yl)-2-oxo-piperidin-3-yl]-benzenesulfonamide;
4-chloro-N-ethyl-N-[1-(2'-methanesulfonyl-biphenyl-4-yl)-2-oxo-piperidin-3-yl]-benzenesulfonamide;
4-chloro-N-[1-(3-fluoro-2'-methanesulfonyl-biphenyl-4-yl)-2-oxo-piperidin-3-yl]-N-(3-pyridylmethyl)-benzenesulfonamide;
4-chloro-N-[1-(3-fluoro-2'-methanesulfonyl-biphenyl-4-yl)-2-oxo-piperidin-3-yl]-N-(2-pyridylmethyl)-benzenesulfonamide;
3-[[1,2-dihydro-1-[2'-(methylsulfonyl)[1,1'-biphenyl]-4-yl]-2-oxo-3-pyridinyl]amino]-benzenecarboximidamide;
3-[(4-methoxyphenyl)amino]-1-[2'-(methylsulfonyl)[1,1'-biphenyl]-4-yl]-2(1H)-pyridinone;
N-[1,2-dihydro-1-[2'-(methylsulfonyl)[1,1'-biphenyl]-4-yl]-2-oxo-3-pyridinyl]-4-methoxy-benzamide;
6-chloro-N-[1,2-dihydro-1-[2'-(methylsulfonyl)[1,1'-biphenyl]-4-yl]-2-oxo-3-pyridinyl]-3-pyridinecarboxamide;
3-[[1,2-dihydro-1-[2'-[(3-hydroxy-1-pyrrolidinyl)methyl][1,1'-biphenyl]-4-yl]-2-oxo-4-(1-pyrrolidinyl)-3-pyridinyl]amino]-benzenecarboximidamide;
3-[[1,2-dihydro-1-[2'-[(3-hydroxy-1-pyrrolidinyl)methyl][1,1'-biphenyl]-4-yl]-2-oxo-4-(1-pyrrolidinyl)-3-pyridinyl]amino]-benzamide;
3-[3-(2'-methanesulfonyl-biphenyl-4-yl)-2-oxo-tetrahydro-pyrimidin-1-ylmethyl]-benzamidine;
4-benzyloxycarbonyl-3-(4-chlorobenzenesulfonylamino)-1-(2'-methanesulfonyl-biphenyl-4-yl)-2-oxo-piperazine;
4-benzyloxycarbonyl-3-(4-methoxybenzenesulfonylamino)-1-(2'-methanesulfonyl-biphenyl-4-yl)-2-oxo-piperazine;
5-chloro-[2-(3-fluoro-2'-methanesulfonyl-biphenyl-4-yl)-3-oxo-1,2,3,4-tetrahydroisoquinolin-4-yl]-thiophene-2-sulfonamide;
3-[1-(2'-dimethylaminomethyl-biphenyl-4-yl)-2-oxo-azepan-3-ylamino]-benzamidine;
N-[3-benzyl-1-(2'-methanesulfonyl-biphenyl-4-yl)-2-oxo-piperidin-3-yl]-4-chlorobenzamide;
[3-(6-chloro-naphthalene-2-sulfonylamino)-1-(2'-methanesulfonyl-biphenyl-4-yl)-2-oxo-piperidin-3-yl]-acetic acid methyl ester;
N-[1-(3-fluoro-2'-methanesulfonyl-biphenyl-4-yl)-2-oxo-piperidin-3-yl]-3-(5-oxo-4,5-dihydro-1H-[1,2,4]triazol-3-yl)-benzenesulfonamide;
1-(3-fluoro-2'-methanesulfonyl-biphenyl-4-yl)-3-[3-(5-oxo-4,5-dihydro-1H-[1,2,4]triazol-3-yl)-phenoxy]-piperidin-2-one;
[1-(3-fluoro-2'-methanesulfonyl-biphenyl-4-yl)-2-oxo-piperidin-3-yl]-benzenesulfonamide;
[1-(3-fluoro-2'-methanesulfonyl-biphenyl-4-yl)-2-oxo-piperidin-3-yl]-pyridin-3-yl-sulfonamide;
5-chloro-3-methyl-N-{1-[3-fluoro-1-2'-(4-hydroxypiperidin-1-ylmethyl)-biphenyl-4-yl]-2-oxo-piperidin-3-yl}-thiophene-2-sulfonamide;
[1-(3-fluoro-2'-methanesulfonyl-biphenyl-4-yl)-2-oxo-piperidin-3-yl]-quinolin-3-yl-sulfonamide;
[1-(3-fluoro-2'-methanesulfonyl-biphenyl-4-yl)-2-oxo-piperidin-3-yl]-quinolin-6-yl-sulfonamide;
[1-(3-fluoro-2'-methanesulfonyl-biphenyl-4-yl)-2-oxo-piperidin-3-yl]-quinoxalin-6-yl-sulfonamide;
[1-(3-fluoro-2'-methanesulfonyl-biphenyl-4-yl)-2-oxo-piperidin-3-yl]-(6-amino-pyridin-3-yl)-sulfonamide;
[1-(3-fluoro-2'-methanesulfonyl-biphenyl-4-yl)-2-oxo-piperidin-3-yl]-indazol-6-yl-sulfonamide;
6-chloronaphthalene-2-sulfonic acid [1-benzyl-4-(2'-dimethylaminomethylbiphenyl-4-yl)-5-oxo-[1,4]-diazepan-6-yl]amide;
5-chloro-N-{1-[2'-(methylsulfonyl)-1,1'-biphenyl-4-yl]-2-oxo-2,3,4,5-tetrahydro-1H-1-benzazepin-3-yl}-2-thiophenesulfonamide;
{(6-chloro-naphthalene-2-sulfonyl)-[1-(3-fluoro-2'-methanesulfonyl-biphenyl-4-yl)-2-oxo-piperidin-3-yl]-amino}-acetic acid methyl ester;
{(6-chloro-naphthalene-2-sulfonyl)-[1-(3-fluoro-2'-methanesulfonyl-biphenyl-4-yl)-2-oxo-piperidin-3-yl]-amino}-acetic acid ethyl ester;
{(6-chloro-naphthalene-2-sulfonyl)-[1-(3-fluoro-2'-methanesulfonyl-biphenyl-4-yl)-2-oxo-piperidin-3-yl]-amino}-acetic acid t-butyl ester;
6-chloro-naphthalene-2-sulfonic acid benzoyl-[1-(3-fluoro-2'-methanesulfonyl-biphenyl-4-yl)-2-oxo-piperidin-3-yl]-amide;
{(6-chloro-naphthalene-2-sulfonyl)-[1-(3-fluoro-2'-methanesulfonylbiphenyl-4-yl)-2-oxo-piperidin-3-yl]amino}acetic acid;
2-{(6-chloronaphthalene-2-sulfonyl)-[1-(3-fluoro-2'-methanesulfonylbiphenyl-4-yl)-2-oxo-piperidin-3-yl]-amino}-N-(2-dimethylaminoethyl)-N-methylacetamide;
2-{(6-Chloro-naphthalene-2-sulfonyl)-[1-(3-fluoro-2'-methanesulfonyl-biphenyl-4-yl)-2-oxo-piperidin-3-yl]-amino}-N-(2-hydroxy-ethyl)-acetamide; and
2-{(6-Chloro-naphthalene-2-sulfonyl)-[1-(3-fluoro-2'-methanesulfonyl-biphenyl-4-yl)-2-oxo-piperidin-3-yl]-amino}-N-(2-dimethylamino-ethyl)-acetamide;
or a pharmaceutically acceptable salt form thereof.

In another embodiment, the present invention provides novel pharmaceutical compositions, comprising: a pharmaceutically acceptable carrier and a therapeutically effective amount of a compound of formula (I) or a pharmaceutically acceptable salt form thereof.

In another embodiment, the present invention provides a novel method for treating a thromboembolic disorder, comprising: administering to a patient in need thereof a therapeutically effective amount of a compound of formula (I) or a pharmaceutically acceptable salt form thereof.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a novel method, comprising: administering a compound of the present invention or a pharmaceutically acceptable salt form thereof in an amount effective to treat a thromboembolic disorder.

In another embodiment, the present invention provides novel monocyclic or bicyclic carbocycles and heterocycles as described above for use in therapy.

In another embodiment, the present invention provides the use of novel monocyclic or bicyclic carbocycles and heterocycles as described above for the manufacture of a medicament for the treatment of a thromboembolic disorder.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon-carbon bonds which may occur in any stable point along the chain, such as ethenyl and propenyl. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl and propynyl. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benztriazolyl, benzisoxazolyl, oxindolyl, benzoxazolinyl, and isatinoyl. Also included are fused ring and spiro compounds containing, for example, the above heterocycles.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable-salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Further examples of prodrugs include amidine prodrugs wherein R is $C(=NR^7)NH_2$ or its tautomer $C(=NH)NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred amidine prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described for example by Chou and Talalay, Adv. Enzyme Regul. 22:27–55 (1984), occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Preparation of the compounds in Scheme 1 commences by the treatment of the appropriately substituted amine $NH_2$-A-B (for prep. see WO97/23212, WO97/30971, WO97/23212, WO97/38984, WO98/01428, WO98/06694, WO98/28269, WO98/28282, WO98/57934, WO98/57937 and WO98/57951) with 5-bromovaleryl chloride (BVC) to afford 1. Bromination can proceed in benzene with $CuBr_2$ according to the procedure by Fort et. al. (*J. Org. Chem.* 1962, 2937) to afford 2. Displacement of the bromide by reaction with a suitably substituted amino or hydroxy compound via an SN2 type of reaction in a solvent like THF, acetonitrile, benzene, or methylene chloride in a presence of a mild base affords compounds of type 3.

Preparation of the compounds of type 7 from 1 can proceed according to the procedures described in the published patent applications cited above. Treatment of 7 with an appropriately substituted amino or hydroxy compound in a solvent such as methanol, ethanol, or THF provides compounds of formula 8. Treatment of 8 with DDQ provides compounds of formula 9. Reduction of 7 or 8 can be accomplished under mild reducing conditions according to the methods known to those in the art to give 10. Conversion of 10 to the intermediate bromide 10a by treatment with $PBr_3$ or carbon tetrabromide and triphenylphospine in an appropriate solvent, followed by an SN2 displacement with a suitably substituted amino or hydroxy compound yields compounds of formula 11. Compounds of formula 1a wherein $G_1$ is a $(CR^{3a}R^{3b})_{1-5}$ can be prepared from compounds of formula 1 by treatment of 1 with a strong base, such as sodium hydride or sodium or lithium hexamethydisilazide, followed by quenching the intermediate anion with a suitably substituted alkyl halide to give 1a. Reaction of compounds of formula 10a with an appropriately functionalized organometallic reagent, such as a Grignard or organolithium reagent, would lead to compounds of formula 10b.

Scheme 1

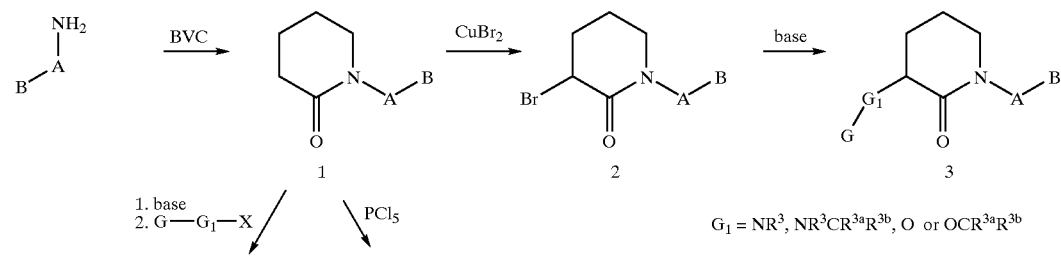

$G_1 = NR^3, NR^3CR^{3a}R^{3b}, O \text{ or } OCR^{3a}R^{3b}$

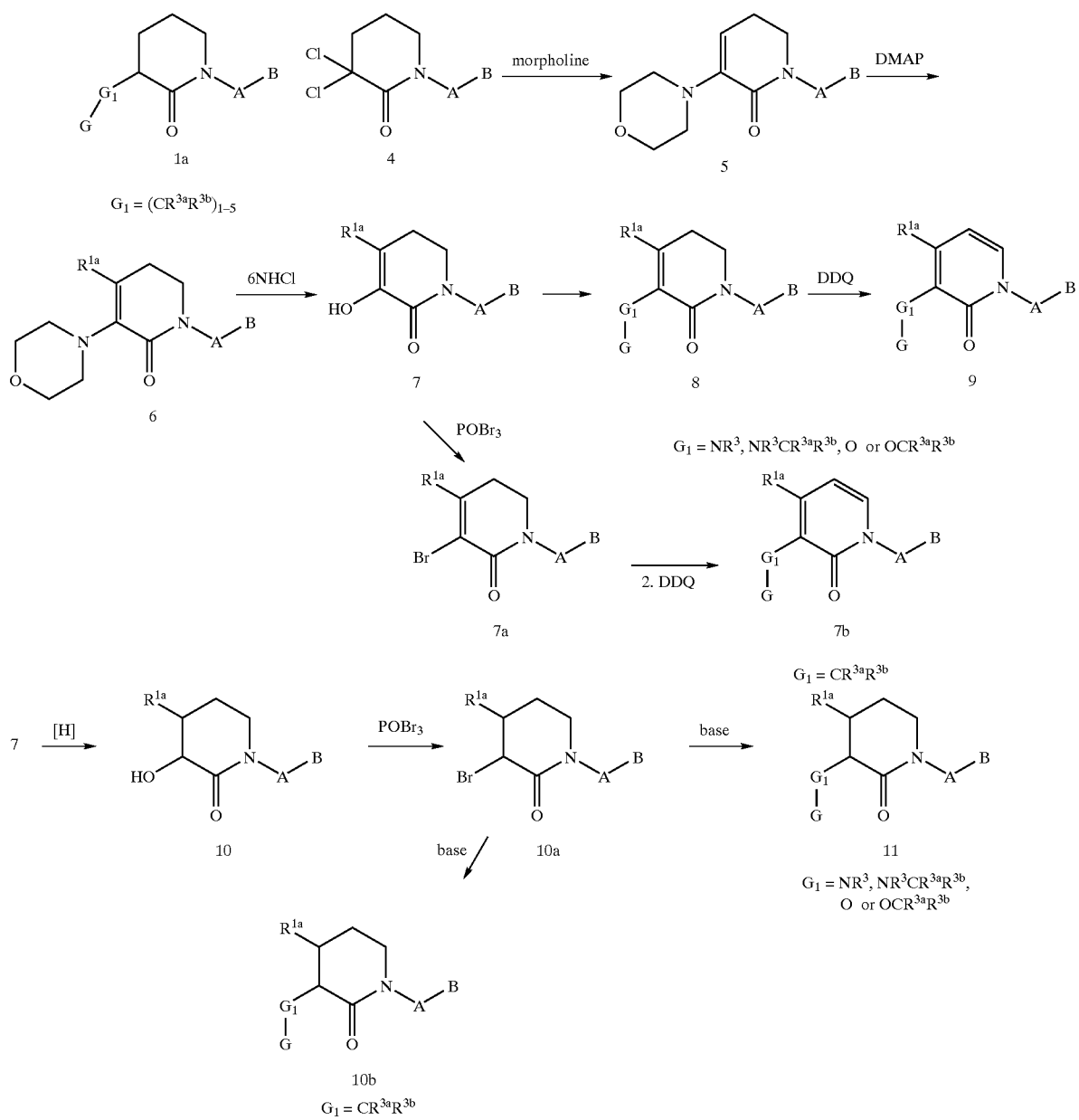

Alternately, when $G_1$ is $SO_2NH$ or $CONH$, compounds of formula I may be prepared from amine 1e which in turn is prepared in three steps from 1b as shown in Scheme 1a. Starting material 1b is prepared according to procedure found in WO00/37131 from a suitably substituted aniline and tetrahydrofuran carboxylic acid. Treatment of 1b with either carbon tetrabromide/triphenyl-phosphine or phosphorus tribromide in a suitable solvent such as methylene chloride provides bromide 1c. Displacement of the bromide with azide and subsequent reduction using triphenylphosphine (Staudinger rxn) or by catalytic hydrogenation provides 1e. Treatment of 1e with a suitably-substituted sulfonyl chloride provides the corresponding sulfonamides which are in turn further elaborated to introduce substituent B by Suzuki, Stille or Ullmann-type coupling methods or other methods known to one skilled in the art. Subsequent modification to the B substituent to introduce the desired functional groups may also be done using established methods. Subsequent alkylation of the sulfonamide nitrogen in the presence of potassium carbonate and an alkyl chloride or bromide provides compounds of the invention where $R^3$ is other than hydrogen. Replacement of the sulfonyl chloride in Scheme 1a with an acid chloride will provide the analogous amide examples of the invention. The substituent B can also be introduced in the early steps of the synthesis prior to the synthesis of the lactam ring to yield an analog of 1e where the Br is replaced by substituent B which is then carried through the rest of the steps to the final targets.

In some cases it is advantageous to introduce the $R^3$ substituent prior to the sulfonyl or acyl group. This may be done by reductive amination of 1e with an appropriate aldehyde in the presence of sodium triacetoxyborohydride or sodium cyanoborohydride to provide a secondary amine which is then sulfonylated or acylated as above.

Scheme 1a

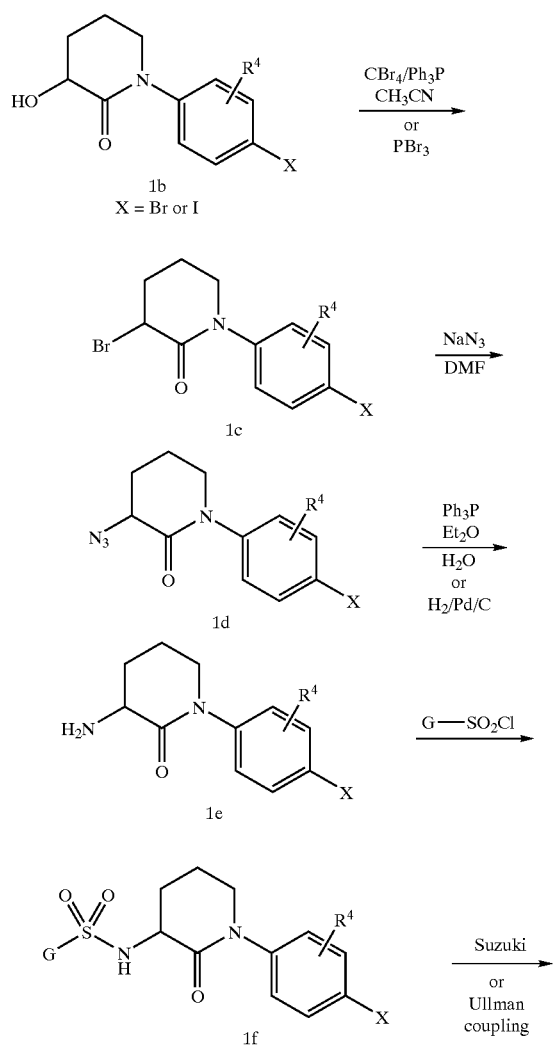

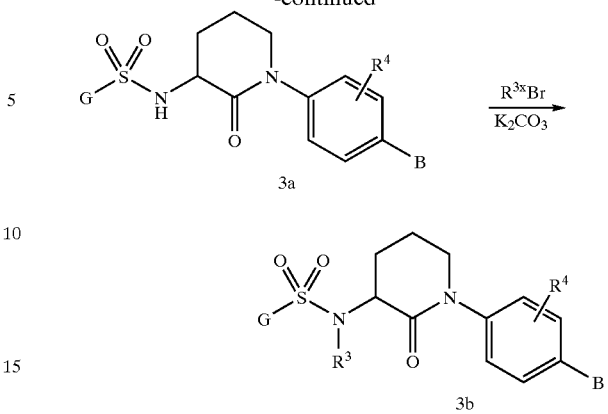

Compounds of this invention wherein ring M is a pyridinone and G1 is linked to ring M through nitrogen can also be prepared from 3-nitropyridinone starting materials as outlined in Scheme 1b. N-Arylation of a 3-nitro-2-pyridinone compound with an appropriately substituted A group precursor by copper-mediated boronic acid coupling (*Tetrahedron* 1999, 55(44) 12757)) provides compounds of formula 7d. Selective reduction of the nitro group to the corresponding amine with tin(II)chloride provides 7e. Introduction of the B substituent and elaboration of the amino group to the desired G or $G_1$-G group can be carried out as described above for the compounds in Schemes 1 and 1a to yield compounds of the invention of formula 9a, 9b and 9c. Additional starting materials for Scheme 1b with alternate $R^{1a}$ substituents can be prepared by starting with a substituted 3-nitro-2-pyridinone, for example, 4-hydroxy-3-nitro-2-pyridinone, which can be converted to the corresponding chloro compound with a reagent such as $POCl_3$ followed by displacement of the chlorine with a nucleophile, such as pyrrolidine, as illustrated in the synthesis of Ex. 68 in the Examples section below.

Scheme 1b

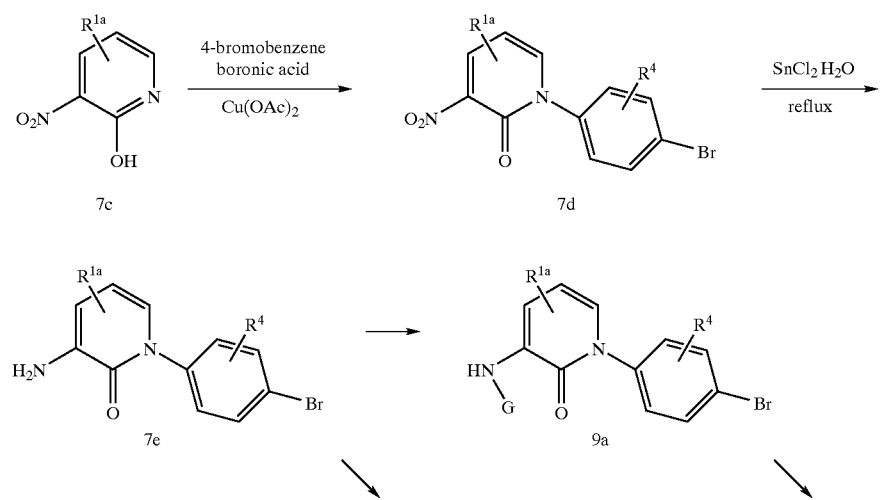

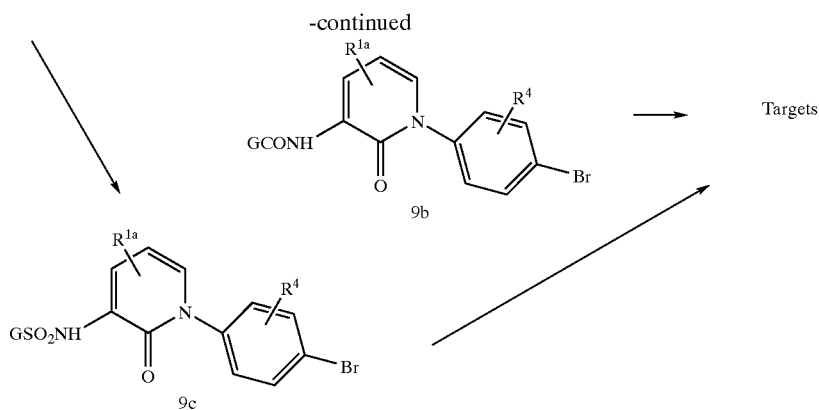

Compounds 15, 17, and 19 could be synthesized as outlined in Scheme 2. $NH_2$-A-B is reacted with 5-hexenoic acid (5-HA) in a presence of a base and an amide bond coupling reagent such as TBTU to give 12. Bromination with $CuBr_2$ (see sch.1), followed by displacement with $G_1$-G ($G_1=NR^3$, $NR^3CR^{3a}R^{3b}$, O, or $OCR^{3a}R^{3b}$) leads to 14. Conversion to 15 follows the methods described by Miller et. al. (*J. Org. Chem.* 1991, 1453). Formation of 17 ($G_1= NR^3$, $NR^3CR^{3a}R^{3b}$, O, or $OCR^{3a}R^{3b}$) and 19 ($G_1=CR^{3a}R^{3b}$) follows procedures outlined in Scheme 1 according to the methods known to those in the art.

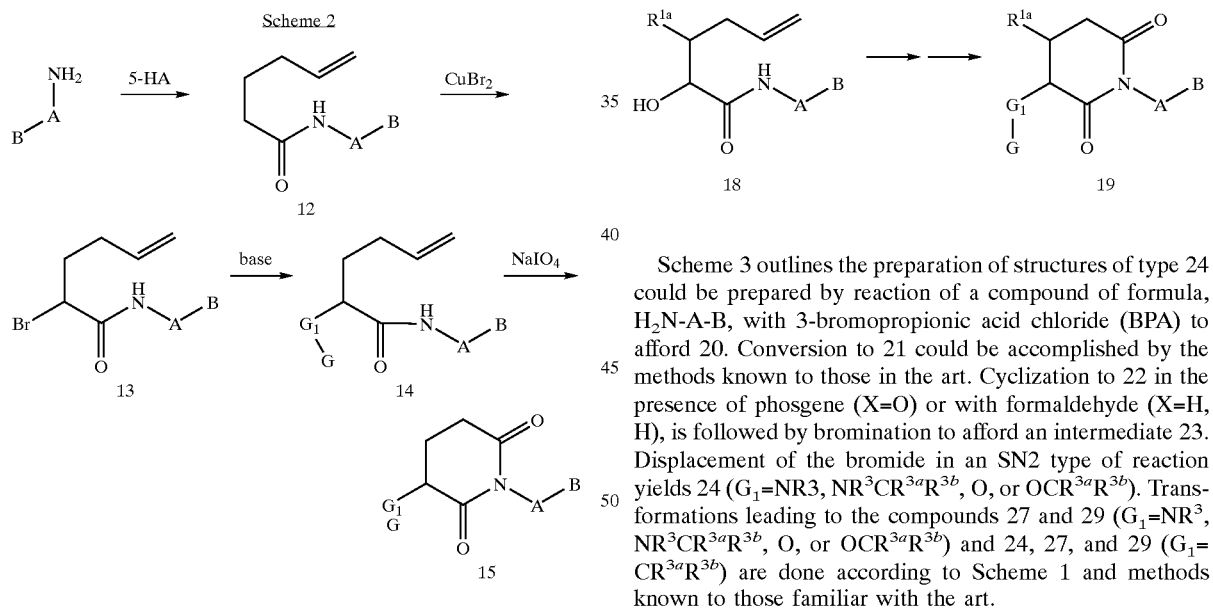

Scheme 3 outlines the preparation of structures of type 24 could be prepared by reaction of a compound of formula, $H_2N$-A-B, with 3-bromopropionic acid chloride (BPA) to afford 20. Conversion to 21 could be accomplished by the methods known to those in the art. Cyclization to 22 in the presence of phosgene (X=O) or with formaldehyde (X=H, H), is followed by bromination to afford an intermediate 23. Displacement of the bromide in an SN2 type of reaction yields 24 ($G_1=NR3$, $NR^3CR^{3a}R^{3b}$, O, or $OCR^{3a}R^{3b}$). Transformations leading to the compounds 27 and 29 ($G_1=NR^3$, $NR^3CR^{3a}R^{3b}$, O, or $OCR^{3a}R^{3b}$) and 24, 27, and 29 ($G_1= CR^{3a}R^{3b}$) are done according to Scheme 1 and methods known to those familiar with the art.

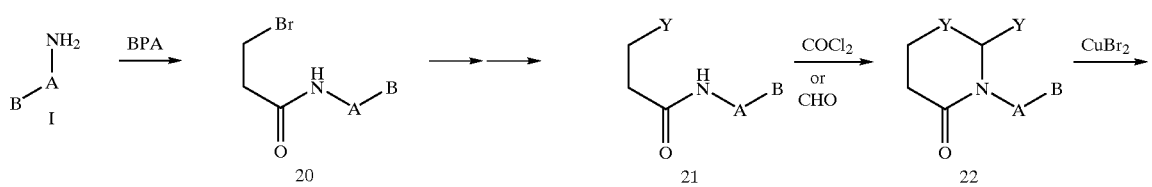

-continued

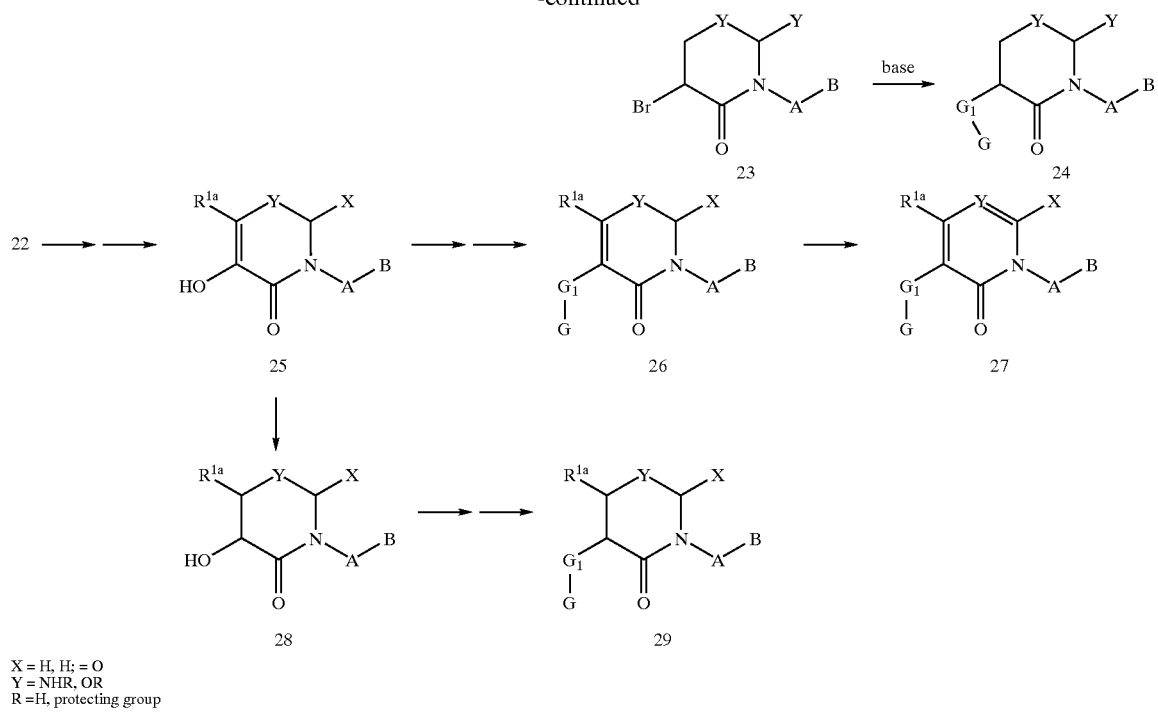

X = H, H; = O
Y = NHR, OR
R = H, protecting group

Compounds of formula 33 and 34 can be prepared as shown in Scheme 4. Compound 30 could be prepared via Suzuki reaction of 3-(4-bromophenyl)-2-propanone and an appropriate boronic acid. Treatment of 30 with base like LDA in an ethereal solvent and 1,3 dibromopropane (DBP) leads to 31. Reaction with NBS in $CCl_4$ following the procedure by Shimazaki et. al. (*Synthesis* 1990, 677) affords bromide 32. Displacement of the bromide in the presence of a mild base via SN2 reaction leads to compound 33 ($G_1$= $NR^3$, $NR^3CR^{3a}R^{3b}$, O, or $OCR^{3a}R^{3b}$). Synthesis of 34 ($Gb=CR^{3a}R^{3b}$), could be accomplished following the sequence of reactions outlined in Scheme 1.

Scheme 4

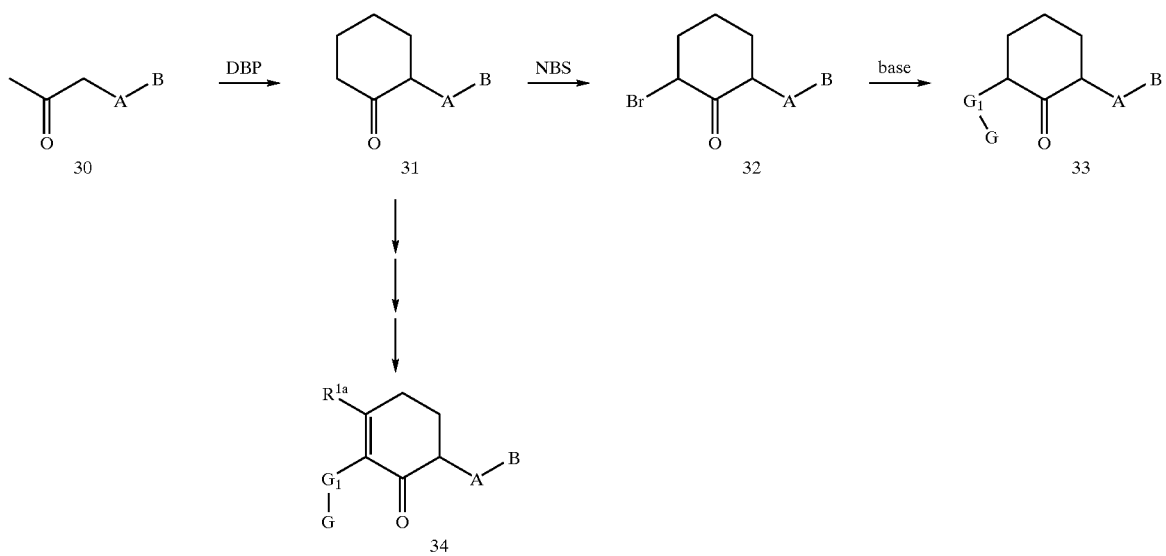

Synthesis of compounds 38 and 40 follows the protocol shown in Scheme 5. Reacting an appropriately substituted commercially available 35 (X=O, tetrahydro-4H-pyranone and X=NZ, 4-piperidone derivative) in DMSO with KOtBu (see Scamehorn et. al.; *J. Org. Chem.* 1984, 4881) affords 36. The further transformations leading to 38 and 40 could proceed according to the chemistry outlined in Schemes 4 and 1.

Scheme 5

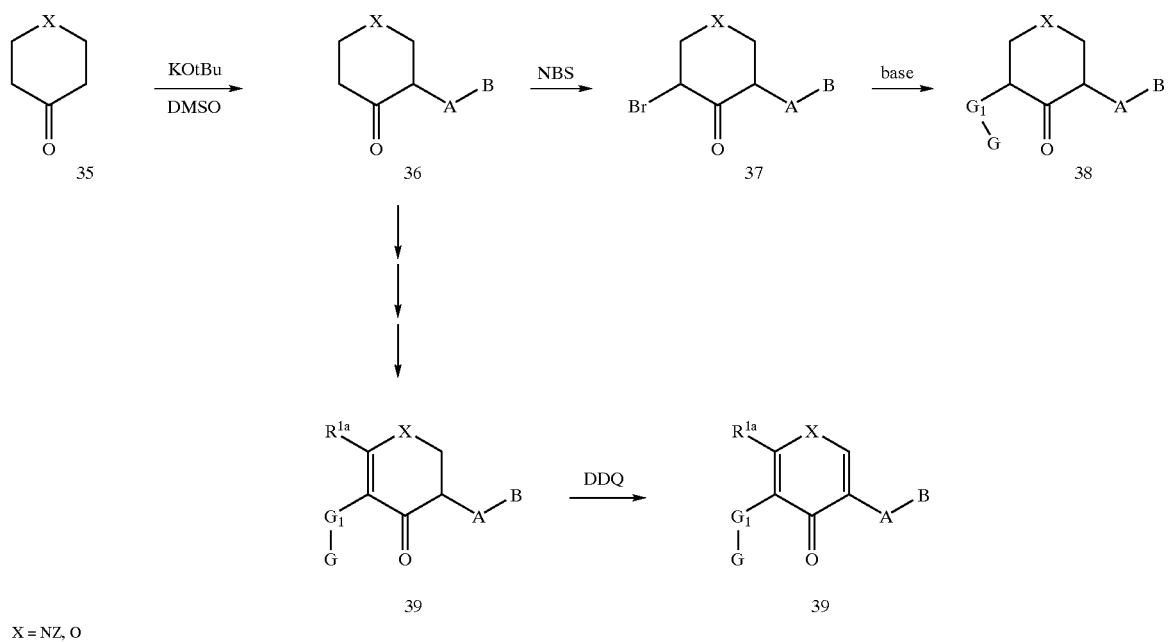

X = NZ, O

In Scheme 6 an appropriately substituted starting material 48 could be converted to 49 following the procedure of Scamehorn et. al. (*J. Org. Chem.* 1984, 4881). The synthesis of the desired compounds 51 and 52 follows the procedures outlined in Schemes 4 and 1.

Synthesis of compounds described in Scheme 7 could be accomplished by reacting the hydrazine 53 (prepared from the corresponding aniline by diazotization, followed by reduction in acidic media) with 4-bromobutanoic acid chloride (BBA) in solvents like THF, EtOAc, or $CH_2Cl_2$ to afford

Scheme 6

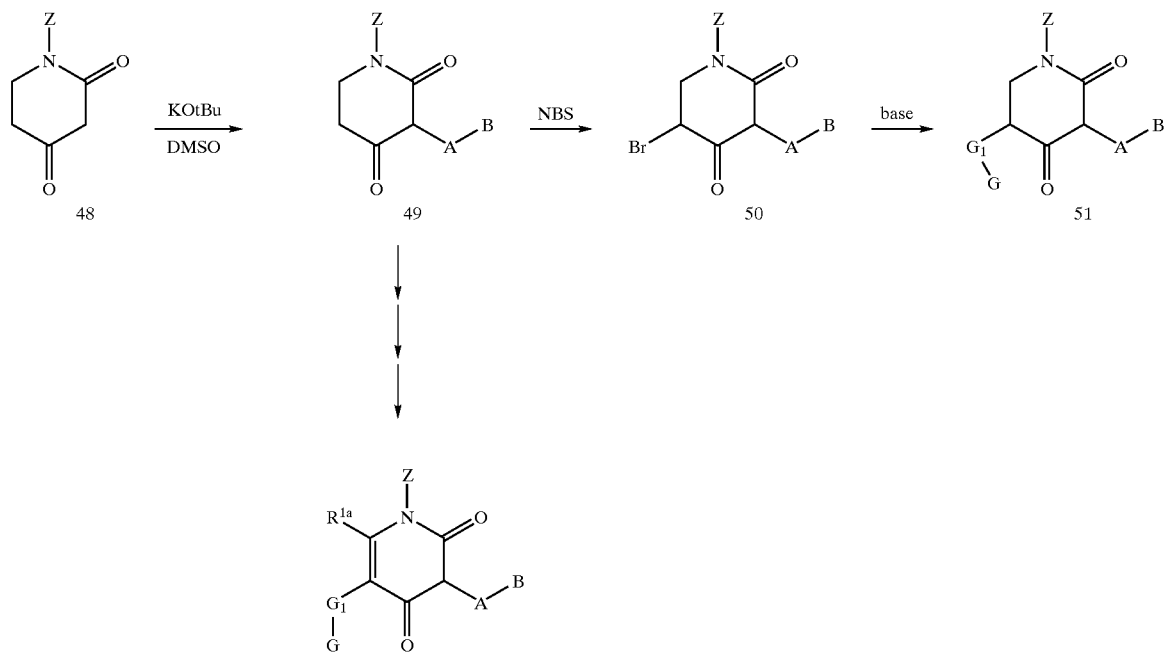

55. The further transformations leading to 57 and 59 proceed according to the chemistry outlined in Schemes 4 and 1.

Scheme 7

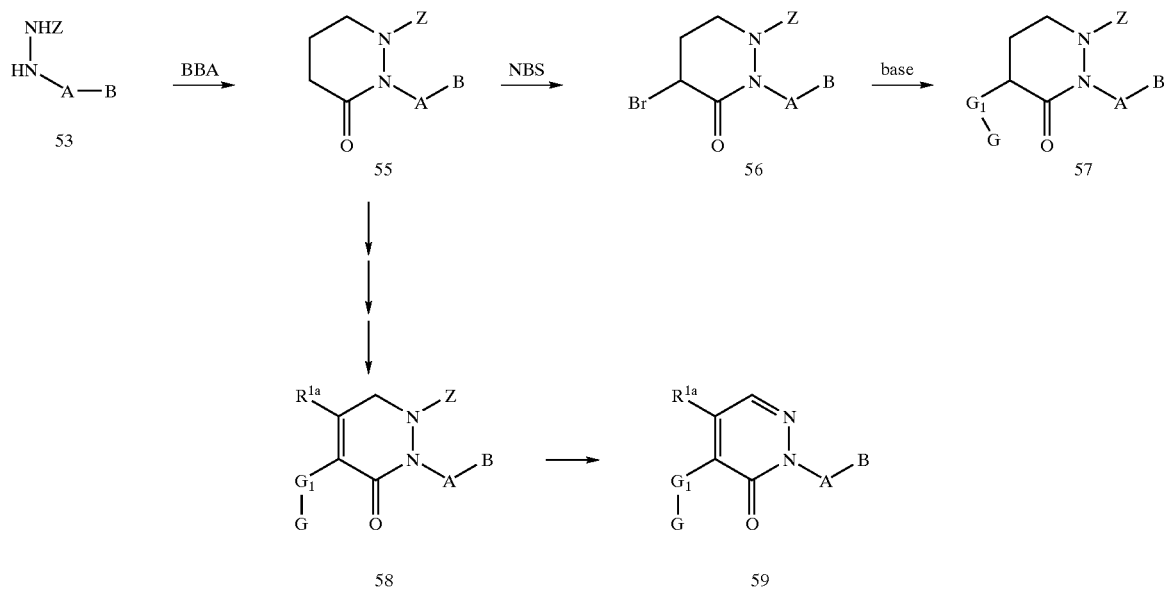

Preparation of the compounds in Scheme 8 can proceed by reacting hydrazine 59 with succinic anhydride in acetic acid following the procedure by Bourel et. al. (*Tet. Lett.* 1996, 4145) to afford compound 60. The further transformations leading to 62 and 63 proceed according to the chemistry outlined in Schemes 4 and 1.

Scheme 8

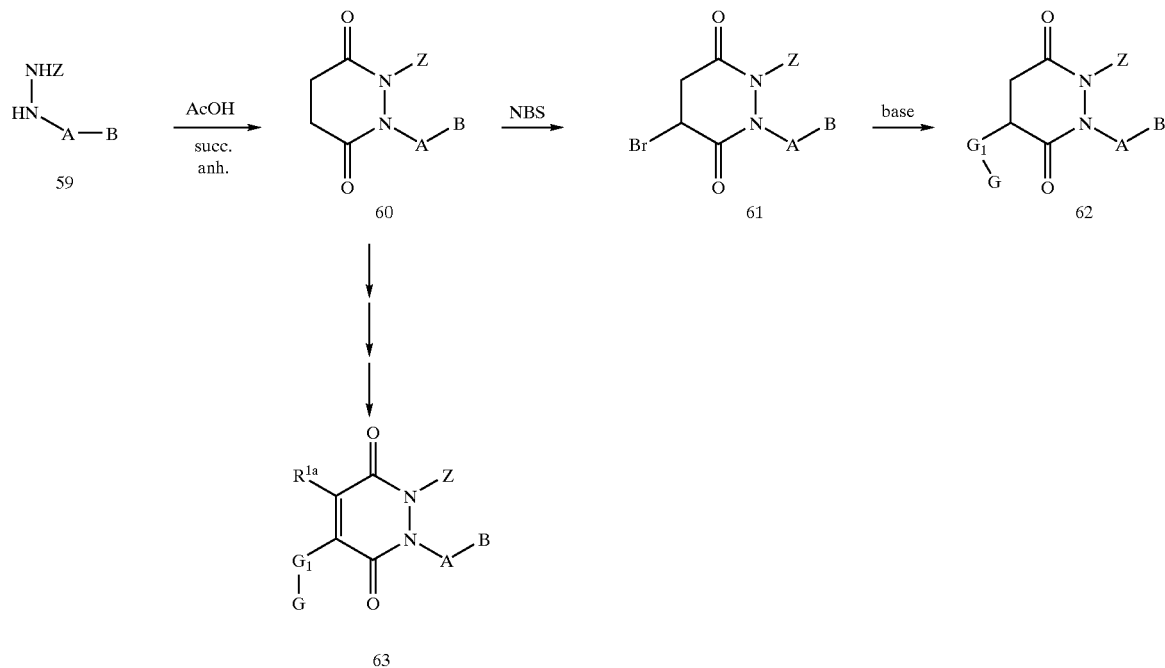

Compounds 66, 67, and 68 in Scheme 9 could be obtained following the procedures outlined in Scheme 1.

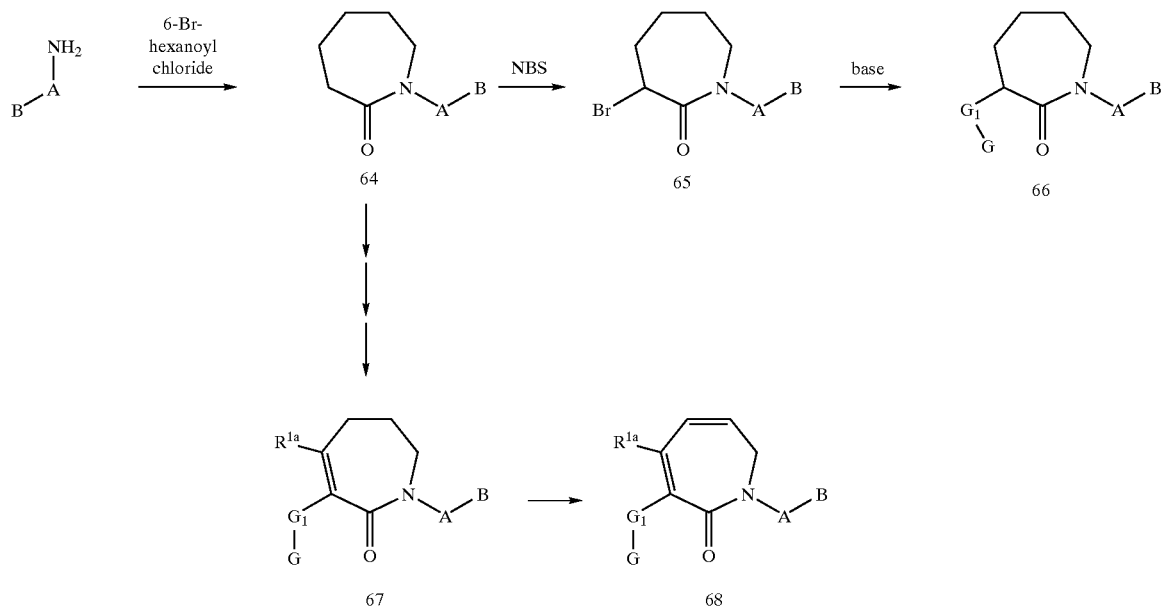

Scheme 9

Alternately, compounds of the invention wherein the core ring M is a caprolactam and the $G_1$ group is —$SO_2NR^3$-can be prepared from α-t-butoxycarbonylamino-ε-caprolactam 64a as outlined in Scheme 9a. Arylation of 64a with 4-bromoiodobenzene under the conditions described by Yin and Buchwald (*Org. Letters* 2000, 2, 1101) provides the 1-(4-bromophenyl) lactam intermediate 65a. Deprotection and treatment with an appropriately substituted sulfonylchloride provides the corresponding sulfonamide 65b. Introduction of the B substituent and optional alkylation as described above provides the targets 66a. Alternately, the B group can be introduced prior to the deprotection and sulfonylation step. The corresponding amide analogs ($G_1$=—$CONR^3$—) can be prepared in similar fashion by substitution of a suitable acylchloride for the sulfonylchloride in Scheme 9a. Compounds with this core ring where $G_1$ is NH are obtained in similar fashion by direct arylation of the amine obtained from deprotection of 65a, either before or after the introduction of the B substituent, using one of several methods known to one skilled in the art of organic synthesis.

Scheme 9a

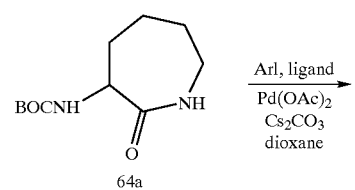

64a

-continued

Compounds of formula 69 (X=OH) can be prepared by reacting an appropriately substitued amine with 3-hydroxypropionic acid, wherein the hydroxyl group can be optionally protected and then deprotected after coupling, in solvents like THF or DMF in a presence of diisopropyl ethyl amine and a coupling reagent such as DCC. Alternately, compounds of formula 69 (X=NHZ) could be prepared by reaction of 3-bromo propionic acid with an appropriately substituted amine ($H_2N$-A-B) in the presence of a peptide bond forming reagent such as TBTU or other methods known in the art followed by displacement of the bromide with an amine of formula $ZNH_2$. Reaction of either of these intermediates with dibromoethane in a suitable solvent such as THF or methylene chloride produces 70 (X=O or NZ). The synthesis of the desired compounds 72 and 73 can be completed following the procedures described above or by other methods known to one skilled in the art of organic synthesis.

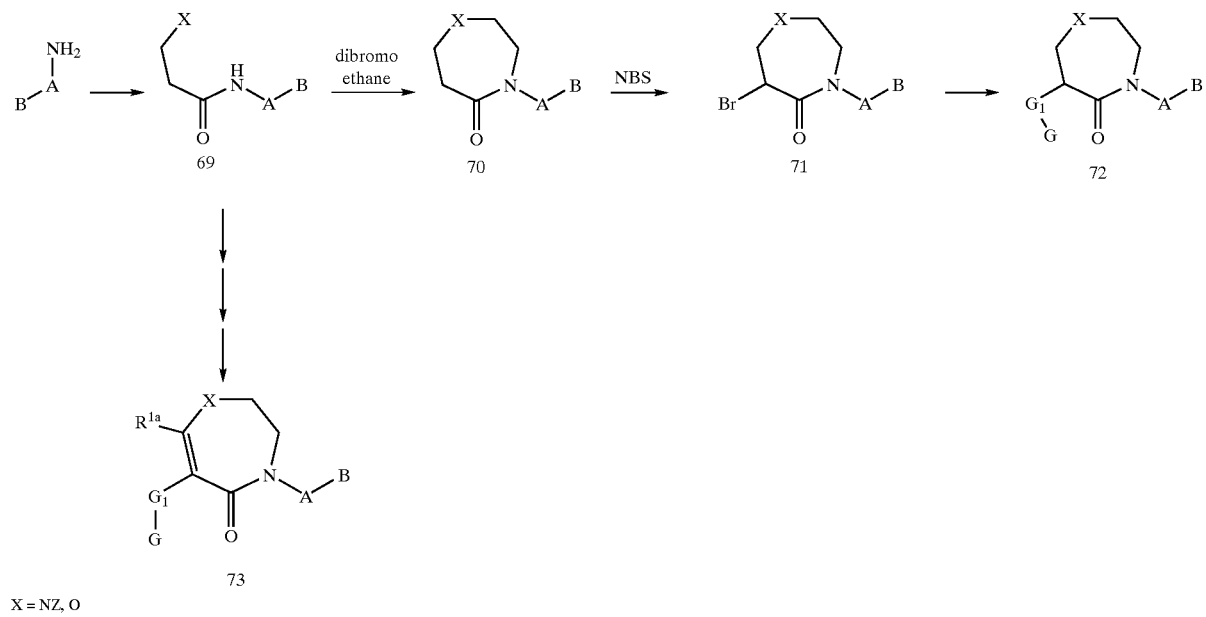

Compounds shown in Scheme 11 could be prepared by treatment of 69 (X=NHZ) (see Scheme 10) with NBS in carbon tetrachloride (see Scheme 4) to give bromide 75, that could be reacted with bromoacetyl bromide in an appropriate solvent under mild basic conditions to afford 76 and its regioisomer. Compounds 77, 77a, 78, and 78a could be prepared following the procedures outlined above followed by separation of regioisomers by suitable chromatographic methods.

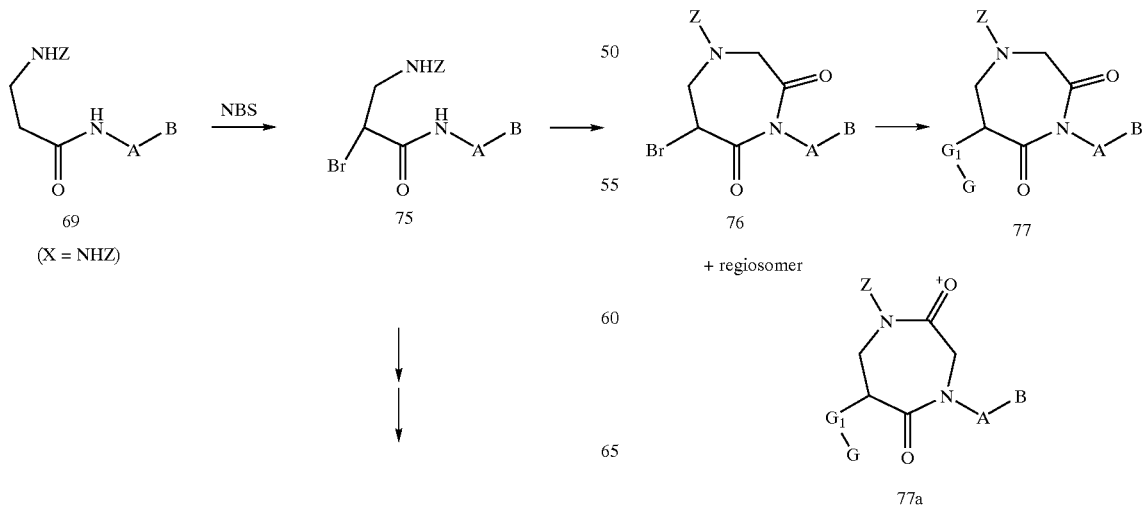

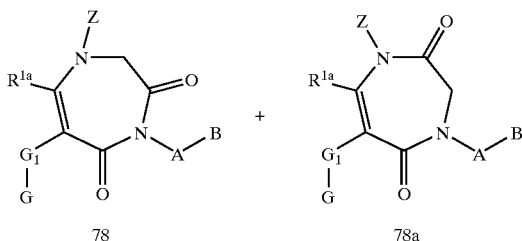

Synthesis of the compounds 82 and 84 could proceed according to Scheme 12. Compound 69 (X=Br) could be converted to 79 by treatment with an appropriately substituted thiol, pretreated with a mild base, in solvents like THF, methylene chloride, ethyl acetate or benzene. Treatment of 79 with 1,2 dibromoethane in the appropriate solvent affords 80. Further transformations are conducted according to Schemes 1 and 4 and are followed by MCPBA oxidations to the target sulfones.

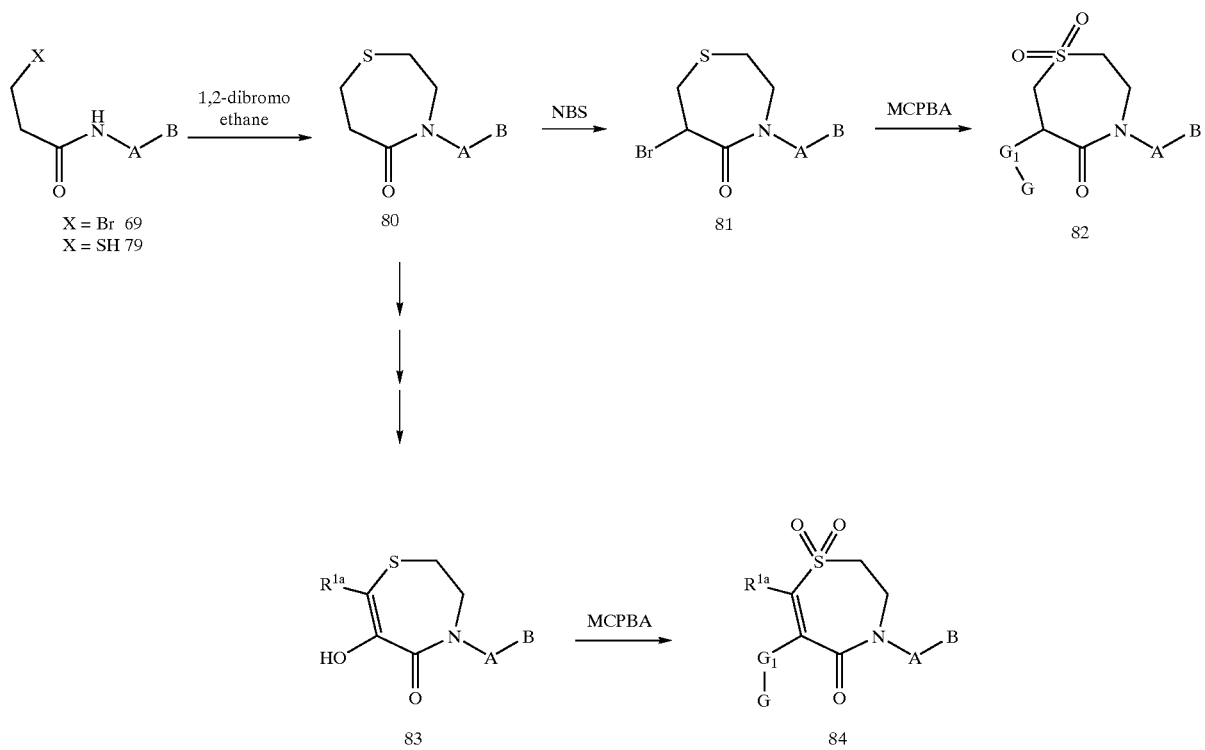

As shown in Scheme 13, synthesis of 86 could be accomplished from compounds of formula 85 via Suzuki or other palladium mediated reactions known to those familiar with the art. (For preparation of 85, see Wally et. al.; *J. Prakt. Chem.* 1994, 86). Further transformations leading to the final compounds 88 and 89 could proceed as outlined in Schemes 1 and 4.

Scheme 13
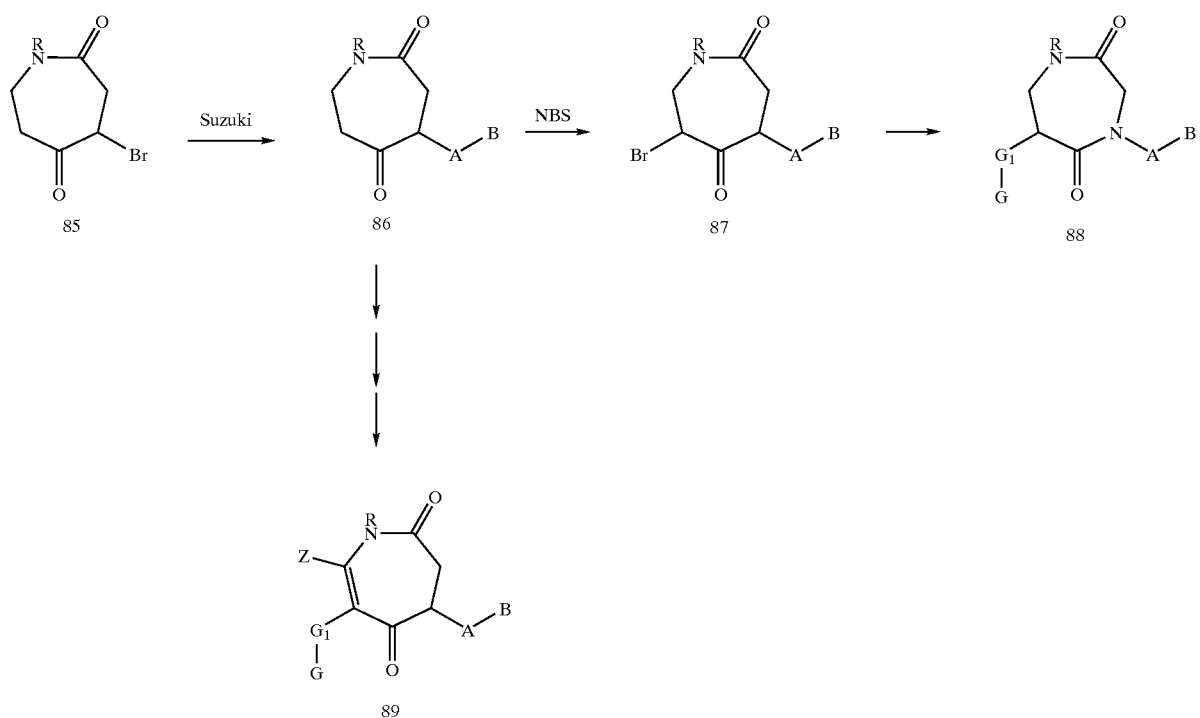
Preparation of compounds in Scheme 14 can proceed via compound 90 that is prepared according to the transformations outlined in Scheme 10. Compound 90 is treated with phosgene in toluene to provide 91, that is then converted to 93 and 95 following the syntheses in Scheme 1 and 14.
Scheme 14
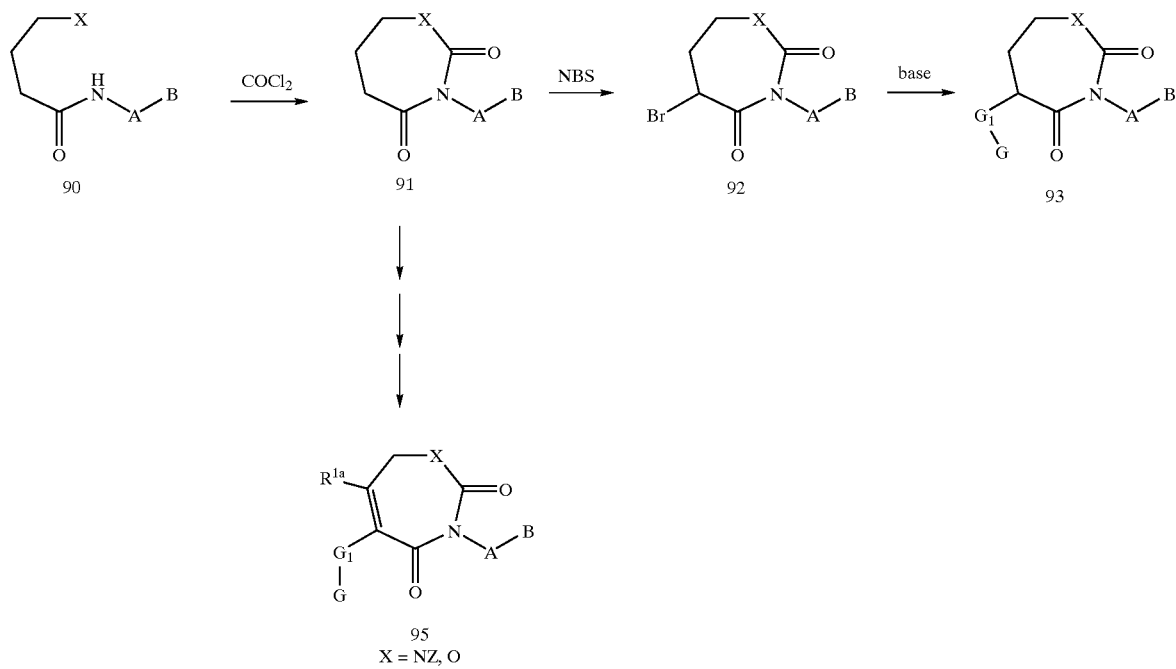

Compounds 98 and 99 could be prepared according to the methods outlined in Scheme 15.

Scheme 15

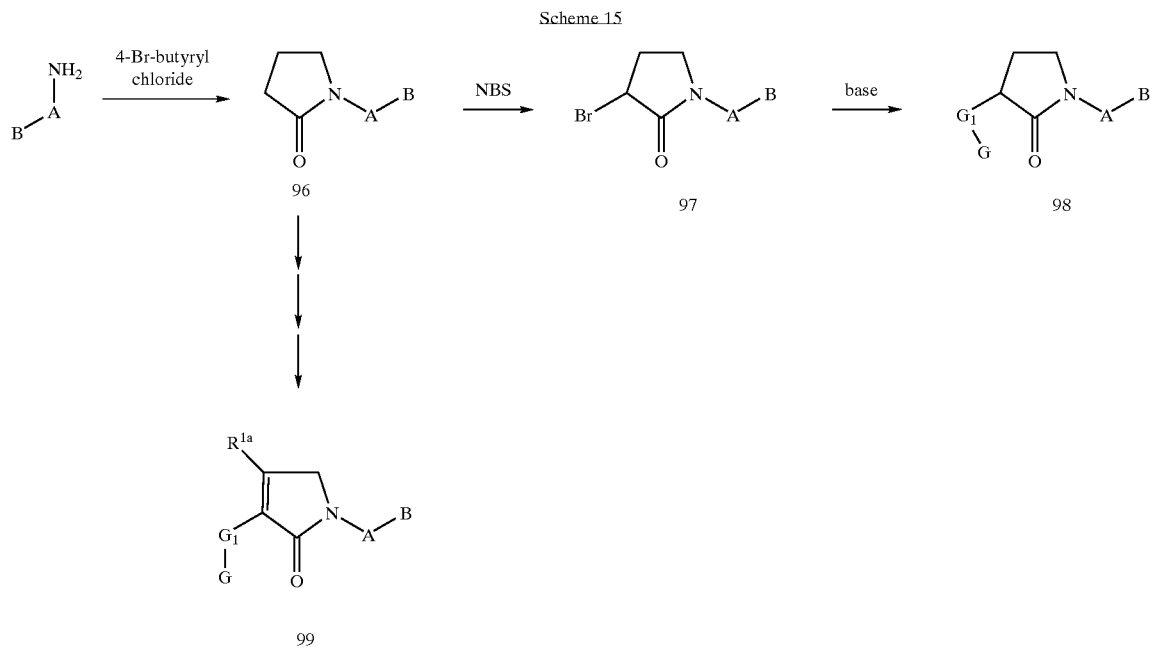

Synthesis of compound 100 from the amine shown could be accomplished by treatment of the amine with succinic anhydride in a presence of the acetic acid. Bromination of 100 with NBS in carbon tetrachloride affords 101. Further transformations leading to the compounds of interest 102 and 103 could be done as described in Scheme 1.

Scheme 16

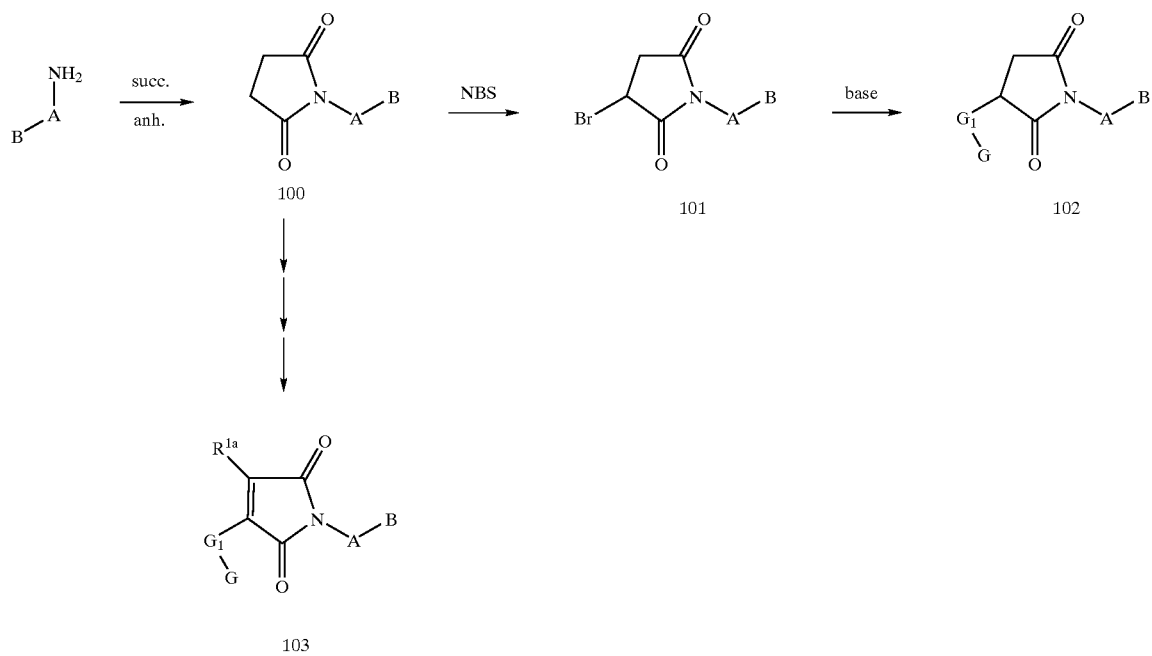

Synthesis of compounds in Scheme 17 proceeds according to the methods described in Scheme 7.

Scheme 17

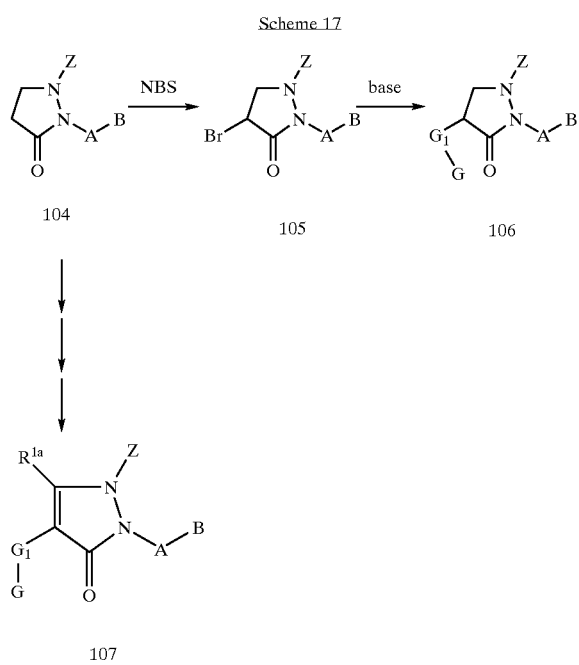

Synthesis of compounds in Scheme 18 proceeds according to the methods described in Scheme 4.

Scheme 18

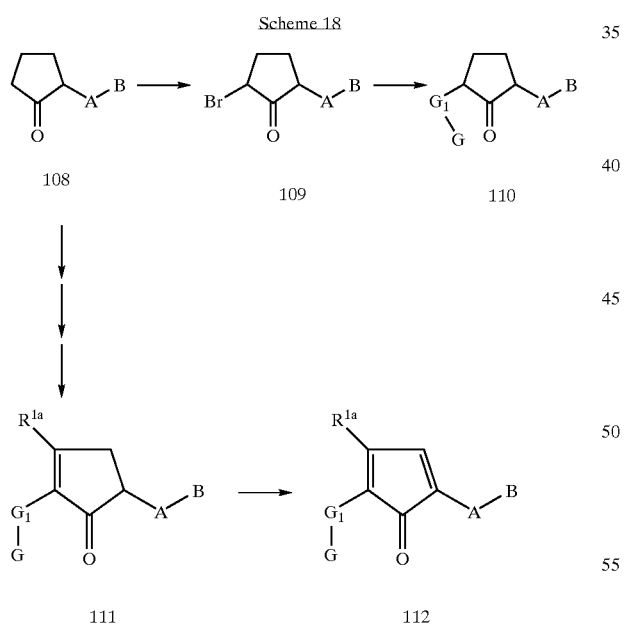

Scheme 19

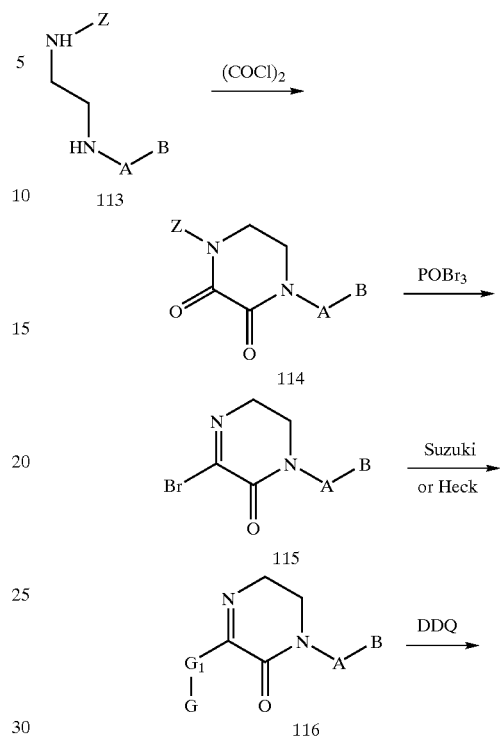

Preparation of the compounds 116 and 117 could be accomplished as outlined in Scheme 19. Closure of an amine 113 to the intermediate 114 could be affected on reaction with oxalyl chloride in a suitable solvent. Treatment with POBr$_3$ affords 115. Pd-mediated coupling via Suzuki or Heck reaction conditions affords 116, that upon treatment with DDQ could be converted to 117.

As shown in Scheme 20, 118 could be prepared from 113 on treatment with bromoacetyl chloride in a suitable solvent such as THF. The synthesis of 120 could proceed according to the synthesis shown in Scheme 1.

Scheme 20

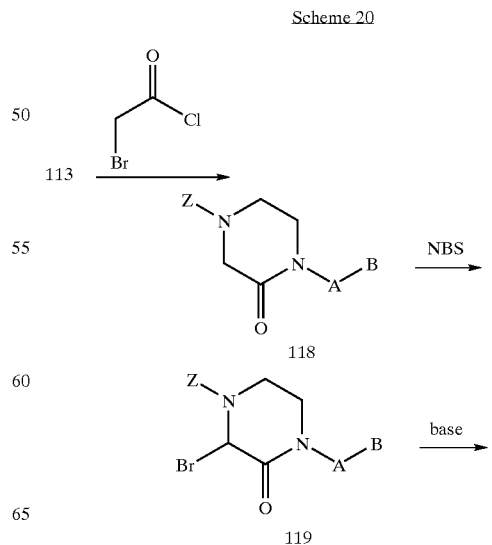

-continued

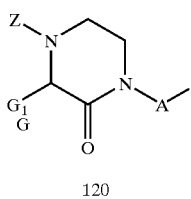

120

Compounds of formula 120 wherein $G_1$ is connected to a central piperazinone ring via a nitrogen may also be prepared as shown in Scheme 20a from commercially available 4-benzyloxycarbonylpiperazin-2-one (120a). Palladium-catalyzed coupling of 120a with p-bromoiodobenzene using methods known in the art provides intermediate 120b. Treatment of 120b with potassium bis(trimethylsilyl)amide followed by trisyl azide and acetic acid provides an azide intermediate 120c which can be selectively reduced to the desired amine 120d with tin dichloride. Sulfonylation, acylation or arylation of 120d followed by introduction of substituent B and final manipulations to introduce the desired functionality as described previously provides the compounds of the invention.

Cyclic ureas of type 122 could be prepared as outlined in Scheme 21. An appropriately substituted amine is reacted with an isocyanate derivative to afford urea 121. Cyclization of 121 to 122 can be carried out by treatment with a dibromo compound according to the methods familiar to those skilled in the art of organic synthesis.

Scheme 21

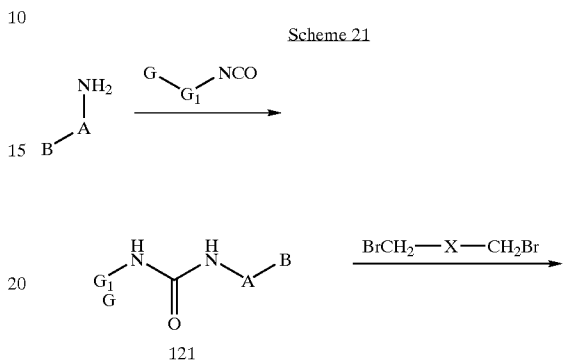

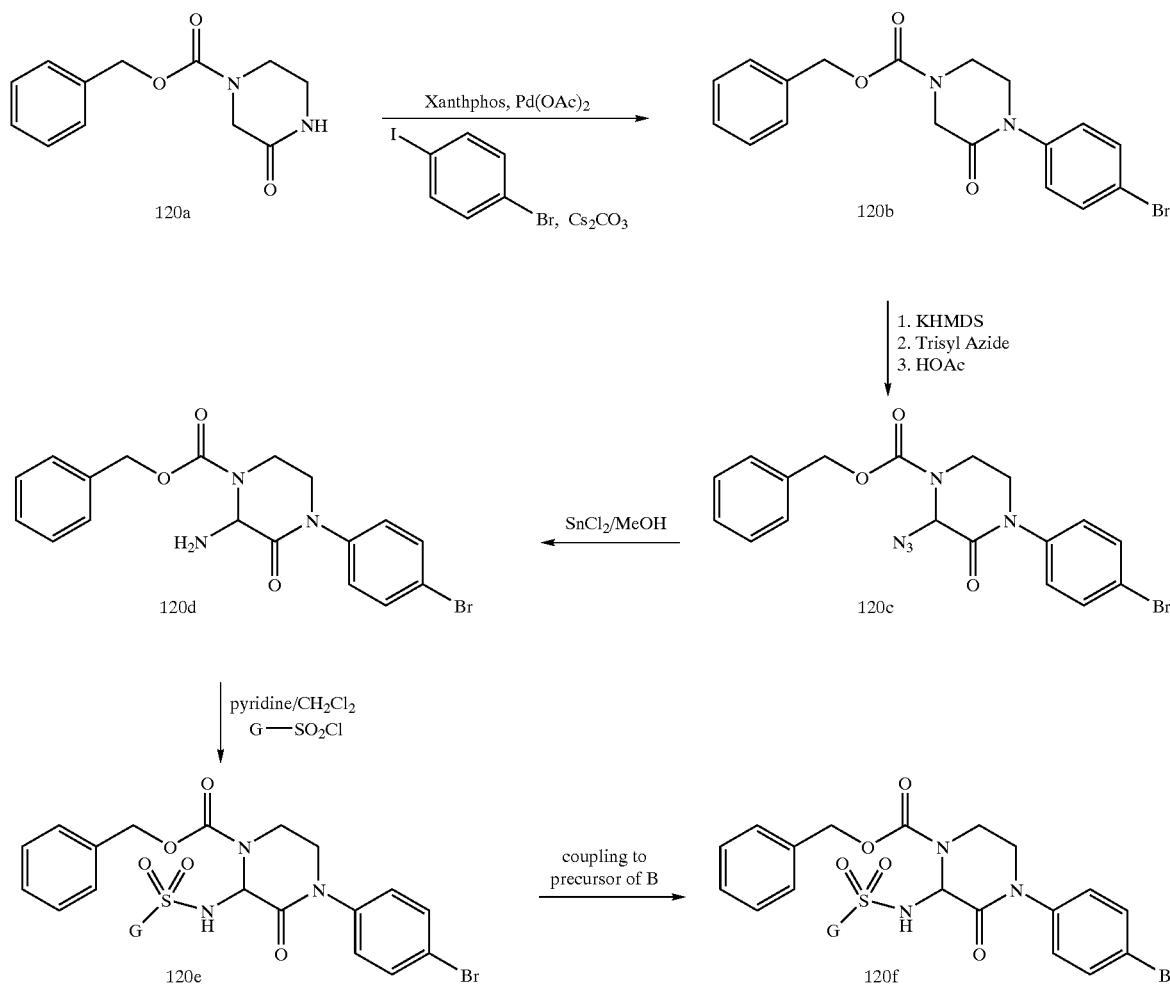

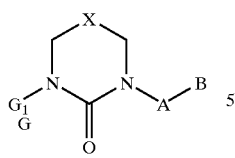

122
X = CH$_2$, (CH$_2$)$_2$, OCH$_2$,
CH$_2$O, NHCH$_2$, CH$_2$NH

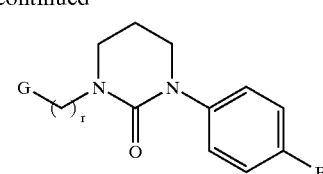

122a

Alternately, cyclic ureas of formula 122a can be prepared as shown in Scheme 21a wherein an isocyanate bearing an appropriately substitued A moiety, for example, 4-bromophenylisocyanate, is reacted with 3-bromopropylamine in the presence of a base such as triethylamine. Suitable solvents for this transformation include methylene chloride or tetrahydrofuran. The resulting urea intermediate 123 can be cyclized by treatment with a base, for example sodium hydroxide in a solvent such as benzene at room temperature or above to provide cyclic urea 124. Alkylation of the unsubstituted urea nitrogen of 124 with an appropriately substituted alkyl halide can be accomplished by treatment of 124 with a strong base such as sodium hydride in a polar solvent such as DMF. Finally, the B group may be introduced onto intermediate 125 by any of the methods already described or known in the art. Subsequent manipulation of the functional groups on the B and G groups provide cyclic urea compounds 122a of this invention.

Compounds of the invention wherein the central ring M is a tetrahydroquinolinone ring system can be prepared as shown in Scheme 22. Addition of an appropriately substituted amine to commercially available isochromanone in the presence of trimethylaluminum affords hydroxyamide 123. Conversion of the hydroxy moiety to the corresponding bromide can be achieved by treatment of 123 with phosphorous tribromide in a suitable solvent such as methylene chloride to give compounds of formula 124. Treatment of 124 with a suitable base, for example, sodium hydride, provides the desired cyclized intermediates 125. The azide moiety can be introduced by treating 125 with a strong base, such as lithium hexamethyldisilazide, and quenching the resulting carbanion with trisyl azide followed by addition of acetic acid. Azide 126 can be reduced to the corresponding amine 127 with tin dichloride. Further elaboration of 127 to introduce the G substituent with or with an additional linking atom can be accomplished by the methods described above or by other methods known to one skilled in the art of organic synthesis to give compounds such as 128, 129 and 130.

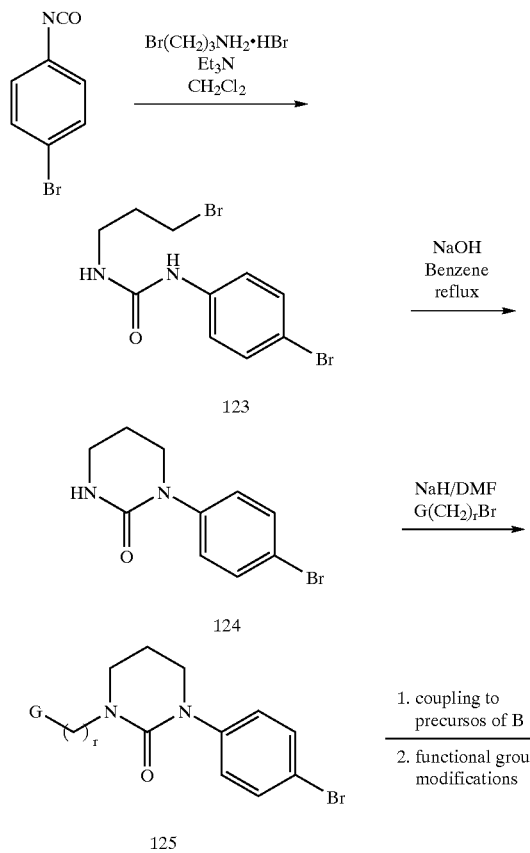

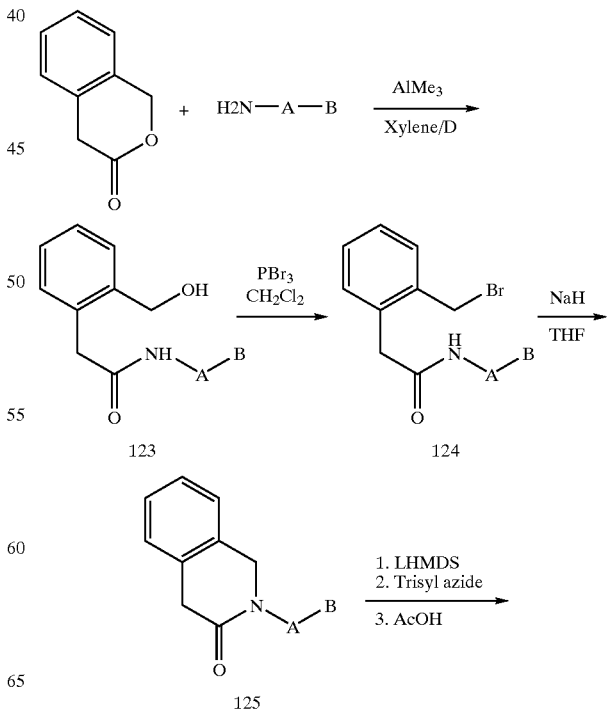

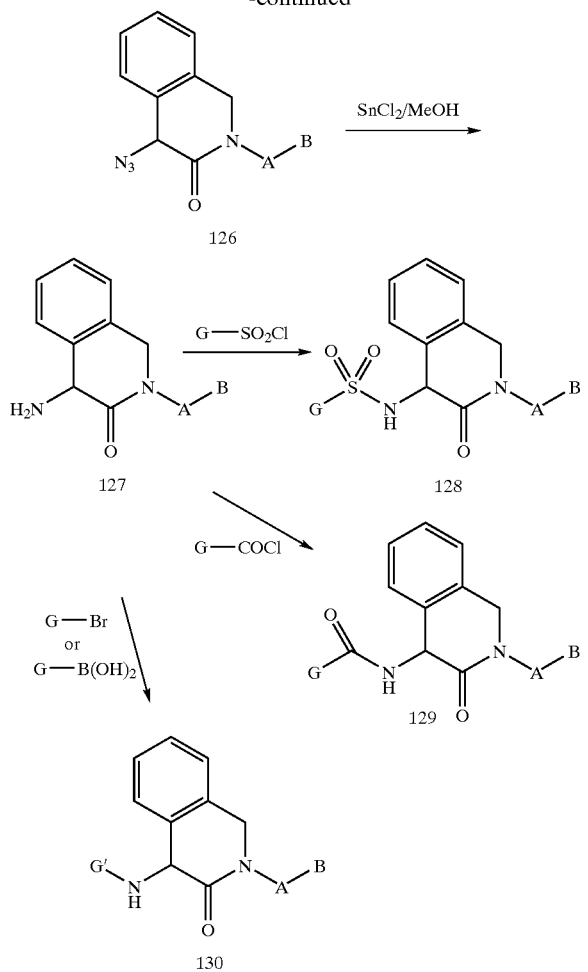

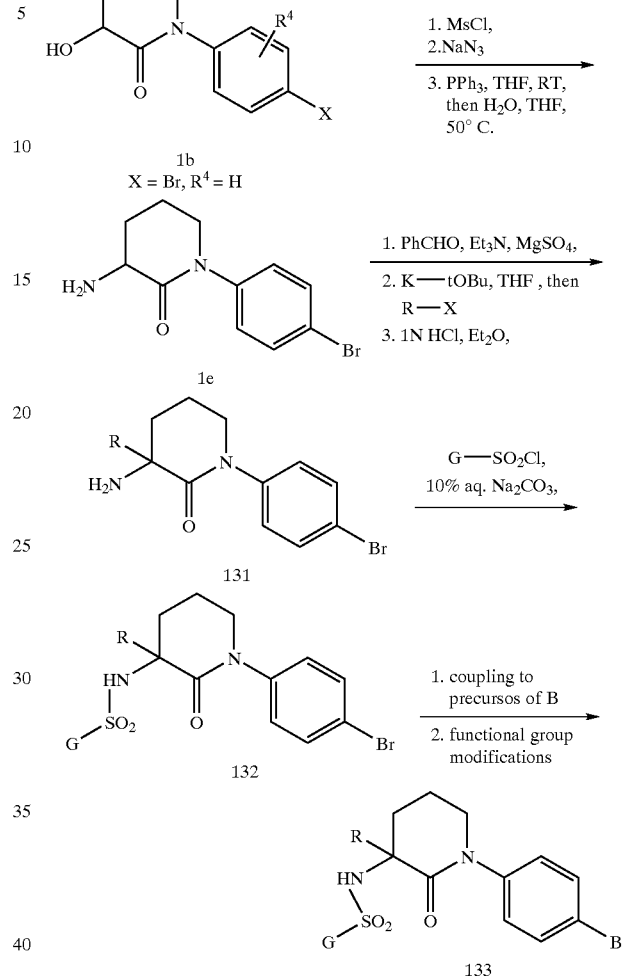

Scheme 23

Compounds of this invention wherein ring M is a 3,3-disubstituted 2-oxo-piperidine system can be prepared as shown in Scheme 23 starting from 1-bromophenyl-3-hydroxy-2-oxopiperidine, 1b. The hydroxyl group can be converted to an amino group via the intermediate azide either through the bromide as described above or alternately by treatment of the alcohol with methanesulfonyl chloride to give a mesylate intermediate which is displaced with azide. Reduction of the azide may be accomplished by any of numerous methods known to one skilled in the art to provide amine 1e. Protection of the amino group as its Schiff base can be achieved by treatment with benzaldehyde in the presence of a suitable base such as triethylamine and a reagent to remove water such as magnesium sulfate. Subsequent deprotonation with a base, such as potassium t-butoxide, treatment of the anion with an alkyl halide and deprotection of the amine provides compounds of formula 131. Reaction of 131 with a suitably substituted sulfonyl chloride provides compounds 132 which can in turn be converted to compounds of the invention of formula 133 by the introduction of the B substituent and modification of functional groups on G and B, if needed, using methods described above or known in the literature. Alternately, the B substituent or alternate A-B groups may be introduced at an earlier point in the synthesis to provide an intermediate $H_2N$-A-B which can be substituted for compound 1b in Scheme 23 to provide additional target compounds. Also as previously described, intermediate 131 can be acylated, alkylated or arylated in place of sulfonylation to provide amide, alkyl amine and aryl amine analogs of 133.

The A-B moieties can be prepared by methods known to those of skill in the art. The following publications, the contents of which are incorporated herein by reference, describe and exemplify means of preparing A-B moieties: WO 97/23212, WO97/30971, WO97/38984, WO98/06694, WO98/01428, WO98/28269, WO98/28282, WO98/57934, WO98/57937, WO99/32454, WO99/50255, WO00/39108, WO00/39131.

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatroban as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine and clopidogrel, including pharmaceutically acceptable salts or prodrugs thereof. Ticlopidine and clopidogrel are also preferred compounds since they are known to be gentle on the gastro-intestinal tract in use. Still other suitable platelet inhibitory agents include IIb/IIIa antagonists, including tirofiban, eptifibatide, and abciximab, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics (or fibrinolytic) agents (or thrombolytics or fibrinolytics), as used herein, denotes agents that lyse blood clots (thrombi). Such agents include tissue plasminogen activator and modified forms thereof, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice. They can also be administered with other therapeutic agents known to those of skill in the art.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Description of appropriate means of adminstration as well as dosages and formulations can be found in WO 97/23212, WO97/30971, WO97/38984, WO98/06694, WO98/01428, WO98/28269, and WO98/28282, the contents of which are incorporated herein by reference.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers)

suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are given for illustration of the invention and are not intended to be limiting thereof.

EXAMPLES

Example 1

3-({1-[3-fluoro-2'-(methylsulfonyl)-[1,1']-biphenyl-4-yl]-2-oxo-3-piperidinyl}oxy)benzonitrile Part A: 3-Bromo-1-(4-bromo-2-fluorophenyl)-2-piperidinone: A solution of 1-(4-bromo-2-fluorophenyl)-3-hydroxy-2-piperidinone (1 g, 3.5 mmol), prepared according to the procedure in WO00/39131 in acetonitrile (20 mL), was treated with carbon tetrabromide (2.3 g, 7 mmol) and triphenylphosphine (1.8 g, 7 mmol). The reaction was stirred at ambient temperature over a period of 3 h, taken up in water, and extracted with ethyl acetate (3×). Ethyl acetate extracts were dried over sodium sulfate and concentrated. The crude residue was purified by flash chromatography (hexane/ethyl acetate, 1:3) to afford the bromide (0.8 g, 67%). LRMS (ES+): 352.1 (M+H)$^+$.

Part B. 3-{[1-(4-Bromo-2-fluorophenyl)-2-oxo-3-piperidinyl]oxy}benzonitrile: A solution of 3-cyanophenol (0.53 g, 4.5 mmol) in tetrahydrofuran (15 mL) was cooled down and treated with sodium hydride (0.18 g, 4.5 mmol) and the compound of Ex. 1, Part A (1.6 g, 4.5 mmol). The reaction was stirred at ambient temperature over a period of 4 h, taken up in water and extracted with ethyl acetate (3×). Ethyl acetate extracts were dried over sodium sulfate and concentrated. The crude residue was, purified by flash chromatography (hexane/ethyl acetate, 1:3) to afford the product (1 g, 59%). LRMS (ES+): 390.3 (M+H)$^+$.

Part C. 3-({1-[3-fluoro-2'-(methylsulfonyl)-[1,1']-biphenyl-4-yl]-2-oxo-3-piperidinyl}oxy)benzonitrile: A solution of the compound of Ex. 1, Part B (0.5 g, 1.3 mmol) and 2-thioanisole boronic acid (0.21 g, 1.3 mmol) in a mixture of tetrahydrofuran (20 mL) and aqueous sodium carbonate (10 mL) was deoxygenated by a rapid stream of nitrogen applied to the system over a period of 20 min, then treated with Pd(0). The reaction was refluxed over a period of 18 h, cooled down, filtered through Celite®, and washed with THF (20 mL). The filtrate was evaporated to dryness, taken up in water, and extracted with ethyl acetate (3×). The ethyl acetate extracts were dried over sodium sulfate and concentrated. The crude residue was purified by flash chromatography (hexane/ethyl acetate, 1:3) to afford coupling product (0.5 g, 90%) which was dissolved in methylene chloride and treated with MCPBA (0.4 g, 2 mmol). The reaction mixture was stirred for 18 h, concentrated and purified through a plug of silica gel (hexane/ethyl acetate, 1:1) to afford the title compound (0.5 g, 93%). LRMS (ES+): 465.5 (M+H)$^+$.

Example 2

({1-[3-fluoro-2'-(methylsulfonyl)-[1,1']-biphenyl-4-yl]-2-oxo-3-piperidinyl}oxy)benzene-carboximidamide A solution of the compound of Ex. 1 (0.1 g, 0.22 mmol) in anhydrous EtOH (20 mL) was bubbled with HCl gas at 0° C. for 15 min. The resulting solution was stirred overnight at room temperature and concentrated in vacuo. The solid was redissolved in anhydrous EtOH (20 mL) and ammonium carbonate (2 g, 2.5 mmol) was added followed by 1 mL pyridine. The resulting solution was stirred overnight at room temperature. The volatile was removed in vacuo and the residue purified by reverse phase HPLC to give the target compound. LRMS (ES+): 482.3 (M+H)$^+$.

Example 3

4-({1-[3-fluoro-2'-(methylsulfonyl)-[1,1']-biphenyl-4-yl]-2-oxo-3-piperidinyl}oxy)benzene-carboximidamide This compound was prepared from 4-cyanophenol and the compound of Ex. 1, Part A following the procedures of Ex. 1, Part B and C, and Ex. 2. LRMS (ES+): 482.5 (M+H)$^+$.

Example 4

3-({1-[2-[(dimethylamino)methyl]-3-fluoro-[1,1']-biphenyl-4-yl]-2-oxo-3-piperidinyl}oxy)benzonitrile A mixture of the compound of Ex. 1, Part B (0.5 g, 1.3 mmol) and 2-formylbenzene boronic acid (0.2 g, 1.3 mmol)

was diluted with THF (20 mL) and 2M sodium carbonate (10 mL), then deoxygenated by a rapid stream of nitrogen applied to the system over a period of 20 min, followed by treatment with Pd(0). The reaction was refluxed over a period of 18 h, cooled down, filtered through Celite®, and washed with THF (20 mL). The filtrate was evaporated to dryness, taken up in water and extracted with ethyl acetate (3×). The ethyl acetate extracts were dried over sodium sulfate and concentrated. The crude residue (0.6 g) was treated with sodium borohydride (0.6 g, 2.8 mmol) and dimethyl amine (1.5 mL, 2M solution in THF). The reaction mixture was stirred for 18 h, diluted with ice water, and extracted with ethyl acetate. Ethyl acetate extracts were dried over sodium sulfate and concentrated. The crude residue was purified by flash chromatography (hexane/ethyl acetate, 1:3) to afford the desired product (0.6 g, 75% over 2 steps). LRMS (ES+): 427.2 (M+H)$^+$.

Example 5

3-({1-[2-[(dimethylamino)methyl]-3-fluoro-[1,1']-biphenyl-4-yl]-2-oxo-3-piperidinyl}oxy)benzenecarboximidamide This compound was prepared from the compound of Ex. 4 by a Pinner reaction according to the procedure described in Example 2. LRMS (ES+): 461.55 (M+H)$^+$.

Example 6

3-({1-[2'-[(dimethylamino)methyl]-[1,1']-biphenyl-4-yl]-2-oxo-3-piperidinyl}oxy)benzenecarboximidamide This compound was prepared from 1-(4-bromophenyl)-3-hydroxy-2-piperidinone following the procedures described in Ex. 1, Part A and B, Ex. 4 and Ex. 5 above. LRMS (ES+): 442.5 (M+H)$^+$.

Example 7

3-({1-[2-[(dimethylamino)methyl]-3-fluoro-[1,1']-biphenyl-4-yl]-2-oxo-3-piperidinyl}amino)benzenecarboximidamide This compound was prepared from 3-aminobenzonitrile and the compound of Ex. 1, Part A according to the procedures described in Ex. 1, Part B and Ex.4 and Ex. 5 above. LRMS (ES+): 460.6 (M+H)$^+$.

Example 8

2,4-dichloro-N-{1-[3-fluoro-2'-(methylsulfonyl)-[1,1']-biphenyl-4-yl]-2-oxo-3-piperidinyl}benzamide Part A. 1-[3-fluoro-2'-(methylsulfanyl)-[1,1']-biphenyl-4-yl]-3-hydroxy-2-piperidinone: A solution of the compound of Ex 1, Part A (5.0 g, 16.3 mmol) and 2-thioanisole boronic acid (2.7 g, 16.3 mmol) in a mixture of tetrahydrofuran (50 mL) and aqueous sodium carbonate (15 mL) was deoxygenated by a rapid stream of nitrogen applied to the system over a period of 20 min., then treated with Pd(0). The reaction was refluxed over a period of 18 h, cooled down, filtered through Celite®, and washed with THF (20 mL). The filtrate evaporated to dryness, taken up in water, and extracted with ethyl acetate (3×). Ethyl acetate extracts were dried over sodium sulfate and concentrated. The crude residue was purified by flash chromatography (hexane/ethyl acetate, 1:3) to afford the product (5 g, 88). LRMS (ES+): 350.5 (M+H)$^+$.

Part B. 3-bromo-1-[3-fluoro-2'-(methylsulfonyl)-[1,1']-biphenyl-4-yl]-2-piperidinone: A solution of the compound of Ex. 8, Part A (1 g, 3.5 mmol) in methylene chloride (20 mL) was treated with PBr$_3$ (0.8 g, 3.5 mmol). The reaction was stirred at ambient temperature over a period of 3 h, taken up in water, and extracted with ethyl acetate (3×). Ethyl acetate extracts were dried over sodium sulfate and concentrated. The crude residue was purified by flash chromatography (hexane/ethyl acetate, 1:3) to afford the bromide (1 g, 50%). LRMS (ES+): 414.1 (M+H)$^+$. The product was dissolved in methylene chloride and treated with MCPBA (1.3 g, 10.5 mmol). The reaction mixture was stirred for 18 h, concentrated, and purified through a plug of silica gel (hexane/ethyl acetate, 1:1) to afford the product (1 g, 93%). LRMS (ES+): 445.5 (M+H)$^+$.

Part C. 3-amino-1-[3-fluoro-2'-(methylsulfonyl)-[1,1]-biphenyl-4-yl]-2-piperidinone: A solution of the compound of Ex. 8, Part B (1 g, 2.4 mmol) in N,N-dimethylformamide (20 mL), was treated with NaN$_3$ (0.2 g, 2.4 mmol). The reaction was stirred at ambient temperature over a period of 18 h, taken up in water, and extracted with ethyl acetate (3×). Ethyl acetate extracts were dried over sodium sulfate and concentrated. The crude residue was purified by flash chromatography (hexane/ethyl acetate, 1:3) to afford the azide, which was dissolved in ether and treated with PPh$_3$ (1.9 g, 7.2 mmol). The reaction mixture was stirred for 18 h, concentrated, and purified through a plug of silica gel (methanol/methylene chloride, 1:10) to afford the amine (0.3 g, 36%). LRMS (ES+): 349.6 (M+H)$^+$.

Part D. 2,4-dichloro-N-{1-[3-fluoro-2'-(methylsulfonyl)-[1,1']-biphenyl-4-yl]-2-oxo-3-piperidinyl}benzamide: A solution of the compound of Ex. 8, Part C (30 mg, 0.09 mmol) and 2,4-dichlorobenzoic acid (17 mg, 0.09 mmol) in N,N-dimethylformamide (5 mL), was treated with TBTU (60 mg, 0.2 mmol) and triethylamine (0.5 mL). The reaction was stirred at ambient temperature over a period of 18 h, taken up in water, and extracted with ethyl acetate (3×). Ethyl acetate extracts were dried over sodium sulfate and concentrated. The crude residue was purified by flash chromatography (methanol/methylene chloride, 1:10) to afford the title compound (20 mg, 39%). LRMS (ES+): 536.4 (M+H)$^+$.

The following amides were similarly prepared by coupling the compound of Ex. 8, Part C with the acid indicated in parentheses in the presence of TBTU and TEA using DMF as solvent.

Example 9

3-chloro-N-{1-[3-fluoro-2'-(methylsulfonyl)-[1,1']-biphenyl-4-yl]-2-oxo-3-piperidinyl}-benzamide: (3-chlorobenzoic acid) LRMS (ES+): 501.9 (M+H)$^+$.

Example 10

3,4-dichloro-N-{1-[3-fluoro-2'-(methylsulfonyl)-[1,1']-biphenyl-4-yl]-2-oxo-3-piperidinyl}-benzamide: (3,4-dichlorobenzoic acid) LRMS (ES+): 536.4 (M+H)$^+$.

Example 11

4-fluoro-N-{1-[3-fluoro-2'-(methylsulfonyl)-[1,1']-biphenyl-4-yl]-2-oxo-3-piperidinyl}-benzamide: (4-fluorobenzoic acid) LRMS (ES+): 485.4 (M+H)$^+$.

Example 12

4-chloro-N-{1-[3-fluoro-2'-(methylsulfonyl)-[1,1']-biphenyl-4-yl]-2-oxo-3-piperidinyl}-benzamide: (4-chlorobenzoic acid) LRMS (ES+): 501.9 (M+H)$^+$.

Example 12a

N-{1-[3-Fluoro-2'-(methylsulfonyl)-[1,1']-biphenyl-4-yl]-2-oxo-3-piperidinyl}-4-methoxy-benzamide: (4-methoxybenzoic acid) LRMS (ES+): 501.9 (M+H)$^+$.

Example 12b
N-{1-[3-Fluoro-2'-(methylsulfonyl)-[1,1']-biphenyl-4-yl]-2-oxo-3-piperidinyl}-3-methoxy-benzamide: (3-methoxybenzoic acid) LRMS (ES+): 501.9 (M+H)$^+$.

Example 13
2-chloro-N-{1-[3-fluoro-21-(methylsulfonyl)-[1,1]-biphenyl-4-yl]-2-oxo-3-piperidinyl}-isonicotinamide: (2-chloroisonicotinic acid) LRMS (ES+): 502.9 (M+H)$^+$.

Example 14
6-chloro-N-{1-[3-fluoro-2'-(methylsulfonyl)-[1,1']-biphenyl-4-yl]-2-oxo-3-piperidinyl}-nicotinamide: (6-chloronicotinic acid) LRMS (ES+): 502.9 (M+H)$^+$.

Example 15
N-{1-[3-fluoro-2'-(methylsulfonyl)-[1,1']-biphenyl-4-yl]-2-oxo-3-piperidinyl}-6-(1H-pyrazol-1-yl)nicotinamide: (6-(1H-pyrazol-1-yl)nicotinic acid) LRMS (ES+): 534.6 (M+H)$^+$.

In similar fashion, the following esters were prepared from the compound of Ex. 8, Part A by TBTU-mediated coupling to the acid indicated in parentheses in the presence of TEA and DMF as solvent following the procedure set out in Ex. 8, Part D. The resulting thiomethyl products were then oxidized to the corresponding methylsulfones using MPCBA in methylene chloride as described above.

Example 16
1-[3-fluoro-21-(methylsulfonyl)-[1,1']-biphenyl-4-yl]-2-oxo-3-piperidinyl}-2-chloronicotinate: (2-chloronicotinic acid) LRMS (ES+): 503.9 (M+H)$^+$.

Example 17
1-[3-fluoro-2'-(methylsulfonyl)-[1,1']-biphenyl-4-yl]-2-oxo-3-piperidinyl4-methoxybenzoate: (4-methoxybenzoic acid) LRMS (ES+): 498.5 (M+H)$^+$.

Example 18
2-({1-[3-fluoro-2'-(methylsulfonyl)-[1,1']-biphenyl-4-yl]-2-oxo-3-piperidinyl}oxy)-5-methoxybenzaldehyde The title compound was obtained from the compound of Ex. 8, Part B, 5-methoxy-2-hydroxybenzaldehyde and sodium hydride in THF as solvent according to the procedure of Ex. 1, Part B. LRMS (ES+): 498.5 (M+H)$^+$.
Similarly prepared from the indicated alcohols or amines were the following:

Example 19
3-[{5-chloro-2-pyridinyl)amino]-1-[3-fluoro-2'-(methylsulfonyl)-[1,1']-biphenyl-4-yl]-2-piperidinone: (5-chloro-2-aminopyridine) LRMS (ES+): 381.6 (M+H)$^+$.

Example 20
1-[3-fluoro-2'-(methylsulfonyl)-[1,1']-biphenyl-4-yl]-3(4-methoxyphenoxy)-2-piperidinone: (p-anisole) LRMS (ES+): 470.5 (M+H)$^+$.

Example 20a
1-[3-fluoro-2'-(methylsulfonyl)-[1,1']-biphenyl-4-yl]-3(4-methoxyanilino)-2-piperidinone: (p-methoxyaniline) LRMS (ES+): 469.3 (M+H)$^+$.

Example 21
2-({1-[3-fluoro-2'-(methylsulfonyl)-[1,1']-biphenyl-4-yl]-2-oxo-3-piperidinyl}oxy)-5-methoxybenzoate: (methyl 2-hydroxy-5-methoxybenzoate) LRMS (ES+): 528.5 (M+H)$^+$.

Example 22
3-[3-(aminomethyl)phenoxy]-1-[3-fluoro-2'-(methylsulfonyl)-[1,1']-biphenyl-4-yl]-2-piperidinone A solution of the nitrile compound of Ex. 1 in MeOH/HOAc was hydrogenated over 10% Pd/C to provide the desired benzyl amine target compound. LRMS (ES+): 469.5 (M+H)$^+$.

Example 23
3-{[2-(anilinomethyl)-4-methoxyphenyl]oxo}-1-[3-fluoro-2'-(methylsulfonyl)-[1,1']-biphenyl-4-yl]-2-piperidinone Reductive amination of the compound of Ex. 18 with aniline in the presence of sodium borohydride in methanol for 2 h provided the title compound. LRMS (ES+): 517.5 (M+H)$^+$.

Example 23a
3-{[2-(4-pyridylaminocarbonyl)-4-methoxyphenyl]oxo}-1-[3-fluoro-2'-(methylsulfonyl)-[1,1']-biphenyl-4-yl]-2-piperidinone This compound was prepared from the compound of Ex. 21 by reaction of the ester with 4-aminopyridine in the presence of trimethylaluminum to give the amide. LRMS (ESI+) 590.6 (M+H)$^+$.

Example 24
3-chloro-N-{1-[3-fluoro-2'-(methylsulfonyl)-[1,1']-biphenyl-4-yl]-2-oxo-3-piperidinyl}-N-methyl-benzamide Alkylation of the compound of Ex. 9 with methyl iodide in the presence of sodium hydride in THF provided the N-methyl amide. LRMS (ES+): 516.0 (M+H)$^+$.

Example 25
N-benzyl-4-chloro-N-{1-[3-fluoro-2'-(methylsulfonyl)-[1,1']-biphenyl-4-yl]-2-oxo-3-piperidinyl}-benzamide Similarly alkylation of the compound of Ex. 12 with benzyl bromide in the presence of sodium hydride in THF gave its N-benzyl amide analog. LRMS (ES+): 592.2 (M+H)$^+$.

The following Examples 26–30 were prepared from 3-amino-1-([3-fluoro-2'-(methylthio)-[1,1']-biphenyl-4-yl-2-piperidinone by coupling with the indicated carboxylic acid in the presence of TBTU and TEA using DMF as solvent.

Example 26
N-{1-[3-fluoro-21-(methylthio)-[1,1']-biphenyl-4-yl]-2-oxo-3-piperidinyl}-1H-indole-5-carboxamide: (indole-5-carboxylic acid) LRMS (ES+): 474.6 (M+H)$^+$.

Example 26a
N-{1-[3-fluoro-2'-(methylthio)-[1,1']-biphenyl-4-yl]-2-oxo-3-piperidinyl}-benzimidazole-5-carboxamide: (imidazole-5-carboxylic acid) LRMS (ES+): 475.5 (M+H)$^+$.

Example 27
N-{1-[3-fluoro-2'-(methylthio)-[1,1']-biphenyl-4-yl]-2-oxo-3-piperidinyl}-1H-pyrazole-4-carboxamide: (4-pyrazole carboxylic acid) LRMS (ES+): 423.4 (M+H)$^+$.

Example 28
N-{1-[3-fluoro-21-(methylthio)-[1,1']-biphenyl-4-yl]-2-oxo-3-piperidinyl}-isonicotinamide: (isonicotinic acid) LRMS (ES+): 436.4 (M+H)$^+$

Example 29
N-{1-[3-fluoro-2'-(methylthio)-[1,1']-biphenyl-4-yl]-2-oxo-3-piperidinyl}-nicotinamide: (nicotinic acid) LRMS (ES+): 436.4 (M+H)$^+$.

Example 29a

N-{1-[3-fluoro-2'-(methylsulfonyl)-[1,1']-biphenyl-4-yl]-2-oxo-3-piperidinyl}-nicotinamide This compound was prepared from the compound of Ex. 29 by oxidation with MCPBA as previously described. LRMS (ESI+) 468.5 (M+H)$^+$.

Example 30
6-amino-N-{1-[3-fluoro-2'-(methylthio)-[1,1']-biphenyl-4-yl]-2-oxo-3-piperidinyl}-nicotinamide: (6-aminonicotinic acid) LRMS (ES+): 451.4 (M+H)$^+$.

Example 31

6-amino-N-{1-[3-fluoro-2'-(methylthio)-[1,1']-biphenyl-4-yl]-2-oxo-3-piperidinyl}-nicotinamide Reductive amination of 3-amino-1-([3-fluoro-2'-(methylthio)-[1,1']-biphenyl-4-yl-2-piperidinone with 4-chlorobenzaldehyde in the presence of sodium borohydride in methanol provided the title compound. LRMS (ES+): 455.9 (M+H)$^+$.

Example 32

3-{[{1-[2'-(aminosulfonyl)-[1,1']-biphenyl-4-yl]-2-oxo-3-piperidinyl}-amino]sulfonyl}benzenecarboximidamide, Trifluoroacetate Salt Part A: 3-bromo-1-[4-bromophenyl]-2-piperidinone: A mixture of 3-hydroxy-1-[4-bromophenyl]-2-piperidinone (10 g, 37.17 mmol) and PBr$_3$ (20.1 g, 74.35 mmol) in CH$_2$Cl$_2$ (200 ml) solution was stirred at r.t. for 18 hr. The reaction was quenched with ice water (100 ml) and extracted with EtOAc. The extracts were washed with water and brine and dried over MgSO$_4$. After filtration and concentration, the product was purified by chromatography on silica gel (2:1/hexane: EtOAc) to give the bromide (8.8 g, 72%) as a white solid. MS (ESI) m/z 372.8, 374.9 [(M+H+ACN)$^+$, 100]. 376.9.

Part B: 3-amino-1-[4-bromophenyl]-2-piperidinone: The compound of Ex. 32, Part A (8.8 g, 26.59 mmol) and NaN$_3$ (5.2 g, 79.76 mmol) in 100 ml DMF was heated at 50° C. in an oil bath for 3 h then cooled to 0° C. and quenched with water. The mixture was extracted with EtOAc and the extracts washed with water and brine, dried over MgSO$_4$, filtrated and concentrated. The residue was purified by chromatography on silica gel (2:1/hexane: EtOAc) to give the azide (7.8 g, 100%) as a solid. MS (AP+) m/z 266.9; 268.9 [(M+H—N2)$^+$, 100]. This azide intermediate (7.8 g, 26.5 mmol) was dissolved in 100 ml Et$_2$O, then Ph$_3$P (6.9 g, 26.5 mmol) was added. After 1.5 hr stirring at r.t., 0.7 ml of water (1.5 eq.) was added. The reaction mixture was stirred for 18 hr. The solvent was removed in vacuo and the residue purified by chromatography on silica gel (2:1/hexane: EtOAc) to give the amine (6.6 g, 93%) as a white solid. MS (ESI) m/z 269.2, 271.2 [(M+H)$^+$ 100].

Part C. N-[1-[4-bromophenyl]oxo-3-piperidinyl]-3-cyanobenzenesulfonamide: The compound of Ex. 32, Part B (0.5 g, 1.86 mmol) was dissolved in CH$_2$Cl$_2$ (5 ml) and 5 ml pyridine added. The solution was cooled to 0° C. in ice bath, and 3-cyanobenzenesulphonyl chloride (0.4 g, 2.05 mmol) was added. The mixture was stirred at 0° C. to r.t. for 18 h, diluted with CH$_2$Cl$_2$, washed with 0.5M HCl, sat. NaHCO$_3$ and brine, dried over MgSO$_4$, filtrated and concentrated. The residue was purified by chromatography on silica gel (1:1 hexane: EtOAc) to give the desired compound (0.35 g, 43%). MS (ESI) m/z 434.0/436.3 [(M+H)+ 25], 497.1/499.1 [(M+Na+AcCN)$^+$, 100].

Part D: 3-{[=1-[2'-(t-butylaminosulfonyl)-[1,1']-biphenyl-4-yl]-2-oxo-3-piperidinyl}-amino]sulfonyl}benzene carboximidamide: A solution of the compound of Ex. 32, Part C (0.35 g. 0.808 mmol) and 2-t-butylaminosulfonylbenzene boronic acid (0.25 g, 0.97 mmol) in a mixture of 30 ml toluene and 12.5 ml ethanol was purged with N$_2$ for 30 min. To this was added 0.8 ml of a 2M soln of sodium carbonate, nBu$_4$NBr (13 mg, 0.04 mmol) and (Ph$_3$P)$_4$Pd (37 mg, 0.03 mmol) and the mixture was heated to reflux for 18 h. Solvents were evaporated and the residue chromatographed on silica gel using 1:1 hexane/ethyl acetate to provide the product (0.4 g, 87%) as a white solid. MS (ESI$^+$) 589.3 (100).

Part E. 3-{[{1-[2'-(aminosulfonyl)-[1,1']-biphenyl-4-yl]-2-oxo-3-piperidinyl}-amino]sulfonyl}benzenecarboximidamide trifluoroacetate salt: The compound of Ex. 32, Part D (0.2 g, 0.35 mmol) was dissolved in 3 ml ethanol and hydroxylamine hydrochloride (74 mg, 1.06 mmol) and triethylamine (0.2 ml, 1.4 mmol) were added. The whole was heated in a 95° C. oil bath for 4 h, cooled to RT, and solvent removed by evaporation. The residue was dried on a vacuum pump and then taken up in 2 m glacial acetic acid. To this was added 49 µL acetic anhydride (0.53 mmol). After stirring for 30 min at room temperature, 20 mg of 5% Pd/C was added and the reaction mixture was placed under a balloon of H$_2$ for 4 h. The catalyst was removed by filtration and washed with ethanol. Combined filtrate and washings were evaporated and the residue dissolved in 3 ml trifluoroacetic acid and stirred overnight at room temperature then heated at 50° C. for 1 h to complete the de-protection of the sulfonamide. Purification by reverse phase HPLC provided the title compound (140 mg, 64%). $^1$H NMR (DMSO-d$_6$) δ 9.49 (s, 2H), 9.13 (s, 2H), 8.38 (m, 1H), 8.24 (m, 2H), 8.02 (m, 2H), 7.82 (m, 1H), 7.59 (m, 2H), 7.36 (m, 2H), 7.29 (m, 3H), 7.23 (m, 2H), 4.10 (m, 1H), 3.60 (m, 2H), 2.11 (m, 1H), 1.95 (m, 2H), 1.86 (m, 1H). MS (ESI) 528.2 [(M+H)$^+$ 100]

Example 33

3-{N-Benzyl-N-[2-oxo-1-(2'-sulfamoyl-biphenyl-4-yl)-piperidin-3-yl]-sulfamoyl}-benzamidine Part A. N-benzyl-N-1-[4-bromophenyl]-2-oxo-3-piperidinyl]-3-cyanobenzenesulfonamide: A mixture of the compound of Ex. 32, Part C (0.8 g, 1.85 mmol) and K$_2$CO$_3$ (0.31 g, 2.22 mmol) in DMF (5 ml) was cooled to 0° C., and benzyl bromide (0.33 g, 1.94 mmol) was added. The reaction mixture was stirred at 0° C. to r.t. for 5 h, diluted with water (100 ml) and extracted with EtOAc. The combined organic layers were washed with water and brine, dried over MgSO$_4$, filtered and concentrated. The residue was purified by chromatography on silica gel (2:1/hexane: EtOAc) to give the desired compound (0.98 g, 100%) Ms (ESI) m/z 524.1, 526.1 [(M+H)$^+$ 35].

Part B. N-Benzyl-N-[1-(2'-t-butylaminosulfonyl-biphenyl-4-yl)2-oxo-piperidin-3-yl]-3-cyanobenzenesulfonamide: This compound was prepared in 68% yield by Suzuki coupling from the compound of Ex. 33, Part A using the procedure described for Ex. 32, Part D.

Part C. 3-{Benzyl-[2-oxo-1-(2'-sulfamoyl-biphenyl-4-yl)-piperidin-3-yl]-sulfamoyl}-benzamidine: The title compound was prepared from the compound of Ex. 33, Part B using the method described for Ex.32, Part E using RaNi catalyst in place of 5% Pd/C. $^1$H NMR (DMSO-d$_6$) δ 9.47 (s, 2H), 9.08 (s, 2H), 8.20 (m, 2H), 8.02 (m, 2H), 7.79 (m, 1H), 7.60 (m, 2H), 7.37 (m, 4H), 7.31 (m, 4H), 7.26 (m, 4H), 4.65 (m, 2H), 4.14 (m, 1H), 3.53 (m, 2H), 2.05 (m, 2H), 1.89 (m, 2H). MS (ESI) 618.2 [(M+H)$^+$, 100].

General Procedure for preparation of Sulfonamide Examples from the Compound of Ex. 8, Part C: The amine from Ex. 8, Part C (25 mg, 0.069 mmol) and a sulfonyl chloride compound (0.104 mmol) were dissolved in 1.5 ml EtOAc, and then 1M K$_2$CO$_3$ solution (0.5 ml) was added. The mixture was stirred at room temperature for 1.5 h. The reaction was diluted with EtOAc (2 ml), and the org. layer was separated and washed with water (2×1 ml). To the organic layer solution was added PS-Trisamine (100 mg) and the mix was stirred at room temperature and overnight. MgSO$_4$ was added followed by filtration and concentration to provide the product. Yield were typically in the 70% to 95% range. Where necessary the products were further purified by either LC/MS or silica gel chromatography.

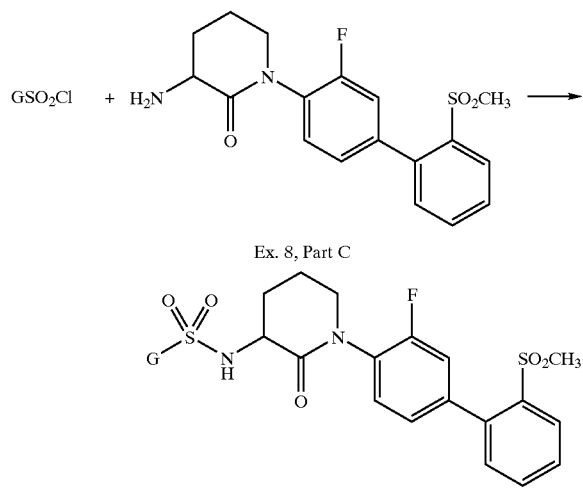

Ex. 8, Part C

Examples 34–52

(See Table 1 Below) were Prepared Using the Above General Procedure

Example 53

5-Chloro-N-[1-(2'-diethylaminomethyl-[1,1']-biphenyl-4-yl)-2-oxo-piperidin-3-yl]-thiophene-2-sulfonamide Part A: 5-Chloro-N-[4-bromophenyl)-2-oxo-piperidin-3-yl]-thiophene-2-sulfonamide: The compound of Ex. 32, Part B (1 g, 3.72 mmol) was dissolved in ethyl acetate (60 ml) and 1M potassium carbonate solution (20 ml) was added. The mixture was stirred vigorously while 5-chloro-2-thiophenesulfonyl chloride (1.2 g, 5.52 mmol) was added in rapid dropwise fashion at room temperature. Stirring was continued under N$_2$ for 1.5–2 h at which time the reaction was transferred to a separatory funnel and phases separated. The organic layer was washed with water and brine, dried over anhydrous Na$_2$SO$_4$, filtered and evaporated. The residue was re-dissolved in a small amount of CH$_2$Cl$_2$ and charged to a pad of silica gel in a 60 ml sintered glass funnel. After washing with ethyl acetate-hexane 3:1, the product was eluted with ethyl acetate-hexane 1:1 (0.75 g 45%). MS 450.9 (M+H)$^+$.

Part B 5-Chloro-N-[1-(2'-formyl-[1,1']-biphenyl-4-yl)-2-oxo-piperidin-3-yl]-thiophene-2-sulfonamide: The compound of Ex. 53, Part A (0.7 g, 1.56 mmol) and 2-formylbenzene boronic acid (0.28 g, 1.87 mmol) were dissolved in a mixture of 30 ml toluene and 12.5 ml ethanol and degassed by evacuation and flushing with N$_2$. To this solution was added 2M aq. Na$_2$CO$_3$ solution (1.56 ml, 3.12 mmol), nBu$_4$NBr (25 mg, 0.078 mmol) and (Ph$_3$P)$_4$Pd (72 mg, 0.78 mm0l) under N$_2$ and the whole was heated to reflux in a 95° C. oil bath overnight. Reaction was cooled to room temperature and partitioned between ethyl acetate and water. Phases were separated and aqueous re-extracted with EtOAc. The combined organic phases were washed with water and brine, dried over anhydrous Na$_2$SO$_4$, filtered and evaporated. The residue was chromatographed on silica gel (hexane-ethyl acetate 65/35 to 50/50) to give the product (0.41 g, 55%). MS 475.0 (M+H)$^+$.

Part C. 5-Chloro-N-[1-(2'-diethylaminomethyl-[1,1']-biphenyl-4-yl)-2-oxo-piperidin-3-yl]-thiophene-2-sulfonamide: The aldehyde of Ex. 53, Part B (50 mg, 0.105 mmol) was charged to a 13 mm test tube and 2–3 ml 1,2-dichloroethane and diethylamine (25 pml, 0.24 mmol) were added. The mixture was agitated using a FirstMate parallel synthesizer for 30 min at room temperature under N$_2$ followed by addition of sodium triacetoxyborohydride (35 mg, 0.165 mmol). Agitation was continued for 48 h. Reaction was quenched with 1 ml 2M NaOH and extracted 3× with CH$_2$Cl$_2$. Extracts were washed with brine, dried over anhydrous Na$_2$SO$_4$, filtered and evaporated. Purification by reverse phase HPLC and lyophilization provided the product as a white solid (19 mg, 34%) $^1$H NMR (DMSO-d$_6$) δ 9.02 (1H, bs), 8.47 (1H, d, J=12 Hz), 7.72 (1H, m). 7.56 (3H, m), 7.39 (5H, s), 7.23 (1H, m), 4.31 (2H, m) 4.12 (1H, m), 3.65 (2H, m), 3.39 (4H, m), 2.98 (1H, m), 2.83 (1H, m), 2.10 (1H, m), 1.97 (2H, m), 1.94 (1H,m), 0.92 (6H, t, J=6.6 Hz). MS 532.4 (M+H)$^+$

Examples 54–57

(See Table 1 below) were similarly prepared from the respective amines and the compound of Ex. 53, Part B

Example 58

3-Amino-N-[1-(3-fluoro-2'-methanesulfonyl-biphenyl-4-yl)-2-oxo-piperidin-3-yl]-benzo[d]isoxazole-5-sulfonamide Part A. 3-cyano-4-fluoro-N-[1-(3-fluoro-2'-methanesulfonyl-biphenyl-4-yl)-2-oxo-piperidin-3-yl]-benzenesulfonamide: A mixture of the compound of Ex. 49 (0.12 g, 0.217 mmol), zinc cyanide (25 mg, 0.217 mmol), tris(dibenzylideneacetone)dipalladium(0) (Pd$_2$(dba)$_3$) (20 mg, 0.0217 mmol), 1,1'-bis(diphenylphosphino)ferrocene (dppf) (24 mg, 0.0433 mmol) and zinc powder (2.8 mg, 0.0433 mmol) in 5 ml N,N-dimethylacetamide was degassed and flushed with nitrogen then heated in a 140° C. oil bath for 20 h. The mixture was cooled to room temperature, diluted with EtOAc and filtered through Celite®. The filtrate was washed with saturated Na$_2$CO$_3$ and brine, dried over anhydrous Na$_2$SO$_4$, filtered and evaporated. Reverse phase HPLC provided the nitrile product (65 mg, 55%). MS 546.4 (M+H)$^+$.

Part B. 3-Amino-N-[1-(3-fluoro-2'-methanesulfonyl-biphenyl-4-yl)-2-oxo-piperidin-3-yl]-benzo[d]isoxazole-5-sulfonamide: A solution of acetoxyhydroxamic acid (54 mg, 0.715 mmol) in 10 ml DMF was treated with potassium carbonate (132 mg, 0.95 mmol) and water (3 ml). This mixture was stirred for 15 min. followed by addition of a solution of the compound of Ex. 58, Part A (65 mg, 0.119 mmol) in 5 ml DMF. The whole was stirred at room temperature for 3 days. Reaction was diluted with ethyl acetate, washed with water and brine, dried over anh. MgSO$_4$, filtered and evaporated. Purification by reverse phase HPLC provided the title compound (18 mg, 27%) after lyophilization. $^1$H NMR (CD$_3$OD) δ 8.40 (1H, s), 8.14 2H, m), 7.63 (2H, m), 7.52 (1H, m), 7.38 (1H, m), 7.25 (3H, m), 4.07 (1H, m), 3.67 (2H, m), 2.76 (3H, s), 2.30 (1H, m), 1.95 (1H,m). MS 559.3 (M+H)$^+$.

Example 58a 3-(3-Amino-benzo[d]isoxazol-5-ylamino)-1-(3-fluoro-2'-methanesulfonyl-biphenyl-4-yl)-piperidin-2-one A mixture of the compound of Ex. 8, Part C (0.372 g, 1.03 mmol), 3-cyano-4-fluorobenzeneboronic acid (0.848 g, 5.15 mmol), copper(II)acetate (0.372 g, 2.06 mmol), triethylamine (0.286 ml, 2.06 mmol), pyridine (0.166 ml, 2.06 mmol) and 4 Å molecular sieves in methylene chloride (15 ml) was stirred for 0.5 h at room temperature. The mixture was then filtered through a page of silca gel which was eluted with EtOAc. The filtrate was evaporated and the resudue purified by column chromatography (silica gel, 0–25% EtOAc in Hexane) to give the product as an oil (0.268 g, 54%) A portion of this product (50 mg, 0.104 mmol) was heated neat with an excess of di-t-butyldicarbonate to 100° C. After cooling to room temperature the BOC-protected amine was isolated in 30% yield (18 mg) after chromatography on silica gel (ethyl acetate/hexane 50—50 to 75–25). This material was added to a mixture of acetoxyhydroxamic acid (6 mg, 2.5 eq) and potassium carbonate (21 mg, 5eq) in DMF/H$_2$O (3:1, 2 ml) which had been pre-stirred for 20 min. The whole was then stirred overnight at room temperature. Reaction mixture was diluted with water and extracted with ethyl acetate. Combined organics were washed with brine, dried over MgSO$_4$, filtered and concentrated in vacuo. Purification by column chromatography (silica gel, 75% EtOAc-hexane to 100% EtOAc) provided the aminobenzisoxazole product (13 mg, 71% yield). Deprotection by stirring in a 1:1 mixture of methylene chloride and trifluoroacetic acid at room temperature for 30 min followed by removal of solvent and reverse phase HPLC provided the title compound as a white powder after lyophilization. (7.8 mg). $^1$H NMR (DMSO-d$_6$) δ 8.12 (1H,d,J=8 Hz), 7.77 (2H,t,J=8 Hz), 7.71 (1H,t,J=7 Hz), 7.46 (2H,m), 7.45 (1H,d,j=11 Hz), 7.29 (1H,d,J=8 Hz), 7.20 (1H,d,J=11 Hz), 7.04 (1H,d,J=8 Hz), 6.98 (1H,s), 4.15 (1H,m), 3.74 (2H,m), 2.91 (3H,s), 2.38 (1H,m), 2.10 (2H, m), 1.88 (1H,m).MS(ESI+) 495.4 (M+H)$^+$.

Example 58b

2-Fluoro-5-[1-(3-fluoro-2'-methanesulfonyl-biphenyl-4-yl)-2-oxo-piperidin-3-ylamino]-N-hydroxy-benzamidine A mixture of acetoxyhydroamic acid (27 mg, 2.5eq) and K$_2$CO$_3$ (98 mg, 5eq) in DMF/H$_2$O (3:1, 4 ml) was stirred at room temperature for 20 min. To this mixture was added 2-fluoro-5-[1-(3-fluoro-2'-methanesulfonyl-biphenyl-4-yl)-2-oxo-piperidin-3-ylamino]-benzonitrile (68 mg, 0.141 mmol) prepared as described under Ex. 58a above. The whole was stirred and heated at 110° C. for 18 h. The mixture was diluted with water and extracted 3× with EtOAc. The combined organic extracts were washed with brine, dried over MgSO$_4$, filtered and evaporated. Purification by reverse phase HPLC yielded the title compound (50 mg, 72%) $^1$H NMR (DMSO-d$_6$) δ 8.11 (1H,d,J=8 Hz), 7.79 (1H,t,J=7, 3 Hz), 7.71 (1H,t,J=7, 73 Hz), 7.46 (2H,m), 7.37 (1H,d,J=11 Hz), 7.28 (1H,d,J=8 Hz), 7.18 (1H,t,J=9.5 Hz), (1H,d,J=11 Hz), 7.28 (1H,d,J=8 Hz), 7.18 (1H,t,J=9.5 Hz), 6.98 (1H,m), 6.85 (1H,m), 4.29 (1H,m), 3.72 (2H,t,J=6.2 Hz), 2.91 (3H,s), 2.28 (1H,m), 2.08 (2H,m), 1.84 (1H,m). MS 515.3 (M+H)$^+$.

Example 58c 1-(3-Fluoro-2'-methanesulfonyl-biphenyl-4-yl)-3-[3-(5-oxo-4,5-dihydro-1H-[1,2,4]triazol-3-yl)-phenylamino]-piperidin-2-one A sample of 3-[1-(3-fluoro-2'-methanesulfonyl-biphenyl-4-yl)-2-oxo-piperidin-3-ylamino]-benzonitrile, prepared from the compound of Ex. 1, part A and 3-cyanoaniline according to the procedure of Ex. 1, Part B, was suspended in a 2:1 mixture of anhydrous MeOH and chloroform and cooled in a 0° C. ice-bath. HCl gas was then bubbled in the mixture for 30 minutes resulting in a clear solution. The reaction vessel was sealed and stored at 0° C. for 18 hours. The mixture was concentrated in vacuo and dried. The resulting residue was suspended in 1,4-dioxane. Semicarbazide hydrochloride (1.7 eq) was then added, followed by N-methylmorpholine (7.2 eq). The mixture was refluxed for 48 hours. The precipitate was filtered and washed with 1,4-dioxane, water, and ether. The solid was pumped dry to afford the title compound. $^1$H NMR (DMSO-d$_6$, 300 MHz) δ 11.87 (s, 1H), 11.56 (s, 1H), 8.11(d, J=8.1 Hz, 1H), 7.75 (m, 2H), 7.47 (m, 2H), 7.37 (d, J=11.0 Hz, 1H), 7.29 (d, J=7.9 Hz, 1H), 7.15 (t, J=7.9 Hz, 1H), 7.08 (br m, 1H), 6.96 (d, J=7.3 Hz, 1H), 6.78 (br d, J=9.5 Hz, 1H), 4.28 (m, 1H), 3.73 (t, J=6.2 Hz, 2H), 2.90 (s, 3H), 2.30 (m, 1H), 2.10 (m, 2H), 1.90 (m, 1H); MS ESI (M+H) 522.4.

Example 58d

N-[1-(3-Fluoro-2'-methanesulfonyl-biphenyl-4-yl)-2-oxo-piperidin-3-yl]-3-(5-oxo-4,5-dihydro-1H-[1,2,4]triazol-3-yl)-benzenesulfonamide This compound was similarly prepared from the compound of Ex 1 using the procedure of Ex. 58c. $^1$H NMR (DMSO-d$_6$, 300 MHz) δ 11.98 (s, 1H), 11.68 (s, 1H), 8.11 (d, J=7.7 Hz, 1H), 7.70 (m, 2H), 7.45 (t, J=7.9 Hz, 1H), 7.30 (m, 6H), 7.20 (m, 1H), 5.10 (m, 1H), 3.65 (m, 2H), 2.84 (s, 3H), 2.30 (m, 1H), 2.05 (m, 3H); MS ESI (M+H) 523.4.

Example 58f 1-(3-Fluoro-2'-methanesulfonyl-biphenyl-4-yl)-3-[3-(5-oxo-4,5-dihydro-1H-[1,2,4]triazol-3-yl)-phenoxy]-piperidin-2-one This compound was prepared 1-(3-Fluoro-2'-methanesulfonyl-biphenyl-4-yl)-3-[3-cyanophenoxy]-piperidin-2-one as described for the preparation of Ex. 58c. $^1$H NMR (DMSO-d$_6$, 300 MHz) δ 11.87 (s, 1H), 11.56 (s, 1H), 8.11(d, J=8.1 Hz, 1H), 7.75 (m, 2H), 7.47 (m, 2H), 7.37 (d, J=11.0 Hz, 1H), 7.29 (d, J=7.9 Hz, 1H), 7.15 (t, J=7.9 Hz, 1H), 7.08 (br m, 1H), 6.96 (d, J=7.3 Hz, 1H), 6.78 (br d, J=9.5 Hz, 1H), 4.28 (m, 1H), 3.73 (t, J=6.2 Hz, 2H), 2.90 (s, 3H), 2.30 (m, 1H), 2.10 (m, 2H), 1.90 (m, 1H); MS ESI (M+H) 522.4.

Table 1 below provides representative Examples, the synthesis of which is described above, of the compounds of Formula (I) of the present invention.

TABLE 1

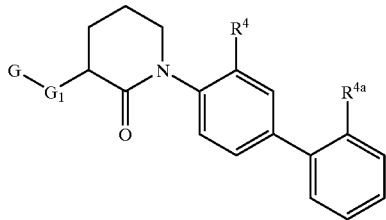

| Ex. # | G | $G_1$ | $R^4$ | $R^{4a}$ | MS (M + H)+ |
|---|---|---|---|---|---|
| 1 | 3-CN-phenyl | O | F | —SO$_2$Me | 465.5 |
| 2 | 3-amidino-phenyl | O | F | —SO$_2$Me | 482.3 |
| 3 | 4-amidino-phenyl | O | F | —SO$_2$Me | 482.5 |
| 4 | 3-CN-phenyl | O | F | —CH$_2$N(Me)$_2$ | 427.2 |
| 5 | 3-amidino-phenyl | O | F | —CH$_2$N(Me)$_2$ | 461.55 |
| 6 | 3-amidino-phenyl | O | H | —CH$_2$N(Me)$_2$ | 442.5 |
| 7 | 3-amidino-phenyl | NH | F | —CH$_2$N(Me)$_2$ | 460.6 |
| 8 | 2,4-diCl-phenyl | CONH | F | —SO$_2$Me | 536.4 |
| 9 | 3-Cl-phenyl | CONH | F | —SO$_2$Me | 501.9 |
| 10 | 3,4-diCl-phenyl | CONH | F | —SO$_2$Me | 536.4 |
| 11 | 4-F-phenyl | CONH | F | —SO$_2$Me | 485.4 |
| 12 | 4-Cl-phenyl | CONH | F | —SO$_2$Me | 501.9 |
| 12a | 4-MeO-phenyl | CONH | F | —SO$_2$Me | 497.1 |
| 12b | 3-MeO-phenyl | CONH | F | —SO$_2$Me | 497.1 |
| 13 | 2-Cl-4-pyridyl | CONH | F | —SO$_2$Ne | 502.9 |
| 14 | 6-Cl-3-pyridyl | CONH | F | —SO$_2$Me | 502.9 |
| 15 | 6-(1H-pyrazol-1-yl)-3-pyridyl | CONH | F | —SO$_2$Me | 534.6 |
| 16 | 2-Cl-3-pyridyl | C(O)O | F | —SO$_2$Me | 503.9 |
| 17 | 4-MeO-phenyl | C(O)O | F | —SO$_2$Me | 498.5 |
| 18 | 4-MeO-2-CHO-phenyl | O | F | —SO$_2$Me | 498.5 |
| 19 | 5-Cl-2-pyridyl | NH | F | —SO$_2$Me | 381.6 |
| 20 | 4-MeO-phenyl | O | F | —SO$_2$Me | 470.5 |
| 20a | 4-MeO-phenyl | NH | F | —SO$_2$Me | 469.3 |
| 21 | 4-MeO-2-(methoxycarbonyl)-phenyl | O | F | —SO$_2$Me | 528.5 |
| 22 | 3-aminomethyl-phenyl | O | F | —SO$_2$Me | 469.5 |
| 23 | 4-MeO-2-anilinomethyl-phenyl | O | F | —SO$_2$Me | 517.5 |
| 23a | 4-MeO-2-(4-pyridyl-aminocarbonyl)-phenyl | O | H | —SO$_2$Me | 590.6 |
| 24 | 3-Cl-phenyl | CONMe | F | —SO$_2$Me | 501.9 |
| 25 | 4-Cl-phenyl | CONBn | F | —SO$_2$Me | 592.2 |
| 26 | 1H-5-indolyl | CONH | F | —SMe | 474.6 |
| 26a | 5-benzimidazolyl | CONH | F | —SMe | 475.5 |
| 27 | 1H-pyrazol-4-yl | CONH | F | —SMe | 423.4 |
| 28 | 4-pyridyl | CONH | F | —SMe | 436.4 |
| 29 | 3-pyridyl | CONH | F | —SMe | 436.4 |
| 29a | 3-pyridyl | CONH | F | —SO$_2$Me | 468.5 |
| 30 | 6-amino-3-pyridyl | CONH | F | —SMe | 451.4 |
| 31 | 4-Cl-phenyl | CH$_2$NH | F | —SMe | 455.9 |
| 32 | 3-amidino-phenyl | SO$_2$NH | H | —SO$_2$NH$_2$ | 528.2 |
| 33 | 3-amidino-phenyl | SO$_2$NBn | H | —SO$_2$NH$_2$ | 618.2 |
| 34 | 4-Cl-phenyl | SO$_2$NH | F | —SO$_2$Me | 537.1 |
| 35 | 6-Cl-naphthyl | SO$_2$NH | F | —SO$_2$Me | 587.3 |
| 36 | 7-Cl-naphthyl | SO$_2$NH | F | —SO$_2$Me | 587.3 |
| 37 | 5-Cl-2-thienyl | SO$_2$NH | F | —SO$_2$Me | 543.0 |
| 38 | 5-(3-isoxazolyl)-2-thienyl | SO$_2$NH | F | —SO$_2$Me | 576.3 |
| 39 | 4-F-phenyl | SO$_2$NH | F | —SO$_2$Me | 521.3 |
| 40 | 4-MeO-phenyl | SO$_2$NH | F | —SO$_2$Me | 533.1 |
| 41 | 4-Et-phenyl | SO$_2$NH | F | —SO$_2$Me | 531.2 |
| 42 | 3-MeO-phenyl | SO$_2$NH | F | —SO$_2$Me | 533.3 |
| 43 | 5-Br-6-Cl-3-pyridyl | SO$_2$NH | F | —SO$_2$Me | 616.2/618.2 |
| 44 | 5-(2-pyridyl)-2-thienyl | SO$_2$NH | F | —SO$_2$Me | 586.3 |
| 45 | 3,4-diF-phenyl | SO$_2$NH | F | —SO$_2$Me | 539.1 |
| 46 | 3-Cl-phenyl | SO$_2$NH | F | —SO$_2$Me | 537.1 |
| 47 | 3,5-diCl-2-thienyl | SO$_2$NH | F | —SO$_2$Me | 577.0 |
| 48 | 4-CN-phenyl | SO$_2$NH | F | —SO$_2$Me | 528.2 |
| 49 | 3-Cl-4-F-phenyl | SO$_2$NH | F | —SO$_2$Me | 555.2 |
| 50 | 1-Me-4-imidazolyl | SO$_2$NH | F | —SO$_2$Me | 507.1 |
| 51 | 2,5-diCl-phenyl | SO$_2$NH | F | —SO$_2$Me | 571.1 |

TABLE 1-continued
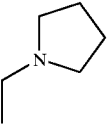
| Ex. # | G | G₁ | R⁴ | R⁴ᵃ | MS (M + H)⁺ |
|---|---|---|---|---|---|
| 52 | 3,5-diCl-phenyl | SO₂NH | F | —SO₂Me | 571.0 |
| 53 | 5-Cl-2-thienyl | SO₂NH | H | —CH₂N(Et)₂ | 532.4 |
| 54 | 5-Cl-2-thienyl | SO₂NH | H | 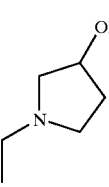 | 530.4 |
| 55 | 5-Cl-2-thienyl | SO₂NH | H | 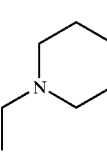 | 546.4 |
| 56 | 5-Cl-2-thienyl | SO₂NH | H | 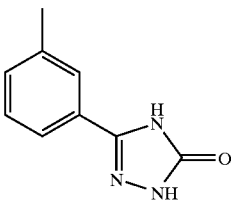 | 560.4 |
| 57 | 5-Cl-2-thienyl | SO₂NH | H | —CH₂N(Me)—CH₂CH₂OH | 534.4 |
| 58 | 3-amino-benzisoxazol-5-yl | SO₂NH | F | —SO₂Me | 559.3 |
| 58a | 3-aminobenzisoxazol-5-yl | NH | F | SO₂Me | 495.4 |
| 58b | 4-F-3-(N-hydroxy-amidino)-phenyl | NH | F | —SO₂Me | 515.3 |
| 58c | 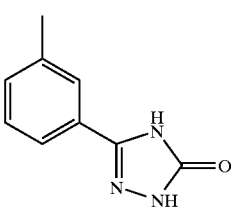 | NH | F | —SO₂Me | 522.4 |
| 58d | 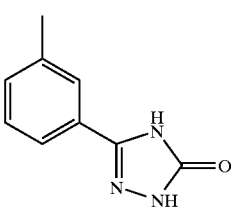 | SO₂NH | F | —SO₂Me | 586.4 |

TABLE 1-continued

| Ex. # | G | G₁ | R⁴ | R⁴ᵃ | MS (M + H)⁺ |
|---|---|---|---|---|---|
| 58e | 3-methylphenyl-(5-oxo-4,5-dihydro-1H-1,2,4-triazol-3-yl) | CONH | F | —SO₂Me | |
| 58f | 3-methylphenyl-(5-oxo-4,5-dihydro-1H-1,2,4-triazol-3-yl) | O | F | —SO₂Me | 523.4 |
| 101 | phenyl | SO₂NH | F | —SO₂Me | 503.4 |
| 102 | 3-pyridyl | SO₂NH | F | —SO₂Me | 504.3 |
| 103 | 5-Cl-3-Me-2-thienyl | SO₂NH | F | —SO₂Me | 607.3 |
| 104 | 3-quinolinyl | SO₂NH | F | —SO₂Me | 554.4 |
| 105 | 6-quinolinyl | SO₂NH | F | —SO₂Me | 554.4 |
| 106 | 6-quinoxalinyl | SO₂NH | F | —SO₂Me | 555.3 |
| 107 | 6-amino-3-pyridyl | SO₂NH | F | —SO₂Me | 519.4 |
| 108 | 6-indazolyl | SO₂NH | F | —SO₂Me | 543.4 |

Examples 59–63 were prepared from Ex. 34 by alkylation with the indicated alkylhalide in the presence of potassium carbonate in DMF as solvent using the procedure described for the synthesis of the compound of Ex. 33, Part A.

TABLE 2

| Ex. No. | Alkylhalide | R | MS (M + H)⁺ |
|---|---|---|---|
| 59 | Benzylbromide | Benzyl | 627.4 |
| 60 | Methyl iodide | Methyl | 551.3 |
| 61 | Ethyl iodide | Ethyl | 565.4 |
| 62 | 2-picolylchloride.HCl | 2-pyridylmethyl | 628.4 |
| 63 | 3-picolylchloride.HCl | 3-pyridylmethyl | 628.4 |

Example 64

3-[[1,2-dihydro-1-[2'-(methylsulfonyl)[1,1'-biphenyl]-4-yl]-2-oxo-3-pyridinyl]amino]-benzenecarboximidamide

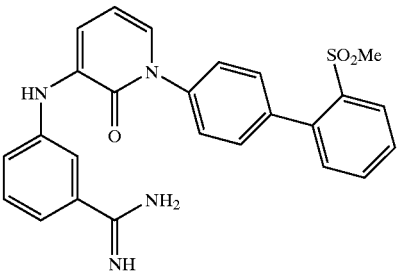

Part A. 1-(4-Bromophenyl)-3-nitro-)-3-2(1H)-pyridinone: 3-Nitro-2-hydroxypyridine (1.00 g, 7.12 mmol), 4-bromophenylboronic acid (2.86 g, 14.24 mmol), copper acetate (2.58 g, 14.24 mmol), triethylamine (2 mL, 14.24 mmol), and pyridine (1.16 mL, 14.24 mmol) were added together with 50 mL of CH₂Cl₂. The mixture was stirred at RT with a drying tube for 36 h. The mixture was filtered through Celite® and washed with CH₂Cl₂. The filtrate was concentrated and chromatographed with 50% EtOAc in hexane to give 1.62 g of the desired product. ¹H NMR (CDCl$_3$) δ 8.40–8.37 (d, J=7.7 Hz, 1H), 7.70–7.69 (d, J=1.3 Hz, 1H), 7.68–7.65 (d, J=8.8 Hz, 2H), 7.30–7.26 (d, J=8.8 Hz, 2H), 6.44–6.39 (t, 1H). MS (AP$^+$): 296.9, (M+H)$^+$.

Part B. 1-[2'-(Methylthio)[1,1'-biphenyl]-4-yl]-3-nitro-2(1H)-pyridinone: The compound of Ex. 64, Part A (1.62 g, 5.49 mmol), 2-methylthiophenylboronic acid (1.38 g, 8.24 mmol), potassium phosphate (4.66 g, 21.96 mmol), and tetrakis(triphenyl-phosphine)palladium (0.32 g, 5% mmol) were added together with 100 mL of dioxane. The mixture was degassed and then refluxed for 5.5 h under N$_2$. After cooling to RT, it was filtered through Celite®, washed with EtOAc and CH$_2$Cl$_2$ concentrated, and chromatographed with CH$_2$Cl$_2$ to give 1.95 g of the desired product. $^1$H NMR (CDCl$_3$) δ 8.42–8.39 (d, J=7.7 Hz, 1H), 7.84–7.81 (d, J=6.9 Hz, 1H), 7.61–7.58 (d, J=8.3 Hz, 2H), 7.447–7.43 (d, J=8.8 Hz, 2H), 7.39–7.23 (m, 4H), 6.44–6.39 (t, 1H), 2.40 (s, 1H); MS (AP$^+$): 339.1, (M+H)$^+$.

Part C. 1-[2'-(Methylsulfonyl)[1,1'-biphenyl]-4-yl]-3-nitro-2(1H)-pyridinone: The compound of Ex. 64, Part B (1.95 g, 5.77 mmol) was dissolved in 50 mL CH$_2$Cl$_2$ and then cooled to 0° C. m-CPBA (4.65 g with 60% purity, 16.16 mmol) was added. The mixture was stirred at 0° C. and then warmed up to RT overnight under N$_2$. The reaction was quenched with saturated Na$_2$SO$_3$. The organic layer was washed with saturated NaHCO$_3$ and brine, dried over Na$_2$SO$_4$, and concentrated to give 2.15 g of the crude product as a yellow solid. MS (AP$^+$): 371.0, (M+H)$^+$.

Part D. 3-Amino-1-[2'-(methylsulfonyl)[1,1'-biphenyl]-4-yl]-2(1H)-pyridinone: To a suspension of the compound of Ex. 64, Part C (2.15 g, 5.81 mmol) in EtOAc (100 mL) was added tin chloride (10.22, 46.4 mmol). The mixture was refluxed for 1.5 h under N$_2$. EtOH (100 mL) was added and the mixture was refluxed for another 1.5 h. The mixture was cooled to RT and water was added. The mixture was filtered through Celite®, washed with 1:5 EtOH/CH$_2$Cl$_2$, and concentrated, and chromatographed with 50% EtOAc in CH$_2$Cl$_2$ to give 0.63 g of the desired product. $^1$H NMR (CDCl$_3$) δ 8.27–8.24 (d, J=8.1 Hz, 1H), 7.72–7.66 (m, 1H), 7.63–7.57 (m, 3H), 7.53–7.50 (d, J=7.8 Hz, 2H), 7.44–7.41 (d, J=7.7 Hz, 1H), 6.91–6.88 (d, J=6.9 Hz, 1H), 6.64–6.61 (d, J=7.0 Hz, 1H), 6.23–6.18 (t, 1H), 2.73 (s, 3H); MS (ES$^+$): 341.3, (M+H)$^+$, 363.3, (M+Na)$^+$.

Part E. 3-[[1,2-dihydro-1-[2'-(methylsulfonyl)-[1,1'-biphenyl]-4-yl]-2-oxo-3-pyridinyl]amino]-benzonitrile:

The compound of Ex. 64, Part D (100 mg, 0.294 mmol), 3-cyanophenylboronic acid (86 mg, 0.588 mmol), pyridine (0.04 mL, 0.647 mmol), triethylamine (0.09 mL, 0.647 mmol), copper acetate (106 mg, 0.588 mmol), and 4 Å molecular sieves were added together with CH$_2$Cl$_2$ (20 mL) in a round-bottom flask equipped with a drying tube. The mixture was stirred at RT overnight, filtered through Celite®, washed with CH$_2$Cl$_2$, concentrated, and chromatographed with 2:3 EtOAc/CH$_2$Cl$_2$ to give 0.14 g of the desired product. $^1$H NMR (CDCl$_3$): δ 8.27–8.24 (d, J=8.0 Hz, 1H), 7.71–7.51 (m, 6H), 7.43–7.27 (m, 5H), 7.22–7.19 (d, J=7.4 Hz, 1H), 7.06–7.03 (d, J=7.0 Hz, 1H), 6.38–6.36 (t, 1H), 2.74 (s, 1H); MS (ES$^+$): 442.4, (M+H)$^+$, 464.2, (M+Na)$^+$.

Part F. 3-[[1,2-dihydro-1-[2'-(methylsulfonyl)-[1,1'-biphenyl]-4-yl]-2-oxo-3-pyridinyl]amino]-benzenecarboximidamide: A solution of the compound of Ex. 64, Part E (0.14 g) in 6 mL of CHCl$_3$ and 4 mL of MeOH was cooled at 0° C. with a ice bath, HCl gas was bubbled in for 15 minutes. The reaction mixture was sealed and put in a refrigerator over the weekend. The solvent was removed and the residue was dried under vacuum to give 0.12 g of a yellow solid. This solid was dissolved in 8 mL of MeOH. Ammonium acetate (147 mg, 19.02 mmol) was added. The mixture was sealed and stirred at RT overnight. The solvent was removed and the residue was purified by HPLC (C18 reverse phase) with 5% TFA in acetonitrile/water to give 52 mg of the benzamidine TFA salt. $^1$H NMR (CD3OD) δ 8.25–8.21 (d, 1H), 7.83–7.74 (t, 1H), 7.72–7.55 (m, 9H), 7.50–7.47 (d, 1H), 7.38–7.33 (d, 1H), 6.59–6.46 (t, 1H), 2.86 (s, 3H); MS (ES$^+$): 459.2, (M+H)$^+$; HPLC purity 97%.

Example 65

3-[(4-Methoxyphenyl)amino]-1-[2'-(methylsulfonyl)[1,1'-biphenyl]-4-yl]-2(1H)-pyridinone

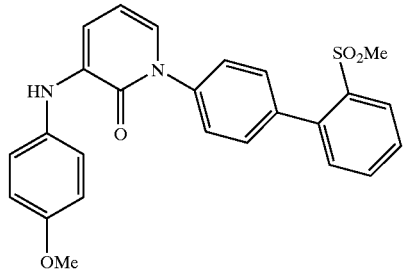

The compound of Ex. 64, Part D (100 mg, 0.294 mmol), 4-methoxyphenylboronic acid (89 mg, 0.588 mmol), pyridine (0.04 mL, 0.647 mmol), triethylamine (0.09 mL, 0.647 mmol), copper acetate (106 mg, 0.588 mmol), and 4 Å molecular sieves were added together with CH$_2$Cl$_2$ (20 mL). The mixture was stirred at RT with a drying tube overnight. It was filtered through Celite®, washed with CH$_2$Cl$_2$, concentrated, and chromatographed with 1:3 EtOAc/CH$_2$Cl$_2$ to give 40 mg of the title compound with some impurities. It was further purified by HPLC in 3:10 EtOAc/CH$_2$Cl$_2$ to give 15 mg of the pure title compound as a brownish solid. $^1$H NMR (CD$_3$Cl) δ 8.27–8.25 (d, J=8.1 Hz, 1H), 7.72–7.53 (m, 6H), 7.45–7.43 (d, J=7.3 Hz, 1H), 7.19–7.16 (d, J=8.8 Hz, 2H), 6.94–6.84 (m, 4H), 6.27–6.22 (t, 1H), 3.83 (s, 3H), 2.73 (s, 3H): MS (ES$^+$): 447.4, (M+H)$^+$.

Example 66

N-[,1,2-dihydro-1-[2'-(methylsulfonyl)[1,1'-biphenyl]-4-yl]-2-oxo-3-pyridinyl]-4-methoxybenzamide

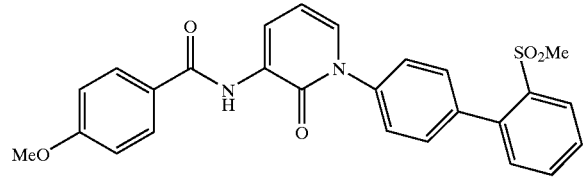

The compound of Ex. 64, Part D (50.0 mg, 0.147 mmol), 4-anisoyl chloride (38.0 mg, 0.221 mmol), and DMAP (45.0 mg, 0.368 mmol) were added together with 6 mL of CH$_2$Cl$_2$. The mixture was stirred at RT overnight under N$_2$. It was concentrated, and chromatographed with 2:3 EtOAc/Hex to give 37 mg of the title compound as a white solid. $^1$H NMR (CDCl$_3$) δ 9.24 (s, 1H), 8.66–8.63 (d, J=7.3 Hz, 1H), 8.28–8.25 (d, J=8.1 Hz, 1H), 7.93–7.90 (d, J=8, 8 Hz, 2H), 7.73–7.59 (m, 4H), 7.55–7.52 (d, J=8.4 Hz, 2H), 7.44–7.41 (d, J=7.3 Hz, 1H), 7.22–7.19 (d, J=7.0 Hz 1H), 6.99–6.96 (d, J=9.2 Hz, 2H), 6.48–6.43 (m, 1H), 3.87 (s, 3H), 2.74 (s, 3H); MS (ES$^+$): 475.3, (M+H)$^+$, 497.3, (M+Na)$^+$.

Example 67

6-chloro-N-[1,2-dihydro-1-[2'-(methylsulfonyl)[1,1'-biphenyl]-4-yl]-2-oxo-3-pyridinyl]-3-pyridinecarboxamide

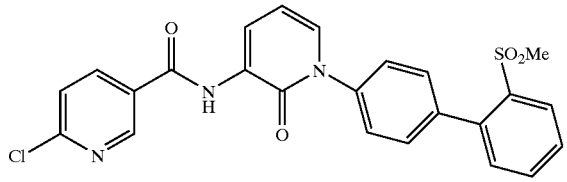

The compound of Ex. 64, Part D (50.0 mg, 0.147 mmol), 2-chloropyridine-5-carbonyl chloride (39.0 mg, 0.221 mmol), and DMAP (45.0 mg, 0.368 mmol) were added together with 6 mL of $CH_2Cl_2$. The mixture was stirred at RT overnight under $N_2$. It was concentrated, and chromatographed with 2:3 EtOAc/Hexane to give 20 mg of the title compound as a white solid. $^1$H NMR (CD$_3$Cl) δ 9.27 (s, 1H), 8.95 (s, 1H), 8.64–8.61 (d, J=7.3 Hz, 1H), 8.28–8.25 (d, J=7.7 Hz, 1H), 8.21–8.17 (d, J=8.4 Hz, 1H), 7.71–7.60 (m, 4H), 7.55–7.41 (m, 4H), 7.29–7.26 (m, 1H), 6.50–6.45 (t, 1H), 2.75 (s, 1H); MS (ES$^+$): 480.3, (M+H)$^+$, 502.3, (M+Na)$^+$.

Example 68

3-[[1,2-dihydro-1-[2'-[(3-hydroxy-1-pyrrolidinyl)methyl][1,1'-biphenyl]-4-yl]-2-oxo-4-(1-pyrrolidinyl)-3-pyridinyl]amino]-benzenecarboximidamide

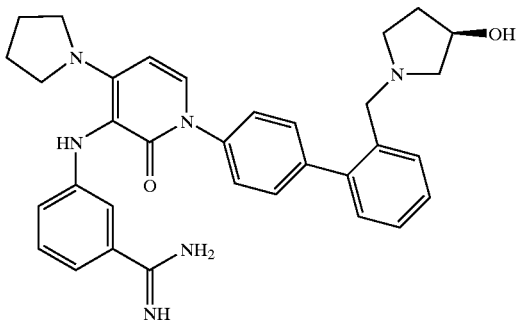

Part A. 4-chloro-3-nitro-2(1H)-pyridinone: To a solution of 2,4-dihydroxy-3-nitropyridine (5.00 g, 32.03 mmol) and benzyltriethylammonium chloride (29.18 g, 128.12 mmol) in 100 mL of $CH_3CN$ was added dropwise phosphorus oxychloride (11.9 mL, 128.12 mmol). The mixture was heated at 60° C. for 1 h and refluxed for 1 h. The solvent was removed and 150 mL of iced water was added. The resulting mixture was stirred at 0° C. for 1.2 h. The precipitate was filtered and dried to give 4.48 g of yellow solid as the desired product. $^1$H NMR (DMSO-d$_6$) δ 7.79–7.76 (d, 1H), 6.61–6.59 (d, 1H); MS (AP$^+$): 216.0, (M+CH$_3$CN+H)$^+$.

Part B: 3-nitro-4-(1-pyrrolidinyl)-2(1H)-pyridinone: The compound of Ex. 68, Part A (0.50 g, 2.86 mmol) and pyrrolidine (0.72 mL, 8.58 mmol) were added together with 30 mL of ethanol. The mixture was refluxed under $N_2$ for 15 minutes. The solvent was removed. The residue was added with $CH_2Cl_2$ and washed with 1N aqueous HCl. The $CH_2Cl_2$ solution was washed with brine, dried over MgSO$_4$, and concentrated to a yellow solid (0.52 g). $^1$H NMR (CDCl$_3$+MeOD-d$_4$) δ 7.21 (d, 1H), 5.98 (d, 1H); 3.40 (m, 4H), 2.01 (m, 4H). MS (AP$^+$): 210.1, (M+H)$^+$.

Part C: 1-(4-bromophenyl)-3-nitro-4-(1-pyrrolidinyl)-2(1H)-pyridinone: The compound of Ex. 68, Part B (0.52 g, 2.49 mmol), 4-bromophenylboronic acid (0.75 g, 3.74 mmol), copper acetate (0.92 g, 4.98 mmol), triethylamine (0.70 mL, 4.98 mmol), and pyridine (0.40 mL, 4.98 mmol) were added together with 20 mL of $CH_2Cl_2$. Molecular sieves (4 Å) were added. The mixture was equipped with a drying tube and stirred at RT for 36 h. The mixture was filtered through Celite® and washed with $CH_2Cl_2$. The filtrate was concentrated and chromatographed with $CH_2Cl_2$ and the EtOAc to give 0.80 g of the desired product. $^1$H NMR (CDCl$_3$) δ 7.53–7.48 (d, 2H), 7.22 (d, 4H), 7.18 (d, 1H), 5.91 (d, 1H), 4.20 (m, 4H), 2.00 (m, 4H). MS (AP$^+$): 363, 365, (M+H)$^+$.

Part D: 3-amino-1-(4-bromophenyl)-4-(1-pyrrolidinyl)-2(1H)-pyridinone: To the compound of Ex. 68, Part C (0.55 g, 1.52 mmol) in 30 mL of EtOAc was added SnCl$_2$ (2.68 g). The mixture was refluxed for 1 h under $N_2$. It was cooled to RT, filtered through Celite®, and washed with EtOAc. The organic layer washed with brine, dried with Na$_2$SO$_4$, and concentrated to give 0.57 g of the title compound as a yellowish solid. $^1$H NMR δ 7.53–7.48 (dd, 2H), 7.23–7.18 (dd, 2H), 6.75–6.72 (d, 1H), 6.02–6.99 (d, 1H), 3.39–3.34 (t, 4H), 1.94–1.84 (m, 4H).

Part E: 3-{[1-(4-bromophenyl)-2-oxo-4-(1-pyrrolidinyl)-1,2-dihydro-3-pyridinyl]amino}benzonitrile: The compound of Ex. 68, Part D (0.57 g, 1.70 mmol), 3-cyanophenylboronic acid (375 mg g, 2.55 mmol), pyridine (0.27 mL, 3.74 mmol), triethylamine (0.53 mL, 3.74 mmol), copper acetate (616 mg, 3.40 mmol), and 4 Å molecular sieves were added together with $CH_2Cl_2$ (20 mL). The mixture was stirred at RT with a drying tube for 1 h. It was filtered through Celite®, washed with $CH_2Cl_2$, concentrated, and chromatographed with $CH_2Cl_2$ to give 1.00 g of a yellow solid as the desired product. $^1$H NMR (CDCl3) δ 7.58–7.53 (dd, 2H), 7.28–7.23 (dd, 2H), 7.20–7.18 (d, 1H), 7.12–7.09 (d, 1H), 7.02–7.70 (dd, 1H), 6.90–6.87 (dd, 1H), 6.75–6.73 (t, 1H), 6.07–6.04 (d, 1H), 5.81 (s, 1H), 3.48–3.44 (t, 4H), 1.88–1.82 (m, 4H); MS (ES$^+$): 435.3–437.3 (M+H)$^+$.

Part F: 3-{[1-(2'-formyl[1,1'-biphenyl]-4-yl)-2-oxo-4-(1-pyrrolidinyl)-1,2-dihydro-3-pyridinyl]amino}-benzonitrile: The compound of Ex. 68, Part E (0.12 g, 0.275 mmol), 2-formylphenylboronic acid (82 mg, 0.55 mmol), potassium phosphate (234 mg, 1.10 mmol), and tetrakis(triphenylphosphine)palladium (31 mg, 10% mmol) were added together with 100 mL of dioxane. The mixture was degassed and then refluxed for 20 h under $N_2$. After cooling to room temperature, the mixture was filtered through Celite®, washed with EtOAc and $CH_2Cl_2$, the filtrate was concentrated, and the residue chromatographed with $CH_2Cl_2$ to give 0.11 g of the desired product. $^1$H NMR (CDCl$_3$) δ 10.00 (s, 1H), 8.07–8.03 (dd, 1H), 7.70–7.65 (t, 1H), 7.63–7.40 (m, 8H), 7.7.30–7.24 (m, 1H), 7.15–7.13 (d, 1H), 7.08–7.05 (d, 1H), 6.69 (s, 1H), 6.37–6.35 (d, 1H), 3.62 (bs, 4H), 1.94–1.90 (bs, 4H); MS (ES$^+$): 461.3, (M+H)$^+$.

Part G: 3-{[1-{2'-[(3-hydroxycyclopentyl)methyl][1,1'-biphenyl]-4-yl}-2-oxo-4-(1-pyrrolidinyl)-1,2-dihydro-3-pyridinyl]amino}benzonitrile: To a solution of the compound of Ex. 68, Part F (0.11 g, 0.239 mmol) in 8 mL of 1,2-dichloroethane was added 3-(R)-pyrrolidinol (0.06 mL, 0.717 mmol). The mixture was stirred for 30 min under N₂, then NaBH(OAc)₃ (101 mg, 0.478 mmol) was added. The resulting mixture was stirred overnight under N₂. The solvent was removed and H₂O was added. It was extracted with EtOAC, dried over Na₂SO₄, and concentrated to give 0.10 g of the desired product. MS (ES⁺): 532.4, (M+H)⁺.

Part H: 3-[[1,2-dihydro-1-[2'-[(3-hydroxy-1-pyrrolidinyl)methyl][1,1'-biphenyl]-4-yl]-2-oxo-4-(1-pyrrolidinyl)-3-pyridinyl]amino]-benzenecarboximidamide:

A solution of the compound of Ex. 68, Part G (0.10 g) in MeOH was cooled at 0° C. with an ice bath, and HCl gas was bubbled in for 15 minutes. The reaction mixture was sealed and put in a refrigerator over the weekend. The solvent was removed and the residue was dried under vacuum to give 0.10 g of the intermediate. MS (ES⁺): 564.5, M+H. The resulting intermediate (50 mg, 0.12 mmol) was dissolved in 8 mL of MeOH. Ammonium acetate (55 mg, 0.72 mmol) was added. The mixture was sealed and stirred at RT overnight. The solvent was removed and the residue was purified by HPLC (C18 reverse phase) with 5% TFA in acetonitrile/water to give 52 mg of the benzamidine TFA salt. ¹H NMR (CD₃OD) δ 7.75–7.25 (bs, 1H, 7.58–7.39 (m, 9H), 7.37–7.26 (t, 1H), 7.03–6.97 (dd, 1H), 6.92–6.82 (bm, 2H), 6.38–6.30 (d, 1H), 4.59–4.33 (bs, 4H), 3.62–3.50 (bs, 4H), 3.25–3.30 (bm, 1H), 3.30–2.80 (bm, 3H), 2.20–1.97 (bm, 1H), 1.86–1.78 (bs, 4H); MS (ES⁺): 549.5, (M+H)⁺. HPLC purity >95%.

Example 69

3-[[1,2-dihydro-1-[2'-[(3-hydroxy-1-pyrrolidinyl)methyl][1,1'-biphenyl]-4-yl]-2-oxo-4-(1-pyrrolidinyl)-3-pyridinyl]amino]-benzamide

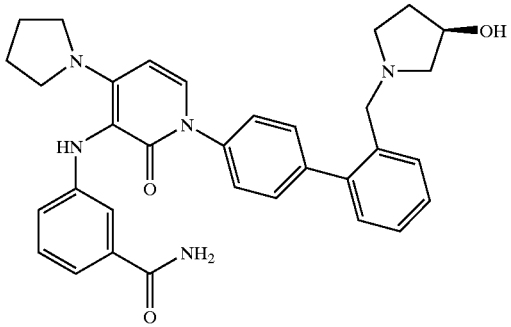

This compound was isolated as a by-product from Part H of Example 68. ¹H NMR (CD₃OD) δ 7.75–7.63 (bs, 1H), 7.58–7.38 (m, 9H), 7.25–7.17 (t, 1H), 7.15–7.11 (d, 1H), 7.07–7.05 (s, 1H), 6.77–6.72 (d, 1H), 4.63–4.58 (bs, 1H), 4.46–4.42 (d, 1H), 4.41–4.33 (bs, 2H), 3.63–3.53 (bm, 4H), 3.25–3.30 (bm, 1H), 3.30–3.28(bm, 3H), 2.20–1.97 (dm, 1H), 1.86–1.78 (bs, 4H); MS (ES⁺): 550.2, (M+H)⁺. HPLC purity >95%.

Example 70

3-[3-(2'-Methanesulfonyl-biphenyl-4-yl)-2-oxo-tetrahydro-pyrimidin-1-ylmethyl]-benzamidine

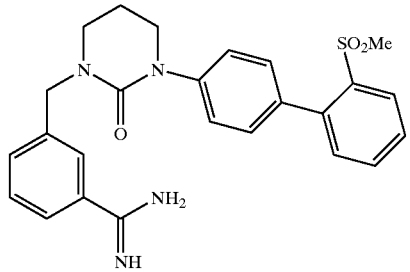

Part A: 1-(4-Bromophenyl)-tetrahydropyrimidin-2-one: 4-Bromophenylisocyanate (5.00 g, 25.3 mmol), and 3-bromopropylamine hydrobromide (5.53 g, 25.3 mmol) were mixed together with 200 mL of CH₂Cl₂. Triethylamine (3.5 mL, 25.3 mmol) was added. The mixture was stirred at RT under N₂ for 2 h. The solvent was removed, the resulting solid was washed with water and dried (8.0 g). The solid was refluxed in benzene (200 mL) and 50% aqueous NaOH (50 mL) for 2 h. The reaction mixture was cooled, diluted with EtOAc, and was then washed with water and brine, dried over MgSO₄ and concentrated to a white solid (6.50 g). ¹H NMR (CDCl₃) δ 7.46 (d, 2), 7.18 (d, 2), 4.92 (bs, 1H), 3.68 (t, 2H), 3.42 (m, 2H), 2.09 (m, 2H). MS (AP⁺): 254.9, 256.9, (M+H)⁺.

Part B: 3-[3-(4-Bromophenyl)-2-oxo-tetrahydropyrimidin-1-ylmethyl]-benzonitrile: The compound from Ex. 70, Part A (0.52 g, 2.04 mmol) was dissolved in 6 mL of DMF. NaH (98 mg of 60% dispersion) was added. The mixture was stirred at room temperature under N₂ for ½ h and α-bromo-m-tolunitrile (0.42 g, 2.14 mmol) was added. The resulting mixture was stirred at RT for 12 h. The reaction mixture was poured into water and extracted with EtOAc. The organic mixture was washed with water and brine, dried over MgSO₄, concentrated, and purified by chromatography on silica gel eluted with EtOAC/hexane (1:3) to give 0.37 g of the desired product. ¹H NMR (CDCl₃) δ 7.59 (m, 3), 7.43 (m, 3H), 7.19 (d, 2), 4.62 (s, 2H), 3.71(t, 2H), 3.32 (t, 2H), 2.10 (m, 2H). MS (AP⁺): 372.0, (M+H)⁺.

Part C: 3-[3-(2'-Methylthio-biphenyl-4-yl)-2-oxo-tetrahydro-pyrimidin-1-ylmethyl]-benzonitrile: The compound of Ex. 70, Part B (0.37 g, 1.0 mmol), 2-methylthiophenylboronic acid (0.34 g, 2.0 mmol), K₃PO₄ (0.85 g, 4.0 mmol), tetrakis-(triphenylphosphine) palladium (0) 57 mg), and dioxane (16 mL) were refluxed under N₂ for 12 h. The reaction mixture was cooled and diluted with EtOAc. It was washed with water and brine, dried over MgSO₄, concentrated, and purified by chromatography on silica gel eluted with EtOAC/hexane (2:3) to give 0.34 g of the desired product. ¹H NMR (CDCl₃) δ 7.60 (m, 3), 7.49–7.18 (m, 9H), 4.62 (s, 2H), 3.80 (t, 2H), 3.37 (t, 2H), 2.38 (s, 3H), 2.05 (m, 2H). MS (ES⁺): 414.4, (M+H)⁺.

Part D: 3-[3-(2'-Methylsulfonyl-biphenyl-4-yl)-2-oxo-tetrahydro-pyrimidin-1-ylmethyl]-benzonitrile: The compound of Ex. 70, Part C (0.31 g, 0.75 mmol) was dissolved in CH₂Cl₂ (16 mL). The mixture was cooled at 0° C. and m-CPBA (0.52 g of 70%) was added. The mixture was stirred at RT under N₂ for 12 h. The reaction was quenched with aqueous Na₂SO₃, diluted with CH₂Cl₂. It was washed with saturated aqueous NaHCO₃ and brine, dried over MgSO₄, concentrated, and purified by chromatography on silica gel eluted with EtOAC/hexane (2:3) to give 0.11 g of the desired product. $^1$H NMR (CDCl$_3$) δ 8.24 (d, 1H), 7.60 (m, 5), 7.0 (m, 6H), 4.65 (s, 2H), 3.82 (t, 2H), 3.39 (t, 2H), 2.67 (s, 3H), 2.15 (m, 2H). MS (ES$^+$): 446.4, (M+H)$^+$.

Part E: 3-[3-(2'-Methylsulfonyl-biphenyl-4-yl)-2-oxo-tetrahydro-pyrimidin-1-ylmethyl]-benzamidine: The compound of Ex. 70, Part D (0.11 g, 0.25 mmol) was dissolved in 6 mL of MeOH and 12 mL of CHCl$_3$. The mixture was cooled in an ice-bath and HCl gas was bubbled in for 15 minutes. The reaction flask was sealed and placed in the refrigerator for 12 h. The solvents were removed and the resulting solid was dried under vacuum. The solid was then dissolved in 10 mL of MeOH and Ammonium acetate (0.28 g, 1.48 mmol) was added. The mixture was sealed and stirred at RT overnight. The solvent was removed and the residue was purified by HPLC (C18 reverse phase) with 5% TFA in acetonitrile/water to give 72 mg of the benzamidine TFA salt. $^1$H NMR (DMSO-d$_6$) δ 9.38 (bs, 2H), 9.10 (bs, 2H), 8.12 (d, 1H), 7.70 (m, 5H), 7.38 (m, 4H), 4.62 (s, 2H), 3.78 (t, 2H), 3.39 (t, 2H), 2.82 (s, 3H), 2.08 (m, 2H). MS (ES$^+$): 463.5, (M+H)$^+$; HPLC purity 96%.

Example 71

4-Benzyloxycarbonyl-3-(4-chlorobenzenesulfonylamino)-1-(2'-methanesulfonyl-biphenyl-4-yl)-2-oxo-piperazine

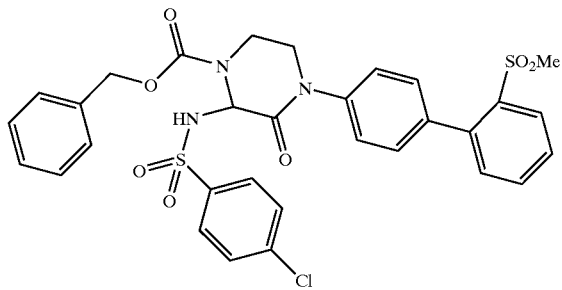

Part A: 4-Benzyloxycarbonyl-1-(4-bromophenyl)-2-oxo-piperazine: 4-Benzyloxycarbonylpiperazin-2-one (18.6 mmol), 4,5-bis(diphenyl-phosphino)-9,9-dimethylxanthene (2.79 mmol), cesium carbonate (27.9 mmol) and palladium acetate (1.86 mmol) were placed in a round bottom flask and it was evacuated and flushed with N$_2$ (3×). Dioxane (200 mL) and p-bromoiodobenzene (18.6 mmol) were then added and evacuation and flushing with N$_2$ were repeated as above. The resulting mixture was heated to 75° C. overnight then cooled and diluted with dichloromethane. The solution was filtered through a pad of Celite® and concentrated to dryness. The residue was purified by flash chromatography eluting with 1:2 EtOAc/Hex to give the product as a yellow solid (48.9%). $^1$H NMR (CDCl$_3$, 300 MHz) δ 7.53 (d, J=8.8 Hz, 2H), 7.37 (m, 5H), 2.87 (d, J=8.7 Hz, 2H), 5.19 (s, 2H), 4.33 (s, 2H), 3.87 (m, 2H), 3.74 (m, 2H); mass spectrum, ESI (M−H) 387.3, 389.3.

Part B. 3-Azido-4-benzyloxycarbonyl-1-(4-bromophenyl)-2-oxo-piperazine: To a solution of the compound of Ex. 71, Part A (1.29 mmol) in 15 mL THF at −78° C. was added 0.5 M KHMDS (1.42 mmol, 2.84 mL) dropwise. After stirring at −78° C. for 5 min, trisyl azide (3.22 mmol) in 5 mL THF was added and stirring was continued for another 5 min before acetic acid (5.80 mmol, 332 μL) was added. The reaction was allowed to warm to room temperature (30 min). The mixture was diluted with saturated ammonium chloride and extracted three times with ethyl acetate. The combined organic layers were washed once with brine, dried (MgSO$_4$), filtered and concentrated in vacuo to give a yellow residue which was purified by flash chromatography on silica gel eluting with 1:1 EtOAc:Hex to give the azide as an off-white oil (74.4%). IR (KBr) 2107 (N$_3$); 1H NMR (CDCl$_3$, 300 MHz) δ 7.54 (d, J=8.7 Hz, 2H), 7.39 (br s, 5H), 7.18 (d, J=8.8 Hz, 2H), 6.0 (br s, 1H), 5.24 (s, 2H), 4.10 (m, 1H), 3.82 (m, 1H), 3.68 (m, 2H). Mass spectrum, ESI (M+Na) 452.1, 454.1.

Part C. 3-Amino-4-benzyloxycarbonyl-1-(4-bromophenyl)-2-oxo-piperazine A solution of the compound of Ex. 71, Part B (0.83 mmol) in 2 mL methanol was added slowly to a stirred suspension of SnCl$_2$ (1.2 mmol) in 5 mL of methanol at 0° C. The mixture was allowed to warm to room temperature after the addition was over and stirring was continued for another 15 min. Methanol was then removed under reduced pressure and the residue was diluted with cold water and made alkaline with 1N NaOH solution. Dichloromethane was added and the biphasic solution was filtered through a sintered glass funnel. The layers were then separated and the aqueous layer was saturated with NaCl and re-extracted with dichloromethane. The combined organic layers were dried (MgSO$_4$) and concentrated to give the product as an off-white foam (96.7%). $^1$H NMR (CDCl$_3$, 300 MHz) δ 7.53 (d, J=8.8 Hz, 2H), 7.38 (m, 5H), 7.17 (d, J=8.8 Hz, 2H), 5.54 (s, 1H), 5.21 (s, 2H), 4.16 (br m, 1H), 3.89 (m, 1H), 3.72 (m, 1H), 3.59 (m, 1H). Mass spectrum, ESI (M+H) 404.1, 406.1.

Part D. 4-Benzyloxycarbonyl-3-(4-chlorosulfonylamino)-1-(4-bromophenyl)-2-oxo-piperazine To a solution of the compound of Ex. 71, Part C (0.50 mmol) in 5 mL dichloromethane was added p-chlorobenzene-sulfonyl chloride (0.74 mmol) and then pyridine (0.60 mL) at room temperature. Solution turned bright yellow after the addition of pyridine. After stirring for an additional 5 min, the mixture was diluted with 1N HCl and then it was extracted three times with ethyl acetate. The combined organic layers were then washed once with brine, dried (MgSO$_4$), filtered and concentrated under vacuo to give a orange residue which was purified by flash chromatography on silica gel eluting with 0–50% EtOAc/Hex to give the sulfonamide product as a white foam (71%). $^1$H NMR (CDCl$_3$, 300 MHz) δ 7.82 (br s, 2H), 7.53 (d, J=8.4 Hz, 2H), 7.40 (br s, 7H), 7.13 (d, J=8.4 Hz, 2H), 5.70 (br m, 2H), 5.18 (s, 2H), 4.18 (br m, 1H), 3.82 (m, 2H), 3.59 (m, 1H). Mass spectrum, ESI (M+H) 578.3, 580.3, (M+Na) 600.2, 602.3.

Part E. 4-Benzyloxycarbonyl-3-(4-chlorobenzenesulfonyl-amino)-1-(2'-(methylthio)-biphenyl-4-yl)-2-oxo-piperazine: The compound of Ex. 71, Part D (0.32 mmol), 2-methylthioboronic acid (0.48 mmol), potassium carbonate (1.3 mmol), and tetrakis(triphenylphosphine)palladium(0) (5 mol %) were placed in a round bottom flask which was flushed twice with N$_2$. To this mixture was added 2:1 toluene/ethanol (15 mL) and the resulting mixture was flushed again with N$_2$ (2×). The mixture was heated to reflux for one hour. The solution was then cooled to room temperature, diluted with water and extracted two times with ethyl acetate. The combined organic extracts were washed with brine, dried (MgSO$_4$), filtered and concentrated under vacuo to give an oil which was purified by flash column chromatography eluting with 1:1 EtOAc:Hex to give the product as an off-white foam (85.9%). $^1$H NMR (CDCl$_3$, 300 MHz) δ 7.80 (br d, 2H), 7.43 (d, J=8.4 Hz, 2H), 7.38 (m, 9H), 7.13 (d, J=8.4 Hz, 2H), 7.20 (m, 2H), 5.72 (s, 1H), 5.68 (br s, 1H), 5.20 (s, 2H), 4.20 (br m, 1H), 3.80 (m, 3H). Mass spectrum, ESI (M+H) 622.4, 624.4, (M+Na) 644.4, 646.4.

Part F. 4-Benzyloxycarbonyl-3-(4-chlorobenzenesulfonyl-amino)-1-(2'-methanesulfonyl-biphenyl-4-yl)-2-oxopiperazine: To a mixture of the compound of Ex. 71, Part E (0.261 mmol) in dichloromethane was added MCPBA (0.652 mmol). After stirring at room temperature for five hours, the mixture was quenched with saturated NaHCO$_3$ and extracted three times with ethyl acetate. The combined organic extracts were washed with once with brine, dried (MgSO$_4$), filtered and concentrated to dryness to give an oily residue which was purified by with flash column chromatography eluting with 3:1 EtOAc/Hex to afford the title compound as a white foam (73.3%). $^1$H NMR (CDCl$_3$, 300 MHz) δ 8.23 (d, J=7.7 Hz, 1H), 7.90 (br s, 2H), 7.61 (m, 2H), 7.52 (d, J=8.4 Hz, 2H) 7.41 (br m, 5H), 7.36 (m, 3H), 7.35 (d, J=8.7 Hz), 5.70 (s, 1H), 5.60 (br s, 1H), 5.21 (s, 2H), 4.23 (br m, 1H), 3.85 (m, 2H), 3.70 (m, 1H). Mass spectrum, ESI (M+Na) 676.4, 678.4, (M−H) 652.4, 654.4.

Example 72

4-Benzyloxycarbonyl-3-(4-methoxybenzenesulfonylamino)-1-(2'-methanesulfonyl-biphenyl-4-yl)-2-oxo-piperazine

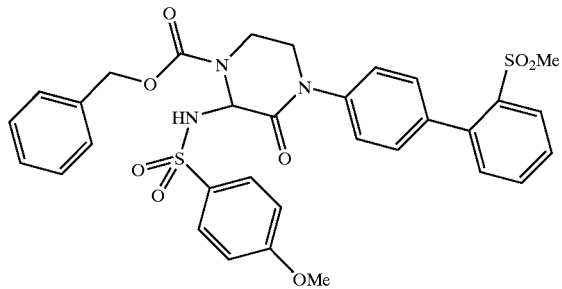

This compound was prepared from the compound of Ex. 71, Part C using 4-methoxysulfonyl chloride and following the same procedures as described for Ex. 71 above. MS (ESI) 650.3 (M+H)$^+$, 672.3 (M+Na)$^+$.

Example 73

5-Chloro-N-[2-(3-fluoro-2'-methanesulfonyl-biphenyl-4-yl)-3-oxo-1,2,3,4-tetrahydro-isoquinolin-4-yl]-thiophene-2-sulfonamide

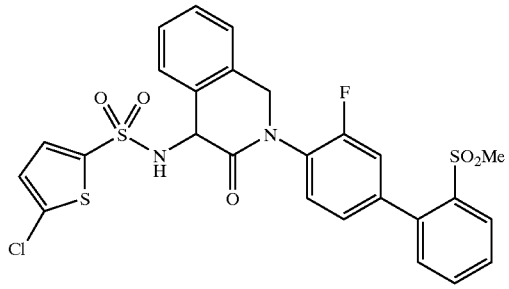

Part A. N-(3-Fluoro-2'-methanesulfonyl-biphenyl-4-yl)-2-(2-hydroxymethylphenyl)-acetamide: To a solution of 2-fluoro-4-[(2-methylsulfonyl)phenyl]aniline (2.43 mmol) in 10 mL of xylene was added 2 M trimethylaluminum in toluene (4 eq). After the addition, stirring was continued at room temperature for 30 min before isochromanone (2 eq) was added in one portion. An exothermic reaction ensued which was further refluxing for three hours, after which the mixture was cooled and then was poured into slurry of silica gel and chloroform. This mixture was stirred for 5 min and then filtered through a sintered glass funnel eluting with methanol. The filtrate was evaporated and the yellow residue was purified by flash column chromatography eluting with 20% EtOAc/Hex to give the amide as an off-white foam (89%). Mass spectrum, ESI (M+H) 414.3, (M+Na) 436.3.

Part B. 2-(2-bromomethylphenyl)-N-(3-Fluoro-2'-methanesulfonyl-biphenyl-4-yl)acetamide: To a mixture of the compound of Ex. 73, Part A (0.38 mmol) in 3 mL of dichloromethane was added phosphorous tribromide (1.3 eq) dropwise at 0° C. After stirring for 5 min at room temperature, the mixture was diluted with water and extracted two times with chloroform. The combined organic extracts were washed once with brine, dried (MgSO$_4$), filtered and concentrated under vacuo to give the bromide as an off-white foam (98%). This compound was not further purified and was carried directly on to the next step. Mass spectrum, ESI (M+H) 476.3, 478.3, (M+Na) 498.3, 500.3.

Part C. 2-(3-Fluoro-2'-methanesulfonyl-biphenyl-4-yl)-1,4-dihydro-2H-isoquinolin-3-one: To a solution of the compound of Ex. 73, Part B (0.36 mmol) in 3 mL of THF was added sodium hydride (2 eq) in one portion at 0° C. After stirring for 5 min, the mixture was diluted with water and extracted two times with ethyl acetate. The combined organic extracts were washed once with brine, dried (MgSO$_4$), filtered and concentrated to dryness to give yellow residue which was purified with flash chromatography eluting with 50% EtOAc/Hex to give the product as an off-white foam (84%). Mass spectrum, ESI (M+H) 396.3.

Part D. 4-Azido-2-(3-fluoro-2'-methanesulfonyl-biphenyl-4-yl)-1,4-dihydro-2H-isoquinolin-3-one: To a solution of the compound of Ex. 73, Part C (0.66 mmol) in 8 mL of THF at −78° C. was added 1 M LHMDS (1.3 eq) drop-wise. After stirring for 5 min, trisyl azide (2 eq) in 3 mL of THF was added to the mixture. After stirring for another 5 min, acetic acid (4.5 eq) was added and the solution was warmed to room temperature (30 min). The mixture was quenched with saturated ammonium chloride and extracted 3 times with ethyl acetate. The organic layer was dried (MgSO4), filtered, and concentrated under vacuo to give a yellow residue which was purified by column chromatography eluting with 50% EtOAc/Hex to give the azide as foam (95%). Mass spectrum, APCI (M+1) 437.1, (M+1−N2) 409.1.

Part E. 4-Amino-2-(3-fluoro-2'-methanesulfonyl-biphenyl-4-yl)-1,4-dihydro-2H-isoquinolin-3-one: 4-Azido-2-(3-fluoro-2'-methanesulfonyl-biphenyl-4-yl)-1,4-dihydro-2H-isoquinolin-3-one: To a stirred suspension of tin(II)chloride (1.5 eq) in 3 mL methanol at 0° C. was added the compound of Ex. 73, Part D (0.48 mmol) in 2 mL of methanol drop-wise. After the addition was over, the mixture was further stirred at room temperature for 2 hours before methanol was removed under reduced pressure. The residue was diluted with water and made alkaline with 1N NaOH solution. Dichloromethane was added and the layers were separated. The aqueous layer was saturated with brine and reextracted with dichloromethane. The combined organic layer was dried with MgSO$_4$, filtered and concentrated in vacuo to give a residue. It was purifed by column chromatography eluting with 10% MeOH/CHCl$_3$ to give the amine as a film (25%). Mass spectrum, ESI (M+H) 411.3.

Part F. 5-Chloro-N-[2-(3-fluoro-2'-methanesulfonyl-biphenyl-4-yl)-3-oxo-1,2,3,4-tetrahydro-isoquinolin-4-yl]-thiophene-2-sulfonamide: To a solution of the compound of Ex. 73, Part E (0.048 mmol) and pyridine (10 eq) in 1 mL of dichloromethane was added 5-chlorothiophene-2-sulfonyl chloride (5 eq). Solution turned bright yellow instantly. After stirring for 5 min, the mixture was diluted with 1N HCl and extracted 3 times with ethyl acetate. The combined organic extracts were washed once with brine, dried (MgSO$_4$), filtered and concentrated under vacuo to give a residue which was purified by flash column chromatography eluting with 50–75% EtOAc/Hex to give the title compound as a foam (64%). $^1$H NMR (CDCl$_3$, 300 MHz) δ 8.23 (d, J=7.4 Hz, 1H), 7.83 (d, J=8.0 Hz, 1H), 7.63 (m, 2H), 7.53 (d, J=4 Hz, 1H), 7.48 (d, J=7.3 Hz, 1H) 7.30 (m, 6H), 6.97 (d, J=4.0 Hz, 1H), 6.16 (d, J=5.9 Hz, 1H), 5.10 (d, J=15.4 Hz, 1H), 4.98 (br s, 1H), 4.58 (d, J=15.4 Hz, 1H), 2.77 (s, 3H); Mass spectrum, ESI (M+H) 591.3.

Example 74

3-[1-(2'-Dimethylaminomethyl-biphenyl-4-yl)-2-oxo-azepan-3-ylamino]-benzamidine

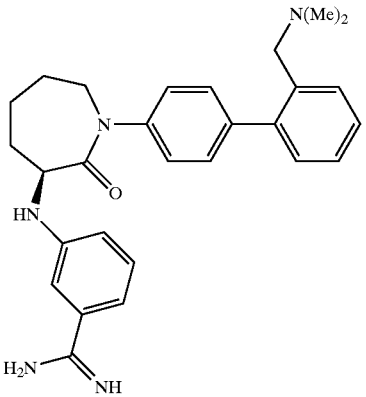

Part A. [1-(4-Bromo-phenyl)-2-oxo-azepan-3-yl]-carbamic acid tert-butyl ester: 3-t-butoxycarbonylamino-2-oxoazepane (4.4 mmol), p-bromoiodobenzene (1 eq), 4,5-bis(diphenyl-phosphino)-9,9-dimethylxanthene (0.15 eq), cesium carbonate (1.5 eq), and palladium acetate (0.1 eq) were placed in a round bottom flask and it was evacuated and flushed 3 times with nitrogen. To this solution, 45 mL of dioxane was added and the resulting solution was evacuated and flushed 3 more times with nitrogen gas. The mixture was allowed to stir at 75° C. overnight. The mixture turned from black to bright yellow suspension. The mixture was cooled and diluted with dichloromethane and then was filtered through a pad of Celite®. The filtrate was removed under reduced pressure and the residue was purified by flash column chromatography eluting with 50% EtOAc/Hex to give the desired product as an off-white foam (68%). Mass spectrum, ESI (M+H) 383.2, 385.2.

Part B. 3-Amino-1-(4-bromo-phenyl)-azepan-2-one: To a solution of the compound of Ex. 74, Part A (2.9 mmol) in 5 mL of dichloromethane was added 5 mL of trifluoroacetic acid. After stirring for 30 min, the excess solvents were evaporated off and the residue was treated with 1N NaOH and extracted 3 times with dichloromethane. The combined organic extracts were washed with brine, dried (MgSO4), filtered and concentrated under vacuo to give the deprotected amino compound as oil (98%). Mass spectrum, ESI (M+H) 283.2, 285.2.

Part C. 3-[1-(4-Bromo-phenyl)-2-oxo-azepan-3-ylamino]-benzonitrile: A mixture of the compound of Ex. 74, Part B (0.35 mmol), 3-cyanophenylboronic acid (1.5 eq), copper acetate (2 eq), triethyl amine (2 eq), pyridine (2 eq), 4 Å molecular sieves was stirred in dichloromethane for 30 min. The mixture was then filtered through a pad of silica gel eluting with ethyl acetate. The filtrate was concentrated under reduced pressure and the residue was purified by column chromatography eluting with 0–25% EtOAc/Hex to give the product as clear oil (44%). Mass spectrum, ESI (M+H) 384.2, 386.2.

Part D. 3-[1-(2'-Formyl-biphenyl-4-yl)-2-oxo-azepan-3-ylamino]-benzonitrile: The compound of Ex. 74, Part C (0.13 mmol), 2-formylphenylboronic acid (1.5 eq), potassium carbonate (4 eq), tetrakis(triphenylphosphine) palladium(0) (5 mol %) were placed in a round bottom flask and was flushed twice with N$_2$. To this mixture was added 2:1 toluene/ethanol (9 mL) and the resulting mixture was flushed again with N$_2$ (2×). The mixture was allowed to heated to reflux overnight. The solution was then cooled to room temperature, diluted with water and extracted two times with ethyl acetate. The combined organic extracts were washed with brine, dried (MgSO$_4$), filtered and concentrated under vacuo to give an oil which was purified by flash column chromatography eluting with 1:1 EtOAc:Hex to give compound the product as an off-white foam (88%). Mass spectrum, ESI (M+H) 410.3 (M+Na) 432.3.

Part E. 3-[1-(2'-Dimethylaminomethyl-biphenyl-4-yl)-2-oxo-azepan-3-ylamino]-benzonitrile: To a solution of the compound of Ex. 74, Part D (0.11 mmol) and dimethylamine hydrochloride (3 eq) in 3 mL of dichloroethane was added diisoproylethylamine (3 eq). After stirring at room temperature for 15 min, sodium triacetoxyborohydride (3 eq) was added to the mixture. After stirring at room temperature overnight, the mixture was diluted with water and extracted two times with dichloromethane. The combined organic extracts were washed with brine, dried (MgSO$_4$), filtered and concentrated under vacuo to give 14 as a yellow film (quantitative). Mass spectrum, ESI (M+H) 439.4.

Part F. 3-[1-(2'-Dimethylaminomethyl-biphenyl-4-yl)-2-oxo-azepan-3-ylamino]-benzamidine: Hydrogen chloride gas was bubbled to a solution of the compound of Ex. 74, Part E (0.21 mmol) in 20 mL of ethanol for 10 min at 0° C. The reaction was sealed with glass stopper and parafilm and was stirred at room temperature overnight. The solvent was then evaporated off and the solid residue was redissolved in ethanol (5 mL) and pyridine (50 μL). To this mixture was then added ammonium carbonate and it was further stirred at room temperature overnight. The excess solvents were evaporated off and the residue was purified by HPLC and the solvent was lypholized off to give the title compound as powder. $^1$H NMR (CD$_3$OD, 300 MHz) δ 7.67 (m, 1H), 7.57 (m, 2H), 7.40 (m, 6H), 7.02 (m, 3H), 4.65 (d, 1H), 4.39 (s, 2H), 4.30 (m, 1H), 3.80 (m, 1H), 2.65 (s, 6H), 2.18 (m, 2H), 2.00 (m, 2H), 1.82 (m, 2H); mass spectrum, ESI (M+H) 456.5.

Example 75

N-[3-Benzyl-1-(2'-methanesulfonyl-biphenyl-4-yl)-2-oxo-piperidin-3-yl]-4-chlorobenzamide

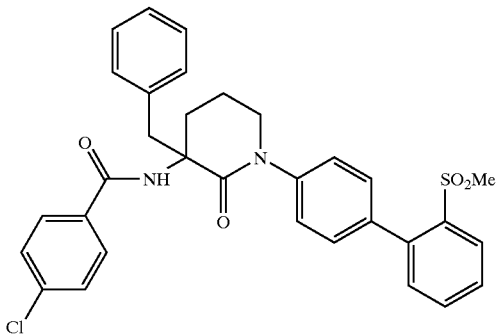

Part A. 3-Amino-1-(4-bromophenyl)-piperidin-2-one: 1-(4-Bromophenyl)-3-hydroxy-2-oxopiperidine (2.66 g, 10 mmol) was stirred in CH$_2$Cl$_2$ at 0° C. under N$_2$. Et$_3$N (2.8 mL, 1.5 eq) was added, followed by dropwise addition of MsCl (0.85 mL, 11 mmol) and addition of DMAP (150 mg). The mixture was warmed up to RT for 7 h. TLC showed completion of the reaction. EtOAc was added, washed with H₂O (1×), brine (2×), dried over MgSO₄, filtered, and concentrated to dryness. The residue was used directly for the next step without purification. It was dissolved in dry DMF (15 mL), and NaN₃ (1.9 g, 29 mmol, 2.9 eq) was added. The mixture was stirred at RT under N₂ O/N. TLC showed completion. EtOAc was added, washed with H₂O (1×), brine (2×), dried over MgSO₄, filtered, and concentrated to dryness. Flash column chromatography (silica gel, CH₂Cl₂:EtOAc=2:1 to 1:1) gave pure azide product (2.25 g, yield: 76%). ¹H NMR (300 MHz, CDCl₃) δ 7.48 (AA'BB', J=8.8 Hz, 2H), 7.13 (48 (AA'BB', J=8.8 Hz, 2H), 4.16 (dd, J=8.3, 6.0 Hz, 1H), 3.56 (m, 2H), 2.16–1.82 (m, 6H). The azide (0.77 g, 2.62 mmol) was stirred in THF (15 mL) at RT. PPh₃ (0.82 g, 3.14 mmol, 1.2 eq) was added as one single portion. The mixture was stirred at RT for 30 min until the emission of N₂ ceased. H₂O (2.9 mL) was added, and the resulting mixture was heated at 50° C. for 5 h. TLC showed completion. The mixture was cooled, and EtOAc was added. It was washed with H₂O (1×), brine (2×), dried over MgSO₄, filtered, and concentrated to dryness. Flash column chromatography (silica gel, CH₂C12, then Et₃N:EtOAc:CH₃OH= 1:50:10 to 2:50:10) gave the amine product as colorless solid (0.70 g, yield: 100%). ¹H NMR (300 MHz, CDCl₃) δ 7.50 (AA'BB', J=8.8 Hz, 2H), 7.14 (AA'BB', J=8.8 Hz, 2H), 3.70 (m, Ha, 1H), 3.57 (m, 2H), 2.31 (m, Hb, 1H), 2.05 (m, 2H), 1.82 (m, 1H).

Part B. 3-Amino-3-benzyl-1-(4-bromophenyl)-piperidin-2-one: The product of Ex 75, Part A (0.61 g, 2.27 mmol) was stirred at 0° C. in dry CH₂Cl₂ (6 mL) under N₂. Benzaldehyde (0.23 mL, 1.0 eq) was added, followed by the addition of MgSO₄ (0.65 g) and Et₃N (0.64 mL, 2.0 eq). The mixture was slowly warmed to RT for 24 h. CH₂Cl₂ (5 mL) was added and stirred for 10 h more. The mixture was filtered, rinsed with Et₂O, washed with H₂O (2×), brine (2×), dried over MgSO₄, filtered, and concentrated to dryness (0.71 g, yield: 88%). The compound was directly used for the next step without purification. ¹H NMR (300 MHz, CDCl₃) δ 8.46 (s, 1H), 7.78 (m, 2H), 7.50 (AA'BB', J=8.8 Hz, 2H), 7.42 (m, 3H), 7.18 (AA'BB', J=8.4 Hz, 2H), 4.10 (t, J=5.9 Hz, 1H), 3.76 (m, 2H), 2.39 (m, 1H), 2.24 (m, 2H), 2.03 (m, 1H). Potassium t-butoxide (0.24 g, 2.16 mmol) was dissolved in dry THF (2 mL) under N₂. A solution of the Schiff base prepared above (0.70 g, 1.97 mmol) in THF (3 mL) was added dropwise to the above stirring solution at RT. The mixture was then stirred at RT for 40 min. PhCH₂Br (0.24 mL, 2.02 mmol) was added to the dark brown solution as one single portion. The color changed to orange yellow. The resulting solution was stirred at RT for 24 h. ¹H NMR (300 MHz, CDCl₃) δ 8.68 (s, 1H), 7.78 (m, 2H), 7.54 (AA'BB', J=8.4 Hz, 2H), 7.47 (m, 3H), 7.33 (m, 5H), 7.08 (AA'BB', J=8.6 Hz, 2H), 3.56 (d, J=12.8 Hz, Ha, 1H), 3.45 (m, 2H), 2.98 (d, J=13.4 Hz, Hb, 1H), 2.24 (m 1), 2.06 (m, 2H), 1.78 (m, 1H). The mixture was dissolved in Et₂O (3 mL), and 1N HCl (20 mL) was added. The reaction was stirred at RT for 5 h. LC-MS showed completion of the reaction. The mixture was extracted with Et₂O (2×). The aqueous layer was basified with 1N NaOH, then extracted with Et₂O (3×), washed with brine, dried over MgSO₄, and concentrated to give the amine product (0.61 g, yield: 87%). ¹H NMR (300 MHz, CDCl₃) δ 7.47 (AA'BB', J=8.8 Hz, 2H), 7.25 (m, 5H), 7.06 (AA'BB', J=8.8 Hz, 2H), 3.49 (m, Ha1, 1H), 3.38 (m, Hb2, 1H), 3.22 (d, J=12.9 Hz, Ha1, 1H), 2.83 (d, J=13.2 Hz, Hb2, 1H), 1.99–1.80 (m, 6H).

Part C. N-[3-Benzyl-1-(4-bromophenyl)-2-oxo-piperidin-3-yl]-4-chlorobenzamide: The compound of Ex. 75, Part B (0.19 g, 0.53 mmol) and p-chlorobenzoyl chloride (0.10 mL, 0.79 mmol) were stirred in dry CH₂Cl₂ (4 mL) at RT under N₂. Disopropylethylamine (0.18 mL, 1.03 mmol) was added dropwise, followed by the addition of DMAP (40 mg). The reaction mixture was stirred at RT for 6 h. It was then quenched with sat'd NH₄Cl, extracted with EtOAc, washed with brine (2×), dried over MgSO₄, and concentrated to dryness. Flash column chromatography (silica gel, hexanes:EtOAc=1:0 to 10:1, to 4:1, then to 1:1) gave the desired product as a colorless amorphous solid (0.23 g, 87%). ¹H NMR (300 MHz, CDCl₃) δ 7.63 (d, J=8.4 Hz, 2H), 7.52 (d, J=8.4 Hz, 2H), 7.34 (m, 4H), 7.28 (m, 3H), 7.19 (d, J=8.4 Hz, 2H), 3.81 (td, J=11.2, 4.6 Hz, 1H), 3.49 (d, J=13.2 Hz, Ha1, 1H), 3.42 (m, 1H), 3.18 (d, J=13.2 Hz, Hb1, 1H), 2.47 (m, 2H), 1.87 (m, 2H).

Part D. N-[3-Benzyl-1-(2'-methanesulfonyl-biphenyl-4-yl)-2-oxo-piperidin-3-yl]-4-chlorobenzamide: The compound of Ex. 75, Part C (0.18 g, 0.36 mmol) and 2-(methylthio) phenylboronic acid (91.5 mg, 0.54 mmol, 1.5 eq) were stirred in toluene (3 mL). Water (0.5 mL) was added followed by Na₂CO₃ (104 mg), then Pd(PPh₃)₄ (41 mg, 0.035 mmol, 10% mol). The mixture was degassed (3×), and heated at 90–100° C. overnight. TLC showed completion. EtOAc was added, extracted with sat'd NH₄C₁, H₂O, then brine, and dried over MgSO₄, and concentrated to dryness. Flash column chromatography (silica gel, hexanes:EtOAc= 1:0 to 1:1) gave the product as colorless crystals (yield: 0.189 g, 96.4%). ¹H NMR (CDCl₃,300 MHz) δ 7.64 (d, J=8.4 Hz, 2H), 7.47 (d, J=8.0 Hz, 2H), 7.45–7.20 (m, 13H), 3.87 (m, 1H), 3.61 (d, J=13.2 Hz, 1H), 3.60 (m, 1H), 3.33 (d, J=13.2 Hz, 1H), 2.71 (m, 1H), 2.50 (m, 1H), 2.38 (s, 3H), 1.97 (m, 2H). RP LC-MS (10–90% CH₃CN in H₂O, t_R=2.87 min) 541.2 (M+H). This product (8 mg, 14.9 mmol) was dissolved in CH₂Cl₂ (1 mL) and stirred at RT under N₂. MCPBA (33 mg, 190 mmol, 13 eq) was added. The mixture was stirred at RT for 1 h. LC-MS showed completion. EtOAc was added, extracted with sat'd NaHCO₃ (2×), brine (2×), dried over MgSO₄, and concentrated to dryness. Flash column chromatography (silica gel, CH₂Cl₂:EtOAc=1:0 then 1:1) gave the product with ~90% purity. This residue was purified by RP LC-MS to give the title compound as a colorless solid (6 mg, yield: 71%). ¹H NMR (300 MHz, CDCl₃) δ 7.64 (d, J=8.4 Hz, 2H), 7.47 (d, J=8.0 Hz, 2H), 7.45–7.20 (m, 13H), 3.98 (m, 1H), 3.65 (m, 1H), 3.59 (d, J=13.6 Hz, Ha1, 1H), 3.29 (d, J=13.2 Hz, Hb1, 1H), 2.71 (m, 1H), 2.50 (m, 1H), 2.68 (s, 3H), 2.60 (m, 2H), 2.01 (m, 2H). RP LC-MS (10–90 CH₃CN in H₂O, t_R=2.50 min) 573.6 (M+H), 595.2 (M+Na)

Example 76

[3-(6-Chloro-naphthalene-2-sulfonylamino)-1-(2'-methanesulfonyl-biphenyl-4-yl)-2-oxo-piperidin-3-yl]-acetic acid methyl ester

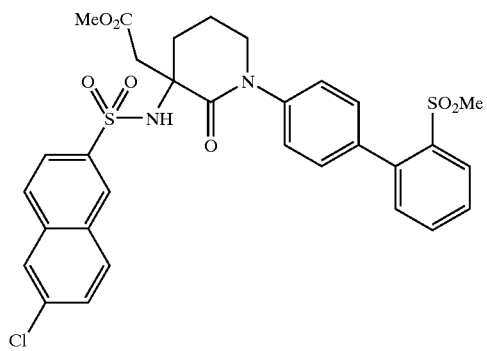

The title compound was prepared from the compound of Ex. 75, Part A in similar fashion by using BrCH₂COOMe in place of benzyl bromide as the alkylating reagent in the procedure of Ex. 75, Part B. $^1$H NMR (300 MHz, $CD_3COCD_3$) δ 8.52 (s, br, 1H), 8.14–8.02 (m, 5H), 7.73 (m, 1H), 7.63 (m, 2H), 7.39 (m, 3H), 7.16 (m, 2H), 3.70 (m, 2H), 3.57 (s, 3H), 3.08 (m, 4H). 2.65 (s, 3H). RP LC-MS (35–98% $CH_3CN$ in $H_2O$, $t_R$=5.27 min in a 9-min run): 583.4 (M+H).

Example 77

6-Chloronaphthalene-2-sulfonic acid [1-benzyl-4-(2'-dimethylaminomethylbiphenyl-4-yl)-5-oxo-[1,4]-diazepan-6-yl]amide

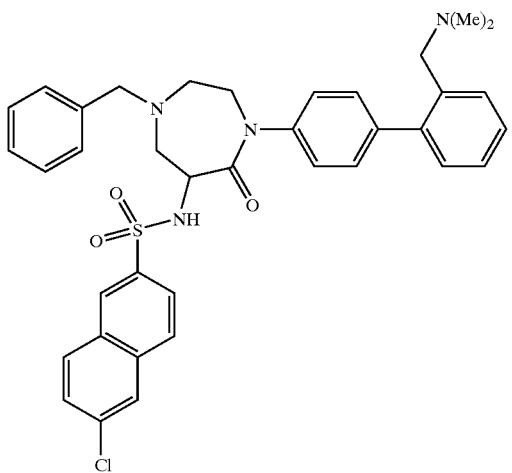

Part A. 1-Benzyl-4-(4-bromo-phenyl)-[1,4]diazepan-5-one: Commercially available 1-benzyl-(1,4)-diazepan-5-one (14.7 mmol), p-bromoiodobenzene (1 eq), 4,5-bis(diphenylphosphino)-9,9-dimethylxanthene (0.15 eq), cesium carbonate (1.5 eq), and palladium acetate (0.1 eq) were placed in a round bottom flask and it was evacuated and flushed 3× with nitrogen. To this mixture was then added 200 mL of dioxane and the resulting solution was again evacuated and flushed 3× times with nitrogen gas. The mixture was allowed to stir at 75° C. overnight during which time the mixture turned from brown to bright yellow suspension. The mixture was cooled and diluted with dichloromethane and then was filtered through a pad of celite. The filtrate was removed under reduced pressure and the residue was purified by flash column chromatography eluting with 50% EtOAc/Hex to give compound 1 as an off-white solid (63%). Mass spectrum, ESI (M+H) 359.3, 361.3.

Part B. 6-Azido-1-benzyl-4-(4-bromo-phenyl)-[1,4] diazepan-5-one: To a solution of diisopropylamine (1.3 eq) in 1 mL THF at −78° C. was added 2.5 n-BuLi (1.3 eq) dropwise. After stirring at −78° C. for 15 min, a solution of the compound of Ex. 77, Part A (0.56 mmol) in 1 mL of THF was added dropwise. After another 15 min, a solution of trisyl azide (1.3 eq) in 1 mL THF was added and stirring was continued for another 5 min before acetic acid (1.3 eq) was added. The reaction was allowed to warm to room temperature overnight. The mixture was diluted with saturated ammonium chloride and extracted three times with ethyl acetate. The combined organic layers were washed once with brine, dried ($MgSO_4$), filtered and concentrated under vacuo to give a yellow residue which was purified by flash column chromatography eluting with 30% EtOAc:Hex to give the azide product as an oil (63%). Mass spectrum, ESI (M+H) 400.3, 402.3.

Part C. 6-Amino-1-benzyl-4-(4-bromo-phenyl)-[1,4] diazepan-5-one: A solution of the compound of Ex. 77, Part B (0.19 mmol) in 2 mL methanol was added slowly to a stirred suspension of $SnCl_2$ (2 eq) in 1 mL of methanol at 0° C. The mixture was allowed to warm to room temperature after the addition was over and stirring was continued overnight. Methanol was then removed under reduced pressure and the residue was diluted with cold water and made alkaline with 1N NaOH solution. Dichloromethane was added and the biphasic solution was filtered through a sintered glass funnel. The layers were then separated and the aqueous layer was saturated with brine and re-extracted with dichloromethane. The combined organic layers were dried ($MgSO_4$) and concentrated to give the amine as an oil (86%). Mass spectrum, ESI (M+H) 374.3, 376.3.

Part D. 6-Chloro-naphthalene-2-sulfonic acid [1-benzyl-4-(4-bromo-phenyl)-5-oxo-[1,4]diazepan-6-yl]-amide: To a solution of the compound of Ex. 77, Part C (0.16 mmol) in 2 mL dichloromethane was added 6-chloronapthalene-2-sulfonyl chloride (1.3 eq) then pyridine (3 eq) at room temperature. After stirring for an additional 5 hours, the excess reagent and solvent were evaporated off and then the residue was purified by flash column chromatography eluting with 0–2% MeOH/CHCl$_3$ to give the sulfonamide product as a clear film (75%). Mass spectrum, ESI (M+H) 598.3, 600.3.

Part E. 6-Chloro-naphthalene-2-sulfonic acid {1-benzyl-5-oxo-4-[2'-(2-oxo-ethyl)-biphenyl-4-yl]-[1,4]diazepa n-6-yl}-amide: The compound of Ex. 77, Part D (0.12 mmol), 2-formylbenzeneboronic acid (1.5 eq), potassium carbonate (4 eq), and tetrakis(triphenylphosphine)palladium(0) (10 mol %) were placed in a round bottom flask and evacuated and flushed twice with $N_2$. To this mixture was added 2:1 toluene/ethanol (9 mL) and the resulting mixture was evacuated and flushed again with $N_2$ (2×). The mixture was allowed to heated to reflux for two hours. The solution was then cooled to room temperature, diluted with water and extracted two times with ethyl acetate. The combined organic extracts were washed with brine, dried ($MgSO_4$), filtered and concentrated in vacuo to give a brown residue which was purified by flash column chromatography eluting with 30% EtOAc:Hex to give the product as a clear film (73%). Mass spectrum, ESI (M+H) 624.4, 626.4.

Part F. 6-Chloro-naphthalene-2-sulfonic acid [1-benzyl-4-(2'-dimethylaminomethyl-biphenyl-4-yl)-5-oxo-[1,4]d iazepan-6-yl]-amide: To a solution of the compound of Ex. 77, Part E (0.09 mmol) and dimethylamine hydrochloride (3 eq) in 3 mL of dichloroethane was added diisoproylethylamine (3 eq). After stirring at room temperature for 15 min, sodium triacetoxyborohydride (3 eq) was added to the mixture. After stirring at room temperature overnight, the mixture was diluted with water and extracted two times with chloroform. The combined organic extracts were washed with brine, dried ($MgSO_4$), filtered and concentrated in vacuo to give the crude product as a yellow film which was purified by column chromatography eluting with 5% MeOH:CHCl$_3$ to give the target as a foam (73%). $^1$H NMR ($CDCl_3$, 300 MHz) δ 8.44 (s, 1H), 7.92 (m, 2H), 7.85 (s, 2H), 7.55 (m, 2H), 7.30 (m, 8H), 7.17 (d, JL=7.5 Hz, 1H), 6.96 (d, J=8.4 Hz, 2H), 6.37 (br d, J=5.1 Hz, 1H), 4.36 (br s, 1H), 3.87 (m, 1H), 3.67 (dd, J=36.1, 13.4 Hz, 2H), 3.60 (br m, 1H), 3.30 (s, 2H), 3.50 (br m, 1H), 2.90 (m, 1H), 2.52 (m, 2H), 2.14 (s, 6H); mass spectrum, ESI (M+H) 653.5, 655.5.

Example 78

5-chloro-N-{1-[2'-(methylsulfonyl)-1,1'-biphenyl-4-yl]-2-oxo-2,3,4,5-tetrahydro-1H-1-benzazepin-3-yl}-2-thiophenesulfonamide

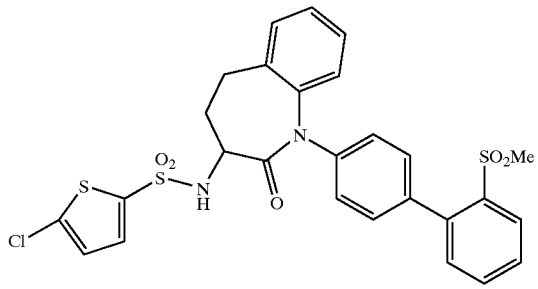

Part A. 2-Bromo-3,4-dihydro-2H-naphthalen-1-one oxime: α-Tetralone: (31.25 g, 0.214 mol) was stirred in MeOH (300 mL). Br$_2$ (11.02 mL, 1.0 eq) was added dropwise during a 1.5 h-period. LC-MS showed completion of the reaction after the addition. NH$_2$OH.HCl (38.10 g, 2.6 eq) was added to the above stirred solution, followed by the addition of H$_2$O (35 mL). The resulting mixture was stirred at RT O/N. LC-MS showed completion of the reaction. H$_2$O (155 mL) was added. The mixture was stirred at RT for 5 h. The light tan oil at the lower level was precipitated out while cooling in an ice bath for 30 min. The precipitate was filtered, and rinsed with H$_2$O. It was azeotroped with toluene (2×50), vacuum dried, and used directly in the next step. LC-MS (ESI$^+$) 240.2, 242.4 (M+H).

Part B. 3-Bromo-1,3,4,5-tetrahydro-benzo[b]azepin-2-one: The product from Ex. 78, Part A (9.0 g, 37.66 mmol) was added portionwise to PPA (48 g) with stirring at 80° C. under N$_2$. The resulting mixture was stirred at 80° C. for 36 h. The hot mixture was poured into ice H$_2$O, extracted with EtOAc (2×), washed with H$_2$O (2×), brine (2×), and dried over MgSO$_4$. The residue was purified by flash column chromatography (silica gel, hexanes: CH$_2$Cl$_2$=1:1 to 0:1, then CH$_2$Cl$_2$: EtOAc=4:1) to produce light tan crystals of the product (3.53 g, 39%). $^1$H NMR (CDCl$_3$) δ 9.03 (br, s, 1H), 7.29–7.07 (m, 4H), 4.53 (m, 1H), 3.05–2.93 (m, 1H), 2.82–2.60 (m, 3H). $^{13}$C NMR (CDCl$_3$) δ 169.6, 136.8, 133.0, 129.7, 128.0, 126.4, 122.5, 47.1, 40.3, 30.3 (10 out of 10 expected peaks obtained). LC-MS (ESI+) 240.2, 242.4 (M+H).

Part C. 3-Azido-1,3,4,5-tetrahydro-benzo[b]azepin-2-one: The product from Ex. 78, Part B (1.9 g, 7.95 mmol) and NaN$_3$ (1.0 g, 15.38 mmol, 2.0 eq) were stirred in DMF at RT under N$_2$ O/N. LC-MS showed completion of the reaction (t$_R$=2.81 min, 10–90% CH$_3$CN in H$_2$O in a 4-min run). EtOAc was added; the organic layer was washed with H$_2$O (2×), brine (2×), dried over MgSO$_4$, and concentrated (ca. 1.8 g, yield: 100%). The crude product was used directly in the next step. $^1$H NMR (CDCl$_3$) δ 8.85 (br, s, 1H), 7.26–7.19 (m, 2H), 7.14 (dd, J=7.7, 1.4 Hz, 1H), 7.05 (d, J=7.7 Hz, 1H), 3.86 (dd, J=11.3, 8.0 Hz, 1H), 2.96 (m, 1H), 2.70 (m, 1H), 2.49 (m, 1H), 2.27 (m, 1H). $^{13}$C NMR (CDCl$_3$) δ 171.4, 136.3, 133.3, 129.6, 128.0, 126.3, 122.4, 59.1, 34.9, 28.3. LC-MS (ESI+) 203.4 (M+H), 405.6 (2M+H).

Part D. 3-Amino-1,3,4,5-tetrahydro-benzo[b]azepin-2-one: The product from Ex. 78, Part C (1.8 g, 8.91 mmol) was stirred in THF (20 mL) at RT. PPh$_3$ (2.8 g, 1.2 eq) was added. The mixture was stirred for 30 min. H$_2$O (6 mL) was added. The mixture was stirred at 50° C. for 3 h. LC-MS showed completion of the reaction. The mixture was concentrated, and acidified with 1N HCl. It was extracted with Et$_2$O (2×). The aqueous layer was basified with 50% NaOH, extracted with CH$_2$Cl$_2$ (2×), washed with brine, dried over MgSO$_4$, and concentrated to dryness to produce 3-amino-1,3,4,5-tetrahydro-2H-1-benzazepin-2-one (1.06 g, 76%). $^1$H NMR (CDCl$_3$) δ 8.69 (br, s, 1H), 7.25 (m, 2H), 7.12 (dd, J=7.5, 1.2 Hz, 1H), 6.99 (dd, J=7.5, 1.2 Hz, 1H), 3.42 (dd, J=11.3, 7.7 Hz, 1H), 2.90 (m, 1H), 2.56 (m, 1H), 2.45 (m, 1H), 1.92 (m, 1H). $^{13}$C NMR (CDCl$_3$) δ 177.4, 136.8, 134.4, 129.6, 127.5, 125.9, 122.0, 51.5, 39.2, 29.0. LC-MS (ESI$^+$) 353.6 (2M+H).

Part E. 3-Amino-1-(4-bromophenyl)-1,3,4,5-tetrahydro-benzo[b]azepin-2-one: The product from Ex. 78, Part D (1.02 g, 5.80 mmol) was stirring in dry CH$_2$Cl$_2$ (15 mL) under N$_2$ at RT. PhCHO (0.58 mL, 1.0 eq) was added, followed by the addition of Et$_3$N (1.63 mL) and MgSO$_4$ (1.65 g). The resulting mixture was stirred at RT for 1 day. The mixture was filtered, rinsed with CH$_2$Cl$_2$, washed with H$_2$O, brine, dried over MgSO$_4$, and concentrated to dryness. The residue (1.3 g, 4.92 mmol) and 4-bromo-1-iodobenzene (1.66 g, 1.2 eq) were stirred in 1,4-dioxane (5 mL) at RT under N$_2$. K$_2$CO$_3$ (1.36 g, 2.0 eq) was added, followed by the addition of CuI (0.19 g, 10% mol) and trans-1,2-cyclohexyldiamine (0.1 ml, 10% mol). The resulting mixture was stirred at 110° C. for 2 h. LC-MS showed 80% of conversion with 20% starting material remaining. The mixture was cooled to RT, and sat'd NH$_4$Cl was added. The mixture was extracted with EtOAc, washed with H$_2$O, brine, and concentrated. The resulting residue was dissolved in Et$_2$O (10 ml). 1N HCl (30 mL) was added. The mixture was stirred at RT for 3 h. LC-MS showed completion of the reaction. The Et$_2$O layer was separated. The aqueous layer was washed with Et$_2$O (2×), basified with 50% aqueous NaOH. It was extracted with CH$_2$Cl$_2$ (2×), washed with brine, and dried over MgSO$_4$. The crude product of 3-amino-1-(4-bromophenyl)-1,3,4,5-tetrahydro-2H-1-benzazepin-2-one was used directly in the next step after vacuum drying. LC-MS (ESI$^+$) 331.4 (M+H), t$_R$=7.72 min (5–98% CH$_3$CN in H$_2$O in a 10-min run).

Part F. [1-(4-Bromophenyl)-2-oxo-2,3,4,5-tetrahydro-1H-benzo[b]azepin-3-yl]carbamic acid tert-butyl ester: The product from Ex. 78, Part E (0.87 g, 2.64 mmol) was stirred in CH$_2$Cl$_2$ (18 mL). (Boc)$_2$O (0.69 g, 1.2 eq) was added as one single portion, followed by the addition of 1N NaOH (3 mL). The resulting mixture was stirred at RT under N$_2$ for 1 h. LC-MS showed completion of the reaction (t$_R$=9.01 min, 5–98% CH$_3$CN in H$_2$O in a 10-min run) with M+H= 333.2. NH$_4$Cl was added, extracted with EtOAc (2×), washed with brine, dried over MgSO$_4$, filtered, and concentrated to give tert-butyl 1-(4-iodophenyl)-2-oxo-2,3,4,5-tetrahydro-1H-1-benzazepin-3-ylcarbamate (1.13 g, 100%). It was used directly in the next step without further purification.

Part G. tert-butyl 1-[2'-(methylthio)-1,1'-biphenyl-4-yl]-2-oxo-2,3,4,5-tetrahydro-1H-1-benzazepin-3-ylcarbamate: The product from Ex. 78, Part F (0.48 g, 1.11 mmol), o-thiomethylphenylboronic acid (0.28 g, 1.5 eq), Na$_2$CO$_3$ (0.24 g, 2.0 eq), and Pd(PPh$_3$)$_4$ (0.13 g, 10% mol) were degassed twice. Toluene (5 mL) and H$_2$O (0.6 mL) were added. The mixture was stirred at 85° C. under N$_2$O/N. LC-MS showed completion of the reaction. NH$_4$Cl was added, extracted with EtOAc (2×), washed with brine, dried over MgSO$_4$, filtered, and concentrated. The residue was purified by flash column chromatography (silica gel, CH$_2$Cl$_2$:hexanes=0:1 to 1:0, them 10–20% EtOAc in CH$_2$Cl$_2$) produced the product (0.28 g, 53%). $^1$H NMR (CDCl$_3$) δ 7.44 (m, 2H), 7.40–7.21 (m, 9H), 6.96 (m, 1H), 7.36–7.10 (m, 7H), 6.92 (d, J=8.8 Hz, 2H), 5.56 (m, 1H), 4.45 (m, 1H), 3.12 (m, 1H), 2.75 (m, 2H), 2.37 (s, 3H), 2.03 (m, 1H), 1.43 (s, 9H). $^{13}$C NMR (CDCl$_3$) δ 171.3, 154.9, 141.3, 140.7, 140.0, 138.9, 137.1, 135.4, 130.1, 129.9, 129.3, 128.1, 127.2, 126.7, 126.0, 125.3, 124.8, 79.6, 60.4, 51.1, 37.1, 28.4, 15.9. LC-MS (ESI$^+$) 475.4 (M+H), 375.4 (M+H-Boc).

Part H. 5-Chloro-thiophene-2-sulfonic acid [1-(2'-methanesulfonyl-biphenyl-4-yl)-2-oxo-2,3,4,5-tetrahydro-1H-benzo[b]azepin-3-yl]-amide: The product from Ex. 78, Part G (0.252 g, 0.53 mmol) was stirred in CH$_2$Cl$_2$ (5 mL) at RT under N$_2$. MCPBA (0.61 g, 4.0 eq) was added as one single portion. LC-MS showed completion of the reaction after 30 min. Sat'd NaHCO$_3$ was added. The mixture was extracted with EtOAc, washed with H$_2$O, brine, dried over MgSO$_4$, and concentrated. The residue was dissolved in CH$_2$CO$_2$ (10 mL). TFA (5 mL) was added. The mixture was stirred at RT for 20 min. LC-MS showed completion of the reaction ($t_R$=0.65 min, 407.6 (M+H)). The solvents were evaporated. EtOAc was added, washed with sat'd NaHCO$_3$, brine, dried over MgSO$_4$, and concentrated. The above residue (0.13 g, 0.32 mmol) and 5-chloro-2-thiophenesulfonic acid (0.10 g, 0.46 mmol) were stirred in CH$_2$Cl$_2$ (2 mL). Aqueous Na$_2$CO$_3$ (10% w/w, 0.6 mL) was added. The mixture was stirred at RT under N$_2$ for 1 h. NH$_4$Cl was added. It was extracted with EtOAc, washed with brine, and concentrated. The residue was purified by prep LC-MS ($t_R$=6.20 min, 5–98% CH$_3$CN in H$_2$O in a 10-min run) to give the target compound as a pure white floatable solid after lyophilization (25 mg, 14%). $^1$H NMR (CDCl$_3$) δ 8.04 (dd, J=7.9, 1.3 Hz, 1H), 7.89 (m, 1H), 7.64 (td, J=7.7, 1.5 Hz, 1H), 7.55 (td, J=7.7, 1.5 Hz, 1H), 7.36–7.10 (m, 7H), 6.92 (d, J=8.8 Hz, 2H), 6.86 (m, 1H), 3.96 (m, 1H), 2.96 (m, 1H), 2.90 (m, 2H), 2.61 (s, 3H), 2.35 (m, 1H), 2.14 (m, 1H). LC-MS (ESI$^+$) 587.2 (M+H).

Examples 79–81 were prepared from Ex. 35 by alkylation with the indicated alkylhalide in the presence of potassium carbonate in DMF as solvent using the procedure described for the synthesis of the compound of Ex. 33, Part A.

TABLE 3

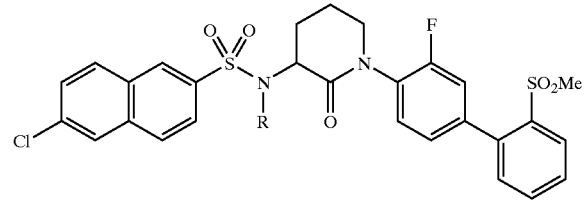

| Ex. # | Alkylhalide | R | MS (M + H)$^+$ |
|---|---|---|---|
| 79 | Ethyl bromoacetate | CH$_2$CO$_2$Me | 681.3 |
| 80 | Ethyl bromoacetate | CH$_2$CO$_2$Et | 673.1, 695.1 (M + Na)$^+$ |
| 81 | t-Butyl bromoacetate | CH$_2$CO$_2$tBu | 701.4, 645.3 (M + H − tBu)$^+$ |
| 82 | Benzylbromide | Benzyl | 677.0 |

Example 83

{(6-Chloro-naphthalene-2-sulfonyl)-[1-(3-fluoro-2'-methanesulfonylbiphenyl-4-yl)-2-oxo-piperidin-3-yl]amino}acetic acid

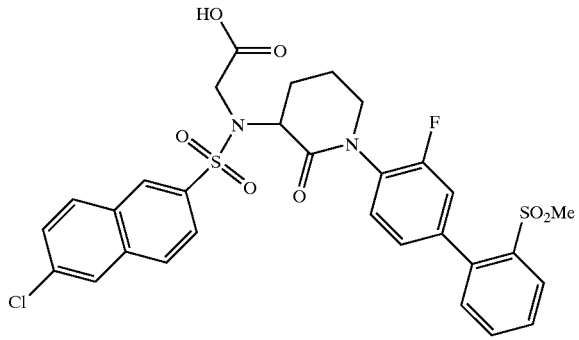

A 50 ml flask was charged with the compound of Ex. 81 (0.300 mg, 0.43 mmoles) and CH$_2$Cl$_2$ (3 ml) and trifluoroacetic acid (3 ml) was added to the rxn mixture. The rxn mixture was stirred at rt under N$_2$ atmosphere for 2 h. The solvent was removed under vacuum and the product dried overnight under high vacuum. $^1$H NMR (CDCl$_3$) δ 8.47 (s,1H), 8.22–8.19 (dd,1H), 7.94–7.90 (m,4H), 7.66–7.54 (m,3H), 7.34–7.23 (m,4H), 3.84–3.78 (m, 1H), 3.63–3.53 (m,2H) 2.71 (s, 3H), 2.69–2.60(m,1H), 2.30–2.30 (m,2H), 2.10–1.98 (m,3H). MS ESI$^+$ 645.3 m/z.

Example 84

2-{(6-Chloronaphthalene-2-sulfonyl)-[1-(3-fluoro-2'-methanesulfonylbiphenyl-4-yl)-2-oxo-piperidin-3-yl]-amino}-N-(2-dimethylaminoethyl)-N-methylacetamide

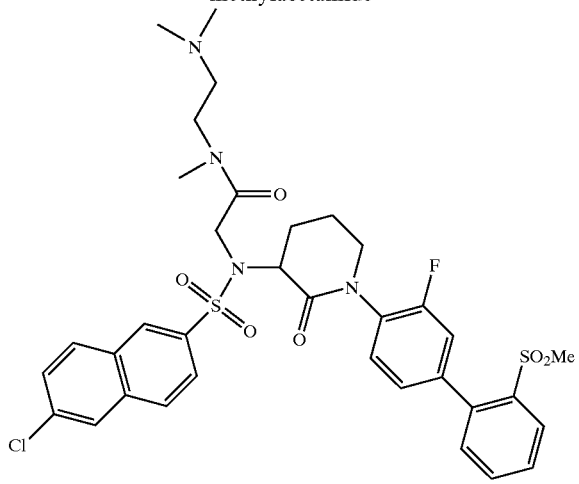

A small vial was charged with the the compound of Ex. 83 (25 mg, 0.039 mmol), 2-dimethylamino-N-methylethylamine (6.0 mg, 0.059 mmol), 4-methyl morpholine (16 mg, 0.156 mmol), Castro's reagent (26 mg, 0.059 mmol), and 1 ml of DMF. The rxn mixture was stirred at rt for 48 hours. The rxn was concentrated and purified by LC/MS to provide the title compound. $^1$H NMR (CDCl$_3$) δ 8.47 (s,1H), 8.22–8.19 (dd,1H), 7.94–7.90 (m,4H), 7.66–7.54 (m,3H), 7.34–7.23 (m,4H), 4.70–4.60 (m,1H), 4.35–4.20 (m,1H), 4.02–3.98(m,1H), 3.98–3.60 (m,3H), 3.60–3.58(m,1H), 3.10(s,3H), 2.90(s,3H), 2.75(s,3H), 2.39–2.35(m,1H) 2.19–2.01(bs,6H). MS ESI$^+$ 729.1 Similarly prepared from the compound of Ex. 83 using the procedure of Ex. 84 and the indicated amine were the following:

TABLE 4

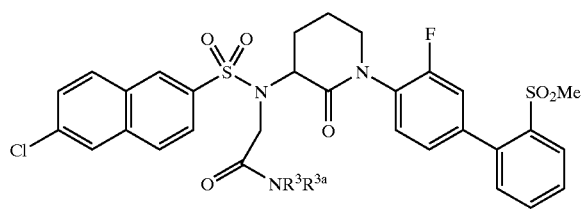

| Ex. # | Amine | NR³R³ᵃ | MS (M + H)⁺ |
|---|---|---|---|
| 85 | 2-aminoethanol | NHCH₂CH₂OH | 688.1 |
| 86 | 2-dimethylaminoethylamine | NHCH₂CH₂NMe₂ | 715.1 |

The following table contains additional representative examples of the present invention. Each entry in each table is intended to be paired with each formulae at the start of the table. For example, in Table 1A, example 1 is intended to be paired with each of the formulae.

The following nomenclature is intended for group A in the following table.

TABLE 1A

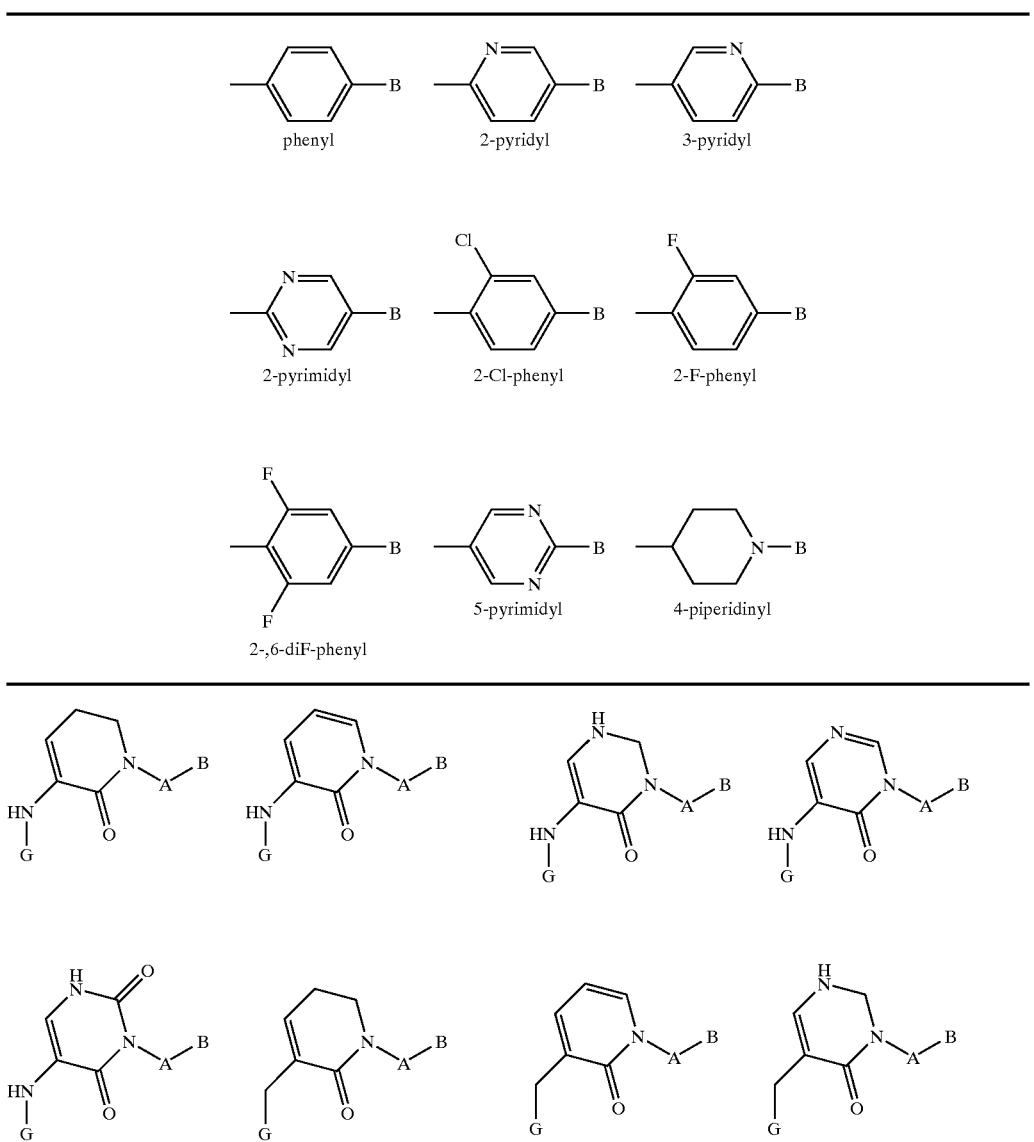

TABLE 1A-continued
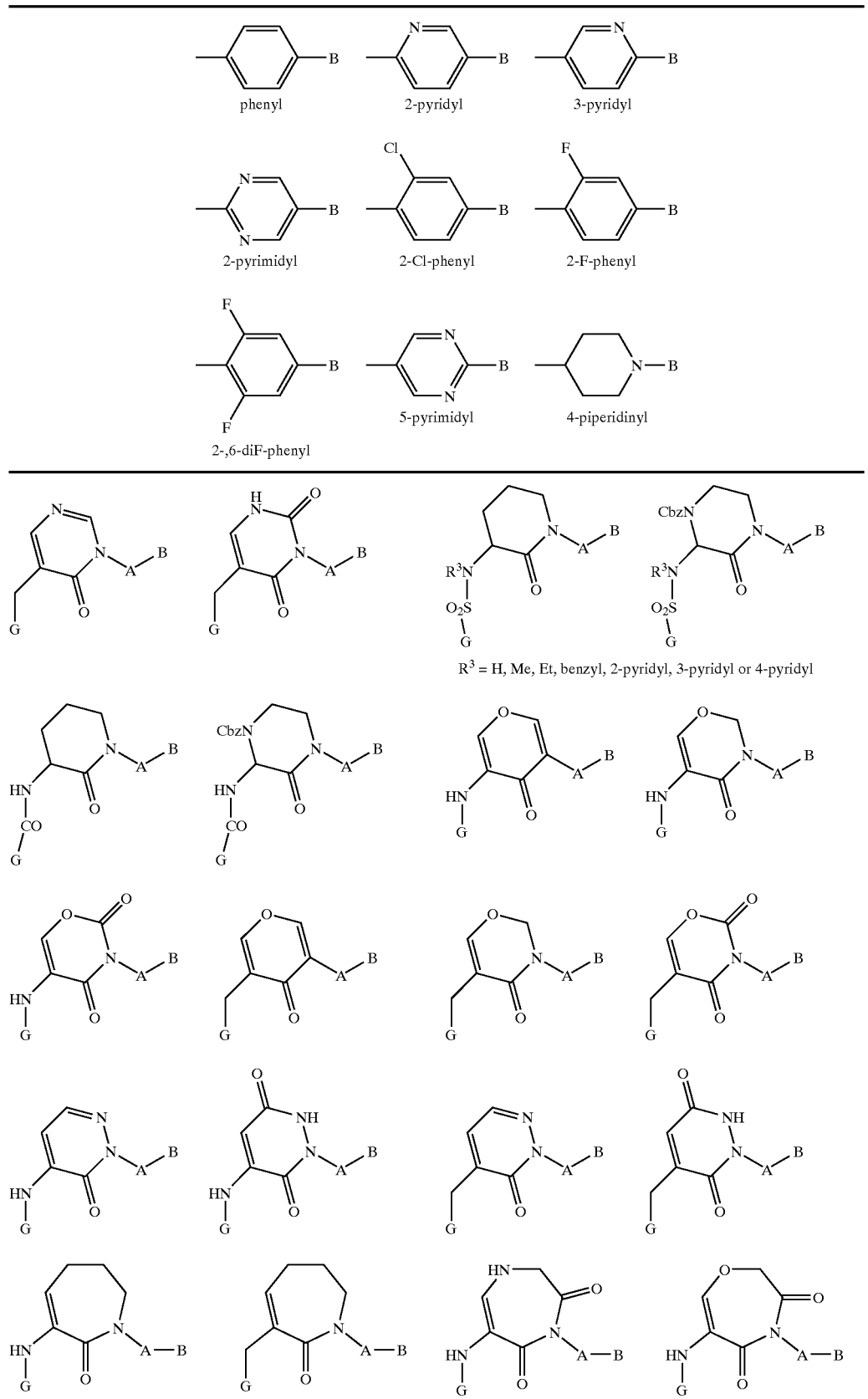

TABLE 1A-continued
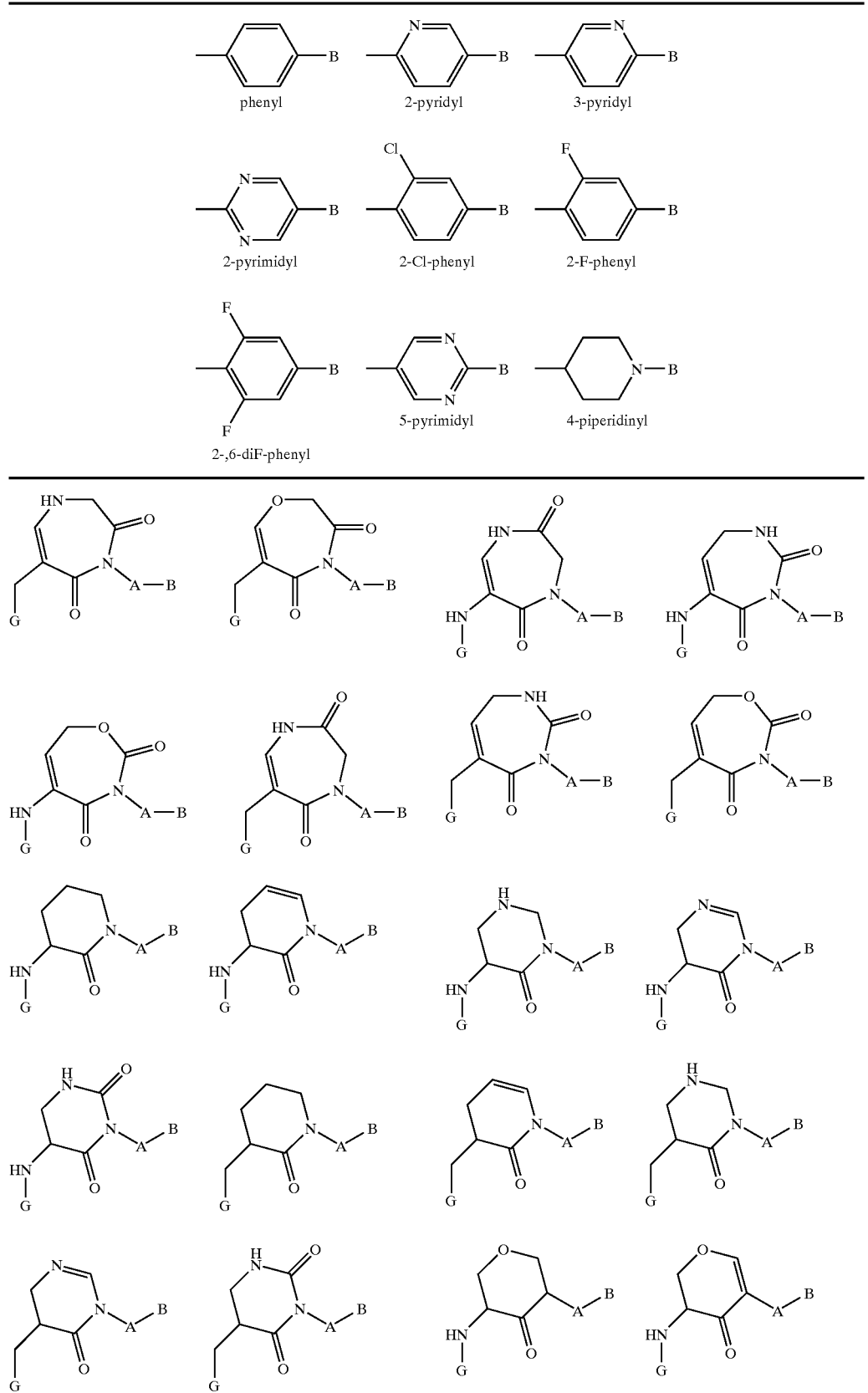

TABLE 1A-continued
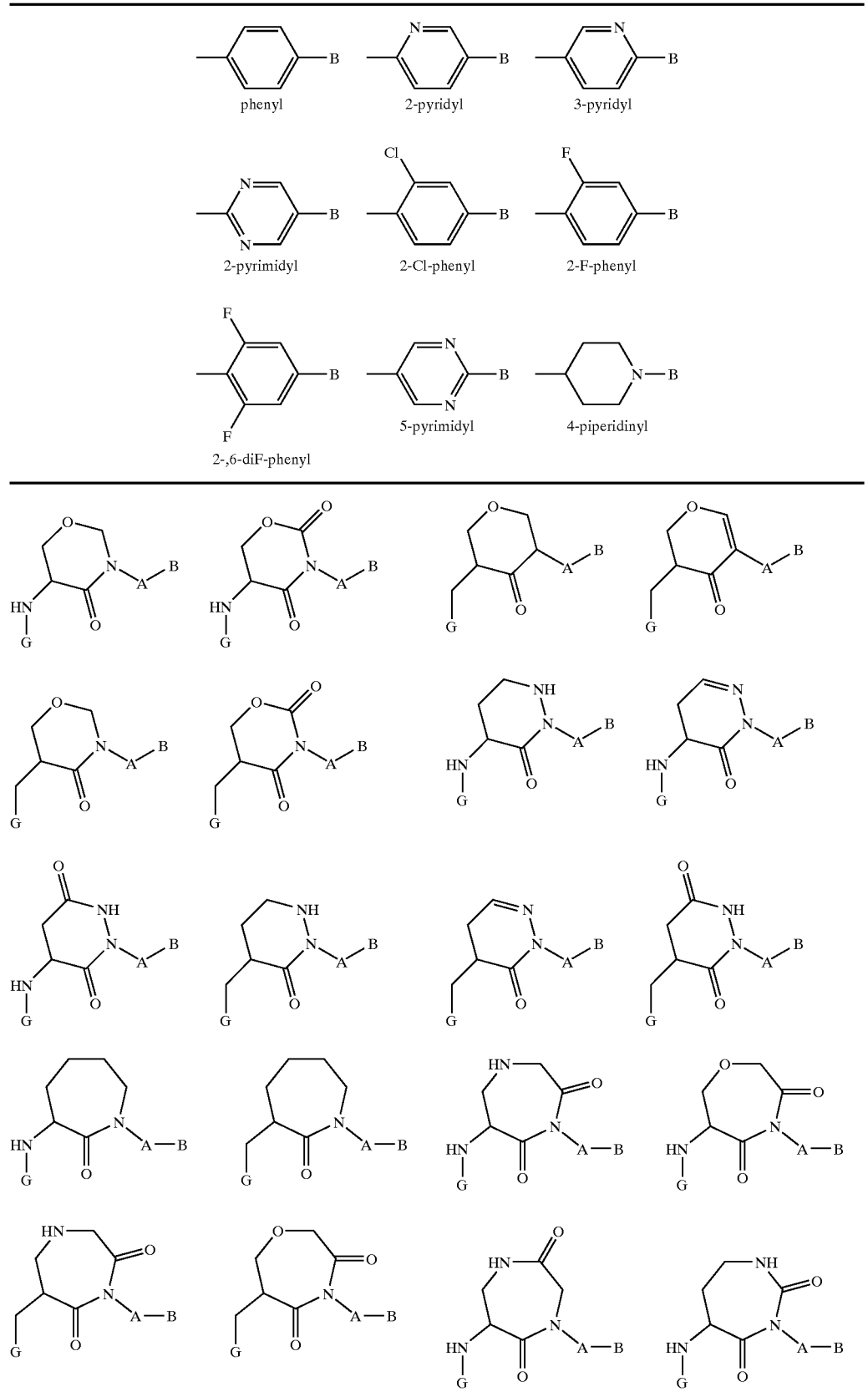

TABLE 1A-continued
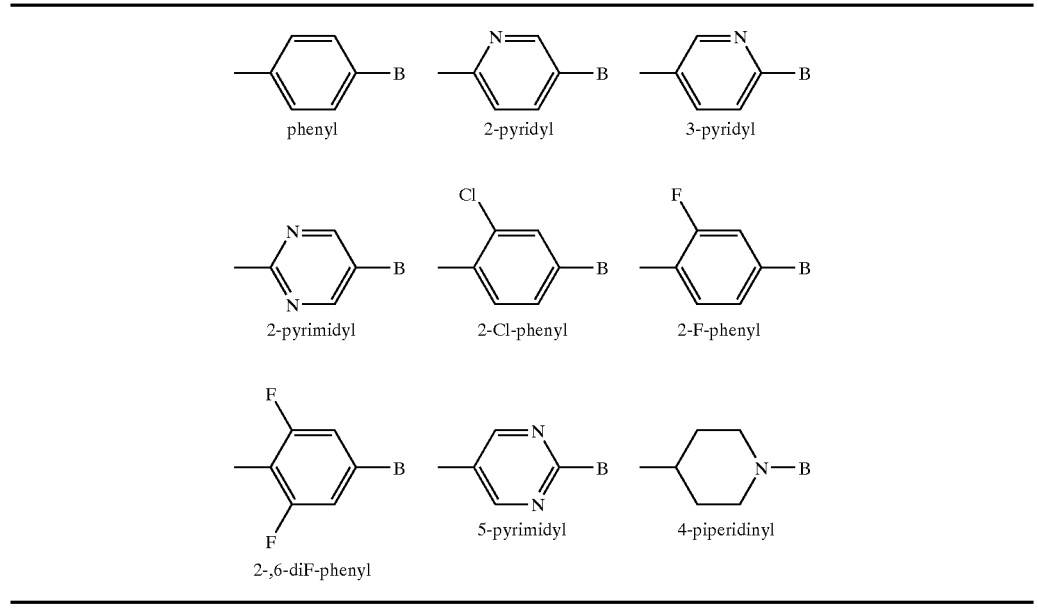
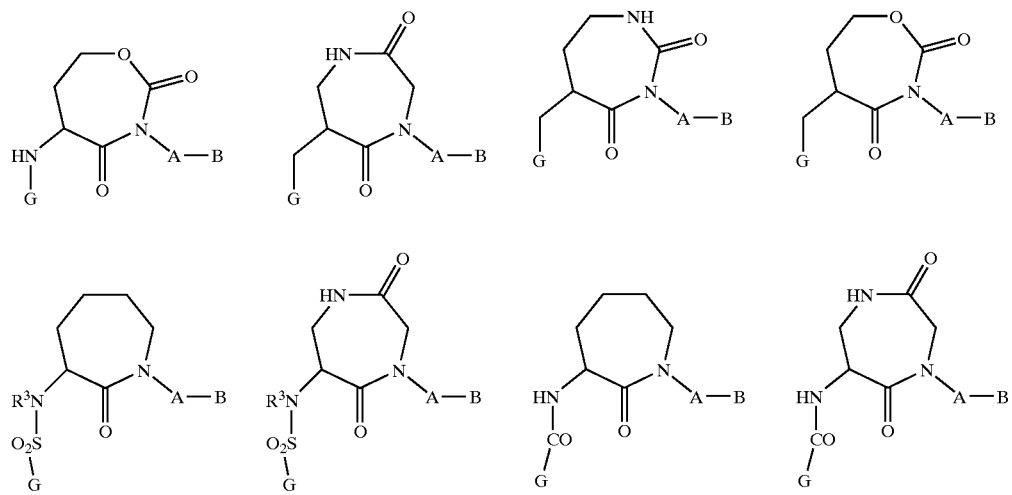
R[3] = H, Me, Et, benzyl, 2-pyridyl, 3-pyridyl or 4-pyridyl
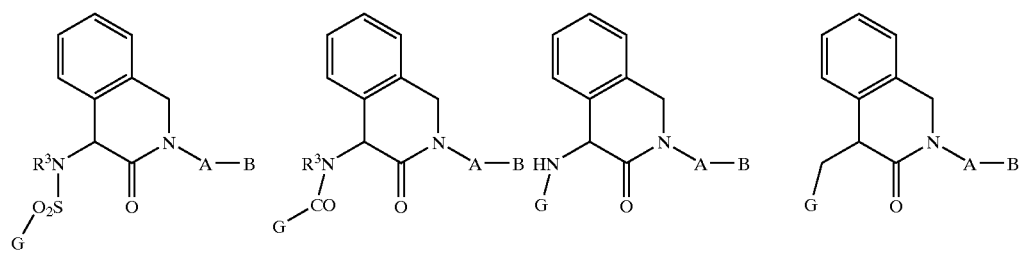
R[3] = H, Me, Et, benzyl, 2-pyridyl, 3-pyridyl or 4-pyridyl
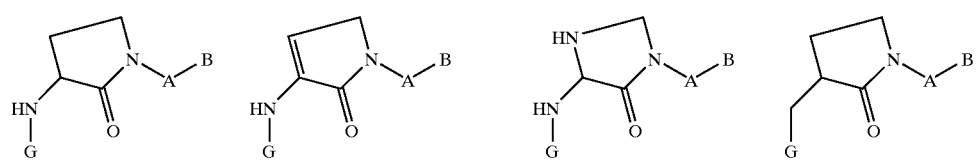

TABLE 1A-continued

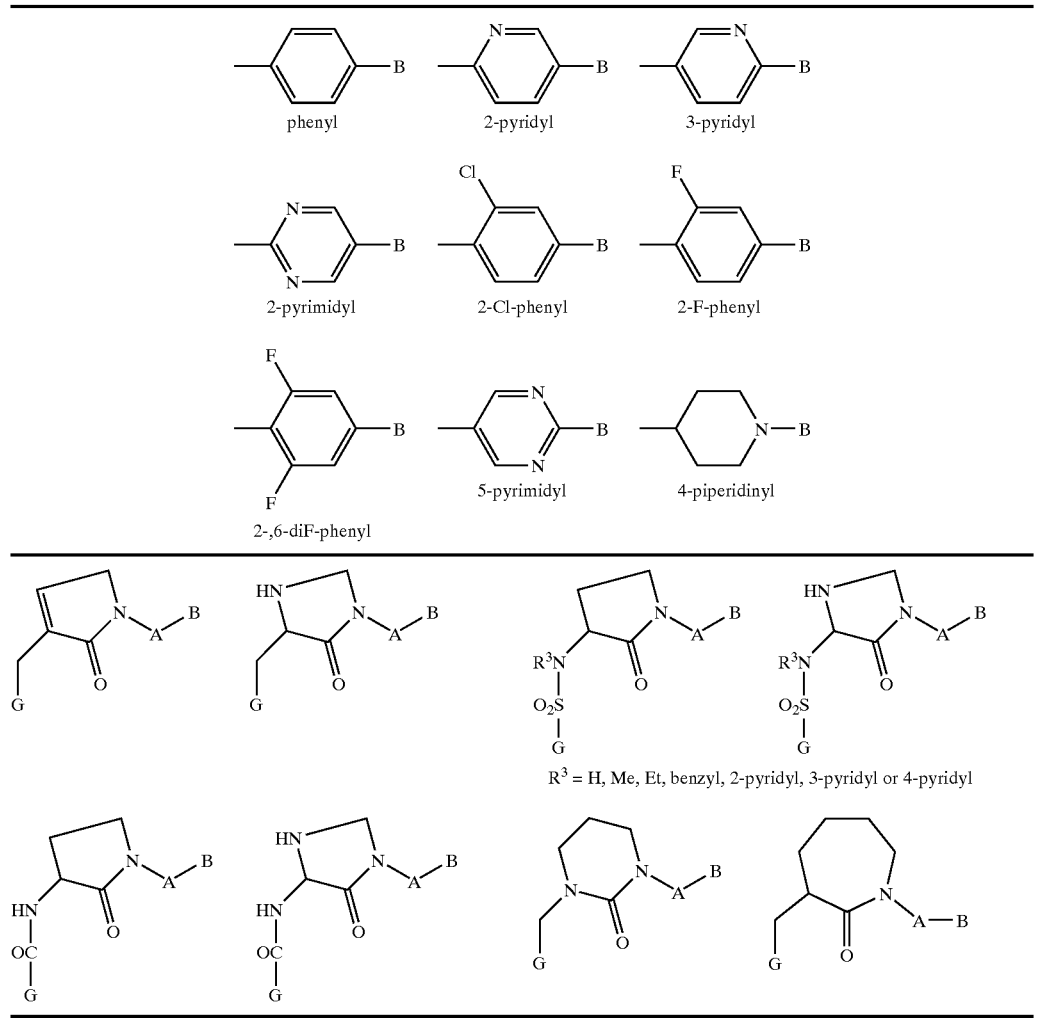

G is 4-(methoxy)phenyl;

| Ex# | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 2-(N,N-dimethylaminomethyl)phenyl |
| 6 | phenyl | 2-(N-pyrrolidinylmethyl)phenyl |
| 7 | phenyl | 1-methyl-2-imidazolyl |
| 8 | phenyl | 2-methyl-1-imidazolyl |
| 9 | phenyl | 2-(dimethylaminomethyl)-1-imidazolyl |
| 10 | phenyl | 2-(N-(cyclopropyl-methyl)aminomethyl)phenyl |
| 11 | phenyl | 2-(N-(cyclobutyl)-aminomethyl)phenyl |
| 12 | phenyl | 2-(N-(cyclopentyl)-aminomethyl)phenyl |
| 13 | phenyl | 2-(N-(3-hydroxypyrrolidinyl)-methyl)phenyl |
| 14 | 2-pyridyl | 2-(aminosulfonyl)phenyl |
| 15 | 2-pyridyl | 2-(methylaminosulfonyl)phenyl |
| 16 | 2-pyridyl | 1-pyrrolidinocarbonyl |
| 17 | 2-pyridyl | 2-(methylsulfonyl)phenyl |
| 18 | 2-pyridyl | 2-(N,N-dimethylaminomethyl)phenyl |
| 19 | 2-pyridyl | 2-(N-pyrrolidinylmethyl)phenyl |
| 20 | 2-pyridyl | 1-methyl-2-imidazolyl |
| 21 | 2-pyridyl | 2-methyl-1-imidazolyl |
| 22 | 2-pyridyl | 2-(dimethylaminomethyl)-1-imidazolyl |
| 23 | 2-pyridyl | 2-(N-(cyclopropyl-methyl)aminomethyl)phenyl |
| 24 | 2-pyridyl | 2-(N-(cyclobutyl)-aminomethyl)phenyl |
| 25 | 2-pyridyl | 2-(N-(cyclopentyl)-aminomethyl)phenyl |
| 26 | 2-pyridyl | 2-(N-(3-hydroxypyrrolidinyl)-methyl)phenyl |
| 27 | 3-pyridyl | 2-(aminosulfonyl)phenyl |
| 28 | 3-pyridyl | 2-(methylaminosulfonyl)phenyl |
| 29 | 3-pyridyl | 1-pyrrolidinocarbonyl |
| 30 | 3-pyridyl | 2-(methylsulfonyl)phenyl |
| 31 | 3-pyridyl | 2-(N,N-dimethylaminomethyl)phenyl |
| 32 | 3-pyridyl | 2-(N-pyrrolidinylmethyl)phenyl |
| 33 | 3-pyridyl | 1-methyl-2-imidazolyl |
| 34 | 3-pyridyl | 2-methyl-1-imidazolyl |
| 35 | 3-pyridyl | 2-(dimethylaminomethyl)-1-imidazolyl |

-continued

| Ex# | A | B |
|---|---|---|
| 36 | 3-pyridyl | 2-(N-(cyclopropyl-methyl)aminomethyl)phenyl |
| 37 | 3-pyridyl | 2-(N-(cyclobutyl)-aminomethyl)phenyl |
| 38 | 3-pyridyl | 2-(N-(cyclopentyl)-aminomethyl)phenyl |
| 39 | 3-pyridyl | 2-(N-(3-hydroxypyrrolidinyl)-methyl)phenyl |
| 40 | 2-pyrimidyl | 2-(aminosulfonyl)phenyl |
| 41 | 2-pyrimidyl | 2-(methylaminosulfonyl)phenyl |
| 42 | 2-pyrimidyl | 1-pyrrolidinocarbonyl |
| 43 | 2-pyrimidyl | 2-(methylsulfonyl)phenyl |
| 44 | 2-pyrimidyl | 2-(N,N-dimethylaminomethyl)phenyl |
| 45 | 2-pyrimidyl | 2-(N-pyrrolidinylmethyl)phenyl |
| 46 | 2-pyrimidyl | 1-methyl-2-imidazolyl |
| 47 | 2-pyrimidyl | 2-methyl-1-imidazolyl |
| 48 | 2-pyrimidyl | 2-(dimethylaminomethyl)-1-imidazolyl |
| 49 | 2-pyrimidyl | 2-(N-(cyclopropyl-methyl)aminomethyl)phenyl |
| 50 | 2-pyrimidyl | 2-(N-(cyclobutyl)-aminomethyl)phenyl |
| 51 | 2-pyrimidyl | 2-(N-(cyclopentyl)-aminomethyl)phenyl |
| 52 | 2-pyrimidyl | 2-(N-(3-hydroxypyrrolidinyl)-methyl)phenyl |
| 53 | 5-pyrimidyl | 2-(aminosulfonyl)phenyl |
| 54 | 5-pyrimidyl | 2-(methylaminosulfonyl)phenyl |
| 55 | 5-pyrimidyl | 1-pyrrolidinocarbonyl |
| 56 | 5-pyrimidyl | 2-(methylsulfonyl)phenyl |
| 57 | 5-pyrimidyl | 2-(N,N-dimethylaminomethyl)phenyl |
| 58 | 5-pyrimidyl | 2-(N-pyrrolidinylmethyl)phenyl |
| 59 | 5-pyrimidyl | 1-methyl-2-imidazolyl |
| 60 | 5-pyrimidyl | 2-methyl-1-imidazolyl |
| 61 | 5-pyrimidyl | 2-(dimethylaminomethyl)-1-imidazolyl |
| 62 | 5-pyrimidyl | 2-(N-(cyclopropyl-methyl)aminomethyl)phenyl |
| 63 | 5-pyrimidyl | 2-(N-(cyclobutyl)-aminomethyl)phenyl |
| 64 | 5-pyrimidyl | 2-(N-(cyclopentyl)-aminomethyl)phenyl |
| 65 | 5-pyrimidyl | 2-(N-(3-hydroxypyrrolidinyl)-methyl)phenyl |
| 66 | 2-Cl-phenyl | 2-(aminosulfonyl)phenyl |
| 67 | 2-Cl-phenyl | 2-(methylaminosulfonyl)phenyl |
| 68 | 2-Cl-phenyl | 1-pyrrolidinocarbonyl |
| 69 | 2-Cl-phenyl | 2-(methylsulfonyl)phenyl |
| 70 | 2-Cl-phenyl | 2-(N,N-dimethylaminomethyl)phenyl |
| 71 | 2-Cl-phenyl | 2-(N-pyrrolidinylmethyl)phenyl |
| 72 | 2-Cl-phenyl | 1-methyl-2-imidazolyl |
| 73 | 2-Cl-phenyl | 2-methyl-1-imidazolyl |
| 74 | 2-Cl-phenyl | 2-(dimethylaminomethyl)-1-imidazolyl |
| 75 | 2-Cl-phenyl | 2-(N-(cyclopropyl-methyl)aminomethyl)phenyl |
| 76 | 2-Cl-phenyl | 2-(N-(cyclobutyl)-aminomethyl)phenyl |
| 77 | 2-Cl-phenyl | 2-(N-(cyclopentyl)-aminomethyl)phenyl |
| 78 | 2-Cl-phenyl | 2-(N-(3-hydroxypyrrolidinyl)-methyl)phenyl |
| 79 | 2-F-phenyl | 2-(aminosulfonyl)phenyl |
| 80 | 2-F-phenyl | 2-(methylaminosulfonyl)phenyl |
| 81 | 2-F-phenyl | 1-pyrrolidinocarbonyl |
| 82 | 2-F-phenyl | 2-(methylsulfonyl)phenyl |
| 83 | 2-F-phenyl | 2-(N,N-dimethylaminomethyl)phenyl |
| 84 | 2-F-phenyl | 2-(N-pyrrolidinylmethyl)phenyl |
| 85 | 2-F-phenyl | 1-methyl-2-imidazolyl |
| 86 | 2-F-phenyl | 2-methyl-1-imidazolyl |
| 87 | 2-F-phenyl | 2-(dimethylaminomethyl)-1-imidazolyl |
| 88 | 2-F-phenyl | 2-(N-(cyclopropyl-methyl)aminomethyl)phenyl |
| 89 | 2-F-phenyl | 2-(N-(cyclobutyl)-aminomethyl)phenyl |

-continued

| Ex# | A | B |
|---|---|---|
| 90 | 2-F-phenyl | 2-(N-(cyclopentyl)-aminomethyl)phenyl |
| 91 | 2-F-phenyl | 2-(N-(3-hydroxypyrrolidinyl)-methyl)phenyl |
| 92 | 2,6-diF-phenyl | 2-(aminosulfonyl)phenyl |
| 93 | 2,6-diF-phenyl | 2-(methylaminosulfonyl)phenyl |
| 94 | 2,6-diF-phenyl | 1-pyrrolidinocarbonyl |
| 95 | 2,6-diF-phenyl | 2-(methylsulfonyl)phenyl |
| 96 | 2,6-diF-phenyl | 2-(N,N-dimethylaminomethyl)phenyl |
| 97 | 2,6-diF-phenyl | 2-(N-pyrrolidinylmethyl)phenyl |
| 98 | 2,6-diF-phenyl | 1-methyl-2-imidazolyl |
| 99 | 2,6-diF-phenyl | 2-methyl-1-imidazolyl |
| 100 | 2,6-diF-phenyl | 2-(dimethylaminomethyl)-1-imidazolyl |
| 101 | 2,6-diF-phenyl | 2-(N-(cyclopropyl-methyl)aminomethyl)phenyl |
| 102 | 2,6-diF-phenyl | 2-(N-(cyclobutyl)-aminomethyl)phenyl |
| 103 | 2,6-diF-phenyl | 2-(N-(cyclopentyl)-aminomethyl)phenyl |
| 104 | 2,6-diF-phenyl | 2-(N-(3-hydroxypyrrolidinyl)-methyl)phenyl |
| 105 | 4-piperidinyl | 2-(aminosulfonyl)phenyl |
| 106 | 4-piperidinyl | 2-(methylaminosulfonyl)phenyl |
| 107 | 4-piperidinyl | 1-pyrrolidinocarbonyl |
| 108 | 4-piperidinyl | 2-(methylsulfonyl)phenyl |
| 109 | 4-piperidinyl | 2-(N,N-dimethylaminomethyl)phenyl |
| 110 | 4-piperidinyl | 2-(N-pyrrolidinylmethyl)phenyl |
| 111 | 4-piperidinyl | 1-methyl-2-imidazolyl |
| 112 | 4-piperidinyl | 2-methyl-1-imidazolyl |
| 113 | 4-piperidinyl | 2-(dimethylaminomethyl)-1-imidazolyl |
| 114 | 4-piperidinyl | 2-(N-(cyclopropyl-methyl)aminomethyl)phenyl |
| 115 | 4-piperidinyl | 2-(N-(cyclobutyl)-aminomethyl)phenyl |
| 116 | 4-piperidinyl | 2-(N-(cyclopentyl)-aminomethyl)phenyl |
| 117 | 4-piperidinyl | 2-(N-(3-hydroxypyrrolidinyl)-methyl)phenyl |

Examples 118–3042 use the corresponding A and B groups from Examples 1–117 and the recited G group.
Examples 118–234, G is 2-(aminomethyl)phenyl;
Examples 234–351, G is 3-(aminomethyl)phenyl;
Examples 352–468, G is 2-(aminomethyl)-3-fluorophenyl;
Examples 469–585, G is 2-(aminomethyl)-4-fluorophenyl;
Examples 586–702, G is 2-(aminomethyl)-5-fluorophenyl;
Examples 703–819, G is 2-(aminomethyl)-6-fluorophenyl;
Examples 820–936, G is 3-amino-phthalazin-5-yl;
Examples 937–1053, G is 3-amino-phthalazin-6-yl;
Examples 1054–1170, G is 1-aminoisoquinolin-6-yl;
Examples 1171–1287, G is 1-aminoisoquinolin-7-yl;
Examples 1288–1404, G is 4-aminoquinazol-6-yl;
Examples 1405–1521, G is 4-aminoquinazol-7-yl;
Examples 1522–1638, G is 3-aminobenzisoxazol-5-yl;
Examples 1639–1755, G is 3-aminobenzisoxazol-6-yl;
Examples 1756–1872, G is 3-aminoisobenzazol-5-yl;
Examples 1873–1989, G is 3-aminoisobenzazol-6-yl;
Examples 1990–2106, G is 4-chlorophenyl;
Examples 2223–2340, G is 6-chloronaphthyl;
Examples 2341–2457, G is 5-chloronaphthyl;
Examples 2457–2574, G is 5-chloro-2-thienyl;
Examples 2575–2691, G is 4-fluorophenyl;
Examples 2692–2808, G is 3,4-difluorophenyl;
Examples 2809–2925, G is 3,5-dichloro-thienyl;
Examples 2926–3042, G is 4-ethyl-phenyl;

Numerous modifications and variations of the present invention are possible in light of the above teachings. It is therefore to be understood that within the scope of the appended claims, the invention may be practiced otherwise that as specifically described herein.

What is claimed is:

1. A compound of Formula I:

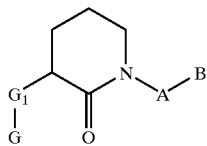

I or a stereoisomer or pharmaceutically acceptable salt thereof, wherein;

the piperidinone ring of formula I is substituted with 0–2 $R^{1a}$;

G is a group of formula IIa or IIb:

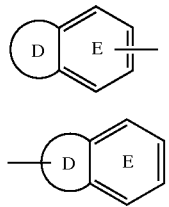

IIa

IIb $G_1$ is selected from O, $NR^{3e}$, $NR^3C(O)$, $OC(O)$, and $NR^{3e}CR^{3a}R^{3b}$;

ring D, including the two atoms of Ring E to which it is attached, is a 6 membered aromatic system consisting of carbon atoms and 0–1 heteroatoms selected from the group consisting of N, O, and $S(O)_p$, and D is substituted with 0–2 R;

E is selected from phenyl and pyridyl and is substituted with 0–2 R;

R is selected from $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-13}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rOR^{3a}$, $(CR^8R^9)_rNR^7C(O)R^7$, $(CR^8R^9)_rS(O)_pNR^7R^8$, $(CR^8R^9)_rNR^7S(O)_pR^{3f}$, $(CR^8R^9)_rS(O)R^{3c}$, $(CR^8R^9)_rS(O)_2R^{3c}$, and $OCF_3$;

alternatively, the bridging portion of ring D is absent, and ring E is selected from phenyl, and pyridyl E is substituted with $R^a$ and $R^b$;

alternatively, ring E is substituted with a 5–6 membered aromatic heterocycle consisting of: carbon atoms and 1–4 heteroatoms selected from the group consisting of N, O, and $S(O)_p$, and said aromatic heterocycle is substituted with $R^a$ and $R^b$;

alternatively, ring E is substituted with a 5–6 membered non-aromatic hetercocycle consisting of: carbon atoms and 1–4 heteroatoms selected from the group consisting of N, O, and $S(O)_p$, and said non-aromatic heterococyle is substituted with $R^a$ and $R^b$, 0–2 carbonyl groups and containing 0–2 double bonds;

$R^a$ and $R^b$, at each occurrence, are independently selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rOR^{3a}$, $(CR^8R^9)_rNR^7C(O)R^{3f}$, $(CR^8R^9)_rS(O)_pNR^7R^8$, $(CR^8R^9)_rNR^7S(O)_pR^{3f}$, $(CR^8R^9)_rS(O)R^{3c}$, $(CR^8R^9)_rS(O)_2R^{3c}$, and $OCF_3$;

A is phenyl substituted with 0–2 $R^4$;

provided that B and ring M are attached to different atoms on A;

B is selected from: Y and X—Y;

X is selected from $-(CR^2R^{2a})_{1-4}-$, $-CR^2(CR^2R^{2b})(CH_2)_r-$, $-C(O)-$, $-C(=NR^{1c})-$, $-CR^2(NR^{1c}R^2)-$, $-CR^2(OR^2)-$, $-CR^2(SR^2)-$, $-C(O)CR^2R^{2a}-$, $-CR^2R^{2a}C(O)$, $-S-$, $-S(O)-$, $-S(O)_2-$, $-SCR^2R^{2a}$, $-S(O)CR^2R^{2a}-$, $-S(O)_2CR^2R^{2a}-$, $-CR^2R^{2a}S-$, $-CR^2R^{2a}S(O)-$, $-CR^2R^{2a}S(O)_2-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2CR^2R^{2a}-$, $-CR^2R^{2a}NR^2-$, O, $-CR^2R^{2a}O-$, and $-OCR^2R^{2a}-$;

Y is selected from:
$-(CH_2)_rNR^2R^{2a}$, provided that X-Y do not form a N—N, O—N, or S—N bond,
$C_{3-10}$ carbocycle substituted with 0–2 $R^{4a}$, and
5–10 membered heterocyclic system containing from 1–4 heteroatoms selected from the group consisting of N, O, and S substituted with 0–2 $R^{4a}$;

provided that B and Y are other than tetrazolyl;

$R^{1a}$, is selected from H, $-(CH_2)_r-R^{1b}$, $-CH=CH-R^{1b}$, $NCH_2R^{1c}$, $OCH_2R^{1c}$, $S(O)_pCH_2R^{1c}$, $NH(CH_2)_2(CH_2)_rR^{1b}$, $O(CH_2)_2(CH_2)_rR^{1b}$, and $S(CH_2)_2(CH_2)_rR^{1b}$, provided that $R^{1a}$ forms other than an N-halo, N—N, N—S, N—O, or N—CN bond with the group to which it is attached;

$R^{1b}$ is selected from H, $C_{1-3}$ alkyl, F, Cl, Br, I, CN, CHO, $(CF_2)_rCF_3$, $(CH_2)_rOR^2$, $NR^2R^{2a}$, $C(O)R^{2c}$, $C(O)OR^2$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-10}$ carbocycle substituted with 0–2 $R^{4a}$, and 5–10 membered heterocycle consisting of carbon atoms and from 1–4 heteroatoms selected from the group consisting of N, O, and $S(O)_p$ substituted with 0–2 $R^{4a}$, provided that $R^{1b}$ forms other than an N-halo, N—N, N—S, N—O, or N—CN bond with the group to which it is attached;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl optionally substituted with 0–2 $R^{4b}$, benzyl, a $C_{3-10}$ carbocycle $(CH_2)_r-$ substituted with 0–2 $R^{4b}$, and (5–6 membered heterocyclic system)-$(CH_2)_r-$ containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl optionally substituted with 0–2 $R^{4b}$, benzyl, a $C_{3-10}$ carbocycle $(CH_2)_r$— substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{2b}$, at each occurrence, is selected from $CF_3$, $C_{1-4}$ alkoxy, $C_{1-6}$ alkyl, benzyl, $C_{3-10}$ carbocycle $(CH_2)_r$— substituted with 0–2 $R^{4b}$, and (5–6 membered heterocyclic system)-$(CH_2)_r$— containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-10}$ carbocycle $(CH_2)_r$— substituted with 0–2 $R^{4b}$, and (5–6 membered heterocyclic system)—$(CH_2)_r$— containing from 1–4 heteroatoms selected from the group consisting of N, O, and S substituted with 0–2 $R^{4b}$;

$R^3$, at each occurrence, is selected from H,
  $C_{1-6}$ alkyl substituted with 0–2 $R^{1a}$;
  $C_{2-6}$ alkenyl substituted with 0–2 $R^{1a}$;
  $C_{2-6}$ alkynyl substituted with 0–2 $R^{1a}$;
  cycloalkyl($C_{0-4}$ alkyl)-substituted with 0–3 $R^{1a}$;
  heterocyclyl($C_{0-4}$ alkyl)-substituted with 0–3 $R^{1a}$;
  aryl($C_{0-4}$ alkyl)-substituted with 0–3 $R^{1a}$;
  heteroaryl($C_{0-4}$ alkyl)-substituted with 0–3 $R^{1a}$;

$R^{3a}$ and $R^{3b}$, at each occurrence, are independently selected from H, $C_{1-4}$ alkyl, phenyl, and benzyl;

$R^{3c}$, at each occurrence, is selected from $C_{1-4}$ alkyl, phenyl, and benzyl;

$R^{3d}$, at each occurrence, is selected from H and $C_{1-4}$ alkyl;

$R^{3e}$, is selected from H, $S(O)_2NHR^3$, $C(O)R^3$, $C(O)NHR^3$, $C(O)OR^{3f}$, $S(O)R^{3f}$, $S(O)_2R^{3f}$,
  $C_{1-6}$ alkyl substituted with 0–2 $R^{1a}$;
  $C_{2-6}$ alkenyl substituted with 0–2 $R^{1a}$;
  $C_{2-6}$ alkynyl substituted with 0–2 $R^{1a}$;
  cycloalkyl($C_{0-4}$ alkyl)-substituted with 0–3 $R^{1a}$;
  heterocyclyl($C_{0-4}$ alkyl)-substituted with 0–3 $R^{1a}$;
  aryl($C_{0-4}$ alkyl)-substituted with 0–3 $R^{1a}$;
  heteroaryl($C_{0-4}$ alkyl)-substituted with 0–3 $R^{1a}$;

$R^{3f}$, at each occurrence, is selected from:
  $C_{1-6}$ alkyl substituted with 0–2 $R^{1a}$;
  $C_{2-6}$ alkenyl substituted with 0–2 $R^{1a}$;
  $C_{2-6}$ alkynyl substituted with 0–2 $R^{1a}$;
  cycloalkyl($C_{0-4}$ alkyl)-substituted with 0–3 $R^{1a}$;
  heterocyclyl($C_{0-4}$ alkyl)-substituted with 0–3 $R^{1a}$;
  aryl($C_{0-4}$ alkyl)-substituted with 0–3 $R^{1a}$;
  heteroaryl($C_{0-4}$ alkyl)-substituted with 0–3 $R^{1a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R$, $S(O)_pR$, $(CF_2)_rCF_3$, $NCH_2R^{1c}$, $OCH_2R^{1c}$, $SCH_2R^{1c}$, $N(CH_2)_2(CH_2)_rR^{1b}$, $O(CH_2)_2(CH_2)_rR^{1b}$, $S(CH_2)_2(CH_2)_rR^{1b}$, and 5–6 membered carbocycle substituted with 0–1 $R^5$, and a 5–6 membered heterocycle consisting of: carbon atoms and 1–4 heteroatoms selected from the group consisting of N, O, and $S(O)_p$ substituted with 0–1 $R^5$;

$R^{4a}$, at each occurrence, is selected from H, =O, $(CH_2)_rOR^2$, $(CH_2)_r$—F, $(CH_2)_r$—Br, $(CH_2)_r$—Cl, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R$, $S(O)_pR$, $(CF_2)_rCF_3$, and 5–6 membered carbocycle substituted with 0–1 $R^5$, and a 5–6 membered heterocycle consisting of: carbon atoms and 1–4 heteroatoms selected from the group consisting of N, O, and $S(O)_p$ substituted with 0–1 $R^5$;

$R^{4b}$, at each occurrence, is selected from H, =O, $(CH_2)_rOR^3$, $(CH_2)_r$—F, $(CH_2)_r$—Cl, $(CH_2)_r$—Br, $(CH_2)_r$—I, $C_{1-4}$ alkyl, $(CH_2)_r$—CN, $(CH_2)_r$—$NO_2$, $(CH_2)_rNR^3R^{3a}$, $(CH_2)_rC(O)R^3$, $(CH_2)_rC(O)OR^{3c}$, $(CH_2)_r$—$NR^3C(O)R^{3a}$, $(CH_2)_r$—$C(O)NR^3R^{3a}$, $(CH_2)_r$—$NR^3C(O)NR^3R^{3a}$, $(CH_2)_r$—$C(=NR^3)NR^3R^{3a}$, $(CH_2)_r$—$NR^3C(=NR^3)NR^3R^{3a}$, $(CH_2)_r$—$SO_2NR^3R^{3a}$, $(CH_2)_r$—$NR^3SO_2NR^3R^{3a}$, $(CH_2)_r$—$NR^3SO_2$—$C_{1-4}$ alkyl, $(CH_2)_r$—$NR^3SO_2CF_3$, $(CH_2)_r$—$NR^3SO_2$-phenyl, $(CH_2)_r$—$S(O)_pCF_3$, $(CH_2)_r$—$S(O)_p$—$C_{1-4}$ alkyl, $(CH_2)_r$—$S(O)_p$-phenyl, and $(CF_2)_rCF_3$;

provided that when $R^{4b}$ is $(CH_2)_rOR^3$, $(CH_2)_rNR^3R^{3a}$, $(CH_2)_rC(O)R^3$, $CH_2)_r$—$NR^3C(O)R^{3a}$, $(CH_2)_r$—$C(O)NR^3R^{3a}$, $(CH_2)_r$—$NR^3C(O)NR^3R^{3a}$, $(CH_2)_r$—$C(=NR^3)NR^3R^{3a}$, $(CH_2)_r$—$NR^3C(=NR^3)NR^3R^{3a}$, $(CH_2)_r$—$SO_2NR^3R^{3a}$, $CH_2)_r$—$NR^3SO_2NR^3R^{3a}$, $(CH_2)_r$—$NR^3SO_2$—$C_{1-4}$alkyl, $(CH_2)_r$—$NR_3SO_2CF_3$, or $(CH_2)_r$—$NR^3SO_2$—phenyl, then the $R^3$ group shown is substituted with 0 $R^{1a}$;

$R^5$, at each occurrence, is selected from H, $C_{1-6}$ alkyl, =O, $(CH_2)_rOR^3$, F, Cl, Br, I, CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $(CF_2)_rCF_3$, phenyl substituted with 0–$R^6$, naphthyl substituted with 0–2 $R^6$, and benzyl substituted with 0–2 $R^6$;

provided that when $R^5$ is $(CH_2)_rOR^3$, $(CH_2)_rNR^3R^{3a}$, $(CH_2)_rC(O)R^3$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, or $NR^3SO_2$-phenyl, then the $R^3$ group shown is substituted with 0 $R^{1a}$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_r$ $C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5–10 membered saturated, partially saturated or unsaturated ring which contains 0–2 additional heteroatoms selected from the group consisting of N, O, and S;

R$^9$, at each occurrence, is selected from H, C$_{1-6}$ alkyl and (CH$_2$)$_n$-phenyl;

n, at each occurrence, is selected from 0, 1, 2, and 3;

p, at each occurrence, is selected from 0, 1, and 2;

r, at each occurrence, is selected from 0, 1, 2, and 3; and t, at each occurrence, is selected from 0, 1, 2, and 3.

2. A compound according to claim 1, wherein:

B is selected from: Y and X—Y;

X is selected from —(CR$^2$R$^{2a}$)$_{1-4}$—, —C(O)—, —C(=NR$^{1c}$)—, CR$^2$(NR$^{1c}$R$^2$)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$—, and —OCR$^2$R$^{2a}$—;

Y is —(CH$_2$)$_r$NR$^2$R$^{2a}$, provided that X—Y do not form a N—N or O—N bond;

alternatively, Y is selected from one of the following carbocyclic and heterocyclic systems which are substituted with 0–2 R$^{4a}$;

cyclopropyl, cyclopentyl, cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl; and alternatively, Y is selected from the following bicyclic heteroaryl ring systems:

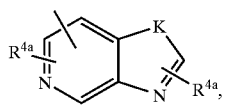
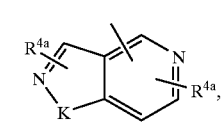
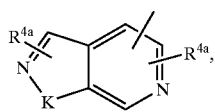
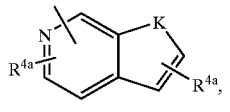
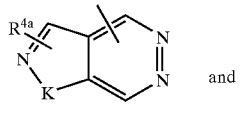

K is selected from O, S, NH, and N.

3. A compound according to claim 2, wherein:

G is selected from the group:

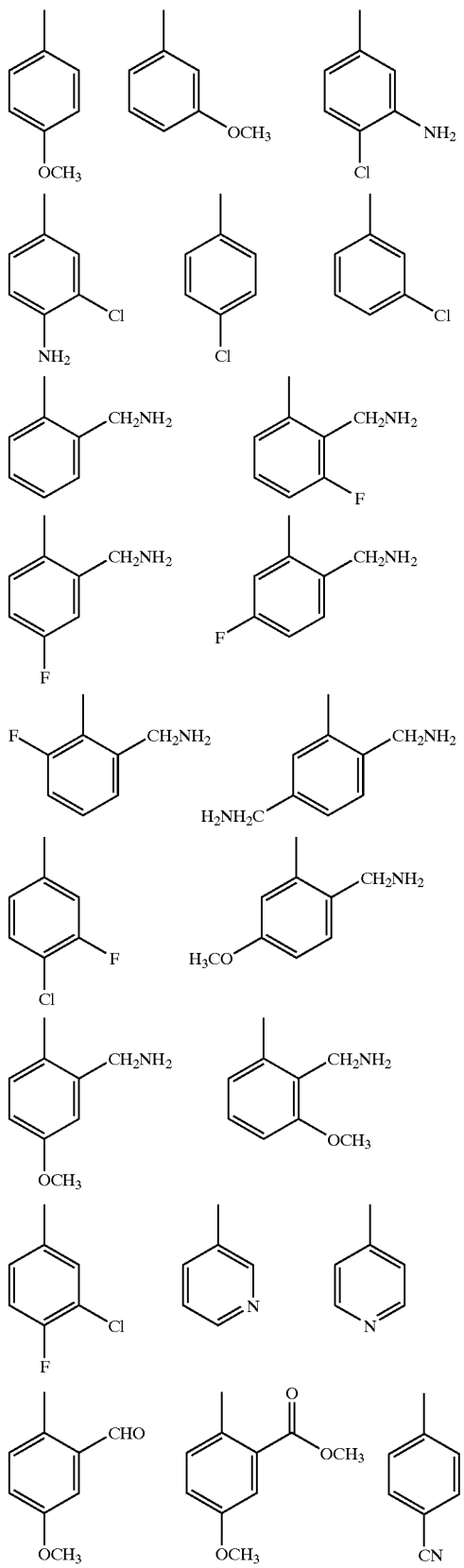

-continued

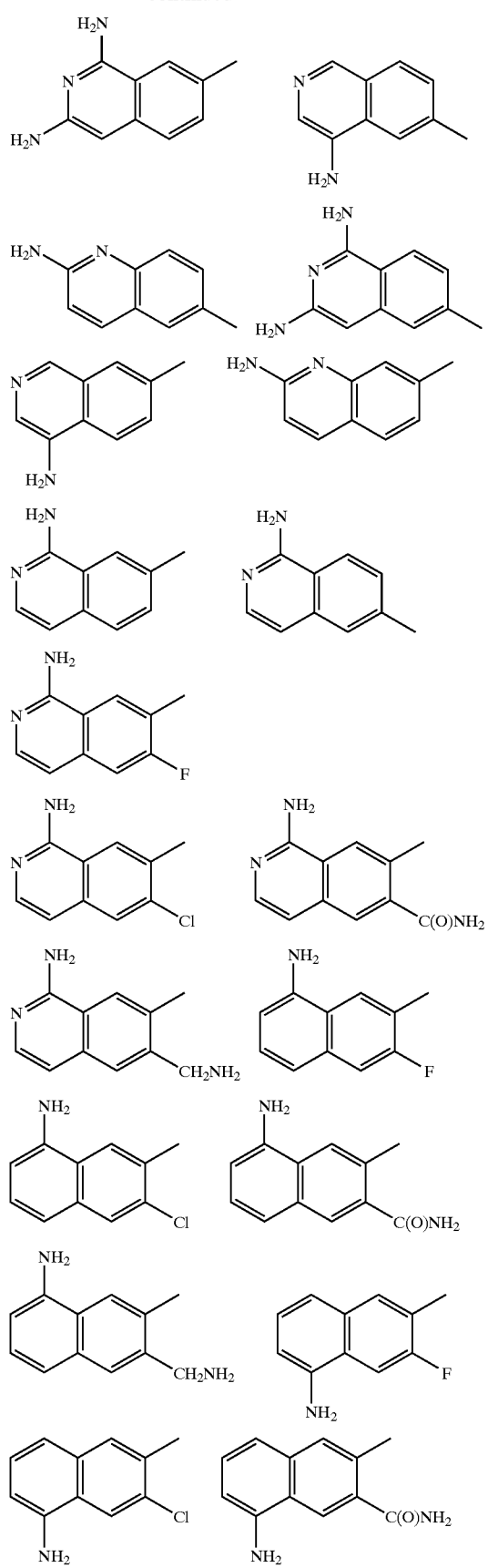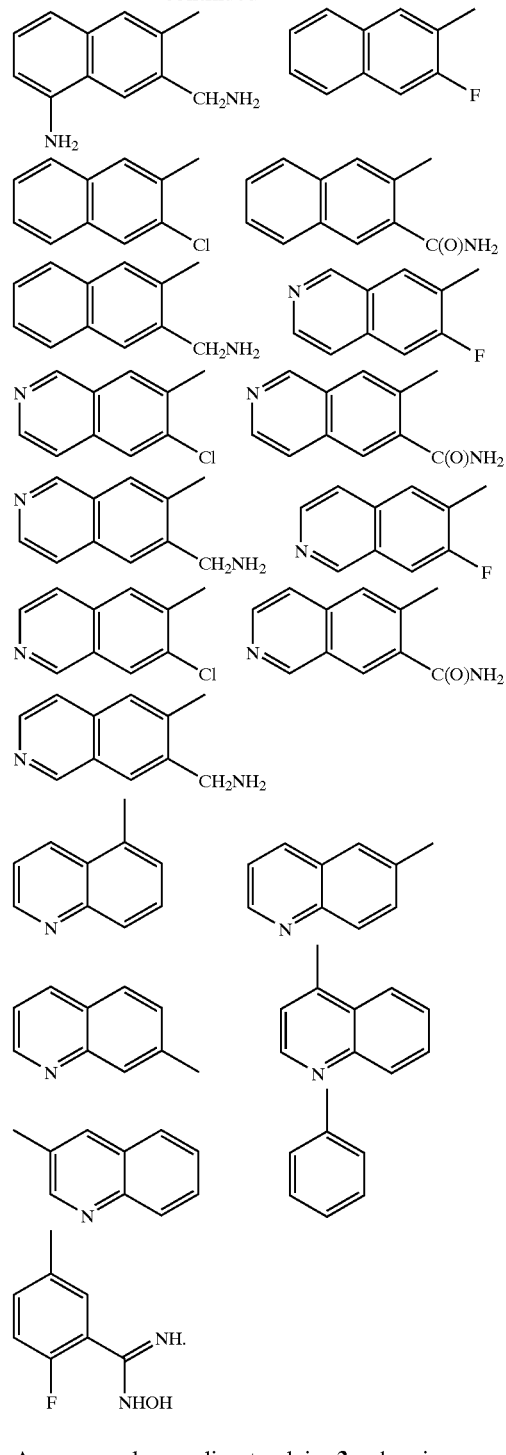
4. A compound according to claim 3, wherein:
G is selected from:
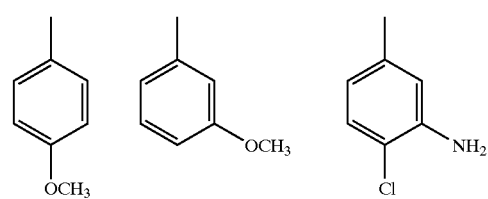

183
-continued
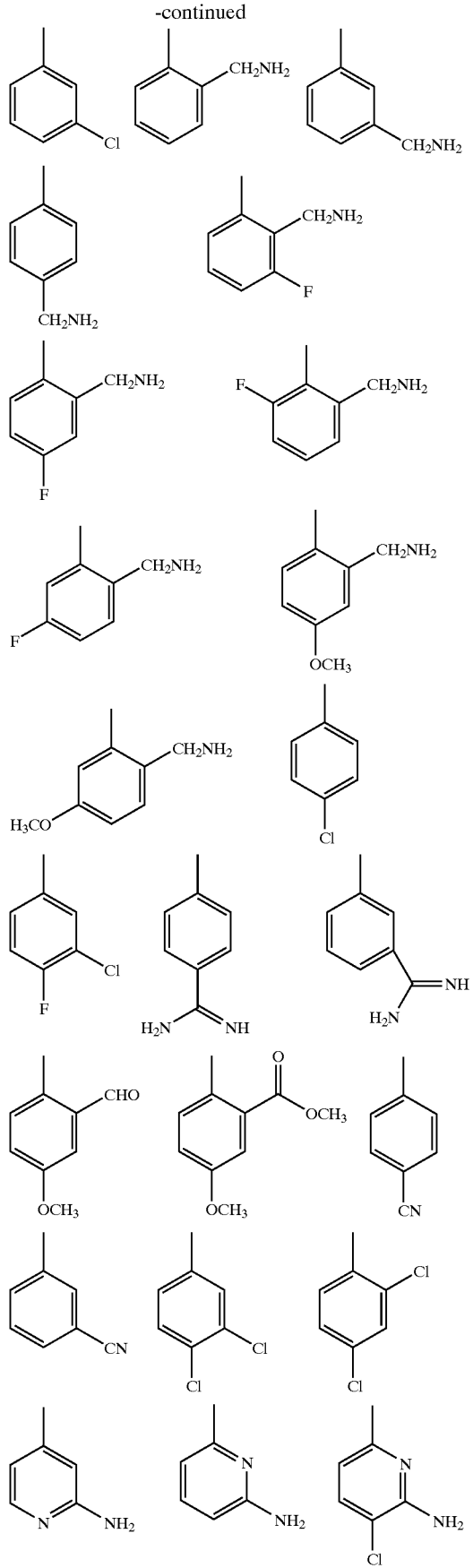
184
-continued
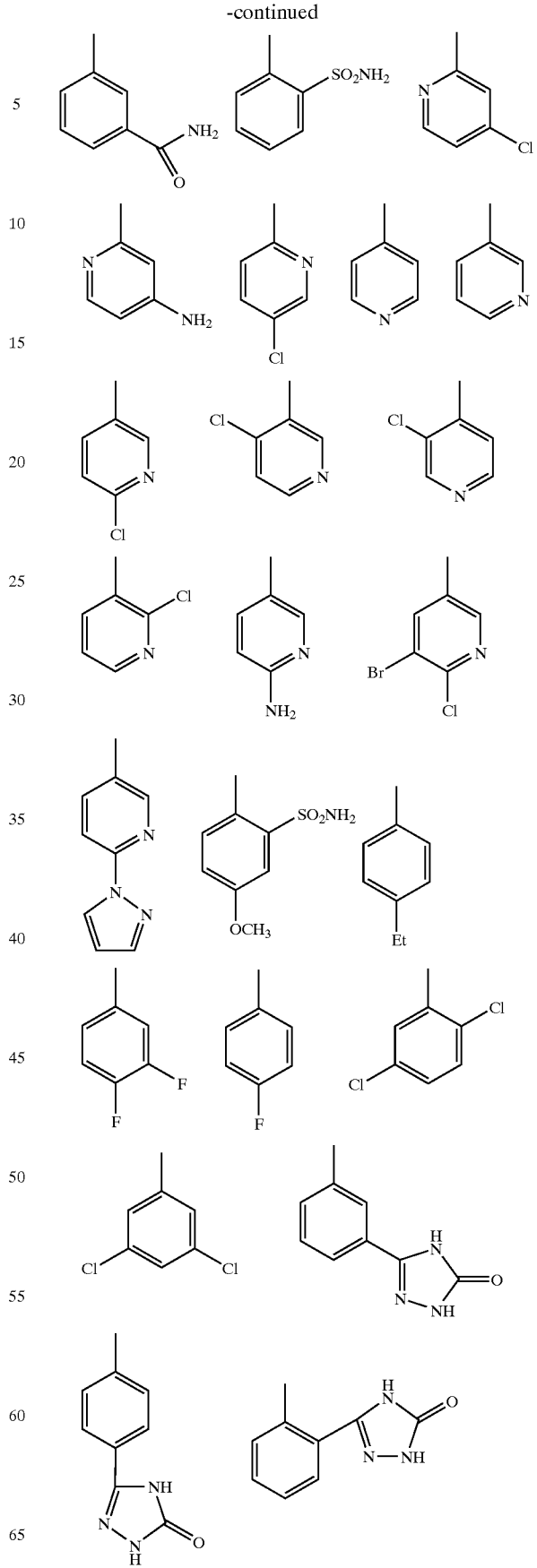

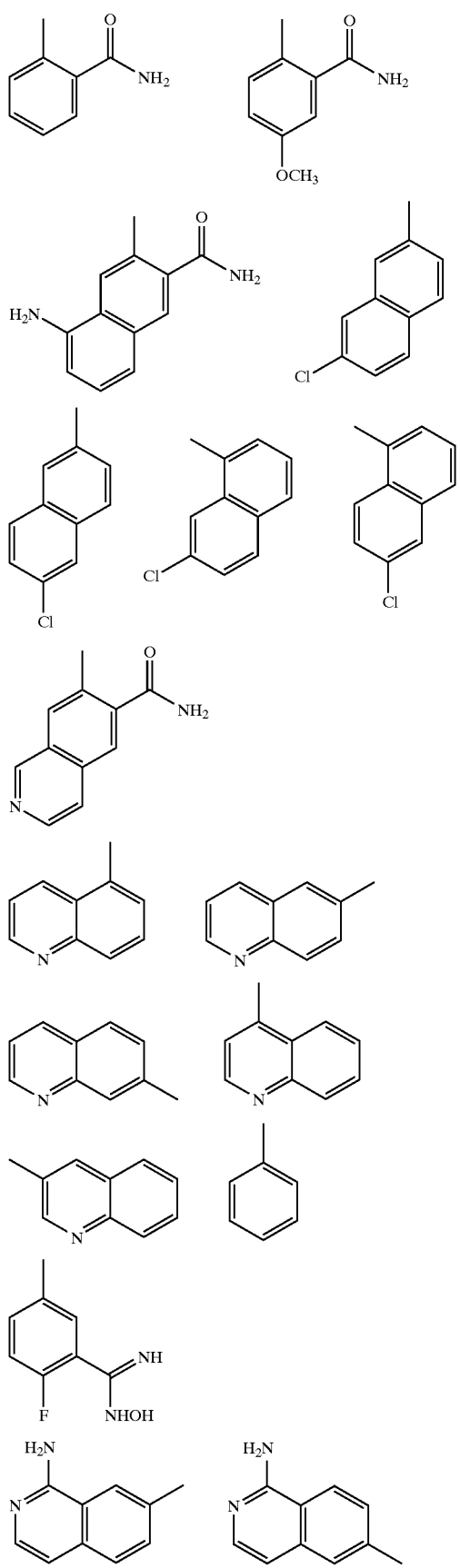

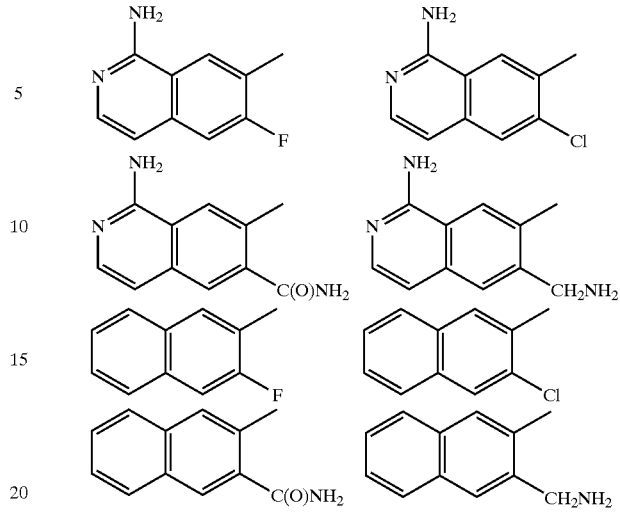

R³, at each occurrence, is selected from H,
C$_{1-4}$ alkyl substituted with 0–2 R$^{1a}$;
C$_{2-4}$ alkenyl substituted with 0–2 R$^{1a}$;
C$_{2-4}$ alkynyl substituted with 0–2 R$^{1a}$;
C$_{3-7}$ cycloalkyl(C$_{0-2}$ alkyl)-substituted with 0–3 R$^{1a}$;
heterocyclyl(C$_{0-2}$ alkyl)-substituted with 0–3 R$^{1a}$;
aryl(C$_{0-2}$ alkyl)-substituted with 0–3 R$^{1a}$;
heteroaryl(C$_{0-2}$ alkyl)-substituted with 0–3 R$^{1a}$;

R$^{3a}$, at each occurrence, is selected from H, C$_{1-4}$ alkyl, and benzyl; and R$^{3b}$, at each occurrence, is selected from H, C$_{1-4}$ alkyl, and benzyl.

5. A compound according to claim 4, wherein:
G is selected from:

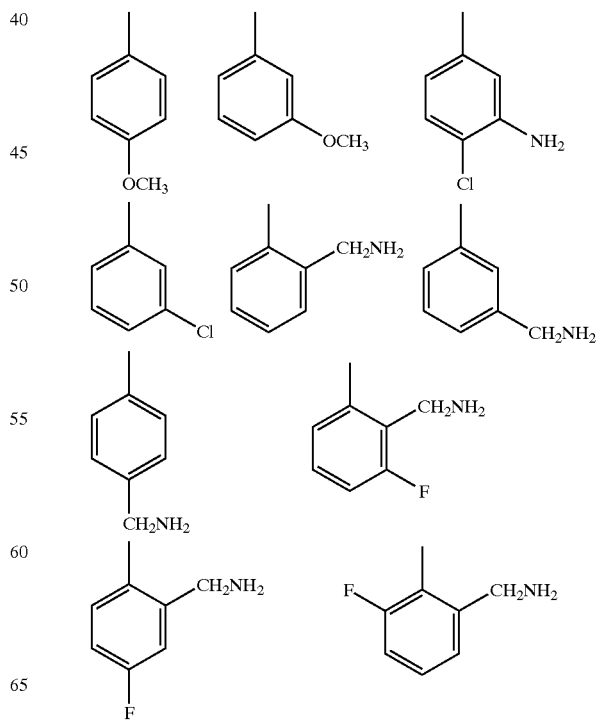

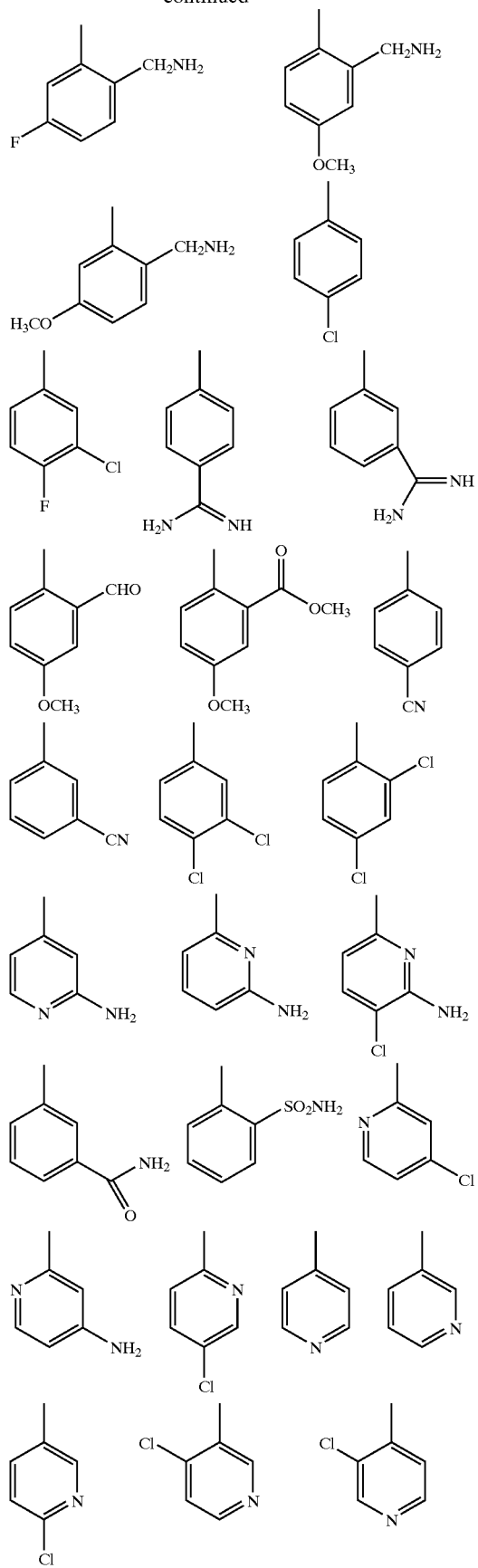
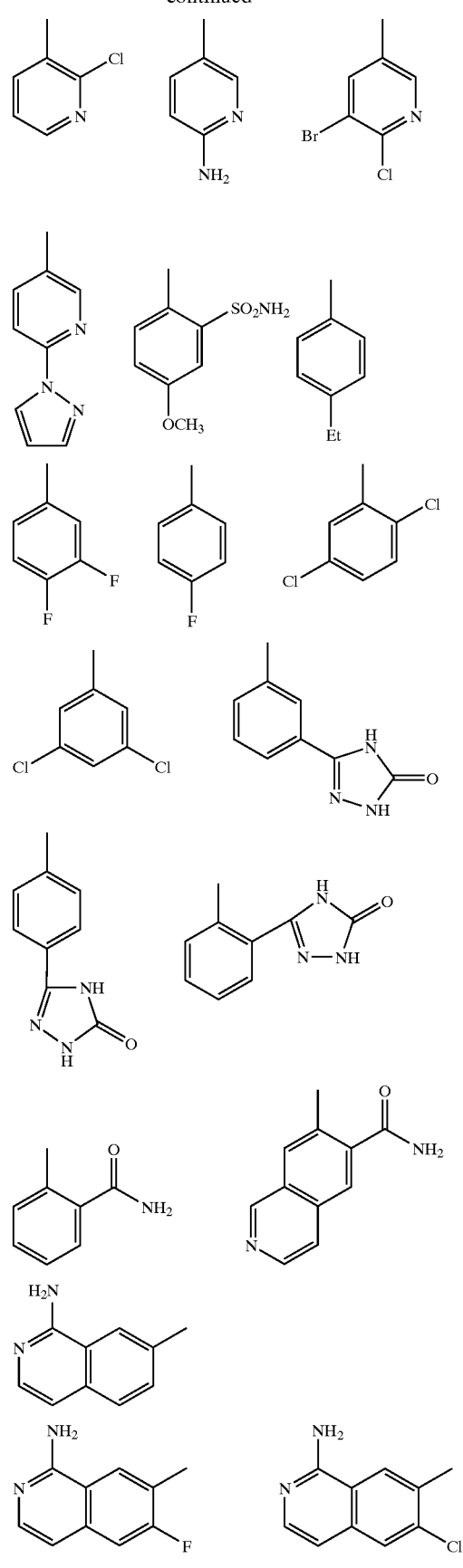

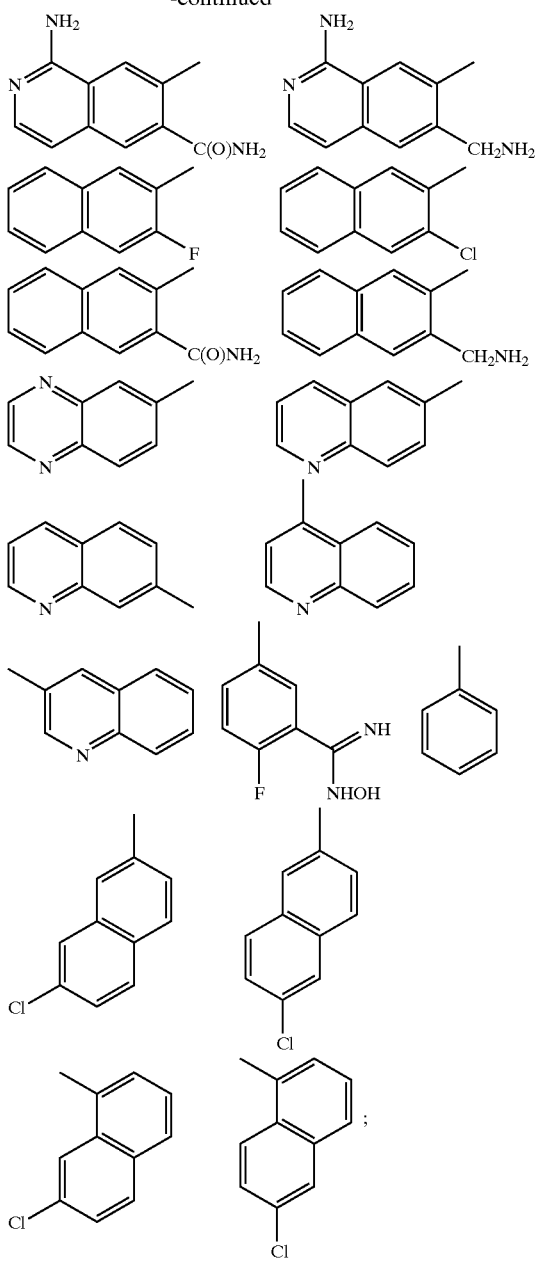

B is selected from phenyl, pyrrolidino, N-pyrrolidino-carbonyl, morpholino, N-morpholino-carbonyl, 1,2,3-triazolyl, imidazolyl, and benzimidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$, and $CH_2CH_3$;

alternatively, $R^2$ and $R^{2a}$, together with the atom to which they are attached, combine to form pyrrolidine substituted with 0–2 $R^{4b}$ or piperidine substituted with 0–2 $R^{4b}$;

$R^4$, at each occurrence, is selected from H, OH, $OR^2$, $(CH_2)OR^2$, $(CH_2)_2OR^2$, F, Br, Cl, I, $C_{1-4}$ alkyl, $NR^2R^{2a}$, $(CH_2)NR^2R^{2a}$, $(CH_2)_2NR^2R^{2a}$, $CF_3$, and $(CF_2)CF_3$;

$R^{4a}$ is selected from H, $C_{1-4}$ alkyl, $CF_3$, $OR^2$, $(CH_2)OR^2$, $(CH_2)_2OR^2$, $NR^2R^{2a}$, $(CH_2)NR^2R^{2a}$, $(CH_2)_2NR^2R^{2a}$, $SR^5$, $S(O)R^5$, $S(O)_2R^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

6. A compound according to claim 5, wherein:

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N,N-diethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, 2-(N-(3-hydroxypyrrolidinyl)methyl)phenyl, and 2-(N-(2-hydroxyethyl)methylamino)-methyl)phenyl.

7. A compound according to claim 1, wherein the compound is selected from the group:

3-({1-[3-fluoro-2'-(methylsulfonyl)-[1,1']-biphenyl-4-yl]-2-oxo-3-piperidinyl}oxy)benzonitrile;

3-({1-[3-fluoro-2'-(methylsulfonyl)-[1,1']-biphenyl-4-yl]-2-oxo-3-piperidinyl}oxy)benzene-carboximidamide;

4-({1-[3-fluoro-2'-(methylsulfonyl)-[1,1']-biphenyl-4-yl]-2-oxo-3-piperidinyl}oxy)benzene-carboximidamide;

3-({1-[2-[(dimethylamino)methyl]-3-fluoro-[1,1']-biphenyl-4-yl]-2-oxo-3-piperidinyl}oxy)benzonitrile;

3-({1-[2-[(dimethylamino)methyl]-3-fluoro-[1,1']-biphenyl-4-yl]-2-oxo-3-piperidinyl}oxy)benzene-carboximidamide;

3-({1-[2'-[(dimethylamino)methyl]-[1,1']-biphenyl-4-yl]-2-oxo-3-piperidinyl}oxy)benzene-carboximidamide;

3-({1-[2-[(dimethylamino)methyl]-3-fluoro-[1,1']-biphenyl-4-yl]-2-oxo-3-piperidinyl}amino)benzene-carboximidamide;

2,4-dichloro-N-{1-[3-fluoro-2'-(methylsulfonyl)-[1,1']-biphenyl-4-yl]-2-oxo-3-piperidinyl}benzamide;

3-chloro-N-{1-[3-fluoro-2'-(methylsulfonyl)-[1,1']-biphenyl-4-yl]-2-oxo-3-piperidinyl}-N-methyl-benzamide;

3,4-dichloro-N-{1-[3-fluoro-2'-(methylsulfonyl)-[1,1']-biphenyl-4-yl]-2-oxo-3-piperidinyl}-benzamide;

4-fluoro-N-{1-[3-fluoro-2'-(methylsulfonyl)-[1,1']-biphenyl-4-yl]-2-oxo-3-piperidinyl}-benzamide;

4-chloro-N-{1-[3-fluoro-2'-(methylsulfonyl)-[1,1']-biphenyl-4-yl]-2-oxo-3-piperidinyl}-benzamide;

2-chloro-N-{1-[3-fluoro-2'-(methylsulfonyl)-[1,1']-biphenyl-4-yl]-2-oxo-3-piperidinyl}-isonicotinamide;

6-chloro-N-{1-[3-fluoro-2'-(methylsulfonyl)-[1,1']-biphenyl-4-yl]-2-oxo-3-piperidinyl}-nicotinamide;

N-{1-[3-fluoro-2'-(methylsulfonyl)-[1,1']-biphenyl-4-yl]-2-oxo-3-piperidinyl}-6-(1H-pyrazol-1-yl) nicotinamide;

1-[3-fluoro-2'-(methylsulfonyl)-[1,1']-biphenyl-4-yl]-2-oxo-3-piperidinyl}-2-chloronicotinate;

1-[3-fluoro-2'-(methylsulfonyl)-[1,1']-biphenyl-4-yl]-2-oxo-3-piperidinyl4-methoxybenzoate;

2-({1-[3-fluoro-2'-(methylsulfonyl)-[1,1']-biphenyl-4-yl]-2-oxo-3-piperidinyl}oxy)-5-methoxybenzaldehyde;

3-[{5-chloro-2-pyridynyl)amino]-1-[3-fluoro-2'-(methylsulfonyl)-[1,1']-biphenyl-4-yl]-2-piperidinone;

1-[3-fluoro-2'-(methylsulfonyl)-[1,1']-biphenyl-4-yl]-3(4-methoxyphenoxy) -2-piperidinone;

2-({1-[3-fluoro-2'-(methylsulfonyl)-[1,1']-biphenyl-4-yl]-2-oxo-3-piperidinyl}oxy)-5-methoxybenzoate;

3-[3-(aminomethyl)phenoxy]-1-[3-fluoro-2'-(methylsulfonyl)-[1,1']-biphenyl-4-yl]-2-piperidinone;

3-chloro-N-{1-[3-fluoro-2'-(methylsulfonyl)-[1,1']-biphenyl-4-yl]-2-oxo-3-piperidinyl}-benzamide;

N-benzyl-4-chloro-N-{1-[3-fluoro-2'-(methylsulfonyl)-[1,1']-biphenyl-4-yl]-2-oxo-3-piperidinyl}-benzamide;

N-{1-[3-fluoro-2'-(methylthio)-[1,1']-biphenyl-4-yl]-2-oxo-3-piperidinyl}-1H-indole-5-carboxamide;

N-{1-[3-fluoro-2'-(methylthio)-[1,1']-biphenyl-4-yl]-2-oxo-3-piperidinyl}-1H-pyrazole-4-carboxamide;

N-{1-[3-fluoro-2'-(methylthio)-[1,1']-biphenyl-4-yl]-2-oxo-3-piperidinyl}-isonicotinamide;

N-{1-[3-fluoro-2'-(methylthio)-[1,1']-biphenyl-4-yl]-2-oxo-3-piperidinyl}-nicotinamide;

6-amino-N-{1-[3-fluoro-2'-(methylthio)-[1,1']-biphenyl-4-yl]-2-oxo-3-piperidinyl}-nicotinamide;

6-amino-N-{1-[3-fluoro-2'-(methylthio)-[1,1']-biphenyl-4-yl]-2-oxo-3-piperidinyl}-nicotinamide;

2-fluoro-5-[1-(3-fluoro-2'-methanesulfonyl-biphenyl-4-yl)-2-oxo-piperidin-3-ylamino]-N-hydroxy-benzamidine;

1-(3-fluoro-2'-methanesulfonyl-biphenyl-4-yl)-3-[3-(5-oxo-4,5-dihydro-1H-[1,2,4]triazol-3-yl)-phenylamino]-piperidin-2-one;

1-(3-fluoro-2'-methanesulfonyl-biphenyl-4-yl)-3-[3-(5-oxo-4,5-dihydro-1H-[1,2,4]triazol-3-yl)-phenoxy]-piperidin-2-one;

or a pharmaceutically acceptable salt form thereof.

8. A pharmaceutical composition, comprising: a pharmaceutically acceptable carrier and a therapeutically effective amount of a compound of claim 1 or a pharmaceutically acceptable salt form thereof.

9. A method for treating a thromboembolic disorder, comprising: administering to a patient in need thereof a therapeutically effective amount of a compound of claim 1 or a pharmaceutically acceptable salt form thereof.

10. A pharmaceutical compostion, comprising: a pharmaceutically acceptable carrier and a therapeutically effective amount of a compound of claim 2 or a pharmaceutically acceptable salt form thereof.

11. A method for treating a thromboembolic disorder, comprising: administering to a patient in need thereof a therapeutically effective amount of a compound of claim 2 or a pharmaceutically acceptable salt form thereof.

12. A pharmaceutical composition, comprising: a pharmaceutically acceptable carrier and a therapeutically effective amount of a compound of claim 3 or a pharmaceutically acceptable salt form thereof.

13. A method for treating a thromboembolic disorder, comprising: administering to a patient in need thereof a therapeutically effective amount of a compound of claim 3 or a pharmaceutically acceptable salt form thereof.

14. A pharmaceutical composition, comprising: a pharmaceutically acceptable carrier and a therapeutically effective amount of a compound of claim 4 or a pharmaceutically acceptable salt form thereof.

15. A method for treating a thromboembolic disorder, comprising: administering to a patient in need thereof a therapeutically effective amount of a compound of claim 4 or a pharmaceutically acceptable salt form thereof.

16. A pharmaceutical composition, comprising: a pharmaceutically acceptable carrier and a therapeutically effective amount of a compound of claim 5 or a pharmaceutically acceptable salt form thereof.

17. A method for treating a thromboembolic disorder, comprising: administering to a patient in need thereof a therapeutically effective amount of a compound of claim 5 or a pharmaceutically acceptable salt form thereof.

18. A pharmaceutical composition, comprising: a pharmaceutically acceptable carrier and a therapeutically effective amount of a compound of claim 6 or a pharmaceutically acceptable salt form thereof.

19. A method for treating a thromboembolic disorder, comprising: administering to a patient in need thereof a therapeutically effective amount of a compound of claim 6 or a pharmaceutically acceptable salt form thereof.

20. A pharmaceutical composition, comprising: a pharmaceutically acceptable carrier and a therapeutically effective amount of a compound of claim 7 or a pharmaceutically acceptable salt form thereof.

21. A method for treating a thromboembolic disorder, comprising: administering to a patient in need thereof a therapeutically effective amount of a compound of claim 7 or a pharmaceutically acceptable salt form thereof.

* * * * *